United States Patent [19]

Fest et al.

[11] Patent Number: 5,213,608
[45] Date of Patent: May 25, 1993

[54] HERBICIDAL SUBSTITUTED SULPHONYLAMIDINOHYDRAZONES

[75] Inventors: Christa Fest, Wuppertal; Ernst R. F. Gesing, Erkrath-Hochdahl; Rolf Kirsten, Monheim; Joachim Kluth, Langenfeld; Reinhard Lantzsch, Wuppertal; Klaus-Helmut Müller, Duesseldorf; Theodor Pfister, Monheim; Hans-Jochem Riebel, Wuppertal; Frank Rosenfeldt, Langenfeld; Hans-Joachim Santel, Leverkusen; Klaus Lürssen; Robert R. Schmidt, both of Bergisch-Gladbach, all of Fed. Rep. of Germany

[73] Assignee: Bayer Aktiengesellschaft, Leverkusen, Fed. Rep. of Germany

[21] Appl. No.: 916,330

[22] Filed: Jul. 16, 1992

Related U.S. Application Data

[62] Division of Ser. No. 583,933, Sep. 17, 1990, Pat. No. 5,167,692.

[30] Foreign Application Priority Data

Oct. 10, 1989 [DE] Fed. Rep. of Germany ....... 3933792
May 31, 1990 [DE] Fed. Rep. of Germany ....... 4017460

[51] Int. Cl.$^5$ .................. C07D 239/42; C07D 401/12; C07D 403/12; A01N 43/54
[52] U.S. Cl. .................. 504/239; 544/320; 544/321; 544/323; 544/324; 544/331; 544/332; 504/242; 504/243
[58] Field of Search ............ 71/92, 90, 91; 544/320, 544/321, 323, 324, 331, 332

[56] References Cited

U.S. PATENT DOCUMENTS 4,743,294  4/1988  Diehr ...................... 71/93
4,797,484  1/1989  Moriya ................... 544/215
4,880,932  11/1989  Moriya ................... 544/320

Primary Examiner—John M. Ford
Attorney, Agent, or Firm—Sprung Horn Kramer & Woods

[57] ABSTRACT

Herbicidal substituted sulphonylamidinohydrazones of the formula

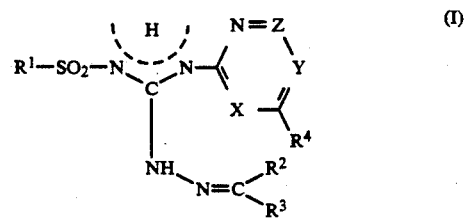

in which
$R^1$ represents in each case optionally substituted aryl, aralkyl or heteroaryl,
$R^2$ represents hydrogen, or represents in each case optionally substituted alkyl, aryl or aralkyl,
$R^3$ represents hydrogen, or represents in each case optionally substituted alkyl, alkenyl, alkadienyl, alkinyl, (hetero)aryl, aralkyl, aralkenyl, alkoxy, alkoxycarbonyl or dialkylamino, or together with $R^2$ represents optionally substituted alkanediyl,
$R^4$ represents hydrogen, halogen, hydroxyl, alkyl, halogenoalkyl, alkoxyalkyl, alkoxy, halogenoalkoxy, alkylthio, halogenoalkylthio, amino, alkylamino or dialkylamino,
X represents nitrogen or a —CH group,
Y represents nitrogen or a —CR$^5$ group where
  $R^5$ represents hydrogen, halogen, cyano, alkyl, formyl, alkyl-carbonyl or alkoxy-carbonyl, and
Z represents nitrogen or a —CR$^6$ group where
  $R^6$ represents hydrogen, halogen, hydroxyl, alkyl, halogenoalkyl, alkoxy, halogenoalkoxy, alkylthio, alkylamino or dialkylamino.

7 Claims, No Drawings

HERBICIDAL SUBSTITUTED SULPHONYLAMIDINOHYDRAZONES

This is a division of application Ser. No. 07/583,933, filed Sep. 17, 1990, now U.S. Pat. No. 5,167,692.

The invention relates to new substituted sulphonylamidinohydrazones, to processes for their preparation, and to their use as herbicides.

It has already been disclosed that certain substituted aminoguanidinoazines, such as, for example, N'-(4,6-dimethyl-pyrimidin-2-yl)-N''-acetylamino-N''''-(2-chlorophenylsulphonyl)-guanidine, have herbicidal properties (cf. EP-A 121,082). However, the herbicidal action of the aminoguanidinoazines known to date is not always entirely satisfactory.

New substituted sulphonylamidinohydrazones have now been found, of the general formula (I)

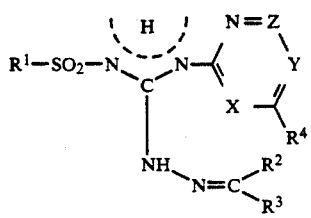
(I)

in which
$R^1$ represents in each case optionally substituted aryl, aralkyl or heteroaryl,
$R^2$ represents hydrogen, or represents in each case optionally substituted alkyl, aryl or aralkyl,
$R^3$ represents hydrogen, or represents in each case optionally substituted alkyl, alkenyl, alkadienyl, alkinyl, (hetero)aryl, aralkyl, aralkenyl, alkoxy, alkoxycarbonyl or dialkylamino, or together with $R^2$ represents optionally substituted alkanediyl,
$R^4$ represents hydrogen, halogen, hydroxyl, alkyl, halogenoalkyl, alkoxyalkyl, alkoxy, halogenoalkoxy, alkylthio, halogenoalkylthio, amino, alkylamino or dialkylamino,
X represents nitrogen or a —CH group,
Y represents nitrogen or a —CR$^5$ group where
  $R^5$ represents hydrogen, halogen, cyano, alkyl, formyl, alkyl-carbonyl or alkoxy-carbonyl, and
Z represents nitrogen or a —CR$^6$ group where
  $R^6$ represents hydrogen, halogen, hydroxyl, alkyl, halogenoalkyl, alkoxy, halogenoalkoxy, alkylthio, alkylamino or dialkylamino.

The general formula (I) represents the individual tautomers of the formulae (IA), (IB) and (IC) which are possible

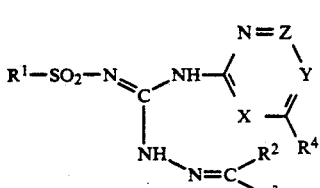
(IA)

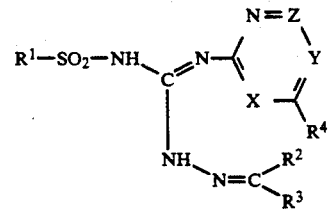
(IB)

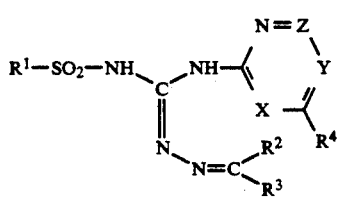
(IC)

and the mixtures of these tautomers, as well as the E- and Z-isomers which are caused by the C-N double bonds which are present in each case, and their mixtures.

The new substituted sulphonylamidinohydrazones of the general formula (I) are obtained when
(a) aminoguanidines of the general formula (II)

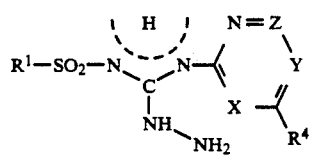
(II)

in which $R^1$, $R^4$, X, Y and Z are as defined above, are reacted with carbonyl compounds of the general formula (III)

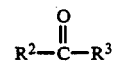
(III)

in which $R^2$ and $R^3$ are as defined above, or with N,N-dialkyl-carboxamide acetals or ketals, if appropriate in the presence of a condensation auxiliary and if appropriate in the presence of a diluent, or when
(b) sulphonyl compounds of the general formula (IV)

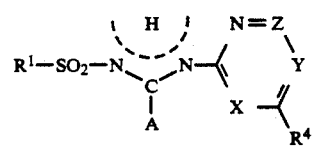
(IV)

in which
$R^1$, $R^4$, X, Y and Z are as defined above and
A represents halogen or one of the leaving groups indicated below

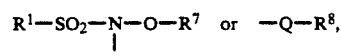

where
$R^1$ is as defined above,
$R^7$ represents alkyl, alkenyl or aralkyl, $R^8$ represents in each case optionally substituted alkyl, aralkyl or aryl and Q represents oxygen or sulphur, are reacted with hydrazones of the general formula (V)

(V)

in which $R^2$ and $R^3$ are as defined above, if appropriate in the presence of a diluent.

The new substituted sulphonylamidinohydrazones of the general formula (I) are distinguished by a powerful herbicidal activity.

Surprisingly, the new compounds of the general formula (I) have a considerably more powerful herbicidal action than previously known compounds which have a similar structure and which act in the same way, such as, for example, the compound N'-(4,6-dimethylpyrimidin-2-yl)-N'''-acetylamino-N''''-(2-chloro-phenylsulphonyl)guanidine (cf. EP-A 121,082).

The present invention preferably relates to compounds of the formula (I) in which $R^1$ represents the radical

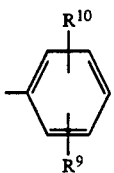

where $R^9$ and $R^{10}$ are identical or different and represent hydrogen, fluorine, chlorine, bromine, iodine, cyano, nitro, $C_1$–$C_6$-alkyl (which is optionally substituted by fluorine, chlorine, bromine, cyano, carboxyl, $C_1$–$C_4$-alkoxycarbonyl, $C_1$–$C_4$-alkylaminocarbonyl, di-($C_1$–$C_4$-alkyl)-amino-carbonyl, hydroxyl, $C_1$–$C_4$-alkoxy, formyloxy, $C_1$–$C_4$-alkyl-carbonyloxy, $C_1$–$C_4$-alkoxy-carbonyloxy, $C_1$–$C_4$-alkylaminocarbonyloxy, $C_1$–$C_4$-alkylthio, $C_1$–$C_4$-alkylsulphinyl, $C_1$–$C_4$-alkylsulphonyl, di-($C_1$–$C_4$-alkyl)-aminosulphonyl, $C_3$–$C_6$-cycloalkyl or phenyl), or represent $C_2$–$C_6$-alkenyl (which is optionally substituted by fluorine, chlorine, bromine, cyano, $C_1$–$C_4$-alkoxy-carbonyl, carboxyl or phenyl), or represent $C_2$–$C_6$-alkinyl (which is optionally substituted by fluorine, chlorine, bromine, cyano, $C_1$–$C_4$-alkoxy-carbonyl, carboxyl or phenyl), or represent $C_1$–$C_4$-alkoxy (which is optionally substituted by fluorine, chlorine, bromine, cyano, carboxyl, $C_1$–$C_4$-alkoxy-carbonyl, $C_1$–$C_4$-alkoxy, $C_1$–$C_4$-alkylthio, $C_1$–$C_4$-alkylsulphinyl or $C_1$–$C_4$-alkylsulphonyl), or represent $C_1$–$C_4$-alkylthio (which is optionally substituted by fluorine, chlorine, bromine, cyano, carboxyl, $C_1$–$C_4$-alkoxycarbonyl, $C_1$–$C_4$-alkylthio, $C_1$–$C_4$-alkylsulphinyl or $C_1$–$C_4$-alkylsulphonyl), or represent $C_3$–$C_6$-alkenyloxy (which is optionally substituted by fluorine, chlorine, bromine, cyano or $C_1$–$C_4$-alkoxy-carbonyl), or represent $C_2$–$C_6$-alkenylthio (which is optionally substituted by fluorine, chlorine, bromine, cyano, nitro, $C_1$–$C_3$-alkylthio or $C_1$–$C_4$-alkoxycarbonyl), $C_3$–$C_6$-alkinyloxy or $C_3$–$C_6$-alkinylthio, or represent the radical —S(O)$_p$—$R^{11}$ where p represents the numbers 1 or 2 and $R^{11}$ represents $C_1$–$C_4$-alkyl (which is optionally substituted by fluorine, chlorine, bromine, cyano or $C_1$–$C_4$-alkoxy-carbonyl), $C_3$–$C_6$-alkenyl, $C_3$–$C_6$-alkinyl, phenyl, $C_1$–$C_4$-alkoxy, $C_1$–$C_4$-alkoxy-$C_1$–$C_4$-alkylamino, $C_1$–$C_4$-alkylamino or di-($C_1$–$C_4$-alkyl)-amino, or represents the radical —NHOR$^{12}$ where $R^{12}$ represents $C_1$–$C_{12}$-alkyl (which is optionally substituted by fluorine, chlorine, cyano, $C_1$–$C_4$-alkoxy, $C_1$–$C_4$-alkylthio, $C_1$–$C_4$-alkylsulphinyl, $C_1$–$C_4$-alkylsulphonyl, $C_1$–$C_4$-alkyl-carbonyl, $C_1$–$C_4$-alkoxycarbonyl, $C_1$–$C_4$-alkylamino-carbonyl or di-($C_1$–$C_4$-alkyl)amino-carbonyl, or represents $C_3$–$C_6$-alkenyl (which is optionally substituted by fluorine, chlorine or bromine), $C_3$–$C_6$-alkinyl, $C_3$–$C_6$-cycloalkyl, $C_3$–$C_6$-cycloalkyl-$C_1$–$C_2$-alkyl, phenyl-$C_1$–$C_2$-alkyl (which is optionally substituted by fluorine, chlorine, nitro, cyano, $C_1$–$C_4$-alkyl, $C_1$–$C_4$-alkoxy or $C_1$–$C_4$-alkoxy-carbonyl), or represents benzhydryl, or represents phenyl (which is optionally substituted by fluorine, chlorine, nitro, cyano, $C_1$–$C_4$-alkyl, trifluoromethyl, $C_1$–$C_4$-alkoxy, $C_1$–$C_2$-fluoroalkoxy, $C_1$–$C_4$-alkylthio, trifluoromethylthio or $C_1$–$C_4$-alkoxycarbonyl), $R^9$ and $R^{10}$ furthermore represent phenyl or phenoxy, or represent amino, $C_1$–$C_4$-alkylcarbonylamino, $C_1$–$C_4$-alkoxy-carbonylamino, $C_1$–$C_4$-alkylaminocarbonylamino or di-($C_1$–$C_4$-alkyl)amino-carbonylamino, or represent the radical —CO—$R^{13}$ where $R^{13}$ represents $C_1$–$C_6$-alkyl, $C_1$–$C_6$-alkoxy (which is optionally substituted by fluorine, chlorine, methoxy or ethoxy), or represents $C_3$–$C_6$-cycloalkoxy, $C_3$–$C_6$-alkenyloxy, $C_1$–$C_4$-alkylthio, $C_1$–$C_4$-alkylamino, $C_1$–$C_4$-alkoxyamino, $C_1$–$C_4$-alkoxy-$C_1$–$C_4$-alkyl-amino or di-($C_1$–$C_4$-alkyl)-amino (each of which is optionally substituted by fluorine and/or chlorine), $R^9$ and $R^{10}$ furthermore represent $C_1$–$C_4$-alkylsulphonyloxy, di-($C_1$–$C_4$-alkyl)-aminosulphonylamino or thiazolyloxy, or represent the radical —CH=N—$R^{14}$ where $R^{14}$ represents $C_1$–$C_6$-alkyl which is optionally substituted by fluorine, chlorine, cyano, carboxyl, $C_1$–$C_4$-alkoxy, $C_1$–$C_4$-alkylthio, $C_1$–$C_4$-alkylsulphinyl or $C_1$–$C_4$-alkylsulphonyl, or represents benzyl which is optionally substituted by fluorine or chlorine, or represents $C_3$–$C_6$-alkenyl or $C_3$–$C_6$-alkinyl, each of which is optionally substituted by fluorine or chlorine, or represents phenyl which is optionally substituted by fluorine, chlorine, bromine, $C_1$–$C_4$-alkyl, $C_1$–$C_4$-alkoxy, trifluoromethyl, trifluoromethoxy or trifluoromethylthio, or represents $C_1$–$C_6$-alkoxy, $C_3$–$C_6$-alkenoxy, $C_3$–$C_6$-alkinoxy or benzyloxy, each of which is optionally substituted by fluorine and/or chlorine, or represents amino, $C_1$–$C_4$-alkylamino, di-($C_1$–$C_4$-alkyl)-amino, phenylamino, $C_1$–$C_4$-alkylcarbonylamino, $C_1$–$C_4$-alkoxy-carbonylamino or $C_1$–$C_4$-alkylsulphonylamino, or represents phenylsulphonylamino which is optionally substituted by fluorine, chlorine, bromine or methyl;

in which formula furthermore $R^1$ represents the radical

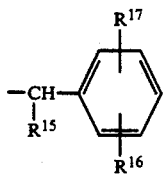

where
R$^{15}$ represents hydrogen or C$_1$–C$_4$-alkyl,
R$^{16}$ and R$^{17}$ are identical or different and represent hydrogen, fluorine, chlorine, bromine, nitro, cyano, C$_1$–C$_4$-alkyl (which is optionally substituted by fluorine and/or chlorine), C$_1$–C$_4$-alkoxy (which is optionally substituted by fluorine and/or chlorine), carboxyl, C$_1$–C$_4$-alkoxycarbonyl, C$_1$–C$_4$-alkylsulphonyl or di-(C$_1$–C$_4$-alkyl)-aminosulphonyl;
in which formula furthermore
R$^1$ represents the radical

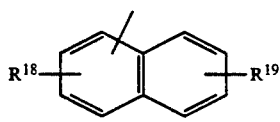

where
R$^{18}$ and R$^{19}$ are identical or different and represent hydrogen, fluorine, chlorine, bromine, nitro, cyano, dimethylamino, C$_1$–C$_4$-alkyl (which is optionally substituted by fluorine and/or chlorine) or C$_1$–C$_4$alkoxy (which is optionally substituted by fluorine and/or chlorine);
in which formula furthermore
R$^1$ represents the radical

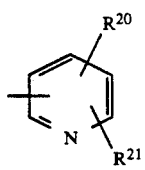

where
R$^{20}$ and R$^{21}$ are identical or different and represent hydrogen, fluorine, chlorine, bromine, nitro, cyano, C$_1$–C$_4$-alkyl (which is optionally substituted by fluorine and/or chlorine), C$_2$–C$_4$-alkenyl (which is optionally substituted by fluorine and/or chlorine), C$_1$–C$_4$-alkoxy (which is optionally substituted by fluorine and/or chlorine), or represent C$_1$–C$_4$-alkylthio, C$_1$–C$_4$-alkylsulphinyl or C$_1$–C$_4$-alkylsulphonyl (each of which is optionally substituted by fluorine and/or chlorine), and also represent di-(C$_1$–C$_4$-alkyl)-aminosulphonyl, C$_1$–C$_4$-alkoxy-carbonyl, dimethylaminocarbonyl or dioxolanyl;
in which formula furthermore
R$^1$ represents the radical

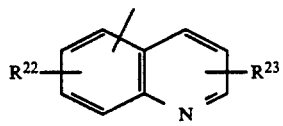

where
R$^{22}$ and R$^{23}$ are identical or different and represent hydrogen, fluorine, chlorine, bromine, C$_1$–C$_4$-alkyl (which is optionally substituted fluorine and/or bromine), C$_1$–C$_4$-alkoxy (which is optionally substituted by fluorine and/chlorine), or represent C$_1$–C$_4$-alkylthio, C$_1$–C$_4$-alkylsulphinyl or C$_1$–C$_4$-alkylsulphonyl (each of which is optionally substituted by fluorine and/or chlorine), or represent di-(C$_1$–C$_4$-alkyl)-aminosulphonyl;
in which formula furthermore
R$^1$ represents the radical

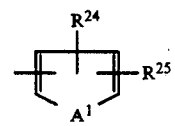

where
R$^{24}$ and R$^{25}$ are identical or different and represent hydrogen, fluorine, chlorine, bromine, cyano, nitro, C$_1$–C$_4$-alkyl (which is optionally substituted by fluorine, chlorine, C$_1$–C$_4$-alkoxy and/or C$_1$–C$_4$-halogenoalkoxy), C$_1$–C$_4$-alkoxy (which is optionally substituted by fluorine and/or chlorine), or C$_1$–C$_4$-alkylthio, C$_1$–C$_4$-alkylsulphinyl or C$_1$–C$_4$-alkylsulphonyl (each of which is optionally substituted by fluorine and/or chlorine), di-(C$_1$–C$_4$-alkyl)-aminosulphonyl, C$_1$–C$_4$-alkoxy-carbonyl, dioxolanyl or 2-thiazolyl, and
A$^1$ represents oxygen, sulphur or the N—Z$^1$ group
where
Z$^1$ represents hydrogen, C$_1$–C$_4$-alkyl (which is optionally substituted by fluorine, chlorine, bromine or cyano), C$_3$–C$_6$-cycloalkyl, benzyl, phenyl (which is optionally substituted by fluorine, chlorine, bromine or nitro), C$_1$–C$_4$-alkylcarbonyl, C$_1$–C$_4$-alkoxy-carbonyl or di-(C$_1$–C$_4$-alkyl)-aminocarbonyl;
in which formula furthermore
R$^1$ represents the radical

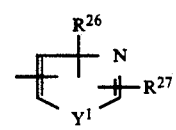

where
R$^{26}$ represents hydrogen, C$_1$–C$_5$-alkyl or halogen,
R$^{27}$ represents hydrogen or C$_1$–C$_5$-alkyl and
Y$^1$ represents oxygen, sulphur or the N—R$^{28}$ group
where
R$^{28}$ represents hydrogen or C$_1$–C$_5$-alkyl;
in which formula furthermore
R$^1$ represents the radical

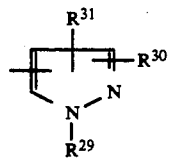

where
R$^{29}$ represents hydrogen, C$_1$-C$_4$-alkyl, phenyl or (iso)quinolinyl,
R$^{30}$ represents hydrogen, halogen, cyano, nitro, C$_1$-C$_4$-alkyl (which is optionally substituted by fluorine and/or chlorine), C$_1$-C$_4$-alkoxy (which is optionally substituted by fluorine and/or chlorine), dioxolanyl or C$_1$-C$_4$-alkoxy-carbonyl, and
R$^{31}$ represents hydrogen, halogen or C$_1$-C$_4$-alkyl;
in which formula furthermore
R$^1$ represents the radical

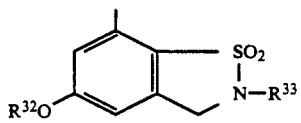

where
R$^{32}$ represents C$_1$-C$_3$-alkyl and
R$^{33}$ represents C$_1$-C$_4$-alkyl,
in which formula furthermore
R$^1$ represents the radical

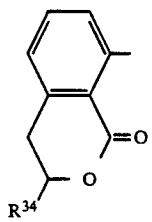

where
R$^{34}$ represents hydrogen or methyl;
in which formula furthermore
R$^1$ represents the radical

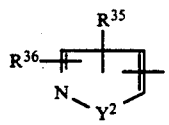

where
R$^{35}$ represents hydrogen, halogen or C$_1$-C$_4$-alkyl,
R$^{36}$ represents hydrogen, halogen, C$_1$-C$_4$-alkyl, C$_1$-C$_4$-halogenoalkyl, C$_1$-C$_4$-alkoxy or C$_1$-C$_4$-halogenoalkoxy, Y$^2$ represents oxygen or sulphur,
in which formula furthermore
R$^1$ represents pentamethylphenyl,
in which formula furthermore
R$^2$ represents hydrogen, or represents C$_1$-C$_6$-alkyl which is optionally substituted by fluorine, chlorine and/or bromine, or represents phenyl or benzyl, each of which is optionally substituted by fluorine, chlorine, bromine, C$_1$-C$_4$-alkyl and/or C$_1$-C$_4$-alkoxy,
R$^3$ represents hydrogen, or represents C$_1$-C$_{20}$-alkyl, C$_2$-C$_{10}$-alkenyl, C$_2$-C$_{10}$-alkinyl or C$_4$-C$_{10}$-alkadienyl, each of which is optionally substituted by fluorine, chlorine and/or bromine, or represents C$_1$-C$_4$-alkoxy-C$_1$-C$_4$-alkyl, or represents C$_1$-C$_4$-alkyl-thio-C$_1$-C$_4$-alkyl, or represents phenyl which is optionally substituted by fluorine, chlorine, bromine, carboxyl, cyano, nitro, amino, C$_1$-C$_4$-alkyl (which is optionally substituted by fluorine and/or chlorine), C$_1$-C$_4$-alkoxy (which is optionally substituted by fluorine and/or chlorine), C$_1$-C$_4$-alkylthio (which is optionally substituted by fluorine and/or chlorine), di-(C$_1$-C$_4$-alkyl)-amino, C$_1$-C$_4$-alkoxy-carbonyl and/or phenoxy (which is optionally substituted by fluorine, chlorine and/or trifluoromethyl), or represents naphthyl, or represents pyridyl, pyrrolyl, furyl, thiazolyl or thienyl, each of which is optionally substituted by cyano, nitro, fluorine, chlorine, bromine, C$_1$-C$_4$-alkyl and/or C$_1$-C$_4$-alkoxy, or represents dithienyl, or represents phenyl-C$_1$-C$_2$-alkyl or phenylethenyl, each of which is optionally substituted by fluorine, chlorine, bromine, C$_1$-C$_4$-alkyl and/or C$_1$-C$_4$-alkoxy, or represents C$_1$-C$_6$-alkoxy, C$_1$-C$_6$-alkoxy-carbonyl or di-(C$_1$-C$_4$-alkyl)-amino, or together with R$^2$ represents C$_2$-C$_6$-alkanediyl which is optionally substituted by fluorine, chlorine, bromine, C$_1$-C$_4$-alkyl and/or C$_1$-C$_4$-alkoxy-carbonyl,
R$^4$ represents hydrogen, fluorine, chlorine, bromine, C$_1$-C$_4$-alkyl, C$_1$-C$_4$-halogenoalkyl, C$_1$-C$_2$-alkoxy-C$_1$-C$_2$-alkyl, bis-(C$_1$-C$_2$-alkoxy)-C$_1$-C$_2$-alkyl, C$_1$-C$_4$-alkoxy, C$_1$-C$_4$-halogenoalkoxy, C$_1$-C$_4$-alkylthio, C$_1$-C$_4$-halogenoalkylthio, amino, C$_1$-C$_4$-alkylamino, dimethylamino or diethylamino,
X represents nitrogen or a —CH group,
Y represents nitrogen or a —CR$^5$ group where
R$^5$ represents hydrogen, fluorine, chlorine, bromine, cyano, methyl, formyl, actyl, methoxycarbonyl or ethoxycarbonyl, and
Z represents nitrogen or a —CR$^6$ group where
R$^6$ represents hydrogen, fluorine, chlorine, bromine, C$_1$-C$_4$-alkyl, trifluoromethyl, C$_1$-C$_4$-alkoxy, difluoromethoxy, C$_1$-C$_4$-alkylthio, C$_1$-C$_4$-alkylamino, dimethylamino or diethylamino.

The invention particularly relates to compounds of the formula (I) in which
R$^1$ represents the radical

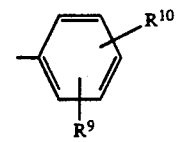

where
R$^9$ represents fluorine, chlorine, bromine, cyano, methyl, trifluoromethyl, methoxy, ethoxy, difluoromethoxy, trifluoromethoxy, C$_1$-C$_3$-alkylthio, C$_1$-C$_3$-alkylsulphinyl, C$_1$-C$_3$-alkylsulphonyl, phenylsulphonyl, dimethylaminosulphonyl, diethylaminosulphonyl, N-methoxy-N-methylaminosulphonyl, phenyl, phenoxy or C$_1$-C$_3$-alkoxycarbonyl, and
R$^{10}$ represents hydrogen, fluorine, chlorine, bromine, methyl or methoxy;
in which formula furthermore
R$^1$ represents the radical

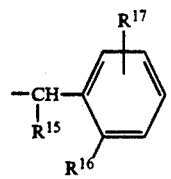

where
R$^{15}$ represents hydrogen,
R$^{16}$ represents fluorine, chlorine, bromine, cyano, methyl, methoxy, ethoxy, difluoromethoxy, trifluoromethoxy, methoxycarbonyl, ethoxycarbonyl, methylsulphonyl or dimethylaminosulphonyl, and
R$^{17}$ represents hydrogen or chlorine;
in which formula furthermore
R$^1$ represents the radical

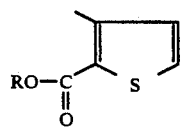

where
R represents C$_1$-C$_2$-alkyl, or
R$^1$ represents the radical

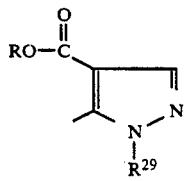

where
R$^{29}$ represents methyl or phenyl and
R represents C$_1$-C$_2$-alkyl, or
R$^1$ represents naphthyl;
in which formula furthermore
R$^2$ represents hydrogen, C$_1$-C$_4$-alkyl or phenyl,
R$^3$ represents C$_1$-C$_{10}$-alkyl, C$_2$-C$_{10}$-alkenyl or C$_4$-C$_{10}$-alkadienyl, or represents phenyl which is optionally substituted by fluorine, chlorine, bromine, carboxyl, cyano, nitro, methyl, ethyl, trifluoromethyl, methoxy, ethoxy, difluoromethoxy, trifluoromethoxy, methylthio, ethylthio, difluoromethylthio, trifluoromethylthio, dimethylamino and/or phenoxy (which is optionally substituted by fluorine, chlorine and/or trifluoromethyl), or represents pyridyl, furyl, thiazolyl or thienyl, each of which is optionally substituted by cyano, nitro, fluorine, chlorine, bromine, methyl, ethyl, methoxy or ethoxy, or represents dithienyl, or represents benzyl or phenylethenyl, or represents C$_1$-C$_4$-alkoxy, C$_1$-C$_4$-alkoxy-carbonyl or dimethylamino, or together with R$^2$ represents butane-1,4-diyl (tetramethylene) or pentane-1,5-diyl (pentamethylene),
R$^4$ represents hydrogen, fluorine, chlorine, bromine, methyl, methoxymethyl, trifluoromethyl, methoxy, ethoxy, difluoromethoxy, methylthio, ethylthio, amino, methylamino, ethylamino, dimethylamino or diethylamino,
X represents nitrogen or a —CH group,
Y represents nitrogen or a —CR$^5$ group where
R$^5$ represents hydrogen, fluorine, chlorine or methyl, and
Z represents nitrogen or a —CR$^6$ group where
R$^6$ represents hydrogen, fluorine, chlorine, bromine, methyl, ethyl, trifluoromethyl, methoxy, ethoxy, propoxy, isopropoxy, difluoromethoxy, methylthio, ethylthio, methylamino, ethylamino, dimethylamino or diethylamino.

If, for example, N'-(4,6-dimethoxypyrimidin-2-yl)-N''-amino-N'''-(2,6-difluorophenylsulphonyl)-guanidine and acetone are used as starting substances, the course of the reaction in process (a) according to the invention can be outlined by the following equation:

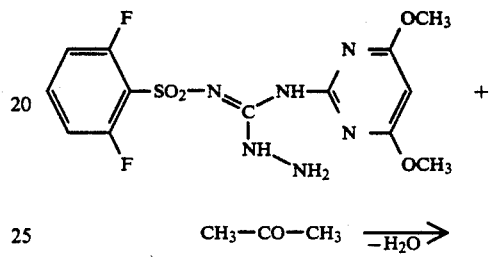

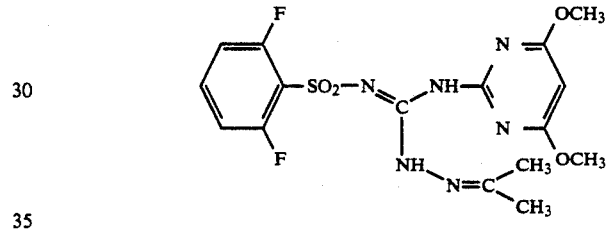

If, for example, N'-(4-methoxy-6-methyl-s-triazin-2-yl)-N''-(2-trifluoromethyl-phenylsulphonyl)-O-methyl-isourea and acetophenone hydrazone are used as starting substances, the course of the reaction in process (b) according to the invention can be outlined by the following equation:

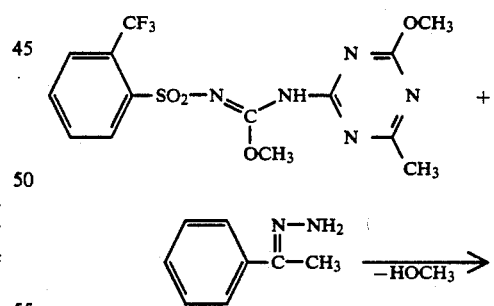

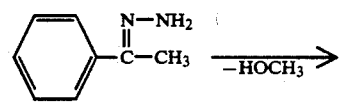

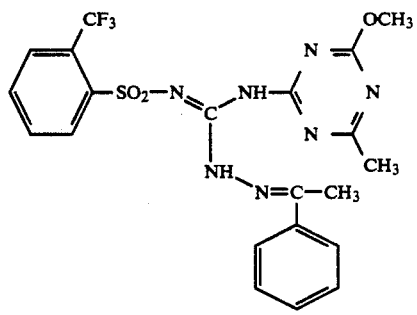

Formula (II) provides a general definition of the aminoguanidines to be used as starting substances in process (a) according to the invention for the preparation of compounds of the formula (I).

In formula (II), $R^1$, $R^4$, X, Y and Z preferably, or in particular, have those meanings which have already been mentioned above in connection with the description of the compounds of the formula (I) according to the invention as being preferred, or particularly preferred, for $R^1$, $R^4$, X, Y and Z.

Examples of the starting substances of the formula (II) are listed in Table 1 below.

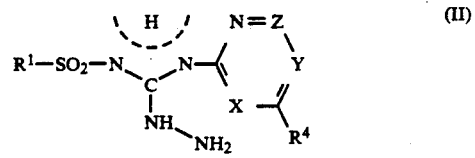
(II)

TABLE 1

| | Examples of the compounds of the formula (II) | | | |
|---|---|---|---|---|
| $R^1$ | $R^4$ | X | Y | Z |
| 2-OCF₃-phenyl | OCH₃ | N | CH | C—OCH₃ |
| 2-COOCH₃-phenyl | OCH₃ | N | CH | C—OCH₃ |
| 2-OCHF₂-phenyl | CH₃ | N | CH | C—CH₃ |
| 2-OCF₃-phenyl | CH₃ | N | N | C—OCH₃ |
| 2-OCF₃-phenyl | OCH₃ | N | N | C—OCH₃ |
| 2-Cl-phenyl | CH₃ | N | CH | C—OCH₃ |
| 3-COOC₂H₅-1-methylpyrazol-4-yl | CH₃ | N | CH | C—CH₃ |
| 3-COOC₂H₅-1-methylpyrazol-4-yl | CH₃ | N | N | C—CH₃ |
| 2-Br-phenyl | CH₃ | N | CH | C—CH₃ |

TABLE 1-continued

Examples of the compounds of the formula (II)

| R¹ | R⁴ | X | Y | Z |
|---|---|---|---|---|
| 2-COOCH₃-phenyl | CH₃ | N | N | C—OCH₃ |
| 2-COOCH₃-phenyl | OCH₃ | N | CH | C—OCH₃ |
| 2-COOC₂H₅-phenyl | CH₃ | N | CH | C—OCH₃ |
| 2-COOC₂H₅-phenyl | OCH₃ | N | CH | C—OCH₃ |
| 2-OCF₃-benzyl (—CH₂—) | OCH₃ | N | CH | C—OCH₃ |
| 2-F-phenyl | OCH₃ | N | N | C—OCH₃ |
| 2-OCF₃-phenyl | C₂H₅ | N | CH | C—OCH₃ |
| 2-COOC₂H₅-phenyl | CH₃ | N | N | C—OCH₃ |
| 2-COOC₂H₅-phenyl | OCH₃ | N | N | C—OCH₃ |
| 2-Cl-phenyl | CH₃ | N | N | C—OCH₃ |
| 2-Cl-phenyl | OCH₃ | N | N | C—OCH₃ |

TABLE 1-continued

Examples of the compounds of the formula (II)

| R¹ | R⁴ | X | Y | Z |
|---|---|---|---|---|
| 2-Br-phenyl | OCH₃ | N | N | C—OCH₃ |
| 2-COOC₂H₅-phenyl | CH₃ | N | CH | C—CH₃ |
| 2-CF₃-phenyl | CH₃ | N | CH | C—CH₃ |
| 2-CF₃-phenyl | OCH₃ | N | CH | C—OCH₃ |
| 2-CF₃-phenyl | CH₃ | N | N | C—OCH₃ |
| 2-OCHF₂-phenyl | OCH₃ | N | CH | C—OCH₃ |
| 2-OCHF₂-phenyl | OCH₃ | N | N | C—OCH₃ |
| 2-OCHF₂-benzyl | OCH₃ | N | CH | C—OCH₃ |
| 2-OCHF₂-benzyl | OCH₃ | N | N | C—OCH₃ |
| 2-COOCH₃-phenyl | C₂H₅ | N | N | C—OCH₃ |
| 2-OCF₃-phenyl | CH₃ | N | CH | C—OC₂H₅ |

TABLE 1-continued

Examples of the compounds of the formula (II)

| R¹ | R⁴ | X | Y | Z |
|---|---|---|---|---|
| 2-(COOCH₃)-benzyl (–CH₂–C₆H₄-COOCH₃) | OCH₃ | N | N | C—OCH₃ |
| 1-methyl-3-methyl-4-(COOC₂H₅)-pyrazol-5-yl | OCH₃ | N | CH | C—OCH₃ |
| 3-methyl-2-(COOCH₃)-thiophen-... (thienyl) | CH₃ | N | N | C—OCH₃ |
| 3-methyl-2-(COOCH₃)-thiophen-... (thienyl) | OCH₃ | N | N | C—OCH₃ |
| 1-methyl-3-methyl-4-(COOCH₃)-pyrazol-5-yl | OCH₃ | N | N | C—OCH₃ |
| 2-C₆H₅-phenyl | OCH₃ | N | CH | C—OCH₃ |
| 2-C₆H₅-phenyl | OCH₃ | N | N | C—OCH₃ |
| 2-(COOC₂H₅)-phenyl | OCH₃ | N | CH | C—Cl |
| 2-CH₃-phenyl | CH₃ | N | N | C—OCH₃ |
| 2-CH₃-4-Cl-phenyl | CH₃ | N | CH | C—CH₃ |
| 2-(COOCH₃)-phenyl | CF₃ | N | CH | C—OCH₃ |

TABLE 1-continued

Examples of the compounds of the formula (II)

| R¹ | R⁴ | X | Y | Z |
|---|---|---|---|---|
| 2-COOCH₃-phenyl | CH₃ | N | CH | C—OCHF₂ |
| 2-COOCH₃-phenyl | OCH₃ | N | CH | C—OCHF₂ |
| 2-COOCH₃-phenyl | OCHF₂ | N | CH | C—OCHF₂ |
| 2-COOCH₃-phenyl | NHCH₃ | N | N | C—OC₂H₅ |
| 2-COOCH₃-phenyl | NHC₂H₅ | N | N | C—OCH₃ |
| 2-COOCH(CH₃)₂-4-Cl-phenyl | CH₃ | N | N | C—OCH₃ |
| 2-COOC₂H₅-4-OCHF₂-phenyl | OCH₃ | N | CH | C—OCH₃ |
| 2-OCH₂CH₂—Cl-phenyl | CH₃ | N | N | C—OCH₃ |
| 2-OCH₂CH₂—OCH₃-phenyl | OCH₃ | N | N | C—OCH₃ |
| 2-COOC₂H₅-phenyl | Cl | N | CH | C—OCH₃ |

TABLE 1-continued

Examples of the compounds of the formula (II)

| R¹ | R⁴ | X | Y | Z |
|---|---|---|---|---|
| 2-(COOCH₃)-phenyl | CH(OCH₃)₂ | N | CH | C—OCH₃ |
| 2-methyl-benzo[d][1,3]dioxin-4-one-8-yl (ethylene-bridged lactone) | NHCH₃ | N | N | C—OC₂H₅ |
| 2-(COOCH₃)-phenyl-CH₂— | OCH₃ | N | CH | C—OCH₃ |
| 3-methyl-isochroman-1-one-8-yl substituted | NHCH₃ | N | N | C—OC₂H₅ |
| 5-CH₃O, 3-CH₃, 2-(SO₂-N(C₄H₉-n)-CH₂)-phenyl | OCH₃ | N | CH | C—OCH₃ |
| 1-(isoquinolin-1-yl)-3-methyl-pyrazol-4-yl-COOC₂H₅ | OCH₃ | N | CH | C—OCH₃ |
| 1-(isoquinolin-1-yl)-3-methyl-pyrazol-4-yl-COOC₂H₅ | OCH₃ | N | N | C—OCH₃ |
| 2-methyl-3-(CON(CH₃)₂)-pyridin-yl | OCH₃ | N | CH | C—OCH₃ |
| 2,6-dimethyl-3-(CON(CH₃)₂)-pyridin-yl | OCH₃ | N | CH | C—OCH₃ |

TABLE 1-continued

Examples of the compounds of the formula (II)

| R¹ | R⁴ | X | Y | Z |
|---|---|---|---|---|
| 6-chloro-3-(N,N-dimethylcarbamoyl)-2-methylpyridin-4-yl (CON(CH₃)₂, Cl, N, CH₃ pyridine) | OCH₃ | N | CH | C—OCH₃ |
| 2-(OCF₃)benzyl | OCH₃ | N | N | C—OCH₃ |
| 2-(OCF₃)benzyl | CH₃ | N | N | C—OCH₃ |
| 2-(OCF₃)benzyl | CH₃ | N | N | C—CH₃ |
| 2-(OCF₃)benzyl | NHCH₃ | N | N | C—OC₂H₅ |
| 2-(OCF₃)benzyl | C₂H₅ | N | N | C—OCH₃ |
| 2-(OCF₃)benzyl | CH₃ | N | N | C—OC₂H₅ |
| 2-(OCHF₂)benzyl | CH₃ | N | N | C—OCH₃ |
| 2-(OCHF₂)benzyl | CH₃ | N | N | C—CH₃ |
| 2-(OCHF₂)benzyl | NHCH₃ | N | N | C—OC₂H₅ |
| 2-(OCHF₂)benzyl | C₂H₅ | N | N | C—OCH₃ |

TABLE 1-continued

Examples of the compounds of the formula (II)

| R¹ | R⁴ | X | Y | Z |
|---|---|---|---|---|
| 2-(OCHF₂)-benzyl (−CH₂−C₆H₄−OCHF₂) | CH₃ | N | N | C—OC₂H₅ |
| 2-(OCF₃)-phenyl, methyl substituted | CF₃ | N | CH | C—OCH₃ |
| 3-methyl-2-(COOCH₃)-thienyl | OCHF₂ | N | CH | C—OCHF₂ |
| 1-methyl-3-methyl-4-(1,3-dioxolan-2-yl)-pyrazolyl | OCH₃ | N | CH | C—OCH₃ |
| 3-methyl-4-methyl-5-(OCH₂−CF₃)-isothiazolyl | OCH₃ | N | CH | C—OCH₃ |
| 3-methyl-4-methyl-5-(OCH₂−CCl₃)-isothiazolyl | OCH₃ | N | N | C—OCH₃ |
| 2-methyl-3-(thiazol-2-yl)-thienyl | OCH₃ | N | CH | C—OCH₃ |
| 2-methyl-3-(OCHF−CF₂−OCH₃)-thienyl | OCH₃ | N | N | C—OCH₃ |
| 2-methyl-3-(CH₂−O−CH₂−CF₃)-thienyl | OCH₃ | N | CH | C—OCH₃ |
| 2-methyl-3-(CHF−CF₃)-thienyl | OCH₃ | N | CH | C—OCH₃ |
| 2-methyl-3-(CF₃)-pyridyl | OCH₃ | N | CH | C—OCH₃ |
| 2-methyl-3-(CF=CF−CF₃)-pyridyl | OCH₃ | N | CH | C—OCH₃ |

TABLE 1-continued
Examples of the compounds of the formula (II)
| R¹ | R⁴ | X | Y | Z |
|---|---|---|---|---|
| 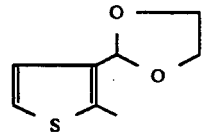 | OCH₃ | N | N | C—OCH₃ |
| 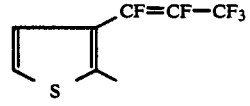 | OCH₃ | N | CH | C—OCH₃ |
| 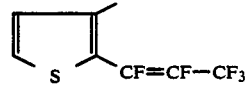 | OCH₃ | N | N | C—OCH₃ |
| 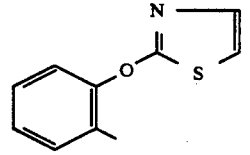 | OCH₃ | N | N | C—OCH₃ |
| 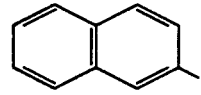 | CH₃ | N | N | C—OCH₃ |
| 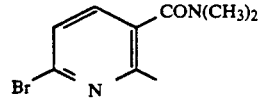 | OCH₃ | N | CH | C—OCH₃ |
| 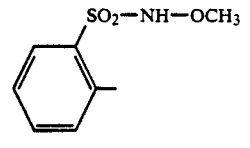 | OCH₃ | N | CH | C—OCH₃ |
| 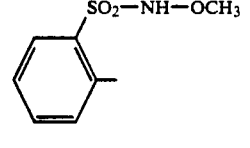 | OCH₃ | N | CH | C—CH₃ |
| 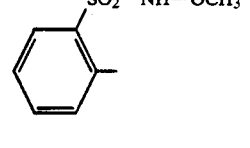 | OCH₃ | N | N | C—OCH₃ |
| 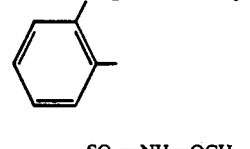 | CF₃ | N | CH | C—OCH₃ |
| 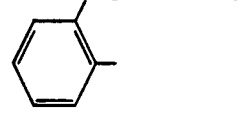 | CH₃ | N | CH | C—CH₃ |

TABLE 1-continued

Examples of the compounds of the formula (II)

| R¹ | R⁴ | X | Y | Z |
|---|---|---|---|---|
| 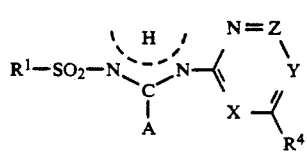 | OCH₃ | N | N | C—CH₃ |

Some of the starting substances of the formula (II) are known (cf. EP-A 224,078, U.S. Pat. No. 4,725,303), and some, as herbicides, are the subject of an earlier, non-prior-published DE Patent Application by the Applicant Company (P 3,818,040.5 dated May 27, 1988).

The compounds of the general formula (II) are obtained when sulphonyl compounds of the general formula (IV)

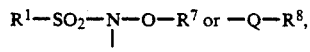   (IV)

in which
R¹, R⁴, X, Y and Z are as defined above and
A represents halogen or one of the leaving groups indicated below $$R^1-SO_2-N-O-R^7 \text{ or } -Q-R^8,$$

where
R¹ is as defined above,
R⁷ represents alkyl, alkenyl or aralkyl,
R⁸ represents in each case optionally substituted alkyl, aralkyl or aryl, and
Q represents oxygen or sulphur,
are reacted with hydrazine or with a hydrazine/water or hydrazine/acid adduct, if appropriate in the presence of an acid acceptor, such as, for example, potassium carbonate, and if appropriate in the presence of a diluent, such as, for example, methanol, ethanol and/or water, at temperatures between −20° C. and +100° C.

Some of the compounds of the formula (II) can also be obtained as outlined below (R as indicated above in the case of R¹²)

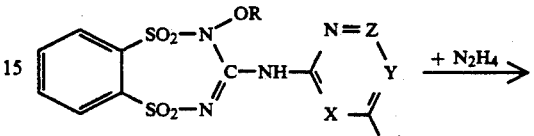

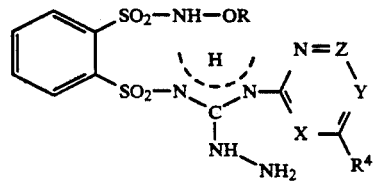

(for reaction principle, see U.S. Pat. No. 4,659,364 and EP-A 173,319).

Formula (IV) provides a general definition of the sulphonyl compounds required as intermediates. In formula (IV), R¹, R⁴, X, Y and Z preferably, or in particular, have those meanings which have already been indicated above in the context of the description of the compounds of the formula (I) according to the invention as being preferred, or particularly preferred, for R¹, R⁴, X, Y and Z, and A preferably represents chlorine or one of the leaving groups indicated below $$R^1-SO_2-N-OR^7 \text{ or } -Q-R^8$$

where
R¹ has the meaning indicated above as being preferred,
R⁷ represents C₁-C₄-alkyl, C₃-C₄-alkenyl or benzyl,
R⁸ represents C₁-C₄-alkyl which is optionally substituted by carboxyl, C₁-C₄-alkoxy-carbonyl or C₁-C₄-alkoxy, or represents benzyl or phenyl, each of which is optionally substituted by fluorine, chlorine, bromine, C₁-C₄-alkyl or C₁-C₄-alkoxy, and
Q represents oxygen or sulphur.

Examples of the compounds of the formula (IV) are listed in Table 2 below.

TABLE 2

Examples of the compounds of the formula (IV)

| A | R¹ | R⁴ | X | Y | Z |
|---|---|---|---|---|---|
| 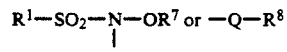 | Cl (phenyl) | CH₃ | N | CH | C—OCH₃ |

TABLE 2-continued
Examples of the compounds of the formula (IV)
| A | R¹ | R⁴ | X | Y | Z |
|---|----|----|---|---|---|
| 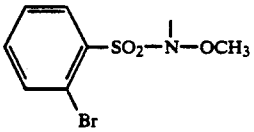 | 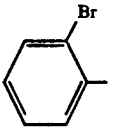 Br | OCH₃ | N | CH | C—OCH₃ |
| 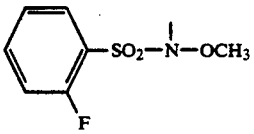 | 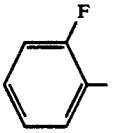 F | OCH₃ | N | CH | C—OCH₃ |
| 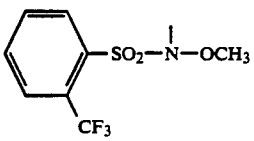 | 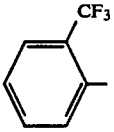 CF₃ | OCH₃ | N | CH | C—OCH₃ |
| 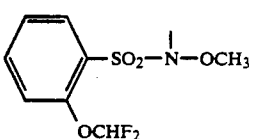 | 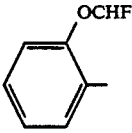 OCHF₂ | OCH₃ | N | CH | C—OCH₃ |
| 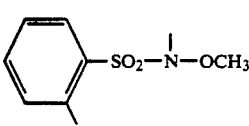 | 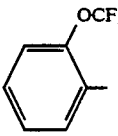 OCF₃ | OCH₃ | N | CH | C—OCH₃ |
| 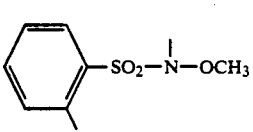 | 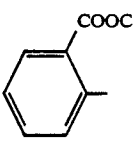 COOCH₃ | CH₃ | N | N | C—OCH₃ |
| 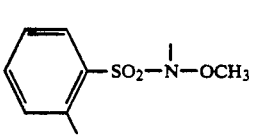 | 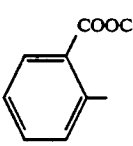 COOC₂H₅ | CH₃ | N | CH | C—CH₃ |
| 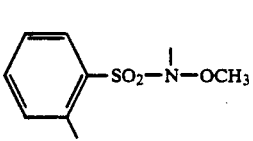 | 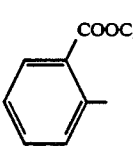 COOC₂H₅ | OCH₃ | N | CH | C—Cl |
| 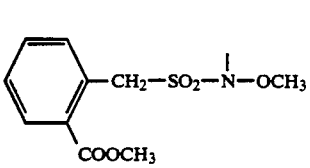 | 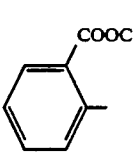 COOCH₃ | OCH₃ | N | CH | C—OCH₃ |
| 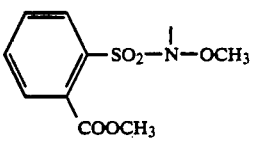 | 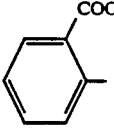 COOCH₃ | OCHF₂ | N | CH | C—OCHF₂ |

TABLE 2-continued

Examples of the compounds of the formula (IV)

| A | R¹ | R⁴ | X | Y | Z |
|---|----|----|---|---|---|
| 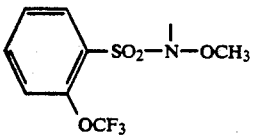 | 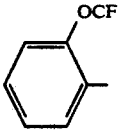 OCF₃ | OCH₃ | N | N | C—OCH₃ |
| —OCH₃ | 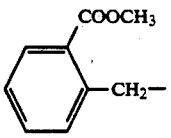 COOCH₃, —CH₂— | OCH₃ | N | CH | C—OCH₃ |
| —SCH₃ | 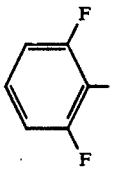 F, F | CH₃ | N | N | C—OCH₃ |
| —OC₆H₅ | 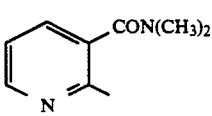 CON(CH₃)₂, N | OCH₃ | N | CH | C—OCH₃ |
| —SC₆H₅ | 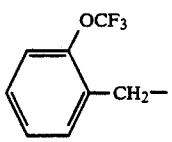 OCF₃, —CH₂— | CH₃ | N | CH | C—OCH₃ |
| —SCH₃ | 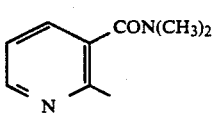 CON(CH₃)₂, N | OCH₃ | N | N | C—OCH₃ |
| —OC₆H₅ | 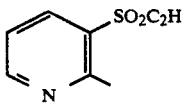 SO₂C₂H₅, N | OCH₃ | N | CH | C—OCH₃ |

The compounds of the formula (IV) are known and/or can be prepared by processes known per se (cf. EP-A 5,986, EP-A 24,215, EP-A 121,082, EP-A 172,957, EP-A 173,321, EP-A 173,956, EP-A 224,078, DE-OS (German Published Specification) 3,634,928 and DE-OS (German Published Specification) 3,634,929).

Formula (III) provides a general definition of the carbonyl compounds furthermore to be used as starting substances in process (a) according to the invention for the preparation of compounds of the formula (I).

In formula (III), $R^2$ and $R^3$ preferably, or in particular, have those meanings which have already been mentioned above in connection with the description of the compounds of the formula (I) according to the invention as being preferred, or particularly preferred, for $R^2$ and $R^3$.

The following may be mentioned as examples of the starting substances of the formula (III): formaldehyde, acetaldehyde, propionaldehyde, butyraldehyde, isobutyraldehyde, valeraldehyde, isovaleraldehyde, benzaldehyde, pyridine-4-, -2- and -3-carbaldehyde, furan-2- and -3-carbaldehyde and thiophene-2- and -3-carbaldehyde, furthermore also acetone, methyl ethyl ketone, methyl propyl ketone, methyl isopropyl ketone, methyl butyl ketone, methyl isobutyl ketone, diethyl ketone, acetophenone, benzophenone, cyclopentanone, cyclohexanone, phenylacetone, chloroacetone, chloral, methyl glyoxylate, ethyl glyoxylate, methyl pyruvate and ethyl pyruvate, phthalaldehydic acid and 6-chloropyridine-3-aldehyde.

N,N-Dialkyl-carboxamide acetals or ketals which can furthermore be employed as starting substances in process (a) according to the invention are preferably N,N-dialkyl-formamide acetals or ketals or N,N-dialkylacetamide acetals or ketals with straight-chain or branched alkyl radicals having 1 to 4 carbon atoms which are bonded to N or O, such as, for example, N,N-dimethyl-formamide dimethyl acetal, N,N-dimethylacetamide dimethyl acetal, N,N-diethylformamide dimethyl acetal, N,N-diethylacetamide dimethyl acetal, N,N-dimethylformamide diethyl acetal, N,N-dimethylacetamide diethyl acetal, N,N-diethylformamide diethyl acetal, N,N-diethylacetamide diethyl acetal, N,N-dimethylformamide dipropyl acetal, N,N-dimethylacetamide dipropyl acetal, N,N-diethylformamide dipropyl acetal, N,N-diethylacetamide dipropyl acetal, N,N-dimethylformamide diisopropyl acetal, N,N-dimethylacetamide diisopropyl acetal, N,N-diethylformamide diisopropyl acetal, N,N-diethylacetamide diisopropyl acetal, N,N-dimethylformamide dibutyl acetal, N,N-dimethylacetamide dibutyl acetal, N,N-diethylformamide dibutyl acetal, N,N-diethylacetamide dibutyl acetal, N,N-dimethylformamide diisobutyl acetal, N,N-dimethylacetamide diisobutyl acetal, N,N-diethylformamide diisobutyl acetal, N,N-diethylacetamide diisobutyl acetal, N,N-dimethylformamide di-sec-butyl acetal, N,N-dimethylacetamide di-sec-butyl acetal, N,N-diethylformamide di-sec-butyl acetal, N,N-diethylacetamide di-sec-butyl acetal, N,N-dimethylformamide di-tert-butyl acetal, N,N-dimethylacetamide di-tert-butyl acetal, N,N-diethylformamide di-tert-butyl acetal and N,N-diethylacetamide di-tert-butyl acetal.

The starting substances of the formula (III) are known chemicals for organic synthesis.

If appropriate, process (a) according to the invention for the preparation of the new compounds of the formula (I) is carried out using diluents. Suitable diluents for this purpose are virtually all inert organic solvents. These preferably include aliphatic and aromatic, optionally halogenated hydrocarbons, such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers, such as diethyl ether, dibutyl ether, glycol dimethyl ether, diglycol dimethyl ether, tetrahydrofuran and dioxane, alcohols, such as methanol, ethanol, propanol, isopropanol, butanol and isobutanol, esters, such as methyl acetate and ethyl acetate, nitriles, such as, for example, acetonitrile and propionitrile, amides, such as, for example, dimethylformamide, dimethylacetamide and N-methyl-pyrrolidone, and also dimethyl sulphoxide, tetramethylene sulphone and hexamethylphosphoric triamide.

If appropriate, process (a) according to the invention is carried out in the presence of a condensation auxiliary. Suitable condensation auxiliaries are preferably the drying agents customary in organic chemistry. These preferably include anhydrous salts, such as, for example, sodium sulphate, magnesium sulphate and potassium carbonate.

When carrying out process (a) according to the invention, the reaction temperatures can be varied within a substantial range. In general, the process is carried out at temperatures between 0° C. and 100° C., preferably at temperatures between 10° C. and 80° C.

Process (a) according to the invention is generally carried out under atmospheric pressure. However, it is also possible to carry out the process under increased or reduced pressure.

For carrying out process (a) according to the invention, between 1 and 1000 moles, preferably between 1 and 500 moles, of carbonyl compound of the formula (III) is generally employed per mole of aminoguanidine of the formula (II).

In general, the reactants are mixed at room temperature or with slight cooling and, if appropriate, stirred at increased temperature until the reaction is complete. Working-up is carried out by customary methods (cf. the Preparation Examples).

Formula (IV) provides a general definition of the sulphonyl compounds to be used as starting substances in process (b) according to the invention for the preparation of compounds of the formula (I). Preferred and particularly preferred subgroups of the sulphonyl compounds (IV) have already been defined above (before Table 2). Examples of the starting substances of the formula (IV) are listed in Table 2 (above).

Formula (V) provides a general definition of the hydrazones furthermore to be used as starting substances in process (b) according to the invention for the preparation of compounds of the formula (I).

In formula (V), $R^2$ and $R^3$ preferably, or in particular, have those meanings which have already been mentioned above in connection with the description of the compounds of the formula (I) according to the invention as being preferred, or particularly preferred, for $R^2$ and $R^3$.

The following may be mentioned as examples of the starting substances of the formula (V):

Acetaldehyde hydrazone, propionaldehyde hydrazone, butyraldehyde hydrazone, isobutyraldehyde hydrazone, valeraldehyde hydrazone, isovaleraldehyde hydrazone, benzaldehyde hydrazone, pyridine-2-, -3- and -4-aldehyde hydrazone, furan-2- and -3-carbaldehyde hydrazone, thiophene-2- and -3-carbaldehyde hydrazone, acetone hydrazone, methyl ethyl ketone hydrazone, methyl propyl ketone hydrazone, methyl isopropyl ketone hydrazone, methyl butyl ketone hydrazone, methyl isobutyl ketone hydrazone, diethyl ketone hydrazone, acetophenone hydrazone, benzophenone hydrazone, cyclopentanone hydrazone and cyclohexanone hydrazone.

The starting substances of the formula (V) are known organic chemicals.

Process (b) according to the invention for the preparation of the new compounds of the formula (I) is preferably carried out using diluents. Suitable diluents in this case are the same organic solvents which have been indicated above as diluents for process (a) according to the invention.

When carrying out process (b) according to the invention, the reaction temperatures can be varied within a substantial range. In general, the process is carried out at temperatures between 0° C. and 150° C., preferably at temperatures between 20° C. and 120° C.

Process (b) according to the invention is generally carried out under atmospheric pressure. However, it is also possible to carry out the process under increased or reduced pressure.

For carrying out process (b) according to the invention, between 1 and 10 moles, preferably between 1 and 5 moles, of hydrazone of the formula (V) is generally employed per mole of sulphonyl compound of the formula (IV).

In general, the reactants are combined at room temperature and, if appropriate, the mixture is stirred at increased temperature until the reaction is complete. Working-up is carried out by customary methods (cf. the Preparation Examples).

The active compounds according to the invention can be used as defoliants, desiccants, agents for destroying broad-leaved plants and, in particular, as weed-killers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus and Taraxacum.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, in lawns, turf and pasture-land and for the selective combating of weeds in annual cultures.

The compounds of the formula (I) according to the invention are particularly suitable for selectively combating dicotyledon weeds in monocotyledon crops by the pre-emergence method as well as the post-emergence method.

The active compounds can be converted into the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations are produced in a known manner, for example by mixing the active compounds with extenders, that is liquid solvents and/or solid carriers, optionally with the use of surface-active agents, that is emulsifying agents and/or dispersing agents and/or foam-forming agents.

In the case of the use of water as an extender, organic solvents can, for example, also be used as auxiliary solvents. As liquid solvents, there are suitable in the main: aromatics, such as xylene, toluene, or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water.

As solid carriers there are suitable: for example ammonium salts and ground natural minerals, such as kaolins, clays, talc, chalk, quartz, attapulgite, montmorillonite or diatomaceous earth, and ground synthetic minerals, such as highly-disperse silica, alumina and silicates, as solid carriers for granules there are suitable: for example crushed and fractionated natural minerals such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumen hydrolysis products; as dispersing agents there are suitable: for example ligninsulphite waste liquors and methylcellulose.

Adhesives such as carboxymethylcellulose and natural and synthetic polymers in the form of powders, granules or latexes, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

For combating weeds, the active compounds according to the invention, as such or in the form of their formulations, can also be used as mixtures with known herbicides, finished formulations or tank mixes being possible.

Suitable herbicides for the mixtures are known herbicides, such as, for example, 1-amino-6-ethylthio-3-(2,2-dimethylpropyl)-1,3,5-triazine-2,4(1H,3H)-dione (AMETHYDIONE) or N-(2-benzothiazolyl)-N,N'-dimethylurea (METABENZTHIAZURON) for combating weeds in cereals; 4-amino-3-methyl-6-phenyl-1,2,4-triazin-5(4H)-one (METAMITRON) for combating weeds in sugar beet, and 4-amino-6-(1,1-dimethylethyl)-3-methylthio-1,2,4-triazin-5(4H)-one (METRIBUZIN) for combating weeds in soya beans; furthermore also 2,4-dichlorophenoxyacetic acid (2,4D); 4-(2,4-dichlorophenoxy)-butyric acid (2,4-DB); 2,4-dichlorophenoxypropionic acid (2,4-DP); 3-isopropyl-2,1,3-benzothiadiazin- 4-one 2,2-dioxide (BENTAZONE); methyl 5-(2,4-dichlorophenoxy)-2-nitrobenzoate (BIFENOX); 3,5-dibromo-4-hydroxy-benzonitrile (BROMOXYNIL); 2-chloro-N{[(4-methoxy-6-methyl-1,3,5-triazin-2-yl)-amino]-carbonyl}-benzenesulphonamide (CHLORSULFURON); N,N-dimethyl-N'-(3-chloro-4-methylphenyl)-urea (CHLORTOLURON); 2-[4-(2,4-dichlorophenoxy)-phenoxy]-propionic acid, its methyl ester or its ethyl ester (DICLOFOP); 2-{(4-[(6-chloro-2-benzoxazolyl)-oxy]-phenoxy}-propanoic acid, its methyl ester or its ethyl ester (FENOXAPROP); [(4-amino-3,5-dichloro-6-fluoro-2-pyridinyl)-oxy]-acetic acid or its 1-methylheptyl ester (FLUROXYPYR); methyl 2-[4,5-dihydro-4-methyl-4-(1-methylethyl)-5-oxo-1H-imidazol-2-yl]-4(5)-methyl-benzoate (IMAZAMETHABENZ); 3,5-diiodo-4-hydroxybenzonitrile (IOXYNIL); N,N-dimethyl-N'-(4-isopropylphenyl)-urea (ISOPROTURON); (2-methyl-4-chlorophenoxy)acetic acid (MCPA); (4-chloro-2-methylphenoxy)-propionic acid (MCPP); N-methyl-2-(1,3-benzothiazol-2-yloxy)acetanilide (MEFENACET); 2-{[[((4-methoxy-6-methyl-1,3,5-triazin-2-yl)amino)-carbonyl]-amino]-sulphonyl}-benzoic acid or its methyl ester (METSULFURON); N-(1-ethyl-propyl)-3,4-dimethyl-2,6-dinitroaniline (PENDIMETHALIN); O-(6-chloro-3-phenyl-pyridazin-4-yl) S-octyl thiocarbamate (PYRIDATE); 4-ethylamino-2-t-butylamino-6-methylthio-s-triazine (TERBUTRYNE); methyl 3-[[[[4-methoxy-6-methyl-1,3,5-triazin-2-yl)-amino]-carbonyl]-amino]-sulphonyl]-thiophene-2-carboxylate (THIAMETURON) and S-2,3,3-trichloroallyl N,N-diisopropylthiocarbamate (TRIALLATE). Surprisingly, some mixtures also show a synergistic action.

Mixtures with other known active compounds, such as fungicides, insecticides, acaricides, nematicides, bird repellants, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants.

They can also be incorporated into the soil before sowing.

The amount of active compound used can vary within a substantial range. It depends essentially on the nature of the desired effect. In general, the amounts used are between 0.01 and 10 kg of active compound per hectare of soil surface, preferably between 0.05 and 5 kg per ha.

The preparation and use of the active compounds according to the invention can be seen from the examples which follow.

PREPARATION EXAMPLES

EXAMPLE 1

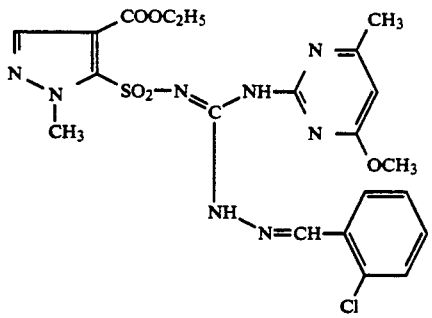

(Process (a))

A mixture of 8.2 g (0.02 mol) of N'-(4-methoxy-6-methyl-pyrimidin-2-yl)-N"-amino-N'"-(1-methyl-4-ethoxycarbonyl-pyrazol-5-yl-sulphonyl)-quanidine, 5.6 g (0.04 mol) of 2-chloro-benzaldehyde and 50 ml of acetonitrile is stirred for 20 hours at 20° C. The product which is obtained in crystalline form is isolated by filtration with suction.

7.5 g (70% of theory) of N'-(4-methoxy-6-methyl-pyrimidin-2-yl)-N"-(2-chloro-benzylideneamino)-N'"-(1-methyl-4-ethoxycarbonyl-pyrazol-5-yl-sulphonyl)-quanidine of melting point 185° C. are obtained.

EXAMPLE 2

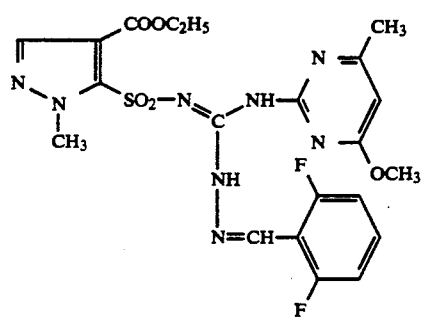

(Process (a))

A mixture of 8.2 g (0.02 mol) of N'-(4-methoxy-6-methyl-pyrimidin-2-yl)-N"-amino-N'"-(1-methyl-4-ethoxycarbonyl-pyrazol-5-yl-sulphonyl)-guanidine, 5.7 g (0.04 mol) of 2,6-difluoro-benzaldehyde and 50 ml of ethanol is stirred for 20 hours at 60° C. After the mixture has cooled to 20° C., the product which is obtained in crystalline form is isolated by filtration with suction.

9.2 g (86% of theory) of N'-(4-methoxy-6-methyl-pyrimidin-2-yl)-N"-(2,6-difluoro-benzylideneamino)-N'"-(1-methyl-4-ethoxycarbonyl-pyrazol-5-yl-sulphonyl)-guanidine of melting point 177° C. are obtained.

EXAMPLE 3

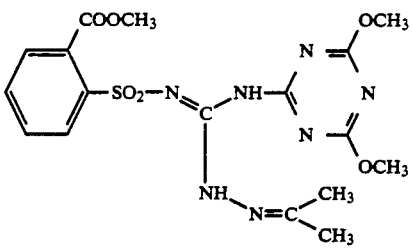

(Process (a))

A mixture of 0.5 g (1.2 mmol) of N'-(4,6-dimethoxy-s-triazin-2-yl)-N"-amino-N'"-(2-methoxycarbonylphenyl sulphonyl)-guanidine, 20 ml of acetone, 2 g of sodium sulphate and 10 ml of methylene chloride is stirred for 20 hours at 20° C. and subsequently filtered. The filter residue is washed with 50 ml of methylene chloride, the mother liquor is evaporated, the residue is brought to crystallization by trituration with diethyl ether, and the crystalline product is isolated by filtration with suction.

0.34 g (62% of theory) of N'-(4,6-dimethoxy-s-triazin-2-yl)-N"-(1-methyl-ethylideneamino)-N'"-(2-methoxycarbonyl-phenylsulphonyl)-guanidine of melting point 175° C. is obtained.

EXAMPLE 4

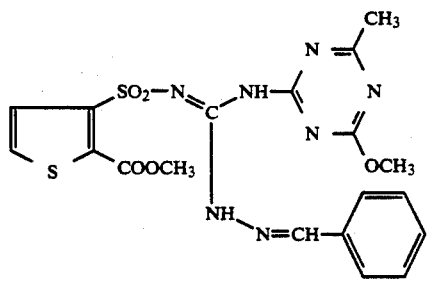

(Process (a))

A mixture of 1.8 g (4.5 mmol) of N'-(4-methoxy-6-methyl-s-triazin-2-yl)-N''-amino-N'''-(2-methoxycarbonyl-thiophen-3-yl-sulphonyl)-guanidine, 0.71 g (6.7 mmol) of benzaldehyde, 2 g of sodium sulphate and 30 ml of chloroform is refluxed for 12 hours and subsequently filtered. The filter residue is washed with 50 ml of chloroform, the filtered chloroform solution is evaporated, the residue is stirred with diethyl ether, and the product which is obtained in crystalline form is isolated by filtration with suction.

2.05 g (94% of theory) of N'-(4-methoxy-6-methyl-s-triazin-2-yl)-N''-benzylideneamino-N'''-(2-methoxycarbonyl-thiophen-3-yl-sulphony)-guanidine of melting point 215° C. are obtained.

EXAMPLE 5

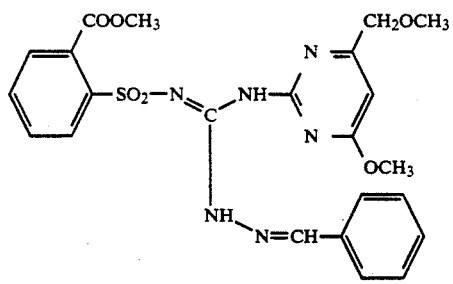

(Process (a))

A mixture of 4.2 g (0.01 mol) of N'-(4-methoxy-6-methoxymethyl-pyrimidin-2-yl)-N''-amino-N'''-(2-methoxycarbonyl-phenylsulphonyl)-guanidine and 50 ml of benzaldehyde is stirred for 7 days at 20° C. The product which is obtained in crystalline form is then isolated by filtration with suction.

2.0 g (39% of theory) of N'-(4-methoxy-6-methoxymethyl-pyrimidin-2-yl)-N''-benzylideneamino-N'''-(2-methoxycarbonyl-phenylsulphonyl)-guanidine of melting point 209° C. are obtained.

EXAMPLE 6

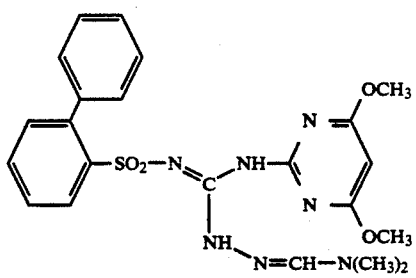

(Process (a))

A mixture of 4.3 g (0.01 mol) of N'-(4,6-dimethoxypyrimidin-2-yl)-N''-amino-N'''-(2-phenyl-phenylsulphonyl)-guanidine and 2 ml of dimethylformamide dimethyl acetal is stirred for 60 minutes at 20° C.; the product which is obtained in crystalline form is then isolated by filtration with suction.

4.6 g (95% of theory) of N'-(4,6-dimethoxypyrimidin-2-yl)-N''-dimethylaminomethyleneamino-N'''-(2-phenyl-phenylsulphonyl)-guanidine of melting point 139° C. are obtained.

EXAMPLE 7

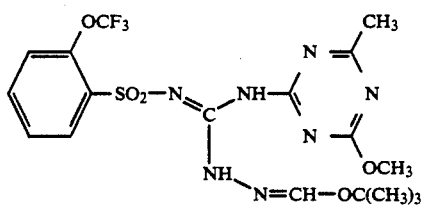

(Process (a))

A mixture of 8.42 g (0.02 mol) of N'-(4-methoxy-6-methyl-s-triazin-2-yl)-N''-amino-N'''-(2-trifluoromethoxy-phenylsulphonyl)-guanidine, 5 ml of dimethylformamide di-tert-butyl acetal and 100 ml of tetrahydrofuran is stirred for 15 hours at 20° C. and then slowly diluted with water to approximately twice the volume. The product which is obtained in crystalline form in this process is isolated by filtration with suction.

2.2 g (22% of theory) of N'-(4-methoxy-6-methyl-s-triazin-2-yl)-N''-(tert-butoxy-methyleneamino)-N'''-(2-trifluoromethoxy-phenylsulphonyl)-guanidine of melting point 182° C. are obtained.

EXAMPLE 8

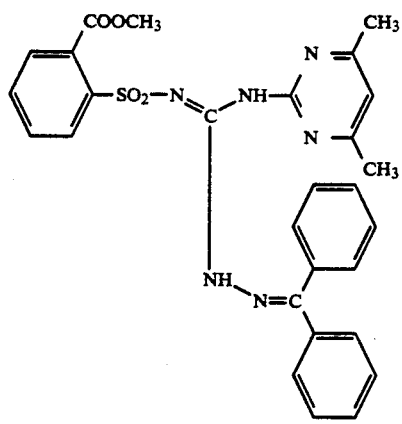

(Process (b))

A mixture of 11.8 g (0.02 mol) of N'-(4,6-dimethyl-pyrimidin-2-yl)-N'''-methoxy-N'',N'''-bis-(2-methoxycarbonyl-phenylsulphonyl)-guanidine, 5.9 g (0.03 mol) of benzophenone hydrazone and 100 ml of dioxane is refluxed for 2 days. After the mixture has cooled, unreacted benzophenone hydrazone is removed by filtration, the filtrate is concentrated, and the residue is recrystallized from ethanol.

4.7 g (43% of theory) of N'-(4,6-dimethylpyrimidin-2-yl)-N''-diphenylmethyleneamino-N'''-(2-methoxycarbonyl-phenylsulphonyl)-guanidine of melting point 153° C. are obtained.

The compounds of the formula (I) listed in Table 3 below are other examples which can be prepared analogously to Examples 1 to 8 and in accordance with the general description of the preparation process according to the invention.

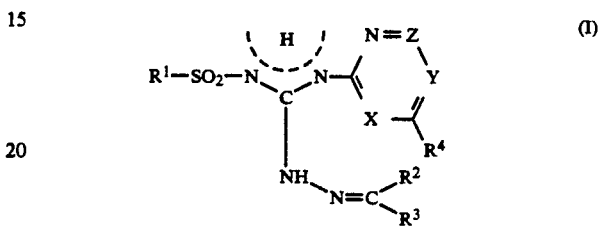

(I)

(The abbreviation "decomp." used in Table 3 means "decomposition").

TABLE 3

Examples of the compounds of the formula (I)

| Ex. No. | R¹ | R² | R³ | R⁴ | X | Y | Z | Melting point (°C.) |
|---|---|---|---|---|---|---|---|---|
| 9 | ethyl 1-methylpyrazole-carboxylate | H | C₆H₅ | CH₃ | N | CH | C—OCH₃ | 182 |
| 10 | ethyl 1-methylpyrazole-carboxylate | CH₃ | CH₃ | CH₃ | N | CH | C—OCH₃ | 168 |
| 11 | ethyl 1-methylpyrazole-carboxylate | —(CH₂)₅— | | CH₃ | N | CH | C—OCH₃ | 188 |
| 12 | ethyl 1-methylpyrazole-carboxylate | CH₃ | C₂H₅ | CH₃ | N | CH | C—OCH₃ | 134 |
| 13 | ethyl 1-methylpyrazole-carboxylate | H | 2-CF₃-C₆H₄ | CH₃ | N | CH | C—OCH₃ | 183 |
| 14 | ethyl 1-methylpyrazole-carboxylate | H | 4-F-C₆H₄ | CH₃ | N | CH | C—OCH₃ | 191 |

TABLE 3-continued

| # | Structure | | | | | | | mp |
|---|---|---|---|---|---|---|---|---|
| 15 | pyrazole-COOC$_2$H$_5$, N-CH$_3$, CH$_3$ | H | 2,6-dichlorophenyl | | CH$_3$ | N | CH | C—OCH$_3$ | 181 |
| 16 | pyrazole-COOC$_2$H$_5$, N-CH$_3$, CH$_3$ | H | 4-OCH$_3$-phenyl | | CH$_3$ | N | CH | C—OCH$_3$ | 193 |
| 17 | pyrazole-COOC$_2$H$_5$, N-CH$_3$, CH$_3$ | H | 2-OCF$_3$-phenyl | | CH$_3$ | N | CH | C—OCH$_3$ | 161 |
| 18 | pyrazole-COOC$_2$H$_5$, N-CH$_3$, CH$_3$ | H | 4-CH$_3$-phenyl | | CH$_3$ | N | CH | C—OCH$_3$ | 186 |
| 19 | pyrazole-COOC$_2$H$_5$, N-CH$_3$, CH$_3$ | H | 4-Cl-phenyl | | CH$_3$ | N | CH | C—OCH$_3$ | 194 |
| 20 | pyrazole-COOC$_2$H$_5$, N-CH$_3$, CH$_3$ | H | 2-F,6-Cl-phenyl | | CH$_3$ | N | CH | C—OCH$_3$ | 175 |
| 21 | pyrazole-COOC$_2$H$_5$, N-CH$_3$, CH$_3$ | H | 2-Cl-phenyl | | OCH$_3$ | N | CH | C—OCH$_3$ | 216 |
| 22 | pyrazole-COOC$_2$H$_5$, N-CH$_3$, CH$_3$ | H | phenyl | | OCH$_3$ | N | CH | C—OCH$_3$ | 189 |
| 23 | pyrazole-COOC$_2$H$_5$, N-CH$_3$, CH$_3$ | CH$_3$ | C$_2$H$_5$ | | OCH$_3$ | N | CH | C—OCH$_3$ | 149 |
| 24 | pyrazole-COOC$_2$H$_5$, N-CH$_3$, CH$_3$ | CH$_3$ | CH$_3$ | | OCH$_3$ | N | CH | C—OCH$_3$ | 182 |

TABLE 3-continued
| | | | | | | | | |
|---|---|---|---|---|---|---|---|---|
| 25 | 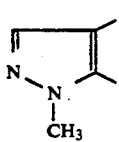 | H |  | OCH₃ | N | CH | C—OCH₃ | 224 |
| 26 | 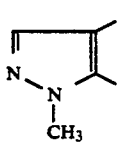 | —(CH₂)₅— | | OCH₃ | N | CH | C—OCH₃ | 148 |
| 27 | 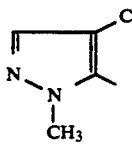 | H | 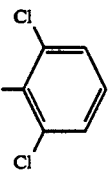 | OCH₃ | N | CH | C—OCH₃ | 202 |
| 28 | 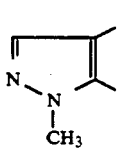 | H | 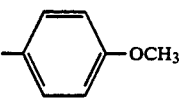 | OCH₃ | N | CH | C—OCH₃ | 211 |
| 29 | 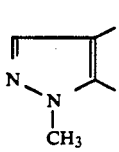 | H |  | OCH₃ | N | CH | C—OCH₃ | 213 |
| 30 | 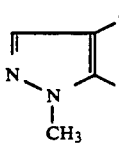 | H | 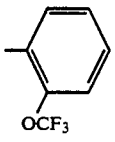 | OCH₃ | N | CH | C—OCH₃ | 152 |
| 31 | 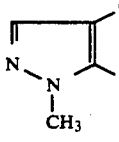 | H | 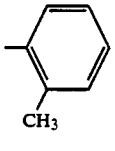 | OCH₃ | N | CH | C—OCH₃ | 200 |
| 32 | 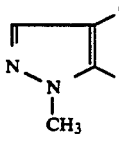 | H | 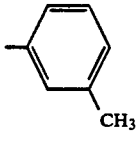 | OCH₃ | N | CH | C—OCH₃ | 180 |
| 33 | 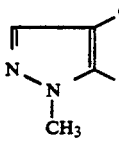 | H | 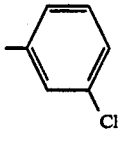 | OCH₃ | N | CH | C—CH₃ | 185 |
| 34 | 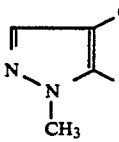 | H | 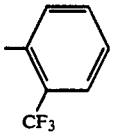 | OCH₃ | N | CH | C—OCH₃ | 165 |

TABLE 3-continued
| | | | | | | | | |
|---|---|---|---|---|---|---|---|---|
| 35 | 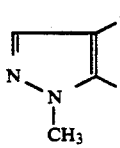 | H | 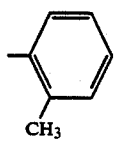 | CH$_3$ | N | CH | C—OCH$_3$ | 186 |
| 36 | 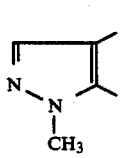 | CH$_3$ CH$_3$ | | CH$_3$ | N | CH | C—CH$_3$ | 164 |
| 37 | 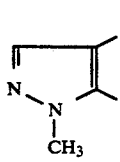 | CH$_3$ C$_2$H$_5$ | | CH$_3$ | N | CH | C—CH$_3$ | 140 |
| 38 | 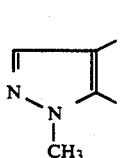 | H | 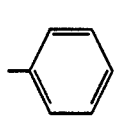 | CH$_3$ | N | CH | C—CH$_3$ | 187 |
| 39 | 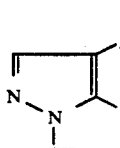 | —(CH$_2$)$_5$— | | CH$_3$ | N | CH | C—CH$_3$ | 176 |
| 40 | 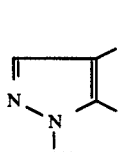 | H | 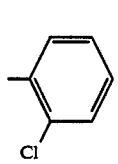 | CH$_3$ | N | CH | C—CH$_3$ | 189 |
| 41 | 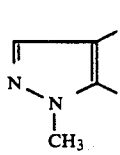 | H | 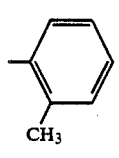 | CH$_3$ | N | CH | C—CH$_3$ | 190 |
| 42 | 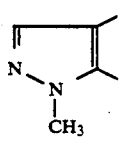 | H | 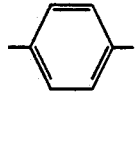 | CH$_3$ | N | CH | C—CH$_3$ | 186 |
| 43 | 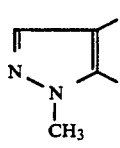 | H | 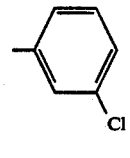 | CH$_3$ | N | CH | C—CH$_3$ | 183 |
| 44 | 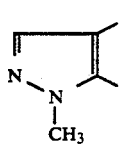 | H | 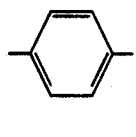 | OCH$_3$ | N | CH | C—OCH$_3$ | 225 |

TABLE 3-continued

| # | Structure | | Ar | | | | mp |
|---|---|---|---|---|---|---|---|
| 45 | pyrazole-COOC₂H₅, N-CH₃ | H | 2,4-dichlorophenyl | OCH₃ | N | CH | C—OCH₃ | 196 |
| 46 | pyrazole-COOC₂H₅, N-CH₃ | H | 2,6-difluorophenyl | OCH₃ | N | CH | C—OCH₃ | 205 |
| 47 | pyrazole-COOC₂H₅, N-CH₃ | H | 3-nitrophenyl | OCH₃ | N | CH | C—OCH₃ | 209 |
| 48 | pyrazole-COOC₂H₅, N-CH₃ | H | 2-nitrophenyl | OCH₃ | N | CH | C—OCH₃ | 192 |
| 49 | pyrazole-COOC₂H₅, N-CH₃ | H | 4-fluorophenyl | CH₃ | N | CH | C—CH₃ | 198 |
| 50 | pyrazole-COOC₂H₅, N-CH₃ | H | 4-methoxyphenyl | CH₃ | N | CH | C—CH₃ | 185 |
| 51 | pyrazole-COOC₂H₅, N-CH₃ | H | 2-(OCF₃)phenyl | CH₃ | N | CH | C—CH₃ | 181 |
| 52 | pyrazole-COOC₂H₅, N-CH₃ | H | 2,6-dichlorophenyl | CH₃ | N | CH | C—CH₃ | 179 |
| 53 | pyrazole-COOC₂H₅, N-CH₃ | H | 2-fluoro-6-chlorophenyl | CH₃ | N | CH | C—CH₃ | 187 |
| 54 | pyrazole-COOC₂H₅, N-CH₃ | H | 2,6-difluorophenyl | CH₃ | N | CH | C—CH₃ | 177 |

TABLE 3-continued

| # | Structure 1 | | Aryl | | | | | m.p. |
|---|---|---|---|---|---|---|---|---|
| 55 | pyrazole-COOC₂H₅, N-CH₃ | H | 4-CH₃-C₆H₄ | CH₃ | N | CH | C—CH₃ | 202 |
| 56 | pyrazole-COOC₂H₅, N-CH₃ | H | 2-CF₃-C₆H₄ | CH₃ | N | CH | C—CH₃ | 185 |
| 57 | pyrazole-COOC₂H₅, N-CH₃ | H | 2,4-Cl₂-C₆H₃ | CH₃ | N | CH | C—CH₃ | 186 |
| 58 | pyrazole-COOC₂H₅, N-CH₃ | H | 2-NO₂-C₆H₄ | CH₃ | N | CH | C—CH₃ | 187 |
| 59 | pyrazole-COOC₂H₅, N-CH₃ | H | 3-NO₂-C₆H₄ | CH₃ | N | CH | C—CH₃ | 197 |
| 60 | pyrazole-COOC₂H₅, N-CH₃ | H | 4-NO₂-C₆H₄ | CH₃ | N | CH | C—CH₃ | 192 |
| 61 | pyrazole-COOC₂H₅, N-CH₃ | H | 4-Cl-3-NO₂-C₆H₃ | CH₃ | N | CH | C—CH₃ | 215 |
| 62 | pyrazole-COOC₂H₅, N-CH₃ | H | 2-NO₂-C₆H₄ | CH₃ | N | CH | C—OCH₃ | 176 |
| 63 | pyrazole-COOC₂H₅, N-CH₃ | H | 3-CH₃-C₆H₄ | CH₃ | N | CH | C—OCH₃ | 174 |
| 64 | pyrazole-COOC₂H₅, N-CH₃ | H | 4-Cl-3-NO₂-C₆H₃ | CH₃ | N | CH | C—OCH₃ | 193 |

TABLE 3-continued

| # | Structure 1 | R | R' | Structure 2 | a | b | c | d | mp |
|---|---|---|---|---|---|---|---|---|---|
| 65 | ethyl 1,5-dimethyl-1H-pyrazole-4-carboxylate | H | | 2,4-dichlorophenyl | CH$_3$ | N | CH | C—OCH$_3$ | 192 |
| 66 | ethyl 1,5-dimethyl-1H-pyrazole-4-carboxylate | H | | 4-chloro-3-nitrophenyl | OCH$_3$ | N | CH | C—OCH$_3$ | 222 |
| 67 | 2,6-dichlorophenyl | CH$_3$ | CH$_3$ | | OCH$_3$ | N | N | C—OCH$_3$ | 213 (decomp.) |
| 68 | 2-(N,N-dimethylsulfamoyl)phenyl | CH$_3$ | CH$_3$ | | OCH$_3$ | N | N | C—OCH$_3$ | 222 |
| 69 | 3-chlorophenyl | CH$_3$ | CH$_3$ | | OCH$_3$ | N | N | C—OCH$_3$ | 146 |
| 70 | 4-chlorophenyl | CH$_3$ | CH$_3$ | | OCH$_3$ | N | N | C—OCH$_3$ | 160 |
| 71 | 2-(methoxycarbonyl)benzyl | —(CH$_2$)$_5$— | | | OCH$_3$ | N | N | C—OCH$_3$ | 173 |
| 72 | 2-(trifluoromethoxy)benzyl | —(CH$_2$)$_5$— | | | OCH$_3$ | N | N | C—OCH$_3$ | 167 |
| 73 | 2-(methoxycarbonyl)phenyl | H | | 2-chloropyridin-5-yl | OCH$_3$ | N | N | C—OCH$_3$ | 230 (decomp.) |
| 74 | 2-(trifluoromethoxy)benzyl | H | C$_6$H$_5$ | | CH$_3$ | N | N | C—OCH$_3$ | 198 |
| 75 | 2-(trifluoromethoxy)benzyl | H | C$_6$H$_5$ | | CH$_3$ | N | N | C—CH$_3$ | 180 |

TABLE 3-continued

| # | R (structure) | | | | | | | mp |
|---|---|---|---|---|---|---|---|---|
| 76 | 2-OCF₃-benzyl | H | C₆H₅ | | C₂H₅ | N | N | C—OCH₃ | 174 |
| 77 | 2-OCF₃-benzyl | H | C₆H₅ | | CH₃ | N | N | C—OC₂H₅ | 186 |
| 78 | 2-Cl-benzyl | H | C₆H₅ | | CH₃ | N | N | C—OC₂H₅ | 184 |
| 79 | 2-Cl-benzyl | H | C₆H₅ | | CH₃ | N | N | C—SCH₃ | 218 |
| 80 | 2,6-Cl₂-phenyl | CH₃ | CH₃ | | CH₃ | N | N | C—OC₂H₅ | 176 |
| 81 | 2,5-dichloro-3-methylthienyl | CH₃ | CH₃ | | CH₃ | N | N | C—OCH₃ | 152 |
| 82 | 2-SO₂N(C₂H₅)₂-phenyl | CH₃ | CH₃ | | CH₃ | N | N | C—OCH₃ | 180 |
| 83 | 3-methyl-2-COOCH₃-thienyl | CH₃ | CH₃ | | CH₃ | N | N | C—OCH₃ | 183 |
| 84 | 2,4-Cl₂-phenyl | CH₃ | CH₃ | | CH₃ | N | N | C—OCH₃ | 187 |
| 85 | 2-OCF₃-phenyl | CH₃ | CH₃ | | CH₃ | N | N | C—OC₂H₅ | 146 |
| 86 | 2-F-phenyl | CH₃ | CH₃ | | OCH₃ | N | N | C—OCH₃ | 194 |

TABLE 3-continued

| # | Aryl | | | | | | | |
|---|---|---|---|---|---|---|---|---|
| 87 | 2-Br-C₆H₄- | CH₃ | CH₃ | | OCH₃ | N | N | C—OCH₃ | 211 |
| 88 | 2-CF₃-C₆H₄- | CH₃ | CH₃ | | OCH₃ | N | N | C—OCH₃ | 152 |
| 89 | 2,4-Cl₂-C₆H₃- | CH₃ | CH₃ | | OCH₃ | N | N | C—OCH₃ | 191 |
| 90 | 2,4-F₂-C₆H₃- | CH₃ | CH₃ | | OCH₃ | N | N | C—OCH₃ | 166 |
| 91 | 2,5-Cl₂-C₆H₃- | CH₃ | CH₃ | | OCH₃ | N | N | C—OCH₃ | 214 |
| 92 | 2-OCF₃-C₆H₄- | CH₃ | CH₃ | | OCH₃ | N | N | C—OCH₃ | 164 |
| 93 | 2-COOCH₃-C₆H₄- | CH₃ | CH₃ | | CH₃ | N | N | C—OCH₃ | 165 |
| 94 | 4-F-C₆H₄- | CH₃ | CH₃ | | CH₃ | N | N | C—OCH₃ | 112 |
| 95 | 2,3-F₂-C₆H₃- | CH₃ | CH₃ | | OCH₃ | N | N | C—OCH₃ | 171 |
| 96 | 2-Cl-C₆H₄- | CH₃ | CH₃ | | CH₃ | N | N | C—CH₃ | 110 |
| 97 | 2-OCF₃-C₆H₄- | H | —CH=C(CH₃)(CH₂)₂—CH=C(CH₃)CH₃ | | OCH₃ | N | N | C—OCH₃ | 152 |

TABLE 3-continued
| 98 | 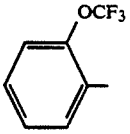 | H | 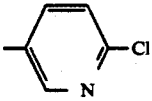 | OCH₃ | N | N | C—OCH₃ | 109 |
| 99 | 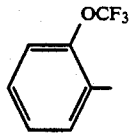 | H | C₆H₅ | OCH₃ | N | N | C—OCH₃ | 174 |
| 100 | 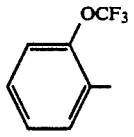 | H | 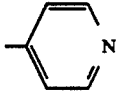 | OCH₃ | N | N | C—OCH₃ | 137 |
| 101 | 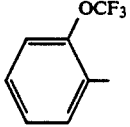 | H | 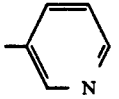 | OCH₃ | N | N | C—OCH₃ | 198 |
| 102 | 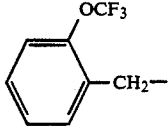 | CH₃ | CH₃ | OCH₃ | N | N | C—OCH₃ | 192 |
| 103 | 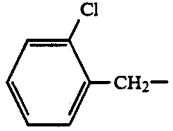 | CH₃ | CH₃ | OCH₃ | N | N | C—OCH₃ | 175 |
| 104 | 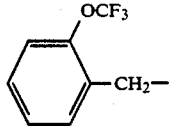 | H | 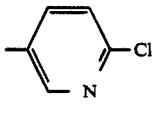 | OCH₃ | N | N | C—OCH₃ | 242 (decomp.) |
| 105 | 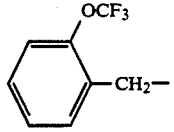 | H | 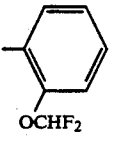 | OCH₃ | N | N | C—OCH₃ | 170 |
| 106 | 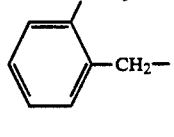 | H | 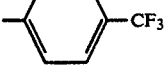 | OCH₃ | N | N | C—OCH₃ | 210 |
| 107 | 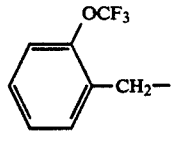 | H | C₆H₅ | OCH₃ | N | N | C—OCH₃ | 199 |
| 108 | 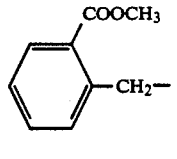 | CH₃ | CH₃ | CH₃ | N | N | C—OCH₃ | 201 |

TABLE 3-continued

| | | | | | | | | |
|---|---|---|---|---|---|---|---|---|
| 109 | 2-(COOCH₃)C₆H₄-CH₂- | CH₃ | CH₃ | | OCH₃ | N | N | C—OCH₃ | 210 |
| 110 | 2-(COOCH₃)C₆H₄-CH₂- | CH₃ | CH₃ | | CH₃ | N | N | C—CH₃ | 200 (decomp.) |
| 111 | 2-(COOCH₃)C₆H₄-CH₂- | CH₃ | CH₃ | | C₂H₅ | N | N | C—OCH₃ | 185 |
| 112 | 2-(COOCH₃)C₆H₄-CH₂- | CH₃ | CH₃ | | CH₃ | N | N | C—SCH₃ | 184 |
| 113 | 2-(COOCH₃)C₆H₄-CH₂- | CH₃ | CH₃ | | CH₃ | N | N | C—OC₂H₅ | 183 |
| 114 | 2-(COOCH₃)C₆H₄-CH₂- | CH₃ | CH₃ | | CH₃ | N | N | C—N(CH₃)₂ | 227 |
| 115 | 2-(OCHF₂)C₆H₄- | CH₃ | CH₃ | | C₂H₅ | N | N | C—OCH₃ | 128 |
| 116 | 2-(OCHF₂)C₆H₄- | CH₃ | CH₃ | | CH₃ | N | N | C—OCH₃ | 177 |
| 117 | 2-(OCHF₂)C₆H₄- | CH₃ | CH₃ | | OCH₃ | N | N | C—OCH₃ | 169 |
| 118 | 2-(OCF₃)C₆H₄-CH₂- | CH₃ | CH₃ | | CH₃ | N | N | C—OCH₃ | 185 |
| 119 | 2-(OCF₃)C₆H₄-CH₂- | CH₃ | CH₃ | | CH₃ | N | N | C—CH₃ | 184 |

TABLE 3-continued

| No. | R | R¹ | R² | R³ | X | Y | Z | mp |
|-----|---|----|----|----|---|---|---|-----|
| 120 | 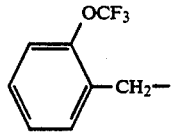 2-OCF₃-benzyl | CH₃ | CH₃ | C₂H₅ | N | N | C—OCH₃ | 175 |
| 121 | 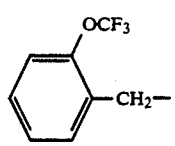 2-OCF₃-benzyl | CH₃ | CH₃ | CH₃ | N | N | C—OC₂H₅ | 210 |
| 122 | 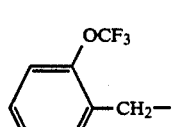 2-OCF₃-benzyl | CH₃ | CH₃ | CH₃ | N | N | C—SCH₃ | 188 |
| 123 | 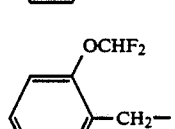 2-OCHF₂-benzyl | CH₃ | CH₃ | OCH₃ | N | N | C—OCH₃ | 163 |
| 124 | 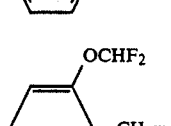 2-OCHF₂-benzyl | CH₃ | CH₃ | CH₃ | N | N | C—CH₃ | 165 |
| 125 | 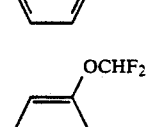 2-OCHF₂-benzyl | CH₃ | CH₃ | CH₃ | N | N | C—OCH₃ | 154 |
| 126 | 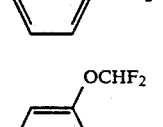 2-OCHF₂-benzyl | CH₃ | CH₃ | C₂H₅ | N | N | C—OCH₃ | 115 |
| 127 | 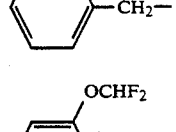 2-OCHF₂-benzyl | CH₃ | CH₃ | CH₃ | N | N | C—OC₂H₅ | 169 |
| 128 | 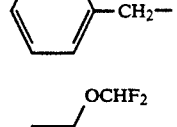 2-OCHF₂-phenyl | CH₃ | CH₃ | CH₃ | N | N | C—CH₃ | 205 |
| 129 | 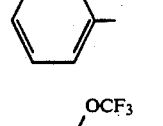 2-OCF₃-phenyl | CH₃ | CH₃ | CH₃ | N | N | C—CH₃ | 179 |
| 130 | 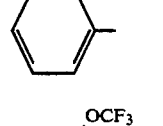 2-OCF₃-benzyl | H | C₆H₅ | CH₃ | N | N | C—SCH₃ | 208 |

TABLE 3-continued

| # | R1 (aryl) | R2 | R3 | R4 | X | Y | Z | mp |
|---|---|---|---|---|---|---|---|---|
| 131 | 2-OCHF₂-benzyl | H | C₆H₅ | OCH₃ | N | N | C—OCH₃ | 227 (decomp.) |
| 132 | 2-OCHF₂-benzyl | H | C₆H₅ | CH₃ | N | N | C—OCH₃ | 207 |
| 133 | 2-OCHF₂-benzyl | H | C₆H₅ | CH₃ | N | N | C—CH₃ | 195 |
| 134 | 2-OCHF₂-benzyl | H | C₆H₅ | C₂H₅ | N | N | C—OCH₃ | 190 |
| 135 | 2-OCHF₂-benzyl | H | C₆H₅ | CH₃ | N | N | C—OC₂H₅ | 212 |
| 136 | 2-OCHF₂-benzyl | CH₃ | CH₃ | CH₃ | N | N | C—SCH₃ | 143 |
| 137 | 2-OCHF₂-benzyl | H | C₆H₅ | CH₃ | N | N | C—SCH₃ | 210 |
| 138 | 2-Cl-benzyl | CH₃ | CH₃ | CH₃ | N | N | C—OC₂H₅ | 168 |
| 139 | 2-SO₂N(CH₃)₂-phenyl | H | 2-OCHF₂-phenyl | CH₃ | N | N | C—OCH₃ | 210 |
| 140 | 2-SO₂N(CH₃)₂-phenyl | H | 4-SCF₃-phenyl | CH₃ | N | N | C—OCH₃ | 200 |
| 141 | 2-SO₂N(CH₃)₂-phenyl | H | 3-CF₃-phenyl | OCH₃ | N | N | C—OCH₃ | 231 (decomp.) |

TABLE 3-continued

| No. | R1 | R2 | Ar | R3 | X | Y | Z | mp (°C) |
|---|---|---|---|---|---|---|---|---|
| 142 | 2-SO$_2$N(CH$_3$)$_2$-phenyl | H | 4-CF$_3$-phenyl | CH$_3$ | N | N | C—OCH$_3$ | 210 |
| 143 | 2-SO$_2$N(CH$_3$)$_2$-phenyl | H | 2-pyridyl | CH$_3$ | N | N | C—OCH$_3$ | 207 (decomp.) |
| 144 | 2-SO$_2$N(CH$_3$)$_2$-phenyl | H | 3-pyridyl | CH$_3$ | N | N | C—OCH$_3$ | 208 (decomp.) |
| 145 | 2-SO$_2$N(CH$_3$)$_2$-phenyl | H | 4-pyridyl | CH$_3$ | N | N | C—OCH$_3$ | 209 (decomp.) |
| 146 | 2-SO$_2$N(CH$_3$)$_2$-phenyl | H | 2-Cl-phenyl | CH$_3$ | N | N | C—OCH$_3$ | 215 |
| 147 | 2-SO$_2$N(CH$_3$)$_2$-phenyl | H | 3-Cl-phenyl | CH$_3$ | N | N | C—OCH$_3$ | 221 (decomp.) |
| 148 | 2-SO$_2$N(CH$_3$)$_2$-phenyl | H | 3-CF$_3$-phenyl | CH$_3$ | N | N | C—OCH$_3$ | 213 |
| 149 | 2-SO$_2$N(CH$_3$)$_2$-phenyl | H | 3-Br-phenyl | CH$_3$ | N | N | C—OCH$_3$ | 222 (decomp.) |
| 150 | 2-SO$_2$N(CH$_3$)$_2$-phenyl | H | 3-CH$_3$-phenyl | CH$_3$ | N | N | C—OCH$_3$ | 238 (decomp.) |
| 151 | 2-SO$_2$N(CH$_3$)$_2$-phenyl | H | 2,6-diF-phenyl | CH$_3$ | N | N | C—OCH$_3$ | 225 (decomp.) |
| 152 | 2-SO$_2$N(CH$_3$)$_2$-phenyl | H | 3-Cl-4-F-phenyl | CH$_3$ | N | N | C—OCH$_3$ | 196 (decomp.) |

TABLE 3-continued

| # | Ar1 | R | Ar2 | R' | X | Y | Z | mp (°C) |
|---|---|---|---|---|---|---|---|---|
| 153 | 2-SO2N(CH3)2-phenyl | H | 4-Br-phenyl | CH3 | N | N | C—OCH3 | 236 (decomp.) |
| 154 | 2-OCHF2-phenyl | H | 2-OCHF2-phenyl | CH3 | N | N | C—OCH3 | 184 |
| 155 | 2-OCHF2-phenyl | H | 4-SCF3-phenyl | CH3 | N | N | C—OCH3 | 149 |
| 156 | 2-OCHF2-phenyl | H | 2-CF3-phenyl | CH3 | N | N | C—OCH3 | 166 |
| 157 | 2-OCHF2-phenyl | H | 4-CF3-phenyl | CH3 | N | N | C—OCH3 | 165 (decomp.) |
| 158 | 2-OCHF2-phenyl | H | 2-pyridyl | CH3 | N | N | C—OCH3 | 176 |
| 159 | 2-OCHF2-phenyl | H | 3-pyridyl | CH3 | N | N | C—OCH3 | 197 |
| 160 | 2-OCHF2-phenyl | H | 4-pyridyl | CH3 | N | N | C—OCH3 | 177 |
| 161 | 2-OCHF2-phenyl | H | 2-Cl-5-pyridyl | CH3 | N | N | C—OCH3 | 200 |
| 162 | 2-OCHF2-phenyl | H | 3-Cl-phenyl | CH3 | N | N | C—OCH3 | 134 |
| 163 | 2-Cl-benzyl | CH3 | CH3 | CH3 | N | N | C—SCH3 | 180 |

TABLE 3-continued

| | | | | | | | | |
|---|---|---|---|---|---|---|---|---|
| 164 | 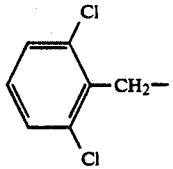 2,6-dichlorobenzyl | CH₃ | CH₃ | CH₃ | N | N | C—OC₂H₅ | 199 |
| 165 | 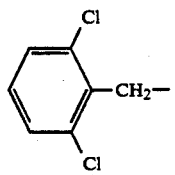 2,6-dichlorobenzyl | H | C₆H₅ | CH₃ | N | N | C—OC₂H₅ | 179 |
| 166 | 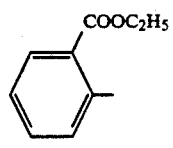 2-COOC₂H₅-phenyl | CH₃ | CH₃ | OCH₃ | N | N | C—OCH₃ | 191 |
| 167 | 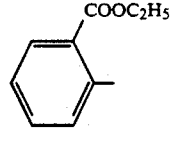 2-COOC₂H₅-phenyl | H | C₆H₅ | OCH₃ | N | N | C—OCH₃ | 192 |
| 168 | 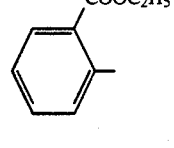 2-COOC₂H₅-phenyl | CH₃ | CH₃ | CH₃ | N | N | C—OCH₃ | 169 |
| 169 | 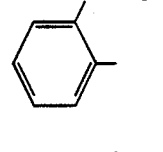 2-COOC₂H₅-phenyl | H | C₆H₅ | CH₃ | N | N | C—OCH₃ | 187 |
| 170 | 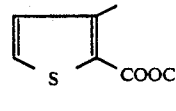 3-methyl-2-COOCH₃-thienyl | CH₃ | CH₃ | CH₃ | N | N | C—SCH₃ | 198 |
| 171 | 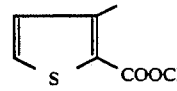 3-methyl-2-COOCH₃-thienyl | H | C₆H₅ | CH₃ | N | N | C—SCH₃ | 211 |
| 172 | 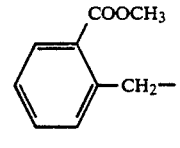 2-COOCH₃-benzyl | H | C₆H₅ | CH₃ | N | N | C—OCH₃ | 156 |
| 173 | 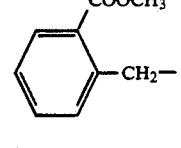 2-COOCH₃-benzyl | H | C₆H₅ | CH₃ | N | N | C—OC₂H₅ | 153 |
| 174 | 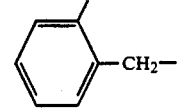 2-COOCH₃-benzyl | H | C₆H₅ | CH₃ | N | N | C—SCH₃ | 165 |

TABLE 3-continued
| | | | | | | | | | |
|---|---|---|---|---|---|---|---|---|---|
| 175 | 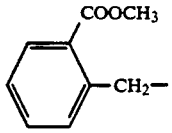 | H | C$_6$H$_5$ | | CH$_3$ | N | N | C—N(CH$_3$)$_2$ | 188 |
| 176 | 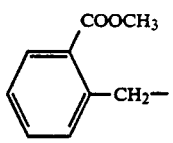 | H | C$_6$H$_5$ | | C$_2$H$_5$ | N | N | C—OCH$_3$ | 121 (decomp.) |
| 177 | 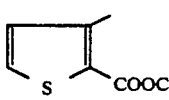 | CH$_3$ | CH$_3$ | | CH$_3$ | N | N | C—OC$_2$H$_5$ | 180 |
| 178 | 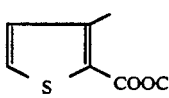 | H | C$_6$H$_5$ | | CH$_3$ | N | N | C—OC$_2$H$_5$ | 216 |
| 179 | 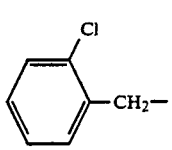 | CH$_3$ | CH$_3$ | | CH$_3$ | N | N | C—OCH$_3$ | 164 |
| 180 | 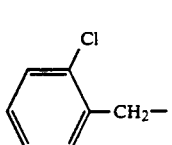 | H | C$_6$H$_5$ | | CH$_3$ | N | N | C—OCH$_3$ | 206 |
| 181 | 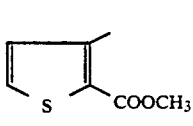 | H | 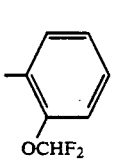 | | CH$_3$ | N | N | C—OC$_2$H$_5$ | 182 |
| 182 | 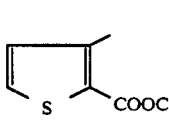 | H | 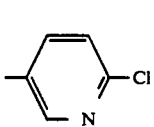 | | CH$_3$ | N | N | C—OC$_2$H$_5$ | 167 (decomp.) |
| 183 | 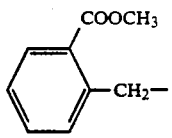 | H | C$_6$H$_5$ | | CH$_3$ | N | N | C—CH$_3$ | 132 |
| 184 | 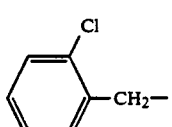 | CH$_3$ | CH$_3$ | | CH$_3$ | N | N | C—OCH$_3$ | 190 |
| 185 | 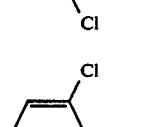 | H | C$_6$H$_5$ | | CH$_3$ | N | N | C—OCH$_3$ | 202 |

TABLE 3-continued
| | | | | | | | | |
|---|---|---|---|---|---|---|---|---|
| 186 | 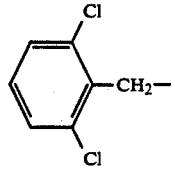 2,6-Cl₂-benzyl | CH₃ | CH₃ | OCH₃ | N | N | C—OCH₃ | 224 |
| 187 | 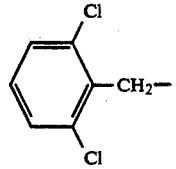 2,6-Cl₂-benzyl | H | C₆H₅ | OCH₃ | N | N | C—OCH₃ | 185 |
| 188 | 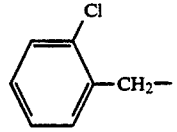 2-Cl-benzyl | CH₃ | CH₃ | CH₃ | N | N | C—CH₃ | 181 |
| 189 | 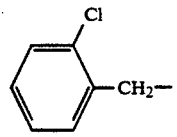 2-Cl-benzyl | H | C₆H₅ | CH₃ | N | N | C—CH₃ | 157 |
| 190 | 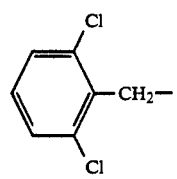 2,6-Cl₂-benzyl | CH₃ | CH₃ | CH₃ | N | N | C—SCH₃ | 200 |
| 191 | 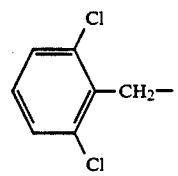 2,6-Cl₂-benzyl | H | C₆H₅ | CH₃ | N | N | C—SCH₃ | 230 |
| 192 | 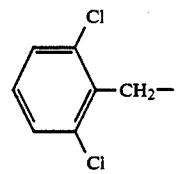 2,6-Cl₂-benzyl | CH₃ | CH₃ | C₂H₅ | N | N | C—OCH₃ | 170 |
| 193 | 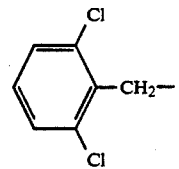 2,6-Cl₂-benzyl | H | C₆H₅ | C₂H₅ | N | N | C—OCH₃ | 190 |
| 194 | 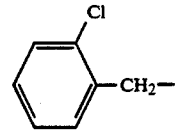 2-Cl-benzyl | CH₃ | CH₃ | C₂H₅ | N | N | C—OCH₃ | 174 |
| 195 | 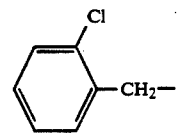 2-Cl-benzyl | H | C₆H₅ | C₂H₅ | N | N | C—OCH₃ | 189 |

TABLE 3-continued

| # | R1 (structure) | | R2 | | | | | m.p. |
|---|---|---|---|---|---|---|---|---|
| 196 | 2-(COOC₂H₅)-phenyl | CH₃ | CH₃ | CH₃ | N | N | C—SCH₃ | 187 |
| 197 | 2-(COOC₂H₅)-phenyl | H | C₆H₅ | | CH₃ | N | N | C—SCH₃ | 207 |
| 198 | 3-methyl-2-(COOCH₃)-thienyl | H | 2-(OCHF₂)-phenyl | | CH₃ | N | N | C—OCH₃ | 195 (decomp.) |
| 199 | 3-methyl-2-(COOCH₃)-thienyl | H | 4-(SCF₃)-phenyl | | CH₃ | N | N | C—OCH₃ | 194 (decomp.) |
| 200 | 3-methyl-2-(COOCH₃)-thienyl | H | 2-(CF₃)-phenyl | | CH₃ | N | N | C—OCH₃ | 173 |
| 201 | 3-methyl-2-(COOCH₃)-thienyl | H | 4-(CF₃)-phenyl | | CH₃ | N | N | C—OCH₃ | 208 |
| 202 | 3-methyl-2-(COOCH₃)-thienyl | H | 2-pyridyl | | CH₃ | N | N | C—OCH₃ | 177 (decomp.) |
| 203 | 3-methyl-2-(COOCH₃)-thienyl | H | 4-pyridyl | | CH₃ | N | N | C—OCH₃ | 174 (decomp.) |
| 204 | 3-methyl-2-(COOCH₃)-thienyl | H | 3-pyridyl | | CH₃ | N | N | C—OCH₃ | 186 (decomp.) |
| 205 | 3-methyl-2-(COOCH₃)-thienyl | H | 6-chloro-3-pyridyl | | CH₃ | N | N | C—OCH₃ | 210 (decomp.) |
| 206 | C₆H₅—CH₂— | H | C₆H₅ | | CH₃ | N | N | C—OCH₃ | 179 |
| 207 | 2-F-C₆H₄—CH₂— | H | C₆H₅ | | CH₃ | N | N | C—OCH₃ | 192 |

TABLE 3-continued
| | | | | | | | | |
|---|---|---|---|---|---|---|---|---|
| 208 | 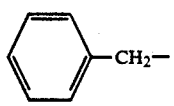 | CH₃ | CH₃ | | CH₃ | N | N | C—OCH₃ | 182 |
| 209 | 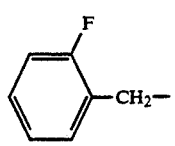 | CH₃ | CH₃ | | CH₃ | N | N | C—OCH₃ | 160 |
| 210 | 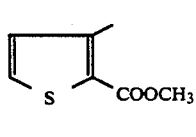 | H | 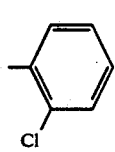 | | CH₃ | N | N | C—OCH₃ | 200 (decomp.) |
| 211 | 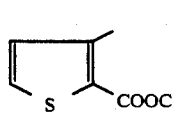 | H | 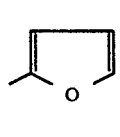 | | CH₃ | N | N | C—OCH₃ | 208 (decomp.) |
| 212 | 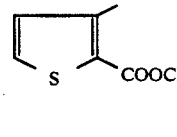 | H | 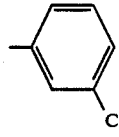 | | CH₃ | N | N | C—OCH₃ | 210 (decomp.) |
| 213 | 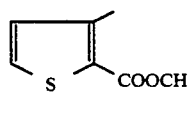 | H | 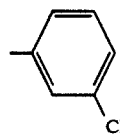 | | CH₃ | N | N | C—OCH₃ | 210 (decomp.) |
| 214 | 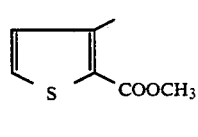 | H | 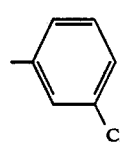 | | CH₃ | N | N | C—OCH₃ | 209 (decomp.) |
| 215 | 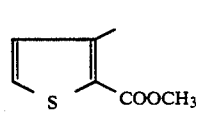 | H | 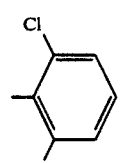 | | CH₃ | N | N | C—OCH₃ | 140 (decomp.) |
| 216 | 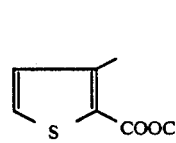 | H | 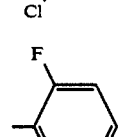 | | CH₃ | N | N | C—OCH₃ | 213 (decomp.) |
| 217 | 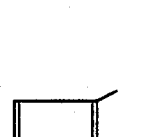 | H | 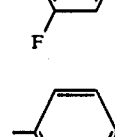 | | CH₃ | N | N | C—OCH₃ | 195 (decomp.) |
| 218 | 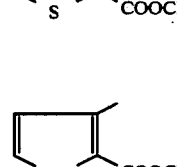 | H | 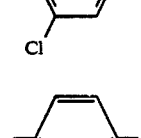 | | CH₃ | N | N | C—OCH₃ | 220 (decomp.) |

TABLE 3-continued
| | | | | | | | |
|---|---|---|---|---|---|---|---|
| 219 | 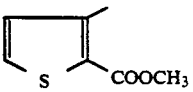 | H | 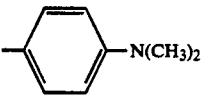 | CH₃ | N | N | C—OCH₃ | 219 (decomp.) |
| 220 | 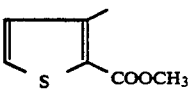 | H | 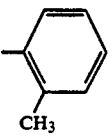 | CH₃ | N | N | C—OCH₃ | 185 (decomp.) |
| 221 | 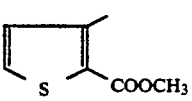 | H | 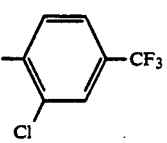 | CH₃ | N | N | C—OCH₃ | 202 (decomp.) |
| 222 | 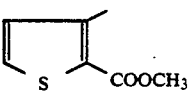 | H | 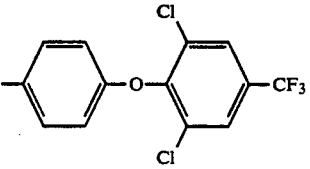 | CH₃ | N | N | C—OCH₃ | 159 (decomp.) |
| 223 | 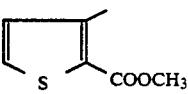 | H | 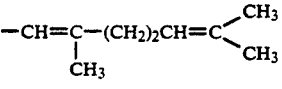 | CH₃ | N | N | C—OCH₃ | 176 |
| 224 | 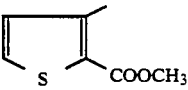 | H | —CH=CH—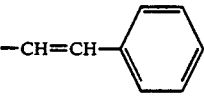 | CH₃ | N | N | C—OCH₃ | 222 (decomp.) |
| 225 | 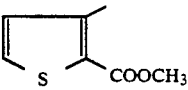 | H | 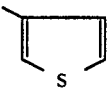 | CH₃ | N | N | C—OCH₃ | 206 |
| 226 | 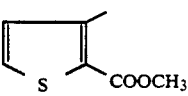 | H | 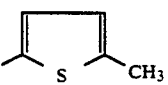 | CH₃ | N | N | C—OCH₃ | 207 (decomp.) |
| 227 | 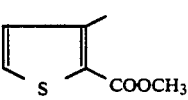 | CH₃ | 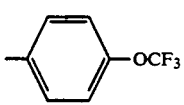 | CH₃ | N | N | C—OCH₃ | 140 |
| 228 | 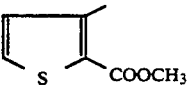 | H | 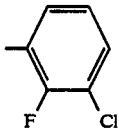 | CH₃ | N | N | C—OCH₃ | 196 (decomp.) |
| 229 | 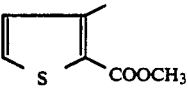 | H | 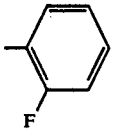 | CH₃ | N | N | C—OCH₃ | 198 (decomp.) |
| 230 | 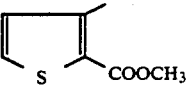 | H | 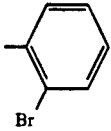 | CH₃ | N | N | C—OCH₃ | 191 (decomp.) |

TABLE 3-continued

| No. | Ar | R1 | R2 | R3 | X | Y | Z | m.p. (°C) |
|---|---|---|---|---|---|---|---|---|
| 231 | 3-methyl-thiophene-2-COOCH₃ | H | CH₃ | CH₃ | N | N | C—OCH₃ | 179 (decomp.) |
| 232 | 3-methyl-thiophene-2-COOCH₃ | H | CH(CH₃)₂ | CH₃ | N | N | C—OCH₃ | 189 |
| 233 | 2-SO₂N(CH₃)₂-phenyl | CH₃ | CH₃ | CH₃ | N | N | C—OCH₃ | 193 (decomp.) |
| 234 | 2-SO₂N(CH₃)₂-phenyl | H | C₆H₅ | CH₃ | N | N | C—OCH₃ | 241 (decomp.) |
| 235 | 2-SO₂N(CH₃)₂-phenyl | H | CH₃ | CH₃ | N | N | C—OCH₃ | 173 (decomp.) |
| 236 | 2-SO₂N(CH₃)₂-phenyl | H | CH(CH₃)₂ | CH₃ | N | N | C—OCH₃ | 174 (decomp.) |
| 237 | 2-COOCH₃-phenyl | H | C₆H₅ | CH₃ | N | N | C—OCH₃ | 198 |
| 238 | 2-COOCH₃-phenyl | H | 3-OCHF₂-phenyl | CH₃ | N | N | C—OCH₃ | 201 |
| 239 | 2-COOCH₃-phenyl | H | 4-SCF₃-phenyl | CH₃ | N | N | C—OCH₃ | 208 |
| 240 | 2-COOCH₃-phenyl | H | 2-CF₃-phenyl | CH₃ | N | N | C—OCH₃ | 165 (decomp.) |
| 241 | 2-COOCH₃-phenyl | H | 4-CF₃-phenyl | CH₃ | N | N | C—OCH₃ | 215 |

TABLE 3-continued

| # | Ar1 | R | Ar2 | R' | X | Y | Z | mp (°C) |
|---|---|---|---|---|---|---|---|---|
| 242 | 2-(COOCH₃)phenyl | H | pyridin-2-yl | CH₃ | N | N | C—OCH₃ | 201 (decomp.) |
| 243 | 2-(SO₂N(CH₃)₂)phenyl | H | 6-chloropyridin-3-yl | CH₃ | N | N | C—OCH₃ | 242 (decomp.) |
| 244 | 2-(SO₂N(CH₃)₂)phenyl | H | 2,6-dichlorophenyl | CH₃ | N | N | C—OCH₃ | 202 (decomp.) |
| 245 | 2-(OCHF₂)phenyl | H | CH₃ | CH₃ | N | N | C—OCH₃ | 139 |
| 246 | 2-(OCHF₂)phenyl | H | CH(CH₃)₂ | CH₃ | N | N | C—OCH₃ | 136 |
| 247 | 2-(OCHF₂)phenyl | H | 3-chlorophenyl | CH₃ | N | N | C—OCH₃ | 182 |
| 248 | 2-(OCHF₂)phenyl | H | 4-chlorophenyl | CH₃ | N | N | C—OCH₃ | 202 |
| 249 | 2-(OCHF₂)phenyl | H | 3-(CF₃)phenyl | CH₃ | N | N | C—OCH₃ | 183 |
| 250 | 2-(OCHF₂)phenyl | H | 3-bromophenyl | CH₃ | N | N | C—OCH₃ | 182 |
| 251 | 2-(OCHF₂)phenyl | H | 3-methylphenyl | CH₃ | N | N | C—OCH₃ | 188 |

TABLE 3-continued
| | | | | | | | | |
|---|---|---|---|---|---|---|---|---|
| 252 | 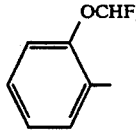 OCHF₂ | H | 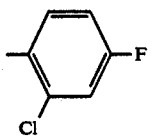 F, Cl | CH₃ | N | N | C—OCH₃ | 154 |
| 253 | 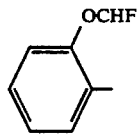 OCHF₂ | H | 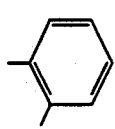 F | CH₃ | N | N | C—OCH₃ | 179 |
| 254 | 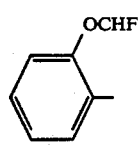 OCHF₂ | H | 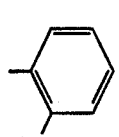 Br | CH₃ | N | N | C—OCH₃ | 174 |
| 255 | 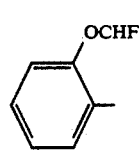 OCHF₂ | H | 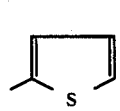 S | CH₃ | N | N | C—OCH₃ | 216 |
| 256 | 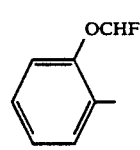 OCHF₂ | H | 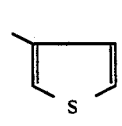 S | CH₃ | N | N | C—OCH₃ | 193 |
| 257 | 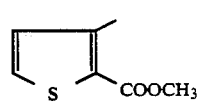 COOCH₃ | CH₃ | CH₃ | CH₃ | N | CH | C—CH₃ | 229 |
| 258 | 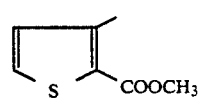 COOCH₃ | CH₃ | C₂H₅ | CH₃ | N | CH | C—CH₃ | 199 |
| 259 | 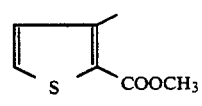 COOCH₃ | CH₃ | COOC₂H₅ | CH₃ | N | CH | C—CH₃ | 222 |
| 260 | 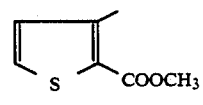 COOCH₃ | H | C₆H₅ | CH₃ | N | CH | C—CH₃ | 222 |
| 261 | 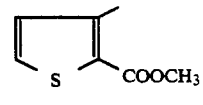 COOCH₃ | H | C₆H₅ | OCH₃ | N | CH | C—OCH₃ | 230 |
| 262 | 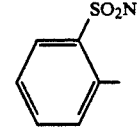 SO₂N(CH₃)₂ | H | C₆H₅ | OCH₃ | N | CH | C—OCH₃ | 239 |
| 263 | 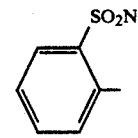 SO₂N(CH₃)₂ | H | C₆H₅ | H | N | CH | C—CH₃ | 212 |

TABLE 3-continued

| # | Ar | R | R' | X | Y | Z | W | mp (°C) |
|---|---|---|---|---|---|---|---|---|
| 264 | 2-CF₃-C₆H₄ | H | C₆H₅ | OCH₃ | N | CH | C—OCH₃ | 229 |
| 265 | 2-OC₂H₅-C₆H₄ | H | C₆H₅ | CH₃ | N | CH | C—CH₃ | 210 |
| 266 | 2-OC₂H₅-C₆H₄ | H | C₆H₅ | OCH₃ | N | CH | C—OCH₃ | 203 |
| 267 | 2-OC₂H₅-C₆H₄ | H | C₆H₅ | CH₃ | N | CH | CH | 186 |
| 268 | 2-CN-C₆H₄-CH₂— | H | C₆H₅ | CH₃ | N | CH | C—OCH₃ | 213 |
| 269 | 2-COOCH₃-C₆H₄ | H | N(CH₃)₂ | CH₃ | N | CH | C—CH₃ | 136 |
| 270 | 2-COOCH₃-C₆H₄ | CH₃ | CH₃ | CH₃ | N | CH | CH | 185 |
| 271 | 2-COOCH₃-C₆H₄ | H | C₆H₅ | CH₃ | N | CH | C—CH₃ | 244 |
| 272 | 2-COOCH₃-C₆H₄ | —(CH₂)₅— | | CH₃ | N | CH | C—CH₃ | 182 |
| 273 | 2-COOCH₃-C₆H₄ | H | CH(CH₃)₂ | CH₃ | N | CH | C—CH₃ | 171 |
| 274 | 2-OCF₃-C₆H₄ | H | C₆H₅ | CH₃ | N | CH | C—CH₃ | ¹H-NMR: δ = 13,5 ppm (N<u>h</u>: in CDCl₃) |

TABLE 3-continued

| | | | | | | | | |
|---|---|---|---|---|---|---|---|---|
| 275 | 2-OCF$_3$-C$_6$H$_4$ | —(CH$_2$)$_5$— | | CH$_3$ | N | CH | C—CH$_3$ | $^1$H-NMR: δ = 13,05 ppm (N<u>H</u>; in CDCl$_3$) |
| 276 | 2-OCF$_3$-C$_6$H$_4$ | H | CH(CH$_3$)$_2$ | CH$_3$ | N | CH | C—CH$_3$ | 205 |
| 277 | 2-OCF$_3$-C$_6$H$_4$ | H | C$_6$H$_5$ | CH$_3$ | N | CH | CH | 200 |
| 278 | 2-COOC$_2$H$_5$-C$_6$H$_4$ | H | C$_6$H$_5$ | CH$_3$ | N | CH | CH | 198 |
| 279 | 2-COOCH$_2$CH$_2$Cl-C$_6$H$_4$ | H | C$_6$H$_5$ | CH$_3$ | N | CH | CH | 180 |
| 280 | 2-COOCH$_3$-C$_6$H$_4$ | CH$_3$ | CH$_3$ | OCH$_3$ | N | CH | C—OCH$_3$ | 200 |
| 281 | 2-OCF$_3$-C$_6$H$_4$ | H | C$_6$H$_5$ | OCH$_3$ | N | CH | C—OCH$_3$ | 218 |
| 282 | 2-COOCH$_3$-C$_6$H$_4$ | H | 2-COOH-C$_6$H$_4$ | CH$_3$ | N | CH | C—CH$_3$ | 240 |
| 283 | 2-COOCH$_3$-C$_6$H$_4$-CH$_2$— | CH$_3$ | CH$_3$ | OCH$_3$ | N | CH | C—OCH$_3$ | 176 |
| 284 | 2-Cl-C$_6$H$_4$ | CH$_3$ | CH$_3$ | CH$_3$ | N | CH | C—CH$_3$ | 223 |
| 285 | 2-OCF$_3$-C$_6$H$_4$ | CH$_3$ | CH$_3$ | CH$_3$ | N | CH | C—CH$_3$ | 225 |

TABLE 3-continued
| | | | | | | | | |
|---|---|---|---|---|---|---|---|---|
| 286 | 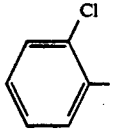 2-Cl-C6H4 | CH3 | CH3 | | OCH3 | N | N | C—OCH3 | 135 |
| 287 | 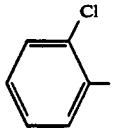 2-Cl-C6H4 | H | 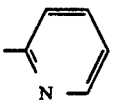 2-pyridyl | OCH3 | N | N | C—OCH3 | 183 |
| 288 | 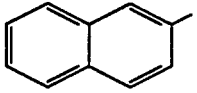 2-naphthyl | CH3 | CH3 | | OCH3 | N | N | C—OCH3 | 182 |
| 289 | 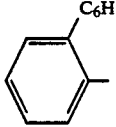 2-C6H5-C6H4 | H | C6H5 | OCH3 | N | N | C—OCH3 | 204 |
| 290 | 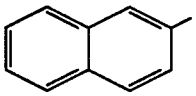 2-naphthyl | H | C6H5 | OCH3 | N | N | C—OCH3 | 191 |
| 291 | 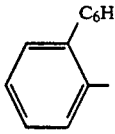 2-C6H5-C6H4 | CH3 | CH3 | OCH3 | N | N | C—OCH3 | 147 |
| 292 | 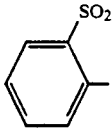 2-SO2C6H5-C6H4 | H | C6H5 | OCH3 | N | N | C—OCH3 | 229 (decomp.) |
| 293 | 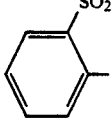 2-SO2C6H5-C6H4 | CH3 | CH3 | OCH3 | N | N | C—OCH3 | 210 |
| 294 | 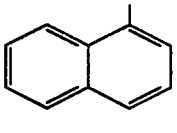 1-naphthyl | H | C6H5 | OCH3 | N | N | C—OCH3 | 209 |
| 295 | 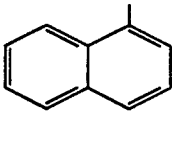 1-naphthyl | CH3 | CH3 | OCH3 | N | N | C—OCH3 | 185 |
| 296 | 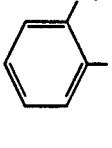 2-C6H5-C6H4 | H | N(CH3)2 | OCH3 | N | N | C—OCH3 | 130 |

TABLE 3-continued
| | | | | | | | | |
|---|---|---|---|---|---|---|---|---|
| 297 | 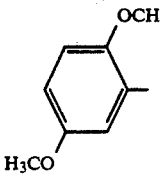 2,4-dimethoxyphenyl | H | C6H5 | OCH3 | N | N | C—OCH3 | 219 |
| 298 | 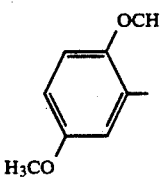 2,4-dimethoxyphenyl | CH3 | CH3 | OCH3 | N | N | C—OCH3 | 185 |
| 299 | 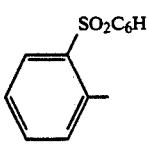 2-(SO2C6H5)phenyl | H | N(CH3)2 | OCH3 | N | N | C—OCH3 | 157 |
| 300 | 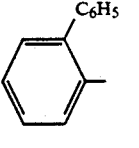 2-phenyl | CH3 | CH3 | CH3 | N | CH | C—CH3 | 242 |
| 301 | 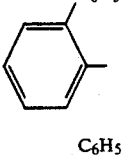 2-phenyl | H | C6H5 | H | N | CH | CH | 214 |
| 302 | 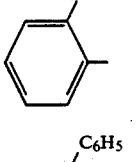 2-phenyl | H | N(CH3)2 | CH3 | N | CH | C—CH3 | 144 |
| 303 | 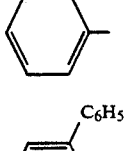 2-phenyl | H | C6H5 | OCH3 | N | CH | C—OCH3 | 206 |
| 304 | 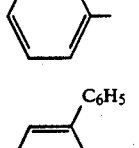 2-phenyl | CH3 | CH3 | OCH3 | N | CH | C—OCH3 | 181 |
| 305 | 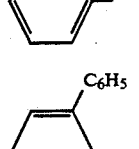 2-phenyl | CH3 | CH3 | CH3 | N | CH | C—OCH3 | 192 |
| 306 | 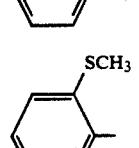 2-phenyl | H | C6H5 | CH3 | N | CH | C—OCH3 | 174 |
| 307 | 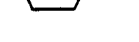 2-SCH3 phenyl | H | C6H5 | OCH3 | N | CH | C—OCH3 | 214 |

TABLE 3-continued

| # | Ar | R | R' | X | A | B | Y | mp (°C) |
|---|---|---|---|---|---|---|---|---|
| 308 | 2-(SCH₃)C₆H₄ | CH₃ | CH₃ | OCH₃ | N | CH | C—OCH₃ | 216 |
| 309 | 2-(SCH₃)C₆H₄ | H | C₆H₅ | CH₃ | N | CH | C—CH₃ | 228 |
| 310 | 2-(SCH(CH₃)₂)C₆H₄ | CH₃ | CH₃ | OCH₃ | N | CH | C—OCH₃ | 153 |
| 311 | 2-(SCH(CH₃)₂)C₆H₄ | H | C₆H₅ | OCH₃ | N | CH | C—OCH₃ | 228 |
| 312 | 2-(SOCH₃)C₆H₄ | CH₃ | CH₃ | OCH₃ | N | CH | C—OCH₃ | 178 |
| 313 | 2-(SOCH₃)C₆H₄ | H | C₆H₅ | OCH₃ | N | CH | C—OCH₃ | 204 |
| 314 | 2-(SCH₃)C₆H₄ | CH₃ | CH₃ | OCH₃ | N | N | C—OCH₃ | 197 |
| 315 | 2-(SCH₃)C₆H₄ | H | C₆H₅ | OCH₃ | N | N | C—OCH₃ | 199 |
| 316 | 2-(SO₂C₆H₅)C₆H₄ | CH₃ | CH₃ | CH₃ | N | N | C—OCH₃ | 144 |
| 317 | 2-(SO₂CH₃)C₆H₄ | CH₃ | CH₃ | OCH₃ | N | N | C—OCH₃ | 175 |
| 318 | 4-COOC₂H₅-2-CH₃-1-methylpyrazol-3-yl | H | 4-CH₃-C₆H₄ | OCH₃ | N | CH | C—OCH₃ | 208 |

TABLE 3-continued

| # | Structure | | | | | | |
|---|---|---|---|---|---|---|---|
| 319 | 2-(SCH₃)-C₆H₄ | CH₃ | CH₃ | CH₃ | N | CH C—CH₃ | 203 |
| 320 | 4-COOC₂H₅-5-methyl-1-phenylpyrazol-3-yl | H | C₆H₅ | CH₃ | N | CH C—CH₃ | 197 |
| 321 | 4-COOC₂H₅-5-methyl-1-phenylpyrazol-3-yl | CH₃ | CH₃ | CH₃ | N | CH C—OCH₃ | 186 |
| 322 | 4-COOC₂H₅-5-methyl-1-phenylpyrazol-3-yl | H | C₆H₅ | CH₃ | N | CH C—OCH₃ | 173 |
| 323 | 4-COOC₂H₅-5-methyl-1-phenylpyrazol-3-yl | CH₃ | CH₃ | CH₃ | N | CH C—CH₃ | 170 |
| 324 | 4-COOC₂H₅-5-methyl-1-phenylpyrazol-3-yl | CH₃ | C₂H₅ | CH₃ | N | CH C—CH₃ | 152 |
| 325 | 4-COOC₂H₅-5-methyl-1-phenylpyrazol-3-yl | —(CH₂)₅— | | CH₃ | N | CH C—CH₃ | 169 |
| 326 | 4-COOC₂H₅-5-methyl-1-phenylpyrazol-3-yl | H | 2-Cl-C₆H₄ | CH₃ | N | CH C—CH₃ | 161 |
| 327 | 4-COOC₂H₅-5-methyl-1-phenylpyrazol-3-yl | H | 2,6-Cl₂-C₆H₃ | CH₃ | N | CH C—CH₃ | 140 |
| 328 | 4-COOC₂H₅-5-methyl-1-phenylpyrazol-3-yl | H | 2,4-Cl₂-C₆H₃ | CH₃ | N | CH C—CH₃ | 218 |

TABLE 3-continued

| No. | Pyrazole | R | Aryl | | | | | m.p. |
|---|---|---|---|---|---|---|---|---|
| 329 | pyrazole-COOC$_2$H$_5$, N-N-C$_6$H$_5$, CH$_3$ | H | 4-Cl-C$_6$H$_4$ | CH$_3$ | N | CH | C—CH$_3$ | 178 |
| 330 | pyrazole-COOC$_2$H$_5$, N-N-C$_6$H$_5$, CH$_3$ | H | 3-Cl-C$_6$H$_4$ | CH$_3$ | N | CH | C—CH$_3$ | 168 |
| 331 | pyrazole-COOC$_2$H$_5$, N-N-C$_6$H$_5$, CH$_3$ | H | 2,3-F$_2$-C$_6$H$_3$ | CH$_3$ | N | CH | C—CH$_3$ | 159 |
| 332 | pyrazole-COOC$_2$H$_5$, N-N-C$_6$H$_5$, CH$_3$ | H | 3-OCF$_3$-C$_6$H$_4$ | CH$_3$ | N | CH | C—CH$_3$ | 137 |
| 333 | pyrazole-COOC$_2$H$_5$, N-N-C$_6$H$_5$, CH$_3$ | H | 4-F-C$_6$H$_4$ | CH$_3$ | N | CH | C—CH$_3$ | 198 |
| 334 | pyrazole-COOC$_2$H$_5$, N-N-C$_6$H$_5$, CH$_3$ | H | 2-F-3-Cl-C$_6$H$_3$ | CH$_3$ | N | CH | C—CH$_3$ | 145 |
| 335 | pyrazole-COOC$_2$H$_5$, N-N-C$_6$H$_5$, CH$_3$ | H | 3-CH$_3$-C$_6$H$_4$ | CH$_3$ | N | CH | C—CH$_3$ | 164 |
| 336 | pyrazole-COOC$_2$H$_5$, N-N-C$_6$H$_5$, CH$_3$ | CH$_3$ | C$_2$H$_5$ | CH$_3$ | N | CH | C—OCH$_3$ | 189 |
| 337 | pyrazole-COOC$_2$H$_5$, N-N-C$_6$H$_5$, CH$_3$ | —(CH$_2$)$_5$— | | CH$_3$ | N | CH | C—OCH$_3$ | 161 |

| # | Ar1 | R | Ar2 | R' | X | Y | Z | mp |
|---|---|---|---|---|---|---|---|---|
| 338 | 2-Me-6-SO₂N(CH₃)₂-phenyl | H | 4-CH₃-phenyl | CH₃ | N | N | C—OCH₃ | 246 (Zers.) |
| 339 | 2-Me-6-OCHF₂-phenyl | H | 2,6-diF-phenyl | CH₃ | N | N | C—OCH₃ | 189 |
| 340 | 2-Me-6-OCHF₂-phenyl | H | 2-furyl | CH₃ | N | N | C—OCH₃ | 205 |
| 341 | 2-Me-6-OCHF₂-phenyl | H | 2-pyrrolyl | CH₃ | N | N | C—OCH₃ | 195 |
| 342 | 2-Me-6-OCHF₂-phenyl | H | 5-Br-2-thienyl | CH₃ | N | N | C—OCH₃ | 195 |
| 343 | 2-Me-6-OCHF₂-phenyl | H | 4-Br-2-thienyl | CH₃ | N | N | C—OCH₃ | 229 |
| 344 | 2-Me-6-OCHF₂-phenyl | H | 5-CH₃-2-thienyl | CH₃ | N | N | C—OCH₃ | 187 |
| 345 | 4-F-benzyl | H | C₆H₅ | CH₃ | N | N | C—OCH₃ | 188 |
| 346 | 3-Cl-benzyl | H | C₆H₅ | CH₃ | N | N | C—OCH₃ | 207 |
| 347 | 4-F-benzyl | CH₃ | CH₃ | CH₃ | N | N | C—OCH₃ | 189 |
| 348 | 3-Cl-benzyl | CH₃ | CH₃ | CH₃ | N | N | C—OCH₃ | 204 |

-continued
| | | | | | | | | |
|---|---|---|---|---|---|---|---|---|
| 349 | 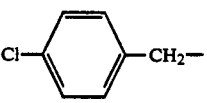 | H | C₆H₅ | | CH₃ | N | N | C—OCH₃ | 215 |
| 350 | 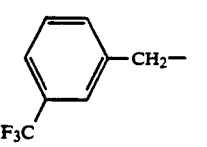 | H | C₆H₅ | | CH₃ | N | N | C—OCH₃ | 225 |
| 351 | 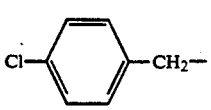 | CH₃ | CH₃ | | CH₃ | N | N | C—OCH₃ | 156 |
| 352 | 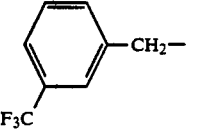 | CH₃ | CH₃ | | CH₃ | N | N | C—OCH₃ | 174 |
| 353 | 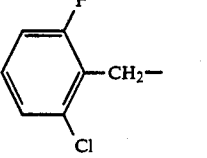 | H | C₆H₅ | | CH₃ | N | N | C—OCH₃ | 191 |
| 354 | 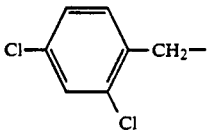 | H | C₆H₅ | | CH₃ | N | N | C—OCH₃ | 190 |
| 355 | 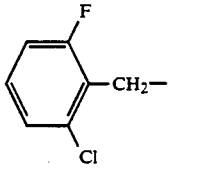 | CH₃ | CH₃ | | CH₃ | N | N | C—OCH₃ | 198 |
| 356 | 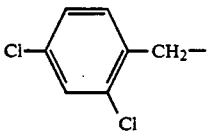 | CH₃ | CH₃ | | CH₃ | N | N | C—OCH₃ | 176 |
| 357 | 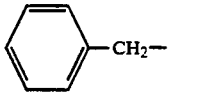 | H | C₆H₅ | | OCH₃ | N | N | C—OCH₃ | 175 |
| 358 | 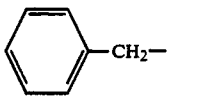 | CH₃ | CH₃ | | OCH₃ | N | N | C—OCH₃ | 189 |
| 359 | 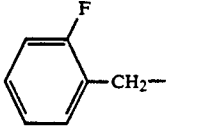 | H | C₆H₅ | | OCH₃ | N | N | C—OCH₃ | 174 |

-continued
| | | | | | | | | |
|---|---|---|---|---|---|---|---|---|
| 360 | 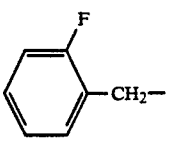 | CH₃ | CH₃ | | OCH₃ | N | N | C—OCH₃ | 185 |
| 361 | 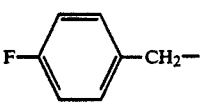 | H | C₆H₅ | | OCH₃ | N | N | C—OCH₃ | 190 |
| 362 | 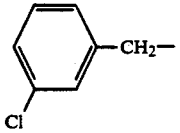 | H | C₆H₅ | | OCH₃ | N | N | C—OCH₃ | 164 |
| 363 |  | CH₃ | CH₃ | | OCH₃ | N | N | C—OCH₃ | 189 |
| 364 | 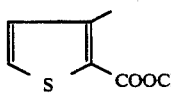 | H |  | CH₃ | N | N | C—OCH₃ | 193 (decomp.) |
| 365 | 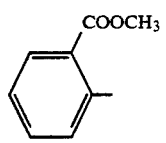 | H | 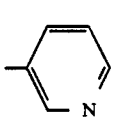 | CH₃ | N | N | C—OCH₃ | 202 (decomp.) |
| 366 | 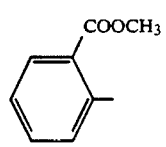 | H | 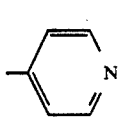 | CH₃ | N | N | C—OCH₃ | 179 (decomp.) |
| 367 | 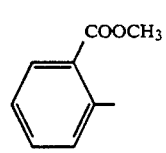 | H | 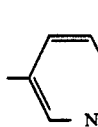 | CH₃ | N | N | C—OCH₃ | 199 (decomp.) |
| 368 | 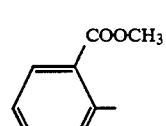 | H | 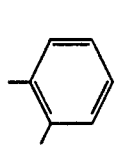 | CH₃ | N | N | C—OCH₃ | 203 |
| 369 | 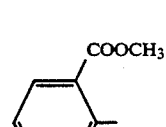 | H | 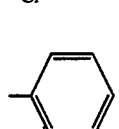 | CH₃ | N | N | C—OCH₃ | 206 |
| 370 | 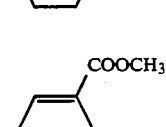 | H |  | CH₃ | N | N | C—OCH₃ | 203 |

-continued

| # | | | | | | | | |
|---|---|---|---|---|---|---|---|---|
| 371 | 2-COOCH₃-phenyl | H | 3-CF₃-phenyl | CH₃ | N | N | C—OCH₃ | 191 |
| 372 | 2-COOCH₃-phenyl | H | 3-Br-phenyl | CH₃ | N | N | C—OCH₃ | 194 |
| 373 | 2-COOCH₃-phenyl | H | 3-CH₃-phenyl | CH₃ | N | N | C—OCH₃ | 182 |
| 374 | 2-COOCH₃-phenyl | H | 2-Cl-4-F-phenyl | CH₃ | N | N | C—OCH₃ | 192 |
| 375 | 2-COOCH₃-phenyl | H | 4-Br-phenyl | CH₃ | N | N | C—OCH₃ | 231 (decomp.) |
| 376 | 2-COOCH₃-phenyl | H | 4-F-phenyl | CH₃ | N | N | C—OCH₃ | 219 |
| 377 | 2-COOCH₃-phenyl | H | 4-CH₃-phenyl | CH₃ | N | N | C—OCH₃ | 227 (decomp.) |
| 378 | 2-COOCH₃-phenyl | H | 4-N(CH₃)₂-phenyl | CH₃ | N | N | C—OCH₃ | 213 |
| 379 | 2-COOCH₃-phenyl | H | 3,5-diCl-phenyl | CH₃ | N | N | C—OCH₃ | 205 |
| 380 | 2-COOCH₃-phenyl | H | 3-CH₃-phenyl | CH₃ | N | N | C—OCH₃ | 210 |

-continued
| | | | | | | | | |
|---|---|---|---|---|---|---|---|---|
| 381 | 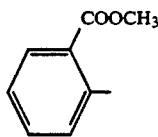 | H | 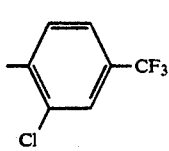 | CH₃ | N | N | C—OCH₃ | 221 |
| 382 | 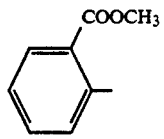 | H | 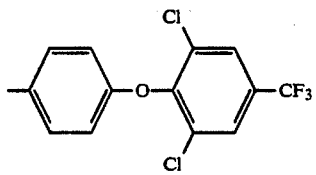 | CH₃ | N | N | C—OCH₃ | 198 |
| 383 | 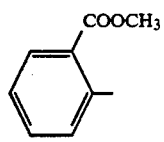 | H | 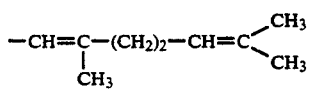 | CH₃ | N | N | C—OCH₃ | 109 |
| 384 | 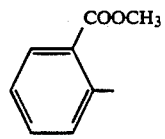 | H | 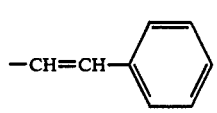 | CH₃ | N | N | C—OCH₃ | 209 |
| 385 | 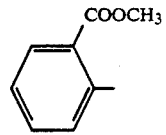 | CH₃ | 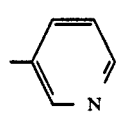 | CH₃ | N | N | C—OCH₃ | 207 |
| 386 | 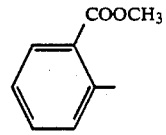 | H | 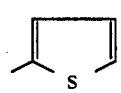 | CH₃ | N | N | C—OCH₃ | 206 (decomp.) |
| 387 | 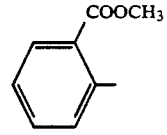 | CH₃ | 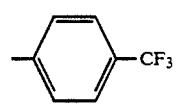 | CH₃ | N | N | C—OCH₃ | 196 (decomp.) |
| 388 | 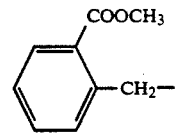 | H | C₆H₅ | CH₃ | N | CH | C—OCH₃ | 180 |
| 389 | 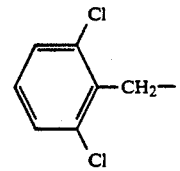 | H | C₆H₅ | CH₃ | N | CH | C—OCH₃ | 146 |
| 390 | 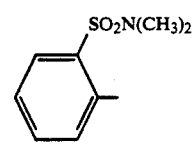 | H | C₆H₅ | CH₃ | N | CH | C—OCH₃ | 206 |

-continued

| | | | | | | | | |
|---|---|---|---|---|---|---|---|---|
| 391 | 2-(N-methyl-N-methoxysulfamoyl)phenyl | H | C$_6$H$_5$ | CH$_3$ | N | CH | C—OCH$_3$ | 217 |
| 392 | 2-chlorobenzyl | H | C$_6$H$_5$ | CH$_3$ | N | CH | CH | 188 |
| 393 | 4-ethoxycarbonyl-5-methyl-1-phenylpyrazol-3-yl | H | C$_6$H$_5$ | OCH$_3$ | N | CH | C—OCH$_3$ | 198 |
| 394 | 4-ethoxycarbonyl-5-methyl-1-phenylpyrazol-3-yl | CH$_3$ | CH$_3$ | OCH$_3$ | N | CH | C—OCH$_3$ | 173 |
| 395 | 4-ethoxycarbonyl-5-methyl-1-phenylpyrazol-3-yl | CH$_3$ | C$_2$H$_5$ | OCH$_3$ | N | CH | C—OCH$_3$ | 149 |
| 396 | 4-ethoxycarbonyl-5-methyl-1-phenylpyrazol-3-yl | H | 2,4-dichlorophenyl | OCH$_3$ | N | CH | C—OCH$_3$ | 238 |
| 397 | 4-ethoxycarbonyl-5-methyl-1-phenylpyrazol-3-yl | H | 4-chlorophenyl | OCH$_3$ | N | CH | C—OCH$_3$ | 208 |
| 398 | 4-ethoxycarbonyl-5-methyl-1-phenylpyrazol-3-yl | H | 2-chlorophenyl | OCH$_3$ | N | CH | C—OCH$_3$ | 173 |
| 399 | 4-ethoxycarbonyl-5-methyl-1-phenylpyrazol-3-yl | H | 3-chlorophenyl | OCH$_3$ | N | CH | C—OCH$_3$ | 181 |
| 400 | 4-ethoxycarbonyl-5-methyl-1-phenylpyrazol-3-yl | H | 2,6-dichlorophenyl | OCH$_3$ | N | CH | C—OCH$_3$ | 145 |

-continued
| | | | | | | | | |
|---|---|---|---|---|---|---|---|---|
| 401 | 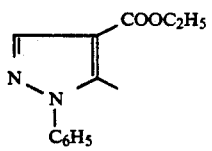 | H | 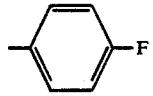 | OCH₃ | N | CH | C—OCH₃ | 206 |
| 402 | 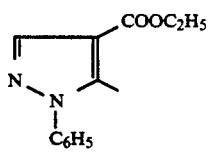 | H | 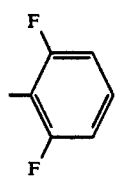 | OCH₃ | N | CH | C—OCH₃ | 176 |
| 403 | 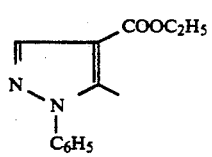 | H | 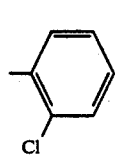 | OCH₃ | N | CH | C—CH₃ | 152 |
| 404 | 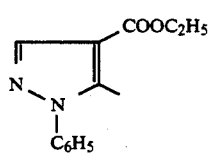 | H | 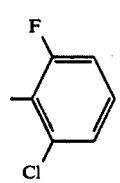 | OCH₃ | N | CH | C—OCH₃ | 175 |
| 405 | 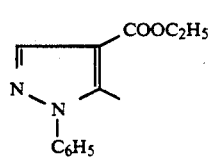 | H | 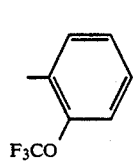 | OCH₃ | N | CH | C—OCH₃ | 154 |
| 406 | 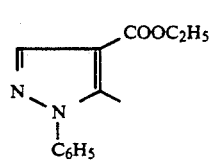 | H | 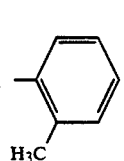 | OCH₃ | N | CH | C—OCH₃ | 161 |
| 407 | 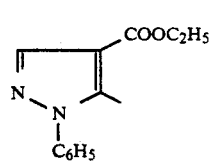 | H | 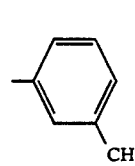 | OCH₃ | N | CH | C—OCH₃ | 159 |
| 408 | 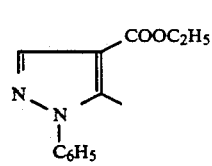 | H | 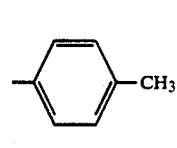 | OCH₃ | N | CH | C—OCH₃ | 195 |
| 409 | 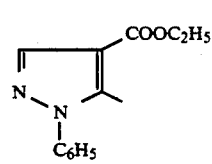 | H | 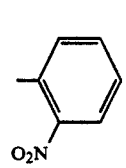 | OCH₃ | N | CH | C—OCH₃ | 123 |
| 410 | 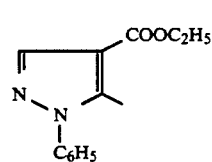 | H | 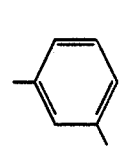 | OCH₃ | N | CH | C—OCH₃ | 196 |

-continued

| | | | | | | | | |
|---|---|---|---|---|---|---|---|---|
| 411 | pyrazole-COOC₂H₅, N-N, C₆H₅ | H | 4-NO₂-C₆H₄ | OCH₃ | N | CH | C—OCH₃ | 225 |
| 412 | pyrazole-COOC₂H₅, N-N, C₆H₅ | H | 2-F₃C-C₆H₄ | OCH₃ | N | CH | C—OCH₃ | 177 |
| 413 | pyrazole-COOC₂H₅, N-N, C₆H₅ | H | 3-Cl-C₆H₄ | OCH₃ | N | CH | C—CH₃ | 166 |
| 414 | pyrazole-COOC₂H₅, N-N, C₆H₅ | H | 4-Cl-C₆H₄ | OCH₃ | N | CH | C—CH₃ | 165 |
| 415 | pyrazole-COOC₂H₅, N-N, C₆H₅ | H | 2,6-Cl₂-C₆H₃ | OCH₃ | N | CH | C—CH₃ | 118 |
| 416 | pyrazole-COOC₂H₅, N-N, C₆H₅ | H | 2-F₃CO-C₆H₄ | OCH₃ | N | CH | C—CH₃ | 139 |
| 417 | pyrazole-COOC₂H₅, N-N, C₆H₅ | H | 2-F-6-Cl-C₆H₃ | OCH₃ | N | CH | C—CH₃ | 147 |
| 418 | pyrazole-COOC₂H₅, N-N, C₆H₅ | H | 4-OCH₃-C₆H₄ | OCH₃ | N | CH | C—OCH₃ | 173 |
| 419 | pyrazole-COOC₂H₅, N-N, C₆H₅ | H | 2,6-F₂-C₆H₃ | OCH₃ | N | CH | C—CH₃ | 189 |
| 420 | pyrazole-COOC₂H₅, N-N, C₆H₅ | H | 3-CH₃-C₆H₄ | OCH₃ | N | CH | C—CH₃ | 143 |

-continued

| No. | (structure 1) | R | (structure 2) | A | X | Y | Z | m.p. |
|---|---|---|---|---|---|---|---|---|
| 421 | 4-COOC₂H₅-5-methyl-1-phenylpyrazol-3-yl | H | 2,4-dichlorophenyl | OCH₃ | N | CH | C—CH₃ | 232 |
| 422 | 4-COOC₂H₅-5-methyl-1-phenylpyrazol-3-yl | —(CH₂)₅— | | OCH₃ | N | CH | C—OCH₃ | 135 |
| 423 | 4-COOC₂H₅-5-methyl-1-phenylpyrazol-3-yl | H | 2-nitrophenyl | OCH₃ | N | CH | C—CH₃ | 152 |
| 424 | 4-COOC₂H₅-5-methyl-1-phenylpyrazol-3-yl | H | 3-nitrophenyl | OCH₃ | N | CH | C—CH₃ | 235 |
| 425 | 2-(COOCH₃)phenyl | H | CH(CH₃)₂ | OCH₃ | N | N | C—OCH₃ | 121 |
| 426 | 2-(COOCH₃)phenyl | H | C₆H₅ | OCH₃ | N | N | C—OCH₃ | 209 |
| 427 | 2-(COOCH₃)phenyl | H | 2-(OCHF₂)phenyl | OCH₃ | N | N | C—OCH₃ | 173 |
| 428 | 2-(COOCH₃)phenyl | H | 4-(SCF₃)phenyl | OCH₃ | N | N | C—OCH₃ | 213 |
| 429 | 2-(COOCH₃)phenyl | H | 2-(CF₃)phenyl | OCH₃ | N | N | C—OCH₃ | 187 |
| 430 | 2-(COOCH₃)phenyl | H | 4-(CF₃)phenyl | OCH₃ | N | N | C—OCH₃ | 139 |
| 431 | 2-(COOCH₃)phenyl | H | 2-pyridyl | OCH₃ | N | N | C—OCH₃ | 168 |

-continued
| | | | | | | | | |
|---|---|---|---|---|---|---|---|---|
| 432 | 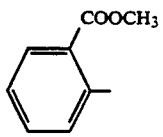 | H | 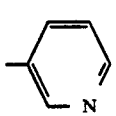 | OCH₃ | N | N | C—OCH₃ | 188 |
| 433 | 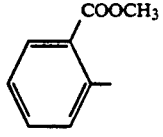 | H | 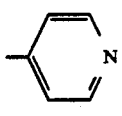 | OCH₃ | N | N | C—OCH₃ | 189 |
| 434 | 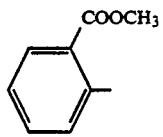 | H | 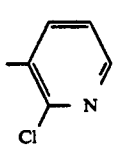 | OCH₃ | N | N | C—OCH₃ | 207 |
| 435 | 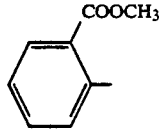 | H | 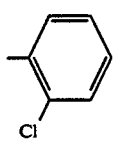 | OCH₃ | N | N | C—OCH₃ | 219 |
| 436 | 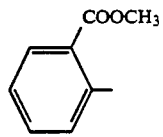 | H | 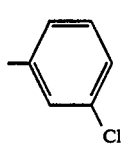 | OCH₃ | N | N | C—OCH₃ | 217 |
| 437 | 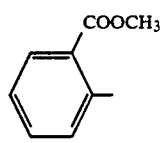 | H | 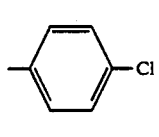 | OCH₃ | N | N | C—OCH₃ | 225 |
| 438 | 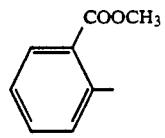 | H | 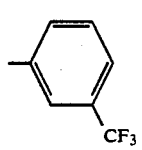 | OCH₃ | N | N | C—OCH₃ | 141 |
| 439 | 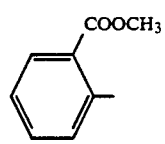 | H | 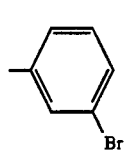 | OCH₃ | N | N | C—OCH₃ | 224 |
| 440 | 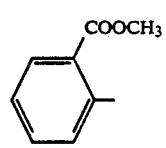 | H | 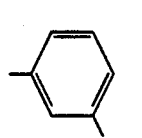 | OCH₃ | N | N | C—OCH₃ | 224 |
| 441 | 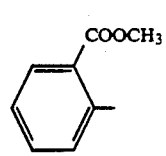 | H | 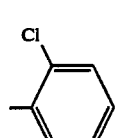 | OCH₃ | N | N | C—OCH₃ | 182 |

-continued
| | | | | | | | | |
|---|---|---|---|---|---|---|---|---|
| 442 | 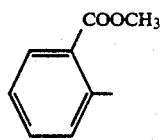 | H | 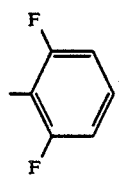 | OCH₃ | N | N | C—OCH₃ | 188 |
| 443 | 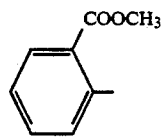 | H | 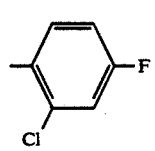 | OCH₃ | N | N | C—OCH₃ | 216 |
| 444 | 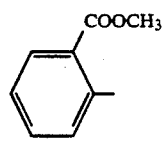 | H | 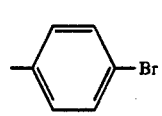 | OCH₃ | N | N | C—OCH₃ | 224 |
| 445 | 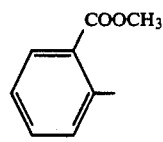 | H | 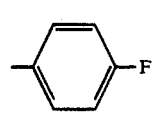 | OCH₃ | N | N | C—OCH₃ | 221 |
| 446 | 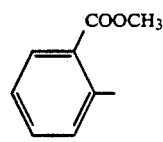 | H | 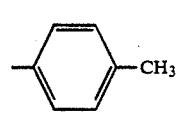 | OCH₃ | N | N | C—OCH₃ | 212 |
| 447 | 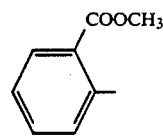 | H | 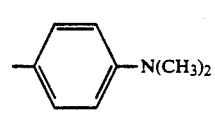 | OCH₃ | N | N | C—OCH₃ | 212 |
| 448 | 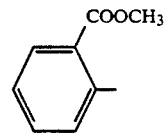 | H | 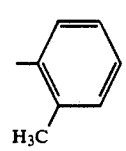 | OCH₃ | N | N | C—OCH₃ | 216 |
| 449 | 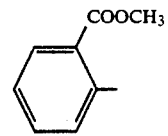 | H | 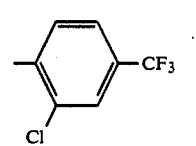 | OCH₃ | N | N | C—OCH₃ | 213 |
| 450 | 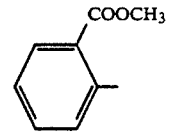 | H | 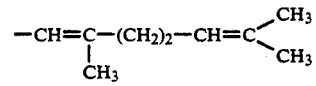 | OCH₃ | N | N | C—OCH₃ | 137 |
| 451 | 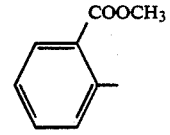 | H | 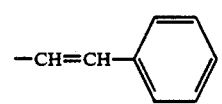 | OCH₃ | N | N | C—OCH₃ | 218 |
| 452 | 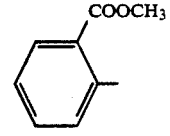 | H | 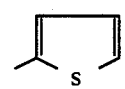 | OCH₃ | N | N | C—OCH₃ | 226 |

-continued
| | | | | | | | | |
|---|---|---|---|---|---|---|---|---|
| 453 | 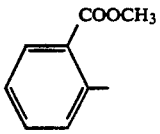 | H | 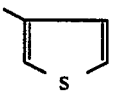 | OCH₃ | N | N | C—OCH₃ | 196 |
| 454 | 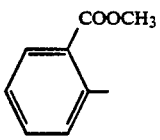 | H | 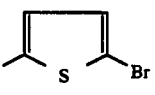 | OCH₃ | N | N | C—OCH₃ | 229 |
| 455 | 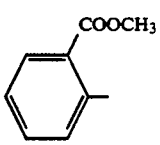 | H | 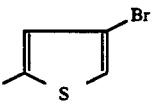 | OCH₃ | N | N | C—OCH₃ | 222 |
| 456 | 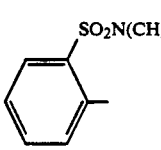 | H | 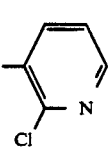 | OCH₃ | N | N | C—CH₃ | 188 |
| 457 | 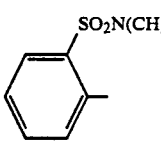 | H | 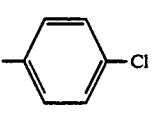 | OCH₃ | N | N | C—CH₃ | 224 |
| 458 | 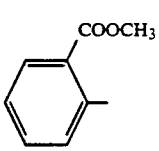 | H | 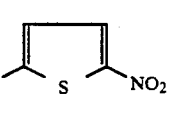 | OCH₃ | N | N | C—OCH₃ | 215 |
| 459 | 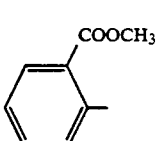 | H | 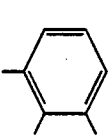 | OCH₃ | N | N | C—OCH₃ | 200 |
| 460 | 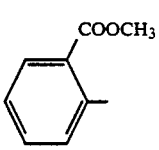 | H | 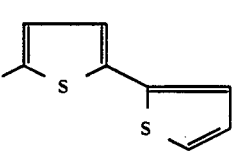 | OCH₃ | N | N | C—OCH₃ | 214 |
| 461 | 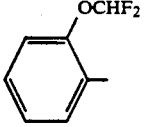 | H | 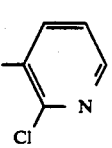 | OCH₃ | N | N | C—CH₃ | 114 |
| 462 | 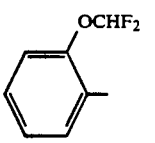 | H | 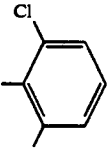 | OCH₃ | N | N | C—CH₃ | 86 |
| 463 | 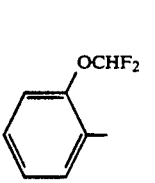 | —(CH₂)₅— | | OCH₃ | N | N | C—CH₃ | 161 |

-continued
| | | | | | | | | |
|---|---|---|---|---|---|---|---|---|
| 464 | 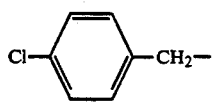 | H | C₆H₅ | | OCH₃ | N | N | C—OCH₃ | 211 |
| 465 | 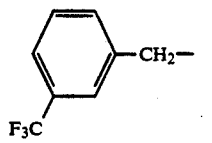 | H | C₆H₅ | | OCH₃ | N | N | C—OCH₃ | 194 |
| 466 | 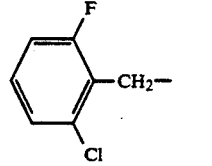 | H | C₆H₅ | | OCH₃ | N | N | C—OCH₃ | 166 |
| 467 | 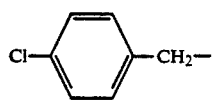 | CH₃ | CH₃ | | OCH₃ | N | N | C—OCH₃ | 178 |
| 468 | 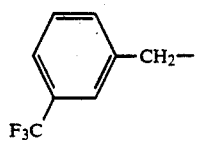 | CH₃ | CH₃ | | OCH₃ | N | N | C—OCH₃ | 166 |
| 469 | 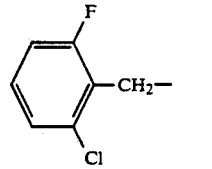 | CH₃ | CH₃ | | OCH₃ | N | N | C—OCH₃ | 195 |
| 470 | 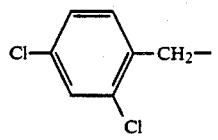 | H | C₆H₅ | | OCH₃ | N | N | C—OCH₃ | 201 |
| 471 | 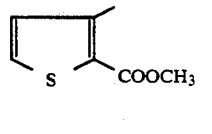 | H | 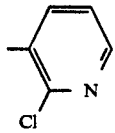 | | OCH₃ | N | N | C—CH₃ | 165 |
| 472 | 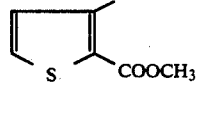 | H | 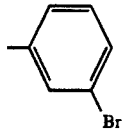 | | OCH₃ | N | N | C—CH₃ | 212 |
| 473 | 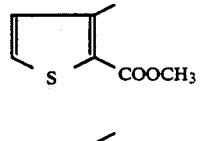 | H | 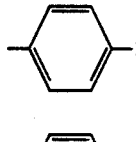 | | OCH₃ | N | N | C—CH₃ | 225 |
| 474 | 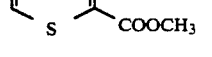 | H | 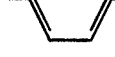 | | OCH₃ | N | N | C—CH₃ | 224 |

-continued
| | | | | | | | |
|---|---|---|---|---|---|---|---|
| 475 | 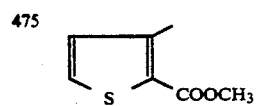 | H | 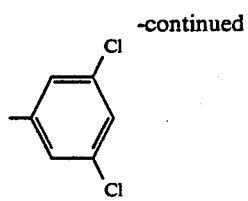 | OCH₃ | N | N | C—CH₃ | 246 |
| 476 | 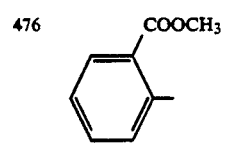 | H |  | OCH₃ | N | N | C—CH₃ | 150 |
| 477 | 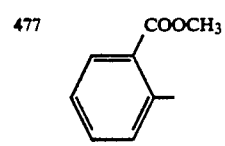 | H | 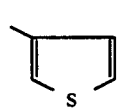 | OCH₃ | N | N | C—CH₃ | 195 (decomp.) |
| 478 | 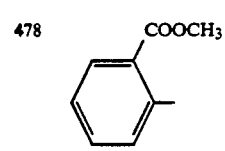 | H | 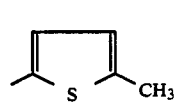 | OCH₃ | N | N | C—CH₃ | 173 (decomp.) |
| 479 | 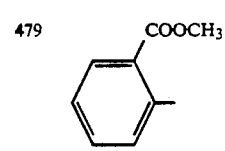 | H | 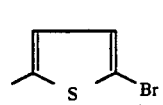 | OCH₃ | N | N | C—CH₃ | 229 (decomp.) |
| 480 | 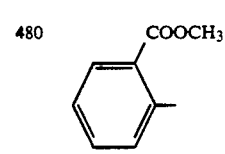 | H | 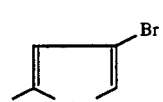 | OCH₃ | N | N | C—CH₃ | 234 |
| 481 | 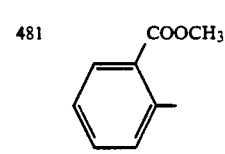 | H | 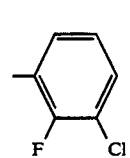 | OCH₃ | N | N | C—CH₃ | 167 |
| 482 | 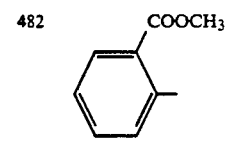 | H | 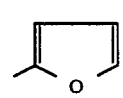 | OCH₃ | N | N | C—CH₃ | 196 |
| 483 | 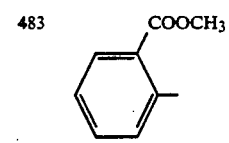 | H | 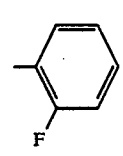 | OCH₃ | N | N | C—CH₃ | 201 |
| 484 | 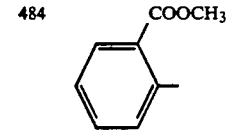 | H | 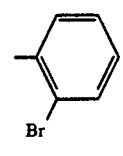 | OCH₃ | N | N | C—CH₃ | 210 |
| 485 | 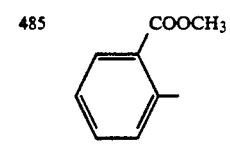 | H | 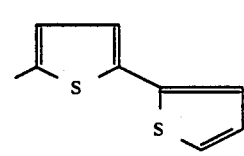 | OCH₃ | N | N | C—CH₃ | 250 |

-continued
| | | | | | | | | |
|---|---|---|---|---|---|---|---|---|
| 486 | 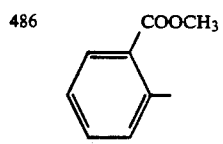 | H | 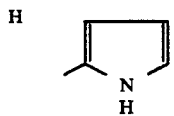 | OCH₃ | N | N | C—CH₃ | 225 |
| 487 | 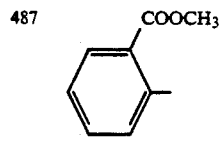 | —(CH₂)₅— | | OCH₃ | N | N | C—CH₃ | 178 |
| 488 | 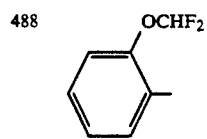 | H | 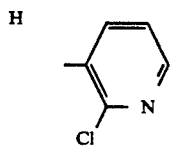 | OCH₃ | N | N | C—OCH₃ | 168 |
| 489 | 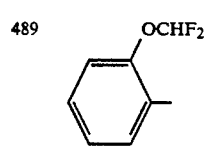 | H | CH₃ | OCH₃ | N | N | C—OCH₃ | 118 |
| 490 | 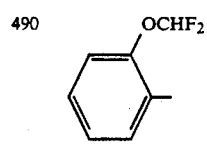 | H | CH(CH₃)₂ | OCH₃ | N | N | C—OCH₃ | 135 |
| 491 | 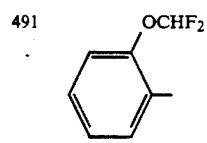 | H | C₆H₅ | OCH₃ | N | N | C—OCH₃ | 243 |
| 492 | 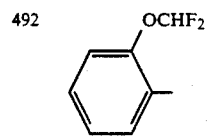 | H | 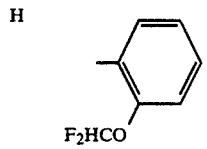 | OCH₃ | N | N | C—OCH₃ | 190 |
| 493 | 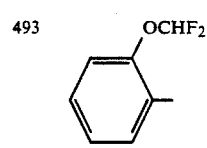 | H | 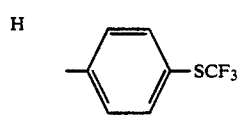 | OCH₃ | N | N | C—OCH₃ | 168 |
| 494 | 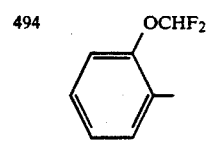 | H | 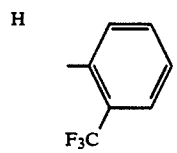 | OCH₃ | N | N | C—OCH₃ | 169 |
| 495 | 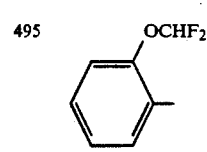 | H | 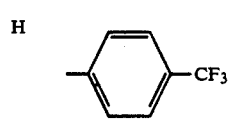 | OCH₃ | N | N | C—OCH₃ | 208 |
| 496 | 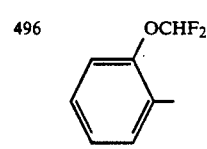 | H | 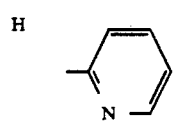 | OCH₃ | N | N | C—OCH₃ | 199 |

-continued
| | | | | | | | | |
|---|---|---|---|---|---|---|---|---|
| 497 | 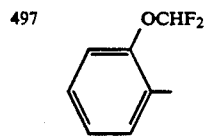 | H | 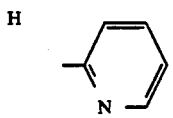 | OCH₃ | N | N | C—OCH₃ | 189 |
| 498 | 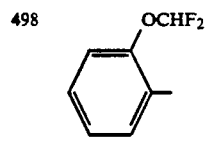 | H | 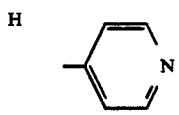 | OCH₃ | N | N | C—OCH₃ | 175 |
| 499 | 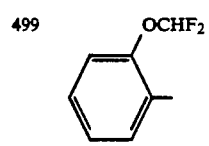 | H | 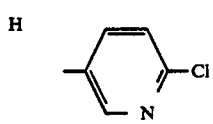 | OCH₃ | N | N | C—OCH₃ | 124 |
| 500 | 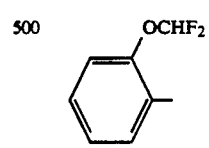 | H | 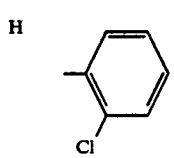 | OCH₃ | N | N | C—OCH₃ | 139 |
| 501 | 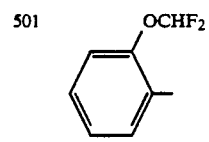 | H | 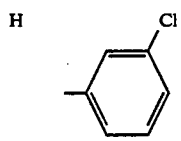 | OCH₃ | N | N | C—OCH₃ | 192 |
| 502 | 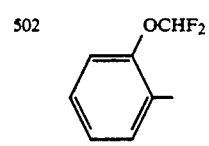 | H | 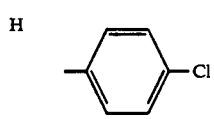 | OCH₃ | N | N | C—OCH₃ | 171 |
| 503 | 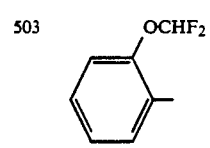 | H | 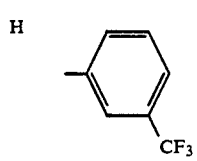 | OCH₃ | N | N | C—OCH₃ | 200 |
| 504 | 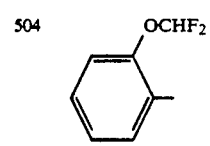 | H | 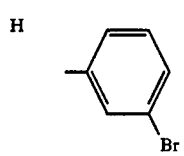 | OCH₃ | N | N | C—OCH₃ | 210 |
| 505 | 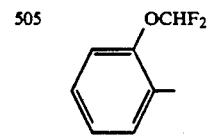 | H | 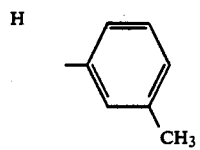 | OCH₃ | N | N | C—OCH₃ | 207 |
| 506 | 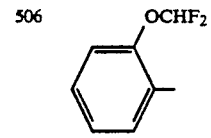 | H | 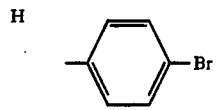 | OCH₃ | N | N | C—OCH₃ | 170 |
| 507 | 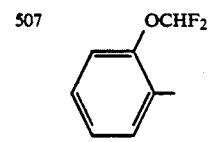 | H | 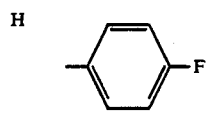 | OCH₃ | N | N | C—OCH₃ | 223 |

-continued
| | | | | | | | |
|---|---|---|---|---|---|---|---|
| 508 | 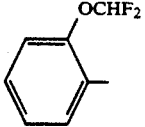 | H | 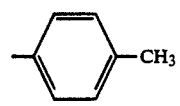 | OCH₃ | N | N | C—OCH₃ 222 |
| 509 | 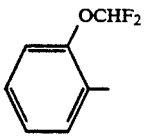 | H | 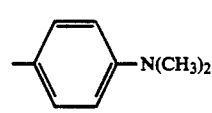 | OCH₃ | N | N | C—OCH₃ 227 |
| 510 | 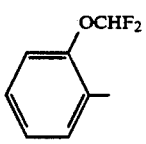 | H | 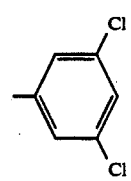 | OCH₃ | N | N | C—OCH₃ 204 |
| 511 | 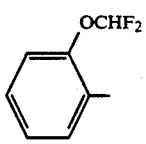 | H | 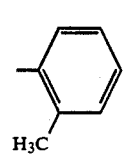 | OCH₃ | N | N | C—OCH₃ 216 |
| 512 | 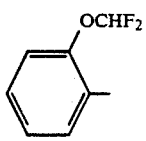 | H | 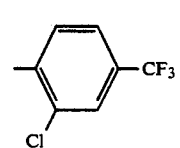 | OCH₃ | N | N | C—OCH₃ 133 |
| 513 | 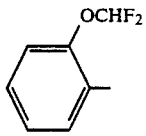 | H | —CH=CH—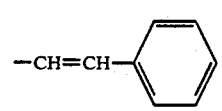 | OCH₃ | N | N | C—OCH₃ 213 |
| 514 | 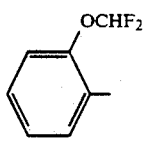 | H | 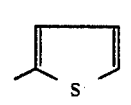 | OCH₃ | N | N | C—OCH₃ 240 |
| 515 | 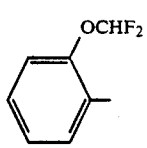 | H | 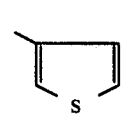 | OCH₃ | N | N | C—OCH₃ 206 |
| 516 | 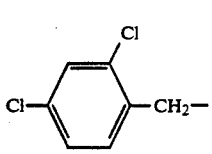 | CH₃ | CH₃ | OCH₃ | N | N | C—OCH₃ 176 |
| 517 | 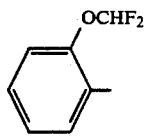 | H | 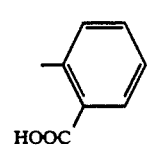 | OCH₃ | N | N | C—OCH₃ 196 |
| 518 | 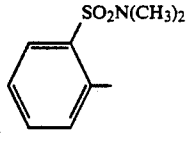 | H | 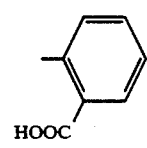 | OCH₃ | N | N | C—CH₃ 180 |

-continued

| # | R1 | | R2 | | | | | m.p. |
|---|---|---|---|---|---|---|---|---|
| 519 | 2-COOCH₃-phenyl | H | 2-HOOC-phenyl | OCH₃ | N | N | C—CH₃ | 184 |
| 520 | 2-OCHF₂-phenyl | H | 2-HOOC-phenyl | OCH₃ | N | N | C—CH₃ | 176 |
| 521 | 2-COOC₂H₅-phenyl | H | 2-HOOC-phenyl | OCH₃ | N | N | C—CH₃ | 212 |
| 522 | 3-Br-phenyl | CH₃ | CH₃ | | OCH₃ | N | N | C—OCH₃ | 185 |
| 523 | 4-Br-phenyl | CH₃ | CH₃ | | OCH₃ | N | N | C—OCH₃ | 159 |
| 524 | 3-Br-phenyl | H | C₆H₅ | OCH₃ | N | N | C—OCH₃ | 172 |
| 525 | 4-Br-phenyl | H | C₆H₅ | OCH₃ | N | N | C—OCH₃ | 185 |
| 526 | 2-OCHF₂-phenyl | H | 2-F-phenyl | OCH₃ | N | N | C—OCH₃ | 194 |
| 527 | 2-OCHF₂-phenyl | —(CH₂)₅— | | OCH₃ | N | N | C—OCH₃ | 187 |
| 528 | 2-SO₂N(CH₃)₂-phenyl | H | CH(CH₃)₂ | OCH₃ | N | N | C—OCH₃ | 103 |
| 529 | 2-SO₂N(CH₃)₂-phenyl | H | phenyl | OCH₃ | N | N | C—OCH₃ | 230 |

-continued

| No. | R1 | R2 | Ar | X | Y | Z | Q | mp(°C) |
|---|---|---|---|---|---|---|---|---|
| 530 | 2-SO₂N(CH₃)₂-phenyl | H | 2-(F₂HCO)-phenyl | OCH₃ | N | N | C—OCH₃ | 217 |
| 531 | 2-SO₂N(CH₃)₂-phenyl | H | 2-(F₃C)-phenyl | OCH₃ | N | N | C—OCH₃ | 231 |
| 532 | 2-SO₂N(CH₃)₂-phenyl | H | 4-(SCF₃)-phenyl | OCH₃ | N | N | C—OCH₃ | 187 |
| 533 | 2-SO₂N(CH₃)₂-phenyl | H | 4-(CF₃)-phenyl | OCH₃ | N | N | C—OCH₃ | 201 |
| 534 | 2-SO₂N(CH₃)₂-phenyl | H | 2-pyridyl | OCH₃ | N | N | C—OCH₃ | 195 |
| 535 | 2-SO₂N(CH₃)₂-phenyl | H | 3-pyridyl | OCH₃ | N | N | C—OCH₃ | 198 (decomp.) |
| 536 | 2-SO₂N(CH₃)₂-phenyl | H | 4-pyridyl | OCH₃ | N | N | C—OCH₃ | 194 |
| 537 | 2-SO₂N(CH₃)₂-phenyl | H | 6-Cl-3-pyridyl | OCH₃ | N | N | C—OCH₃ | 212 |
| 538 | 2-SO₂N(CH₃)₂-phenyl | H | 2-Cl-3-pyridyl | OCH₃ | N | N | C—OCH₃ | 199 |
| 539 | 2-SO₂N(CH₃)₂-phenyl | H | 2-Cl-phenyl | OCH₃ | N | N | C—OCH₃ | 230 |
| 540 | 2-SO₂N(CH₃)₂-phenyl | H | 3-Cl-phenyl | OCH₃ | N | N | C—OCH₃ | 219 |

-continued
| | | | | | | | | |
|---|---|---|---|---|---|---|---|---|
| 541 | 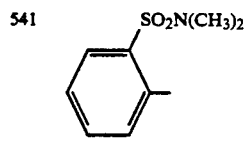 | H | 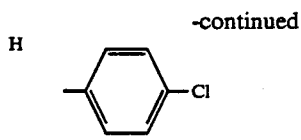 | OCH$_3$ | N | N | C—OCH$_3$ | 240 |
| 542 | 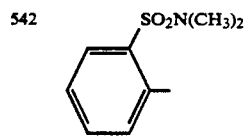 | H | 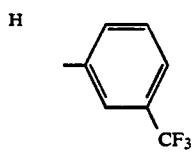 | OCH$_3$ | N | N | C—OCH$_3$ | 198 |
| 543 | 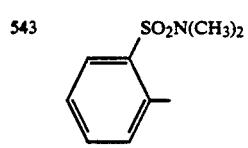 | H | 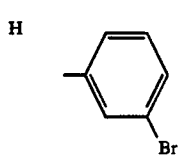 | OCH$_3$ | N | N | C—OCH$_3$ | 231 |
| 544 | 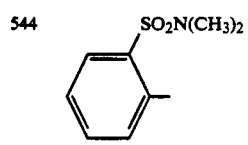 | H | 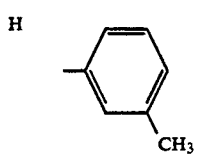 | OCH$_3$ | N | N | C—OCH$_3$ | 218 |
| 545 | 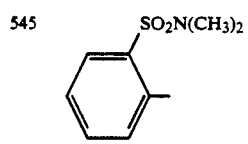 | H | 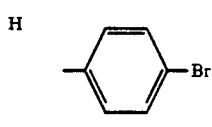 | OCH$_3$ | N | N | C—OCH$_3$ | 248 (decomp.) |
| 546 | 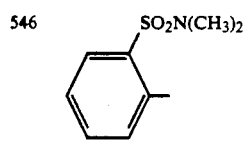 | H | 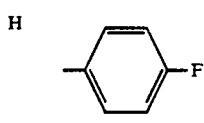 | OCH$_3$ | N | N | C—OCH$_3$ | 239 |
| 547 | 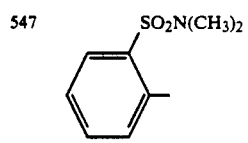 | H | —CH=CH—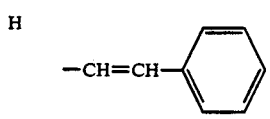 | OCH$_3$ | N | N | C—OCH$_3$ | 230 |
| 548 | 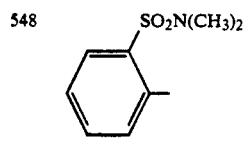 | H | 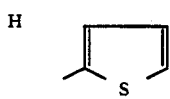 | OCH$_3$ | N | N | C—OCH$_3$ | 248 |
| 549 | 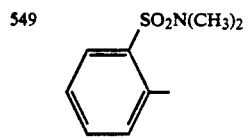 | H | 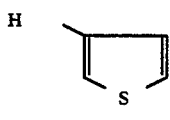 | OCH$_3$ | N | N | C—OCH$_3$ | 236 |
| 550 | 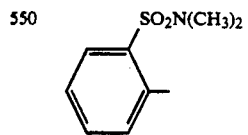 | H | 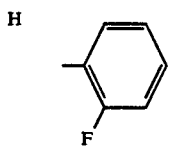 | OCH$_3$ | N | N | C—OCH$_3$ | 221 |
| 551 | 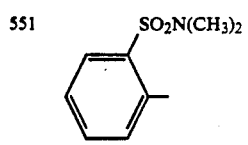 | H | 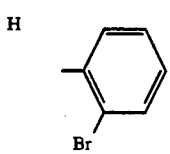 | OCH$_3$ | N | N | C—OCH$_3$ | 226 |

-continued
| | | | | | | | |
|---|---|---|---|---|---|---|---|
| 552 | 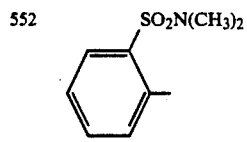 | —(CH₂)₅— | | OCH₃ | N | N | C—OCH₃ | 179 |
| 553 | 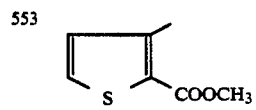 | CH₃ | CH₃ | OCH₃ | N | N | C—OCH₃ | 215 |
| 554 | 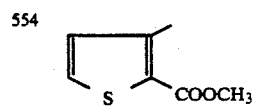 | H | CH₃ | OCH₃ | N | N | C—OCH₃ | 145 |
| 555 | 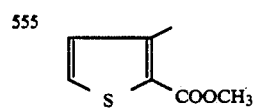 | H | CH(CH₃)₂ | OCH₃ | N | N | C—OCH₃ | 164 |
| 556 | 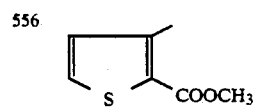 | H | C₆H₅ | OCH₃ | N | N | C—OCH₃ | 209 |
| 557 | 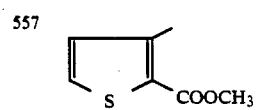 | H | 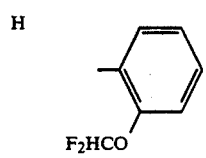 | OCH₃ | N | N | C—OCH₃ | 165 |
| 558 | 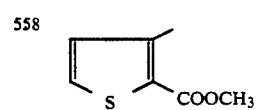 | H | 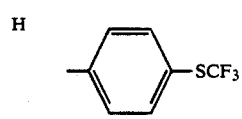 | OCH₃ | N | N | C—OCH₃ | 185 |
| 559 | 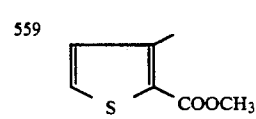 | H | 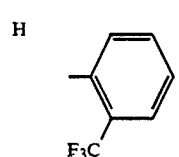 | OCH₃ | N | N | C—OCH₃ | 119 (decomp.) |
| 560 | 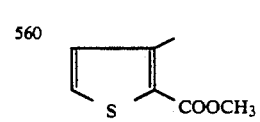 | H | 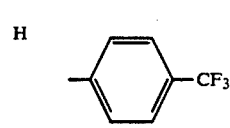 | OCH₃ | N | N | C—OCH₃ | 196 |
| 561 |  | H | 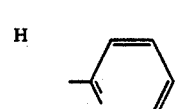 | OCH₃ | N | N | C—OCH₃ | 193 |
| 562 | 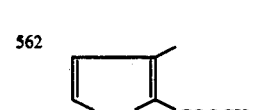 | H | 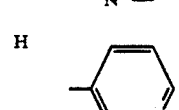 | OCH₃ | N | N | C—OCH₃ | 191 (decomp.) |
| 563 | 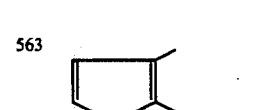 | H | 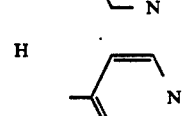 | OCH₃ | N | N | C—OCH₃ | 159 |
| 564 | 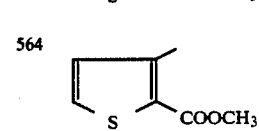 | H | 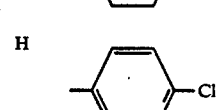 | OCH₃ | N | N | C—OCH₃ | 130 |

-continued

| # | Structure 1 | (H) | Structure 2 | R1 | X | Y | R2 | mp |
|---|---|---|---|---|---|---|---|---|
| 565 | 3-methylthiophene-2-COOCH₃ | H | 2-chloropyridin-3-yl | OCH₃ | N | N | C—OCH₃ | 183 |
| 566 | 3-methylthiophene-2-COOCH₃ | H | 2-chlorophenyl | OCH₃ | N | N | C—OCH₃ | 215 |
| 567 | 3-methylthiophene-2-COOCH₃ | H | 3-chlorophenyl | OCH₃ | N | N | C—OCH₃ | 233 |
| 568 | 3-methylthiophene-2-COOCH₃ | H | 4-chlorophenyl | OCH₃ | N | N | C—OCH₃ | 218 |
| 569 | 3-methylthiophene-2-COOCH₃ | H | 3-CF₃-phenyl | OCH₃ | N | N | C—OCH₃ | 235 |
| 570 | 3-methylthiophene-2-COOCH₃ | H | 3-bromophenyl | OCH₃ | N | N | C—OCH₃ | 225 |
| 571 | 3-methylthiophene-2-COOCH₃ | H | 3-methylphenyl | OCH₃ | N | N | C—OCH₃ | 205 |
| 572 | 3-methylthiophene-2-COOCH₃ | H | 4-bromophenyl | OCH₃ | N | N | C—OCH₃ | 221 |
| 573 | 3-methylthiophene-2-COOCH₃ | H | 4-fluorophenyl | OCH₃ | N | N | C—OCH₃ | 205 |
| 574 | 3-methylthiophene-2-COOCH₃ | H | —CH=CH—phenyl | OCH₃ | N | N | C—OCH₃ | 212 |
| 575 | 3-methylthiophene-2-COOCH₃ | H | 2-methylfuran-5-yl | OCH₃ | N | N | C—OCH₃ | 201 |

-continued
| | | | | | | | |
|---|---|---|---|---|---|---|---|
| 576 | 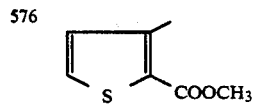 | H | 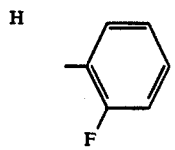 | OCH₃ | N | N | C—OCH₃ 226 |
| 577 | 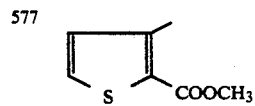 | H | 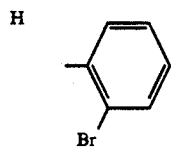 | OCH₃ | N | N | C—OCH₃ 219 |
| 578 | 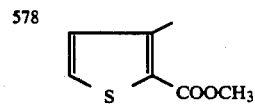 | 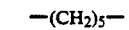 —(CH₂)₅— | | OCH₃ | N | N | C—OCH₃ 203 |
| 579 | 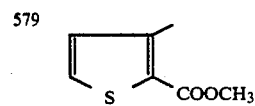 | H | 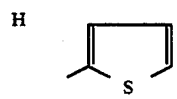 | OCH₃ | N | N | C—OCH₃ 239 |
| 580 | 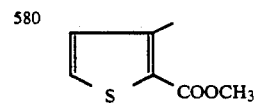 | H | 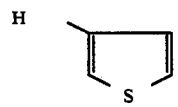 | OCH₃ | N | N | C—OCH₃ 209 |
| 581 | 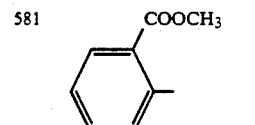 | 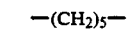 —(CH₂)₅— | | OCH₃ | N | N | C—OCH₃ 167 |
| 582 | 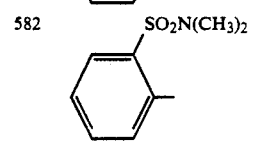 | H | 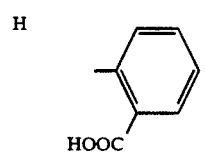 | OCH₃ | N | N | C—OCH₃ 238 |
| 583 | 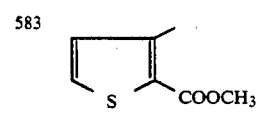 | H | 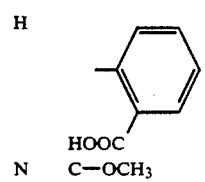 | OCH₃ N | N | C—OCH₃ | 225 (decomp.) |
| 584 | 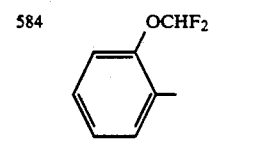 | H |  C₆H₅ | OCH₃ | N | N | C—CH₃ 192 |
| 585 | 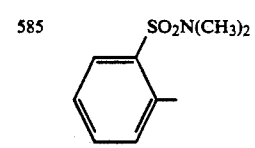 | H | 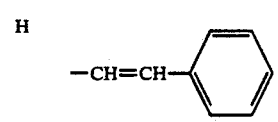 —CH=CH— | OCH₃ | N | N | C—CH₃ 249 |
| 586 | 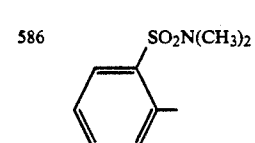 | H |  | OCH₃ | N | N | C—CH₃ 236 |

| # | R1 | R2 | R3 | X | A | B | Y | mp |
|---|---|---|---|---|---|---|---|---|
| 587 | 2-CH₃-C₆H₄-SO₂N(CH₃)₂ (ortho-SO₂N(CH₃)₂) | H | 2-F-C₆H₄ | OCH₃ | N | N | C—CH₃ | 241 |
| 588 | 2-CH₃-C₆H₄-SO₂N(CH₃)₂ | H | 2-Br-C₆H₄ | OCH₃ | N | N | C—CH₃ | 208 |
| 589 | 2-CN-C₆H₄-CH₂— | CH₃ | CH₃ | OCH₃ | N | N | C—OCH₃ | 214 |
| 590 | 2-CN-C₆H₄-CH₂— | H | C₆H₅ | OCH₃ | N | N | C—OCH₃ | 227 |
| 591 | 2-COOCH₃-C₆H₄-CH₂— | H | C₆H₅ | OCH₃ | N | N | C—OCH₃ | 203 |
| 592 | 2-CH₃-C₆H₄-SO₂N(CH₃)₂ | —(CH₂)₅— | | OCH₃ | N | N | C—CH₃ | 174 |
| 593 | 3-CH₃-2-COOCH₃-thienyl | —(CH₂)₅— | | OCH₃ | N | N | C—CH₃ | 177 |
| 594 | 3-CH₃-2-COOCH₃-thienyl | H | 2-HOOC-C₆H₄ | OCH₃ | N | N | C—CH₃ | 115–123 |
| 595 | 2-COOCH₃-C₆H₄- | H | C₆H₅ | OC₂H₅ | N | N | C—CH₃ | 85–93 |
| 596 | 2-CH₃-C₆H₄-SO₂N(CH₃)(OCH₃) | H | 2-F₃C-C₆H₄ | OCH₃ | N | N | C—OCH₃ | 205–210 |
| 597 | 2-CH₃-C₆H₄-SO₂N(CH₃)(OCH₃) | H | 4-CF₃-C₆H₄ | OCH₃ | N | N | C—OCH₃ | 205–207 |

-continued

| No. | Structure (col 1) | (col 2) | (col 3) | (col 4) | (col 5) | (col 6) | (col 7) | m.p. |
|---|---|---|---|---|---|---|---|---|
| 598 | 2-[SO₂N(CH₃)(OCH₃)]-phenyl | H | 4-F-C₆H₄ | OCH₃ | N | N | C—OCH₃ | 225 |
| 599 | 2-[SO₂N(CH₃)(OCH₃)]-phenyl | H | 2-Cl-C₆H₄ | OCH₃ | N | N | C—OCH₃ | 203–206 |
| 600 | 2-[SO₂N(CH₃)(OCH₃)]-phenyl | H | 4-SCF₃-C₆H₄ | OCH₃ | N | N | C—OCH₃ | 210 |
| 601 | 2-[SO₂N(CH₃)(OCH₃)]-phenyl | H | —CH=CH—C₆H₅ | OCH₃ | N | N | C—OCH₃ | 233–235 |
| 602 | 2-[SO₂N(CH₃)(OCH₃)]-phenyl | —(CH₂)₅— | | OCH₃ | N | N | C—OCH₃ | 194 |
| 603 | 2-[SO₂N(CH₃)(OCH₃)]-phenyl | H | C(CH₃)₃ | OCH₃ | N | N | C—OCH₃ | 175–177 |
| 604 | 2-[SO₂N(CH₃)(OCH₃)]-phenyl | H | CH(CH₃)₂ | OCH₃ | N | N | C—OCH₃ | 156–157 |
| 605 | 2-[SO₂N(CH₃)(OCH₃)]-phenyl | CH₃ | CH₂CH(CH₃)₂ | OCH₃ | N | N | C—OCH₃ | 169 |
| 606 | 2-[COOCH(CH₃)₂]-phenyl | CH₃ | CH₃ | OCH₃ | N | N | C—CH₃ | 158 |
| 607 | 2-[COOCH(CH₃)₂]-phenyl | H | C₆H₅ | OCH₃ | N | N | C—CH₃ | 190 |

-continued

| # | R1 | R2 | R3 | X | A | B | D | mp |
|---|---|---|---|---|---|---|---|---|
| 608 | 2-COOCH(CH₃)₂-phenyl | CH₃ | CH₃ | | OCH₃ | N | N | C—C₂H₅ | 148–150 |
| 609 | 2-COOCH(CH₃)₂-phenyl | H | C₆H₅ | | OCH₃ | N | N | C—C₂H₅ | 170 |
| 610 | 2-SO₂N(CH₃)(OCH₃)-phenyl | H | CH₃ | | OCH₃ | N | N | C—OCH₃ | 145 |
| 611 | 2-SO₂N(CH₃)(OCH₃)-phenyl | H | 5-methyl-furan-2-yl | | OCH₃ | N | N | C—OCH₃ | 174 |
| 612 | 2-SO₂N(CH₃)(OCH₃)-phenyl | H | pyridin-2-yl | | OCH₃ | N | N | C—OCH₃ | 166–170 |
| 613 | 2-SO₂N(CH₃)(OCH₃)-phenyl | H | pyridin-3-yl | | OCH₃ | N | N | C—OCH₃ | 166–168 |
| 614 | 2-SO₂N(CH₃)(OCH₃)-phenyl | H | pyridin-4-yl | | OCH₃ | N | N | C—OCH₃ | 173–174 |
| 615 | 2-SO₂N(CH₃)(OCH₃)-phenyl | H | 2-chloro-5-methyl-thiazol-4-yl (substituted) | | OCH₃ | N | N | C—OCH₃ | 87–100 |
| 616 | 2-SO₂N(CH₃)(OCH₃)-phenyl | H | 2-chloro-4-methyl-5-chloro-thiazol | | OCH₃ | N | N | C—OCH₃ | 216 |
| 617 | 2-OCF₃-phenyl | H | C₆H₅ | | OC₂H₅ | N | N | C—CH₃ | 175 |

-continued
| | | | | | | | | |
|---|---|---|---|---|---|---|---|---|
| 618 | 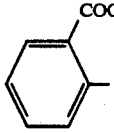 COOCH(CH₃)₂ | CH₃ | CH₃ | OC₂H₅ | N | N | C—CH₃ | 152 |
| 619 | 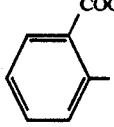 COOCH(CH₃)₂ | H | C₆H₅ | OC₂H₅ | N | N | C—CH₃ | 162 |
| 620 | 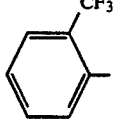 CF₃ | H | 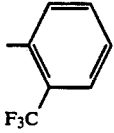 F₃C | OCH₃ | N | N | C—OCH₃ | 209 |
| 621 | 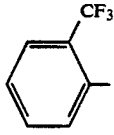 CF₃ | H | 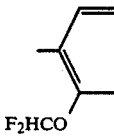 F₂HCO | OCH₃ | N | N | C—OCH₃ | 195-198 |
| 622 | 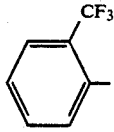 CF₃ | H | C₆H₅ | OCH₃ | N | N | C—OCH₃ | 200 |
| 623 | 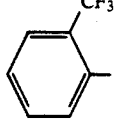 CF₃ | H | 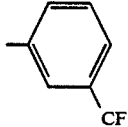 CF₃ | OCH₃ | N | N | C—OCH₃ | 209-211 |
| 624 | 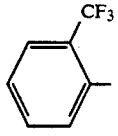 CF₃ | H | 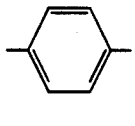 CF₃ | OCH₃ | N | N | C—OCH₃ | 175-177 |
| 625 | 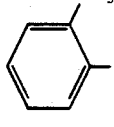 CF₃ | H | 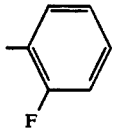 F | OCH₃ | N | N | C—OCH₃ | 217 |
| 626 | 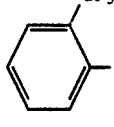 CF₃ | H | 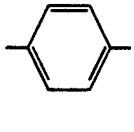 F | OCH₃ | N | N | C—OCH₃ | 231 |
| 627 | 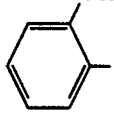 OCF₃ | CH₃ | CH₃ | OCH₃ | N | N | C—C₂H₅ | 151 |
| 628 | 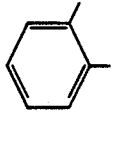 OCHF₂ | CH₃ | CH₃ | SCH₃ | N | N | C—CH₃ | 141 |

| | | | | | | | | |
|---|---|---|---|---|---|---|---|---|
| 629 | 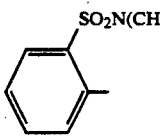 SO₂N(CH₃)₂ | H | C₆H₅ | | SCH₃ | N | N | C—CH₃ | 226 |
| 630 | 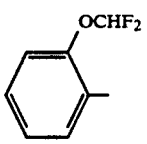 OCHF₂ | H | C₆H₅ | | SCH₃ | N | N | C—CH₃ | 169 |
| 631 | 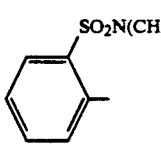 SO₂N(CH₃)₂ | CH₃ | CH₃ | | SCH₃ | N | N | C—CH₃ | 228 |
| 632 | 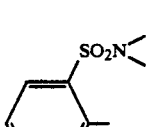 SO₂N(CH₃)(OCH₃) | H | 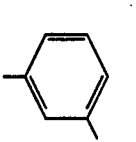 CF₃ | | OCH₃ | N | N | C—OCH₃ | 202–204 |
| 633 | 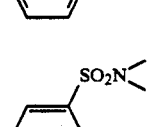 SO₂N(CH₃)(OCH₃) | H | 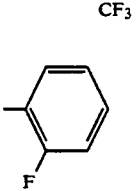 F | | OCH₃ | N | N | C—OCH₃ | 194–197 |
| 634 | 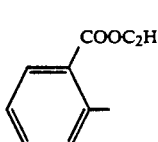 COOC₂H₅ | CH₃ | CH₃ | | OC₂H₅ | N | N | C—CH₃ | 184–185 |
| 635 | 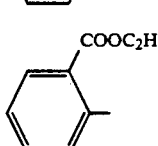 COOC₂H₅ | H | C₆H₅ | | OC₂H₅ | N | N | C—CH₃ | 147 |
| 636 | 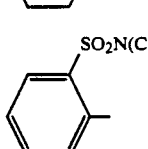 SO₂N(CH₃)₂ | CH₃ | CH₃ | | OC₂H₅ | N | N | C—CH₃ | 214–217 |
| 637 | 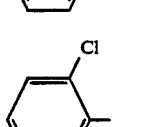 Cl | H | C₆H₅ | | OCH₃ | N | N | C—OCH₃ | 192 |
| 638 | 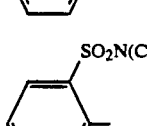 SO₂N(CH₃)₂ | H | C₆H₅ | | OC₂H₅ | N | N | C—CH₃ | 204 |
| 639 | 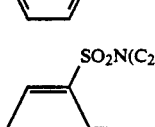 SO₂N(C₂H₅)₂ | H | 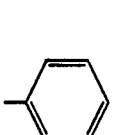 CF₃ | | OCH₃ | N | N | C—CH₃ | 151 |

-continued
| | | | | | | | | |
|---|---|---|---|---|---|---|---|---|
| 640 | 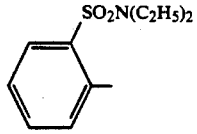 | H | 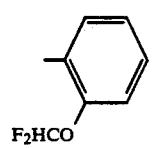 | OCH₃ | N | N | C—CH₃ | 179 |
| 641 | 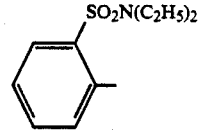 | H | 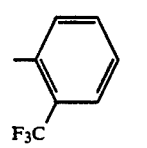 | OCH₃ | N | N | C—CH₃ | 204–207 |
| 642 | 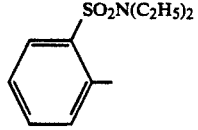 | H | 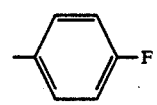 | OCH₃ | N | N | C—CH₃ | 236 |
| 643 | 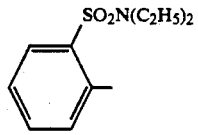 | H | 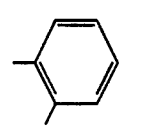 | OCH₃ | N | N | C—CH₃ | 230 |
| 644 | 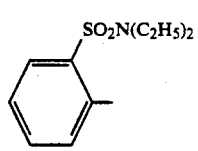 | H | 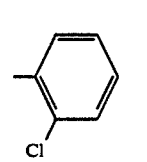 | OCH₃ | N | N | C—CH₃ | 198–203 |
| 645 | 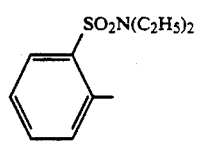 | H | 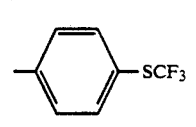 | OCH₃ | N | N | C—CH₃ | 213–215 |
| 646 | 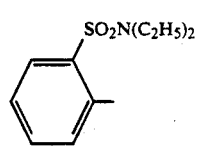 | H | —CH=CH—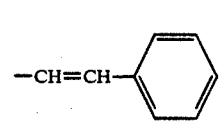 | OCH₃ | N | N | C—CH₃ | 223–226 |
| 647 | 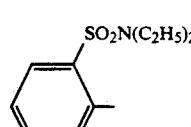 | —(CH₂)₅— | | OCH₃ | N | N | C—CH₃ | 200 |
| 648 | 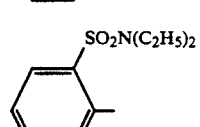 | H | CH(CH₃)₂ | OCH₃ | N | N | C—CH₃ | 166–172 |
| 649 | 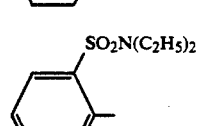 | H | C(CH₃)₃ | OCH₃ | N | N | C—CH₃ | 173–175 |
| 650 | 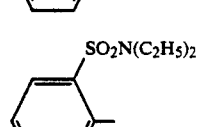 | H | 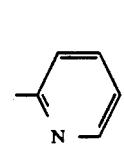 | OCH₃ | N | N | C—CH₃ | 217 |

| No. | R1 | R2 | R3 | | | | | m.p. |
|---|---|---|---|---|---|---|---|---|
| 651 | 2-SO₂N(C₂H₅)₂-phenyl | H | pyridin-3-yl | OCH₃ | N | N | C—CH₃ | 180–184 |
| 652 | 2,6-Cl₂-phenyl | H | 4-CF₃-phenyl | OCH₃ | N | N | C—CH₃ | 167–173 |
| 653 | 2,6-Cl₂-phenyl | H | CH₃ | OCH₃ | N | N | C—CH₃ | 144–149 |
| 654 | 2,6-Cl₂-phenyl | H | pyridin-2-yl | OCH₃ | N | N | C—CH₃ | 171 |
| 655 | 2,6-Cl₂-phenyl | H | pyridin-3-yl | OCH₃ | N | N | C—CH₃ | 122 |
| 656 | 2,6-Cl₂-phenyl | H | pyridin-4-yl | OCH₃ | N | N | C—CH₃ | 195 |
| 657 | 2-COOC₃H₇-phenyl | CH₃ | CH₃ | OCH₃ | N | N | C—CH₃ | 160 |
| 658 | 2-COOC₃H₇-phenyl | H | C₆H₅ | OCH₃ | N | N | C—CH₃ | 173–182 |
| 659 | 2,6-Cl₂-phenyl | H | 2-HOOC-phenyl | OCH₃ | N | N | C—CH₃ | 192 |
| 660 | 2-COOC₃H₇-phenyl | H | C₆H₅ | OCH₃ | N | N | C—C₂H₅ | 141 |

-continued
| | | | | | | | | |
|---|---|---|---|---|---|---|---|---|
| 661 | 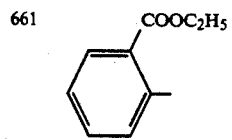 | H | 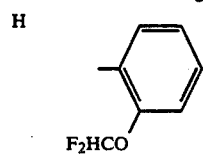 | OCH₃ | N | N | C—CH₃ | 159 |
| 662 | 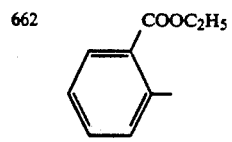 | H | 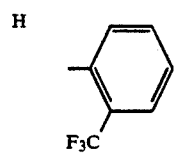 | OCH₃ | N | N | C—CH₃ | 125 |
| 663 | 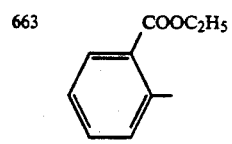 | H | 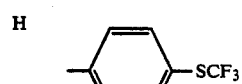 | OCH₃ | N | N | C—CH₃ | 163 |
| 664 | 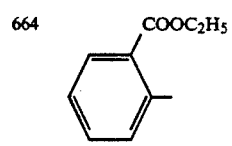 | H | 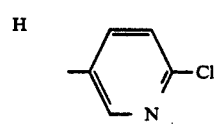 | OCH₃ | N | N | C—CH₃ | 191 |
| 665 | 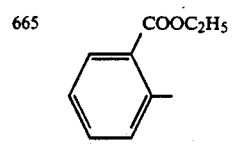 | H | 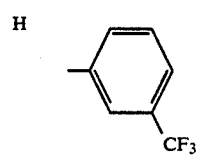 | OCH₃ | N | N | C—CH₃ | 160–162 |
| 666 | 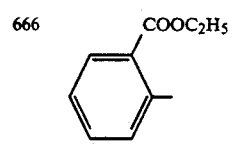 | H | 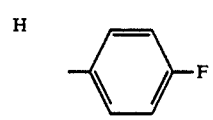 | OCH₃ | N | N | C—CH₃ | 186 |
| 667 | 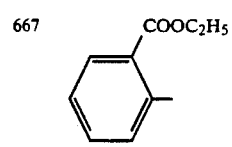 | H | 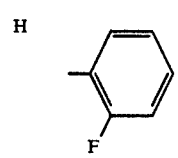 | OCH₃ | N | N | C—CH₃ | 192 |
| 668 | 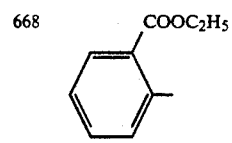 | —(CH₂)₅— | | OCH₃ | N | N | C—CH₃ | 166 |
| 669 | COOC₂H₅ | H | | OCH₃ | N | N | C—CH₃ | 254 |
| 670 | SO₂N(C₂H₅)₂ | H | | OCH₃ | N | N | C—OCH₃ | 182 |
| 671 | SO₂N(C₂H₅)₂ | H | | OCH₃ | N | N | C—OCH₃ | 205–210 |

| | | | | | | | | |
|---|---|---|---|---|---|---|---|---|
| 672 | 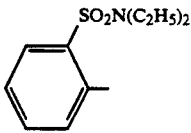SO$_2$N(C$_2$H$_5$)$_2$ | H | 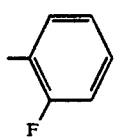F | OCH$_3$ | N | N | C—OCH$_3$ | 200 |
| 673 | 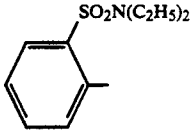SO$_2$N(C$_2$H$_5$)$_2$ | H | 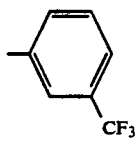CF$_3$ | OCH$_3$ | N | N | C—OCH$_3$ | 182 |
| 674 | 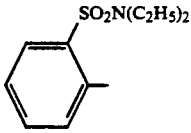SO$_2$N(C$_2$H$_5$)$_2$ | H | 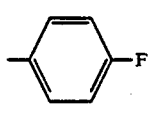F | OCH$_3$ | N | N | C—OCH$_3$ | 235 |
| 675 | 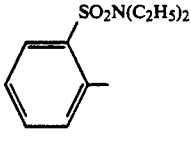SO$_2$N(C$_2$H$_5$)$_2$ | H | 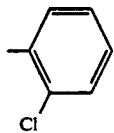Cl | OCH$_3$ | N | N | C—OCH$_3$ | 194 |
| 676 | 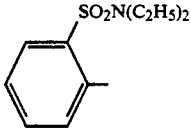SO$_2$N(C$_2$H$_5$)$_2$ | H | 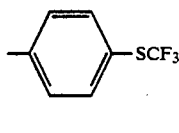SCF$_3$ | OCH$_3$ | N | N | C—OCH$_3$ | 203 |
| 677 | 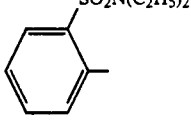SO$_2$N(C$_2$H$_5$)$_2$ | H | C$_6$H$_5$ | OCH$_3$ | N | N | C—OCH$_3$ | 216–218 |
| 678 | 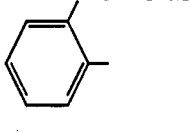SO$_2$N(C$_2$H$_5$)$_2$ | —(CH$_2$)$_5$— | | OCH$_3$ | N | N | C—OCH$_3$ | 171 |
| 679 | 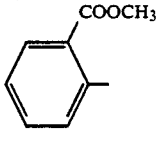COOCH$_3$ | H | C$_6$H$_5$ | OCH$_3$ | N | N | C—C$_2$H$_5$ | 170 |
| 680 | 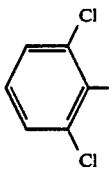Cl Cl | H | 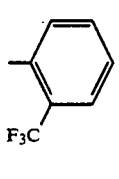F$_3$C | OC$_2$H$_5$ | N | N | C—CH$_3$ | 202–204 |
| 681 | 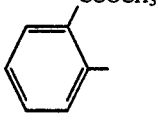COOCH$_3$ | CH$_3$ | CH$_3$ | OC$_2$H$_5$ | N | N | C—CH$_3$ | 160–163 |
| 682 | 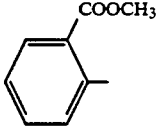COOCH$_3$ | H | 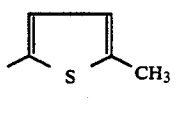CH$_3$ S CH$_3$ | OCH$_3$ | N | N | C—OCH$_3$ | 211–212 |

| | | | | | | | |
|---|---|---|---|---|---|---|---|
| 683 | 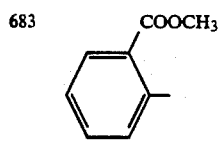 | H | 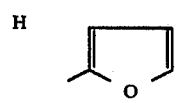 | OCH$_3$ | N | N | C—OCH$_3$ 219-220 |
| 684 | 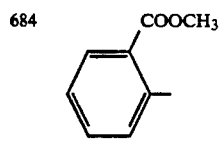 | H | 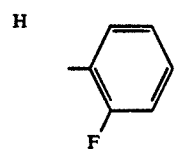 | OCH$_3$ | N | N | C—OCH$_3$ 208-209 |
| 685 | 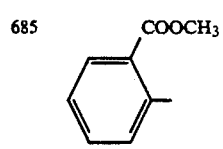 | H | 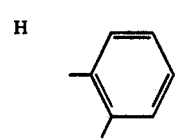 | OCH$_3$ | N | N | C—OCH$_3$ 223-224 |
| 686 | 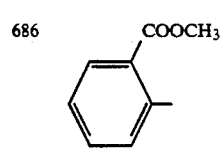 | H | 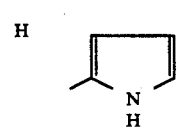 | OCH$_3$ | N | N | C—OCH$_3$ 205 |
| 687 | 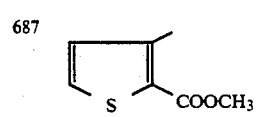 | H | 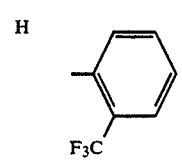 | OC$_2$H$_5$ | N | N | C—CH$_3$ 160-165 |
| 688 | 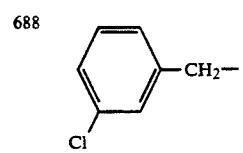 | CH$_3$ | CH$_3$ | OCH$_3$ | N | N | C—OCH$_3$ 217 |
| 689 | 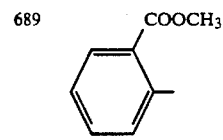 | CH$_3$ | CH$_3$ | OCH$_3$ | N | N | C—C$_2$H$_5$ 138-140 |
| 690 | 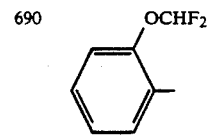 | H | 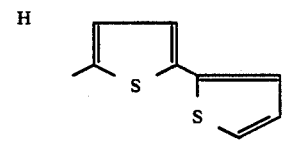 | OCH$_3$ | N | N | C—CH$_3$ 249-251 |
| 691 | 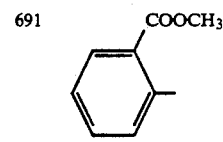 | H | 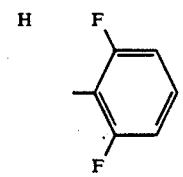 | OCH$_3$ | N | N | C—CH$_3$ 180-183 |
| 692 | 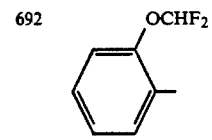 | H | 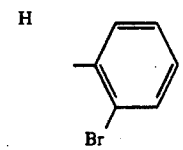 | OCH$_3$ | N | N | C—OCH$_3$ 134-139 |

-continued

| # | Aryl | | | | | | | mp |
|---|---|---|---|---|---|---|---|---|
| 693 | 2,5-dibromophenyl | CH₃ | CH₃ | OCH₃ | N | N | C—OCH₃ | 220 |
| 694 | 2,5-dibromophenyl | H | C₆H₅ | OCH₃ | N | N | C—OCH₃ | 143–145 |
| 695 | 2,5-difluorophenyl | CH₃ | CH₃ | OCH₃ | N | N | C—OCH₃ | 198–200 |
| 696 | 2,5-difluorophenyl | H | C₆H₅ | OCH₃ | N | N | C—OCH₃ | 176–178 |
| 697 | 4-fluorophenyl | CH₃ | CH₃ | OCH₃ | N | N | C—OCH₃ | 163–167 |
| 698 | 3-chloro-4-fluorophenyl | CH₃ | CH₃ | OCH₃ | N | N | C—OCH₃ | 153–155 |
| 699 | 3-(trifluoromethyl)phenyl | CH₃ | CH₃ | OCH₃ | N | N | C—OCH₃ | 129–134 |
| 700 | 4-fluorophenyl | H | C₆H₅ | OCH₃ | N | N | C—OCH₃ | 192–200 |
| 701 | 3-chloro-4-fluorophenyl | H | C₆H₅ | OCH₃ | N | N | C—OCH₃ | 117–122 |
| 702 | 3-(trifluoromethyl)phenyl | H | C₆H₅ | OCH₃ | N | N | C—OCH₃ | 177 |

-continued
| | | | | | | | | |
|---|---|---|---|---|---|---|---|---|
| 703 | 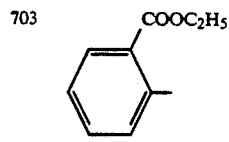 | H | 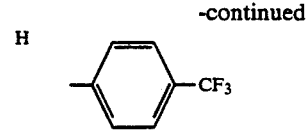 | OCH₃ | N | N | C—CH₃ | 199 |
| 704 | 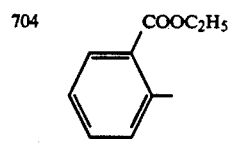 | H | 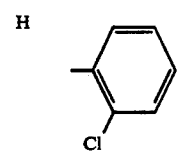 | OCH₃ | N | N | C—CH₃ | 140–144 |
| 705 | 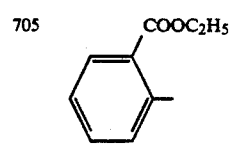 | H | 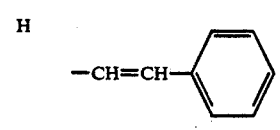 | OCH₃ | N | N | C—CH₃ | 175–179 |
| 706 | 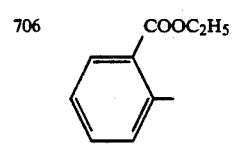 | H | CH(CH₃)₂ | OCH₃ | N | N | C—CH₃ | 137–140 |
| 707 | 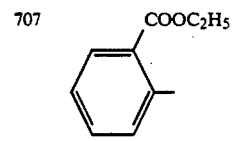 | H | C(CH₃)₃ | OCH₃ | N | N | C—CH₃ | 176–180 |
| 708 | 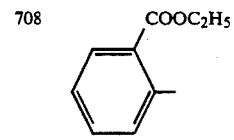 | CH₃ | CH₂CH(CH₃)₂ | OCH₃ | N | N | C—CH₃ | 136–139 |
| 709 | 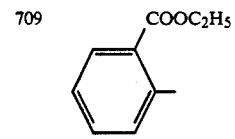 | H | CH₃ | OCH₃ | N | N | C—CH₃ | 130–132 |
| 710 | 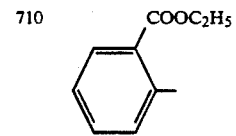 | H | C₆H₅ | OCH₃ | N | N | C—C₂H₅ | 172 |
| 711 | 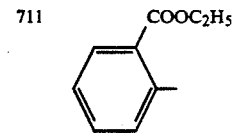 | CH₃ | CH₃ | OCH₃ | N | N | C—C₂H₅ | 137–142 |
| 712 | 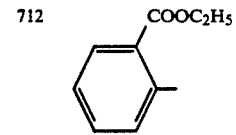 | H | 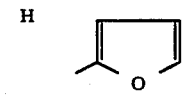 | OCH₃ | N | N | C—CH₃ | 128–136 |
| 713 | 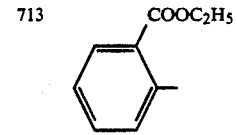 | H | 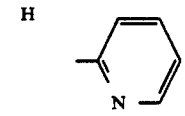 | OCH₃ | N | N | C—CH₃ | 182–188 |

-continued

| | | | | | | | | |
|---|---|---|---|---|---|---|---|---|
| 714 | 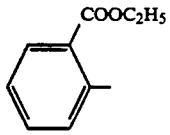 COOC$_2$H$_5$ | H | 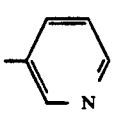 | OCH$_3$ | N | N | C—CH$_3$ | 156–166 |
| 715 | 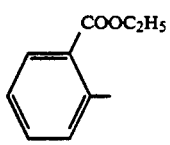 COOC$_2$H$_5$ | H | 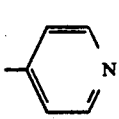 | OCH$_3$ | N | N | C—CH$_3$ | 157–163 |
| 716 | 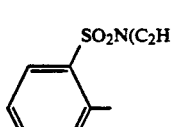 SO$_2$N(C$_2$H$_5$)$_2$ | H | C$_6$H$_5$ | OCH$_3$ | N | N | C—OCH$_3$ | 227–228 |
| 717 | 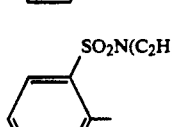 SO$_2$N(C$_2$H$_5$)$_2$ | H | C$_6$H$_5$ | OCH$_3$ | N | N | C—CH$_3$ | 228–231 |
| 718 | 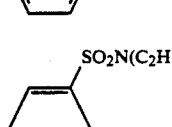 SO$_2$N(C$_2$H$_5$)$_2$ | CH$_3$ | CH$_3$ | OCH$_3$ | N | N | C—OCH$_3$ | 158–172 |
| 719 | 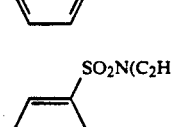 SO$_2$N(C$_2$H$_5$)$_2$ | H |  | OCH$_3$ | N | N | C—OCH$_3$ | 182 |
| 720 | 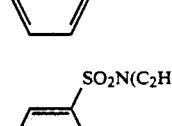 SO$_2$N(C$_2$H$_5$)$_2$ | H | 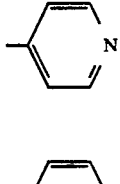 | OCH$_3$ | N | N | C—OCH$_3$ | 189–193 |
| 721 | 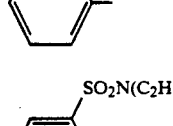 SO$_2$N(C$_2$H$_5$)$_2$ | H | 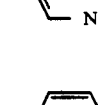 | OCH$_3$ | N | N | C—OCH$_3$ | 188–191 |
| 722 | 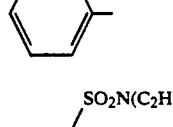 SO$_2$N(C$_2$H$_5$)$_2$ | H | 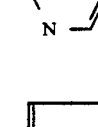 | OCH$_3$ | N | N | C—OCH$_3$ | 219–221 |
| 723 | 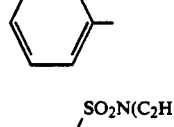 SO$_2$N(C$_2$H$_5$)$_2$ | H | CH$_3$ | OCH$_3$ | N | N | C—OCH$_3$ | 125–132 |
| 724 | 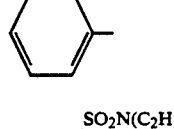 SO$_2$N(C$_2$H$_5$)$_2$ | CH$_3$ | CH$_2$CH(CH$_3$)$_2$ | OCH$_3$ | N | N | C—OCH$_3$ | 168 |

-continued

| | | | | | | | | |
|---|---|---|---|---|---|---|---|---|
| 725 | SO₂N(C₂H₅)₂ (on phenyl with ortho substituent) | H | C(CH₃)₃ | OCH₃ | N | N | C—OCH₃ | 180–182 |
| 726 | SO₂N(C₂H₅)₂ (on phenyl with ortho substituent) | H | CH(CH₃)₂ | OCH₃ | N | N | C—OCH₃ | 187–189 |
| 727 | SO₂N(CH₃)₂ (on phenyl with ortho substituent) | CH₃ | CH₃ | CH₃ | N | N | C—CH₃ | 246–251 (d.) |
| 728 | Cl (on phenyl with ortho substituent) | CH₃ | CH₃ | OCH₃ | N | N | C—CH₃ | 170–176 |
| 729 | Cl (on phenyl with ortho substituent) | H | C₆H₅ | OCH₃ | N | N | C—CH₃ | 212–218 |
| 730 | OCF₃ (on phenyl with ortho substituent) | CH₃ | CH₃ | OCH₃ | N | N | C—CH₃ | 146 |
| 731 | OCF₃ (on phenyl with ortho substituent) | H | C₆H₅ | OCH₃ | N | N | C—CH₃ | 170 |
| 732 | CF₃ (on phenyl with ortho substituent) | CH₃ | CH₃ | OCH₃ | N | N | C—CH₃ | 180–181 |
| 733 | CF₃ (on phenyl with ortho substituent) | H | CH₃ | OCH₃ | N | N | C—CH₃ | 197 |
| 734 | SO₂N(CH₃)(OCH₃) (on phenyl with ortho substituent) | CH₃ | CH₃ | OCH₃ | N | N | C—CH₃ | 191 |
| 735 | F (on phenyl with ortho substituent) | CH₃ | CH₃ | OCH₃ | N | N | C—CH₃ | 185 |

-continued

| # | Structure | | | | | | | |
|---|---|---|---|---|---|---|---|---|
| 736 | 2-CH₃, 6-SO₂N(CH₃)(OCH₃)-C₆H₃ | H | C₆H₅ | OCH₃ | N | N | C—CH₃ | 223 |
| 737 | 2-F-C₆H₄ | H | C₆H₅ | OCH₃ | N | N | C—CH₃ | 230 |
| 738 | 2-Cl-C₆H₄ | CH₃ | CH₃ | OC₂H₅ | N | N | C—CH₃ | 163–167 |
| 739 | 2-Cl-C₆H₄ | H | C₆H₅ | OC₂H₅ | N | N | C—CH₃ | 178–180 |
| 740 | 2-CH₃, 6-SO₂N(CH₃)(OCH₃)-C₆H₃ | CH₃ | CH₃ | SCH₃ | N | N | C—CH₃ | 187–191 |
| 741 | 2-CH₃, 6-SO₂N(CH₃)(OCH₃)-C₆H₃ | H | C₆H₅ | SCH₃ | N | N | C—CH₃ | 219–223 |
| 742 | 2-CH₃, 6-SO₂N(CH₃)(OCH₃)-C₆H₃ | CH₃ | CH₃ | OCH₃ | N | N | C—C₂H₅ | 171–175 |
| 743 | 2-CH₃, 6-SO₂N(CH₃)(OCH₃)-C₆H₃ | H | C₆H₅ | OCH₃ | N | N | C—C₂H₅ | 204–207 |
| 744 | 2-F-C₆H₄ | CH₃ | CH₃ | OCH₃ | N | N | C—C₂H₅ | 146 |
| 745 | 2-F-C₆H₄ | H | C₆H₅ | OCH₃ | N | N | C—C₂H₅ | 215 |

| | | | | | | | | | |
|---|---|---|---|---|---|---|---|---|---|
| 746 | 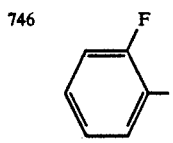 | H | C$_6$H$_5$ | | SCH$_3$ | N | N | C—CH$_3$ | 220–223 |
| 747 | 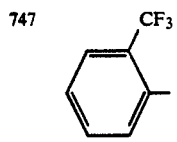 | CH$_3$ | CH$_3$ | | OCH$_3$ | N | N | C—C$_2$H$_5$ | 148 |
| 748 | 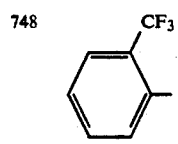 | H | C$_6$H$_5$ | | OCH$_3$ | N | N | C—C$_2$H$_5$ | 185–188 |
| 749 | 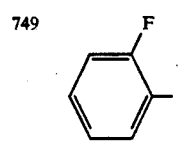 | H | C$_6$H$_5$ | | OC$_2$H$_5$ | N | N | C—CH$_3$ | 195 |
| 750 | 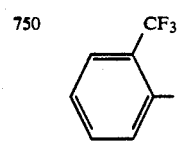 | CH$_3$ | CH$_3$ | | OC$_2$H$_5$ | N | N | C—CH$_3$ | 152 |
| 751 | 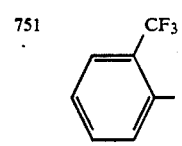 | H | C$_6$H$_5$ | | OC$_2$H$_5$ | N | N | C—CH$_3$ | 209 |
| 752 | 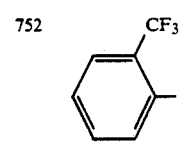 | H | CH(CH$_3$)$_2$ | | OCH$_3$ | N | N | C—CH$_3$ | 143–147 |
| 753 | 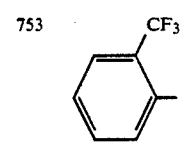 | H | C(CH$_3$)$_3$ | | OCH$_3$ | N | N | C—CH$_3$ | 136–138 |
| 754 | 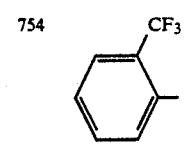 | CH$_3$ | CH$_2$CH(CH$_3$)$_2$ | | OCH$_3$ | N | N | C—CH$_3$ | 126 |
| 755 | 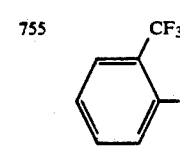 | H | CH$_3$ | | OCH$_3$ | N | N | C—CH$_3$ | 142–144 |
| 756 | 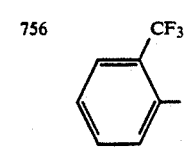 | H | (furan) | | OCH$_3$ | N | N | C—CH$_3$ | 147–158 |

-continued

| No. | R1 | R2 | R3 | | | | | mp (°C) |
|---|---|---|---|---|---|---|---|---|
| 757 | 2-CF₃-phenyl | H | 2-pyridyl | OCH₃ | N | N | C—CH₃ | 174–179 |
| 758 | 2-SO₂N(CH₃)₂-phenyl | CH₃ | CH₂CH(CH₃)₂ | OCH₃ | N | N | C—CH₃ | ¹H NMR*) δ = 4,03 ppm (OCH₃) |
| 759 | 2-SO₂N(CH₃)₂-phenyl | CH₃ | CH₂CH(CH₃)₂ | OCH₃ | N | N | C—OCH₃ | 180–184 |
| 760 | 2-CF₃-phenyl | H | 3-pyridyl | OCH₃ | N | N | C—CH₃ | 180–185 |
| 761 | 2-SO₂N(CH₃)₂-phenyl | H | CH(C₂H₅)₂ | OCH₃ | N | N | C—OCH₃ | 135 |
| 762 | 2-SO₂N(CH₃)₂-phenyl | H | CH(C₂H₅)₂ | OCH₃ | N | N | C—CH₃ | 124 |
| 763 | 2-SO₂N(CH₃)₂-phenyl | H | —CH=CH₂ | OCH₃ | N | N | C—OCH₃ | 189–191 |
| 764 | 2-OCF₃-phenyl | H | 2-(F₂HCO)-phenyl | OCH₃ | N | N | C—CH₃ | 154 |
| 765 | 2-OCF₃-phenyl | H | 2-(F₃C)-phenyl | OCH₃ | N | N | C—CH₃ | 160–162 |
| 766 | 2-OCF₃-phenyl | H | 2-F-phenyl | OCH₃ | N | N | C—CH₃ | 149–158 |
| 767 | 2-OCF₃-phenyl | H | 4-F-phenyl | OCH₃ | N | N | C—CH₃ | 187–189 |

| | | | | | | | | |
|---|---|---|---|---|---|---|---|---|
| 768 | 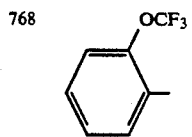 OCF$_3$ | H | 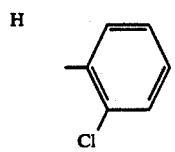 Cl | OCH$_3$ | N | N | C—CH$_3$ | 171–174 |
| 769 | 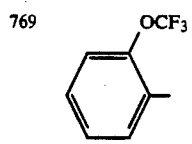 OCF$_3$ | H | —CH=CH— 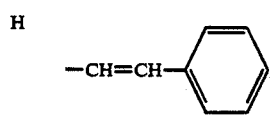 | OCH$_3$ | N | N | C—CH$_3$ | 182 |
| 770 | 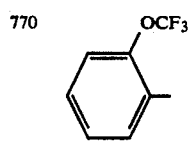 OCF$_3$ | H | CH(CH$_3$)$_2$ | OCH$_3$ | N | N | C—CH$_3$ | 128 |
| 771 | 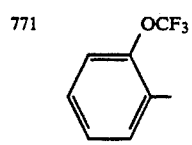 OCF$_3$ | H | C(CH$_3$)$_3$ | OCH$_3$ | N | N | C—CH$_3$ | 139–141 |
| 772 | 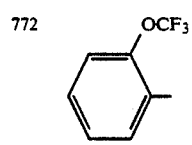 OCF$_3$ | H | CH$_3$ | OCH$_3$ | N | N | C—CH$_3$ | 137 |
| 773 | 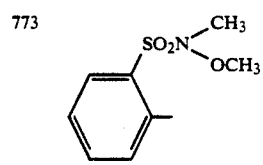 SO$_2$N(CH$_3$)(OCH$_3$) | H | 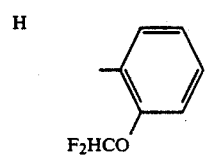 F$_2$HCO | OCH$_3$ | N | N | C—OCH$_3$ | 182 |
| 774 | 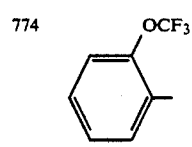 OCF$_3$ | H | 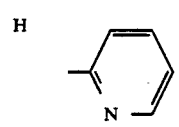 N | OCH$_3$ | N | N | C—CH$_3$ | 166 |
| 775 | 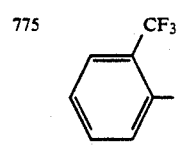 CF$_3$ | H | 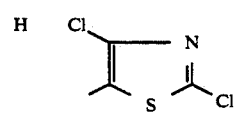 | OCH$_3$ | N | N | C—CH$_3$ | 196–199 |
| 776 | 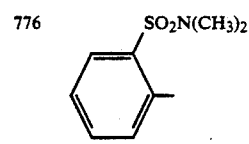 SO$_2$N(CH$_3$)$_2$ | CH$_3$ | C$_2$H$_5$ | OCH$_3$ | N | N | C—OCH$_3$ | 196–204 (decomp.) |
| 777 | 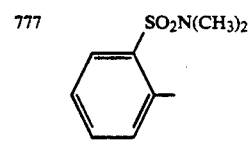 SO$_2$N(CH$_3$)$_2$ | CH$_3$ | C$_2$H$_5$ | OCH$_3$ | N | N | C—CH$_3$ | 190–196 |
| 778 | 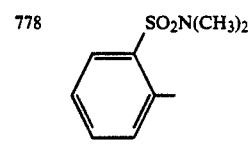 SO$_2$N(CH$_3$)$_2$ | CH$_3$ | CH$_2$OCH$_3$ | OCH$_3$ | N | N | C—CH$_3$ | 165–170 |

-continued

| # | Ar | R | R' | X | A | B | Y | mp |
|---|---|---|---|---|---|---|---|---|
| 779 | 2-SO₂N(CH₃)₂-C₆H₄ | H | -C(CH₃)=CHC₂H₅ | OCH₃ | N | N | C-CH₃ | 178 |
| 780 | 2-OCF₃-C₆H₄ | H | C₆H₅ | OCH₃ | N | N | C-C₂H₅ | 157 |
| 781 | 2-CF₃-C₆H₄ | H | 2-Cl-C₆H₄ | OCH₃ | N | N | C-OCH₃ | 202 |
| 782 | 2-CF₃-C₆H₄ | H | 4-SCF₃-C₆H₄ | OCH₃ | N | N | C-OCH₃ | 152 |
| 783 | 2-CF₃-C₆H₄ | H | -CH=CH-C₆H₅ | OCH₃ | N | N | C-OCH₃ | 200-203 |
| 784 | 2-CF₃-C₆H₄ | H | CH(CH₃)₂ | OCH₃ | N | N | C-OCH₃ | 150-153 |
| 785 | 2-CF₃-C₆H₄ | -(CH₂)₅- | | OCH₃ | N | N | C-OCH₃ | 145 |
| 786 | 2-CF₃-C₆H₄ | H | C(CH₃)₃ | OCH₃ | N | N | C-OCH₃ | 70-78 |
| 787 | 2-COOC₃H₇-C₆H₄ | CH₃ | CH₃ | OCH₃ | N | N | C-OCH₃ | 185-189 |
| 788 | 2-COOC₃H₇-C₆H₄ | H | C₆H₅ | OCH₃ | N | N | C-OCH₃ | 180-183 |
| 789 | 2-COOCH(CH₃)₂-C₆H₄ | CH₃ | CH₃ | OCH₃ | N | N | C-OCH₃ | 191 |

| No. | R1 (aryl substituent) | R2 | R3 | X | A | B | Y | mp (°C) |
|---|---|---|---|---|---|---|---|---|
| 790 | 2-COOCH(CH₃)₂-C₆H₄ | H | C₆H₅ | OCH₃ | N | N | C—OCH₃ | 201-202 |
| 791 | 2-CF₃-C₆H₄ | H | 4-CF₃-C₆H₄ | OCH₃ | N | N | C—CH₃ | 188-190 |
| 792 | 2-CF₃-C₆H₄ | H | 4-pyridyl | OCH₃ | N | N | C—CH₃ | 144 |
| 793 | 2,6-Cl₂-C₆H₃ | H | 3-F-C₆H₄ | OCH₃ | N | N | C—CH₃ | 205-207 |
| 794 | 2-CF₃-C₆H₄ | H | 3-F-C₆H₄ | OCH₃ | N | N | C—CH₃ | 175-177 |
| 795 | 2-CF₃-C₆H₄ | H | 3-F-C₆H₄ | OCH₃ | N | N | C—OCH₃ | 177 |
| 796 | 2-COOCH₂CH₂Cl-C₆H₄ | CH₃ | CH₃ | OCH₃ | N | N | C—OCH₃ | 201-203 |
| 797 | 2-COOCH₂CH₂Cl-C₆H₄ | H | C₆H₅ | OCH₃ | N | N | C—OCH₃ | 151 |
| 798 | 2-COOCH₂CH₂Cl-C₆H₄ | CH₃ | CH₃ | OCH₃ | N | N | C—CH₃ | 180 |
| 799 | 2-COOCH₂CH₂Cl-C₆H₄ | H | C₆H₅ | OCH₃ | N | N | C—CH₃ | 172 |
| 800 | 2-CF₃-C₆H₄ | CH₃ | CH₂CH(CH₃)₂ | OCH₃ | N | N | C—OCH₃ | 122-123 |

-continued

| | Ar | R | R' | X | A | B | Y | m.p. (°C) |
|---|---|---|---|---|---|---|---|---|
| 801 | 2-CF₃-C₆H₄ | H | CH₃ | OCH₃ | N | N | C—OCH₃ | 153–159 |
| 802 | 2-CF₃-C₆H₄ | H | 2-furyl (5-methylfuran-2-yl) | OCH₃ | N | N | C—OCH₃ | 204–205 |
| 803 | 2-CF₃-C₆H₄ | H | 2-pyridyl | OCH₃ | N | N | C—OCH₃ | 160–166 |
| 804 | 2-CF₃-C₆H₄ | H | 3-pyridyl | OCH₃ | N | N | C—OCH₃ | 139 (decomp.) |
| 805 | 2-CF₃-C₆H₄ | H | 2-HOOC-C₆H₄ | OCH₃ | N | N | C—OCH₃ | 211 |
| 806 | 2-CF₃-C₆H₄ | H | 4-methyl-5-chloro-2-chlorothiazol-yl | OCH₃ | N | N | C—OCH₃ | 152–158 |
| 807 | 2-CF₃-C₆H₄ | H | 4-methyl-5-chloro-2-chlorothiazol-yl | OCH₃ | N | N | C—OCH₃ | 153 |
| 808 | 2-(COOCH₂CH₂Cl)-C₆H₄ | CH₃ | CH₃ | OCH₃ | N | N | C—C₂H₅ | 165 |
| 809 | 2-(COOCH₂CH₂Cl)-C₆H₄ | H | C₆H₅ | OCH₃ | N | N | C—C₂H₅ | 154 |
| 810 | 2-(COOCH₂CH₂Cl)-C₆H₄ | CH₃ | CH₃ | OC₂H₅ | N | N | C—CH₃ | 165–166 |
| 811 | 2-(COOCH₂CH₂Cl)-C₆H₄ | H | C₆H₅ | OC₂H₅ | N | N | C—CH₃ | 148 |

| | | | | | | | | |
|---|---|---|---|---|---|---|---|---|
| 812 | 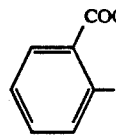 COOCH₂CH₂OCH₃ | CH₃ | CH₃ | OCH₃ | N | N | C—OCH₃ | 158 |
| 813 | 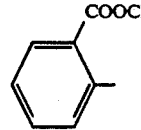 COOCH₂CH₂OCH₃ | H | C₆H₅ | OCH₃ | N | N | C—OCH₃ | 157 |
| 814 | 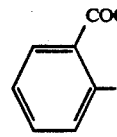 COOCH₂CH₂OCH₃ | CH₃ | CH₃ | OCH₃ | N | N | C—CH₃ | 160 |
| 815 | 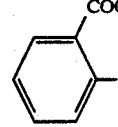 COOCH₂CH₂OCH₃ | H | C₆H₅ | OCH₃ | N | N | C—CH₃ | 153 |
| 816 | COOC₂H₅ | H | 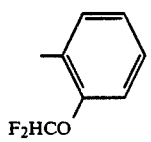 F₂HCO | OCH₃ | N | N | C—OCH₃ | 155 |
| 817 | COOC₂H₅ | H | F₃C- | OCH₃ | N | N | C—OCH₃ | 171–172 |
| 818 | COOC₂H₅ | H | -CF₃ | OCH₃ | N | N | C—OCH₃ | 171 |
| 819 | COOC₂H₅ | H | -CF₃ | OCH₃ | N | N | C—OCH₃ | 205 |
| 820 | COOC₂H₅ | H | -F | OCH₃ | N | N | C—OCH₃ | 189 |
| 821 | COOC₂H₅ | H | -F | OCH₃ | N | N | C—OCH₃ | 187 |
| 822 | COOC₂H₅ | H | -F | OCH₃ | N | N | C—OCH₃ | 200–203 |

-continued

| No. | R¹ (aryl) | R² | R³ | col1 | col2 | col3 | col4 | mp |
|---|---|---|---|---|---|---|---|---|
| 823 | 2-(COOC₂H₅)-phenyl | H | 2-Cl-phenyl | OCH₃ | N | N | C—OCH₃ | 188–190 |
| 824 | 2-(COOC₂H₅)-phenyl | H | 4-SCF₃-phenyl | OCH₃ | N | N | C—OCH₃ | 195–196 |
| 825 | 2-(COOC₂H₅)-phenyl | H | 2-HOOC-phenyl | OCH₃ | N | N | C—OCH₃ | 201–202 |
| 826 | 2-(COOC₂H₅)-phenyl | H | —CH=CH—phenyl | OCH₃ | N | N | C—OCH₃ | 201–202 |
| 827 | 2-(COOC₂H₅)-phenyl | —(CH₂)₅— | | OCH₃ | N | N | C—OCH₃ | 164–165 |
| 828 | 2-(COOC₂H₅)-phenyl | H | CH(CH₃)₂ | OCH₃ | N | N | C—OCH₃ | 135–138 |
| 829 | 2-(COOC₂H₅)-phenyl | H | C(CH₃)₃ | OCH₃ | N | N | C—OCH₃ | 150–151 |
| 830 | 2-Cl-3-CH₃-phenyl | H | 2-(F₂HCO)-phenyl | OCH₃ | N | N | C—OCH₃ | 187 |
| 831 | 2-Cl-3-CH₃-phenyl | H | 2-(F₃C)-phenyl | OCH₃ | N | N | C—OCH₃ | 113–118 |
| 832 | 2-Cl-3-CH₃-phenyl | H | 3-CF₃-phenyl | OCH₃ | N | N | C—OCH₃ | 187 |

| | | | | | | | | |
|---|---|---|---|---|---|---|---|---|
| 833 | 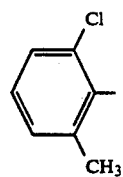 | H | 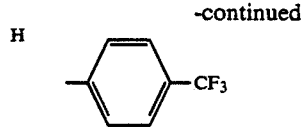 | OCH₃ | N | N | C—OCH₃ | 200–205 |
| 834 | 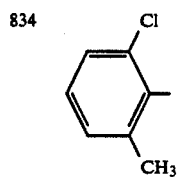 | H | 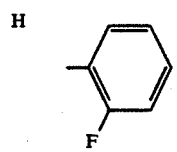 | OCH₃ | N | N | C—OCH₃ | 189 |
| 835 | 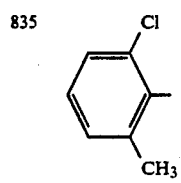 | H | 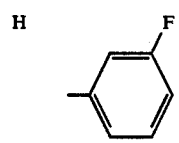 | OCH₃ | N | N | C—OCH₃ | 193–194 |
| 836 | 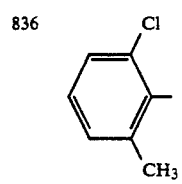 | H | 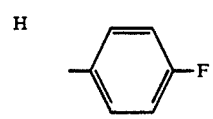 | OCH₃ | N | N | C—OCH₃ | 170 |
| 837 | 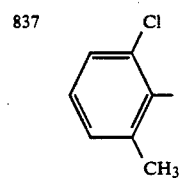 | H | 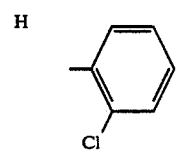 | OCH₃ | N | N | C—OCH₃ | 220–222 |
| 838 | 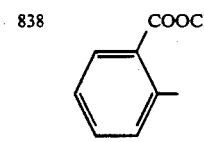 | CH₃ | CH₃ | OCH₃ | N | N | C—C₂H₅ | 142 |
| 839 | 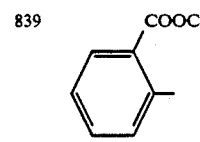 | H | C₆H₅ | OCH₃ | N | N | C—C₂H₅ | 140–141 |
| 840 | 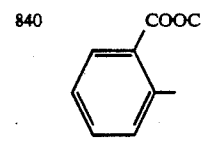 | H | C₆H₅ | OC₂H₅ | N | N | C—CH₃ | 150–152 |
| 841 | 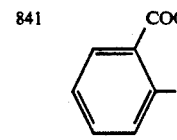 | CH₃ | CH₃ | OC₂H₅ | N | N | C—CH₃ | 149–152 |
| 842 | 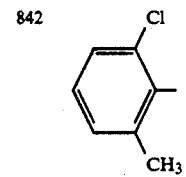 | H | 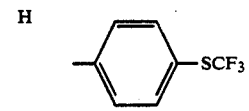 | OCH₃ | N | N | C—OCH₃ | 177 |

-continued
| | | | | | | | | |
|---|---|---|---|---|---|---|---|---|
| 843 | 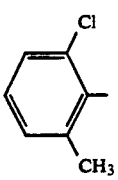 | H | 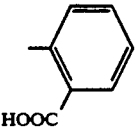 | OCH₃ | N | N | C—OCH₃ | 180 |
| 844 | 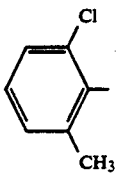 | H | —CH=CH—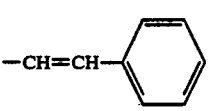 | OCH₃ | N | N | C—OCH₃ | 165–168 |
| 845 | 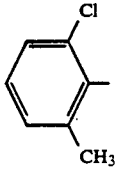 | —(CH₂)₅— | | OCH₃ | N | N | C—OCH₃ | 193–195 |
| 846 | 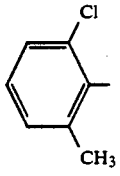 | H | CH(CH₃)₂ | OCH₃ | N | N | C—OCH₃ | 165–168 |
| 847 | 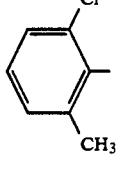 | H | C(CH₃)₃ | OCH₃ | N | N | C—OCH₃ | 84 |
| 848 | 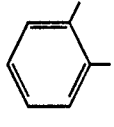 | H | 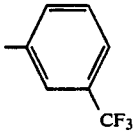 | OCH₃ | N | N | C—CH₃ | 175–176 |
| 849 | 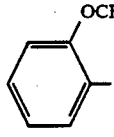 | H | 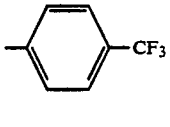 | OCH₃ | N | N | C—CH₃ | 158 |
| 850 | 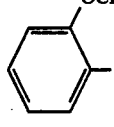 | H | 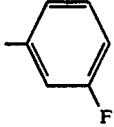 | OCH₃ | N | N | C—CH₃ | 153–160 |
| 851 | 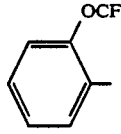 | H | 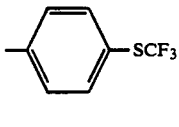 | OCH₃ | N | N | C—CH₃ | 139 |

-continued
| | 201 | | | 202 | | | | |
|---|---|---|---|---|---|---|---|---|
| 852 | 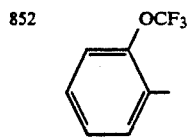 | H | 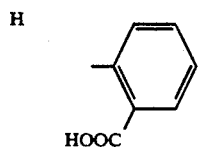 | OCH₃ | N | N | C—CH₃ | 183-186 |
| 853 | 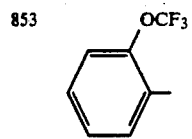 | —(CH₂)₅— | | OCH₃ | N | N | C—CH₃ | 140 |
| 854 | 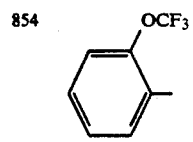 | CH₃ | CH₂CH(CH₃)₂ | OCH₃ | N | N | C—CH₃ | 102 |
| 855 | 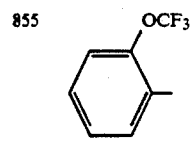 | H | 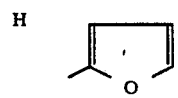 | OCH₃ | N | N | C—CH₃ | 168 |
| 856 | 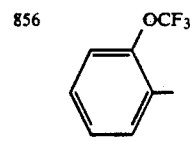 | H | 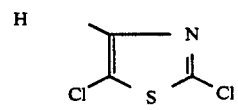 | OCH₃ | N | N | C—CH₃ | 176-178 |
| 857 | 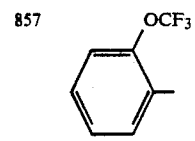 | H | 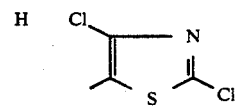 | OCH₃ | N | N | C—CH₃ | 198 |
| 858 | 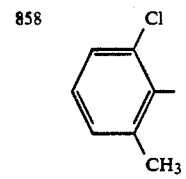 | H | 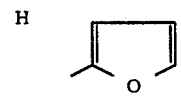 | OCH₃ | N | N | C—OCH₃ | 139 |
| 859 | 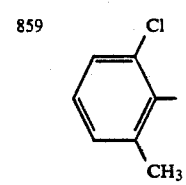 | H | 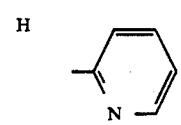 | OCH₃ | N | N | C—OCH₃ | 145-161 |
| 860 | 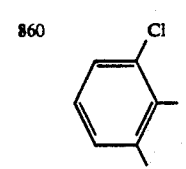 | H | 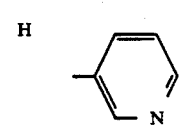 | OCH₃ | N | N | C—OCH₃ | 172 |
| 861 | 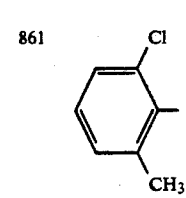 | H | 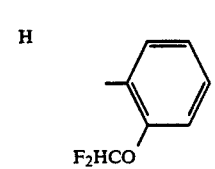 | OCH₃ | N | N | C—OCH₃ | 195-197 |

| | | | | | | | | |
|---|---|---|---|---|---|---|---|---|
| 862 | 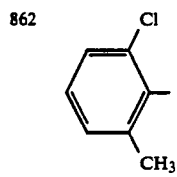 | H | 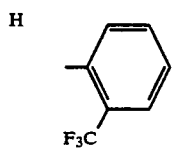 | OCH₃ | N | N | C—OCH₃ | 126–131 |
| 863 | 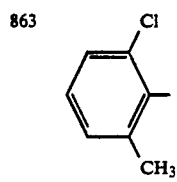 | H | 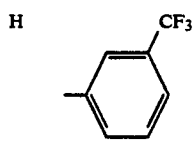 | OCH₃ | N | N | C—OCH₃ | 198–202 |
| 864 | 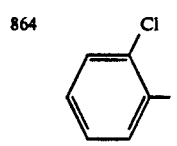 | CH₃ | CH₃ | OCH₃ | N | N | C—C₂H₅ | 175–177 |
| 865 | 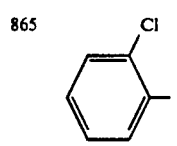 | H | C₆H₅ | OCH₃ | N | N | C—C₂H₅ | 189 |
| 866 | 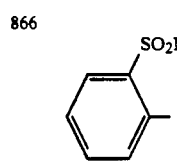 | H | C₆H₅ | OCH₃ | N | N | C—OCH₃ | 198–200 |
| 867 | 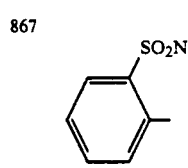 | CH₃ | CH₃ | OCH₃ | N | N | C—OCH₃ | 203–206 |
| 868 | 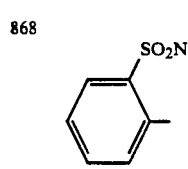 | CH₃ | CH₃ | CH₃ | N | N | C—CH₃ | 239 |
| 869 | 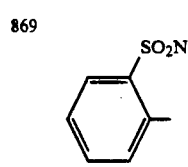 | H | C₆H₅ | CH₃ | N | N | C—CH₃ | 238–243 |
| 870 | 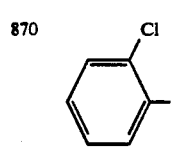 | CH₃ | CH₃ | SCH₃ | N | N | C—CH₃ | 188 |
| 871 | 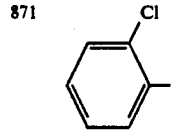 | H | C₆H₅ | SCH₃ | N | N | C—CH₃ | 216 |

-continued
| | 205 | | | | 206 | | | | |
|---|---|---|---|---|---|---|---|---|---|
| 872 | 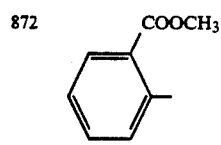 COOCH₃ | CH₃ | CH₃ | | SCH₃ | N | N | C—CH₃ | 182–187 |
| 873 | 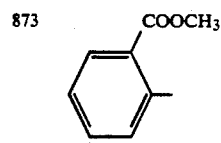 COOCH₃ | H | C₆H₅ | | SCH₃ | N | N | C—CH₃ | 210 |
| 874 | 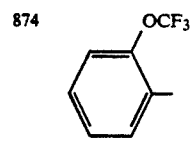 OCF₃ | CH₃ | CH₃ | | SCH₃ | N | N | C—CH₃ | 162–165 |
| 875 | 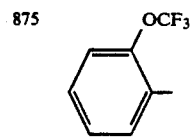 OCF₃ | H | C₆H₅ | | SCH₃ | N | N | C—CH₃ | 149 |
| 876 | 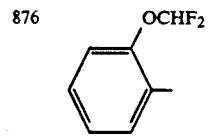 OCHF₂ | H | C₆H₅ | | OC₂H₅ | N | N | C—CH₃ | 199 |
| 877 | 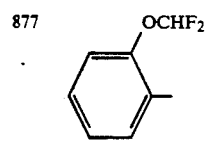 OCHF₂ | CH₃ | CH₃ | | OC₂H₅ | N | N | C—CH₃ | 150–155 |
| 878 | 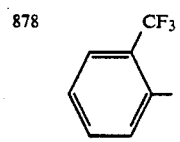 CF₃ | CH₃ | CH₃ | | SCH₃ | N | N | C—CH₃ | 158 |
| 879 | 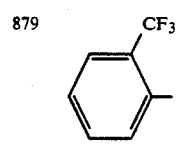 CF₃ | H | C₆H₅ | | SCH₃ | N | N | C—CH₃ | 206 |
| 880 | 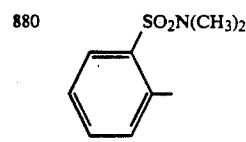 SO₂N(CH₃)₂ | CH₃ | CH₃ | | OCH₃ | N | N | C—C₂H₅ | 196 |
| 881 | 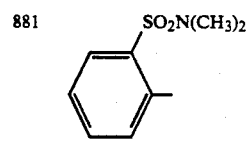 SO₂N(CH₃)₂ | H | C₆H₅ | | OCH₃ | N | N | C—C₂H₅ | 188–191 |
| 882 | 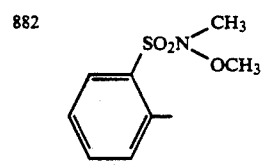 SO₂N(CH₃)(OCH₃) | CH₃ | CH₃ | | OC₂H₅ | N | N | C—CH₃ | 189–193 |

-continued

| No. | Ar1 | R | Ar2 | R' | X | Y | Z | mp |
|---|---|---|---|---|---|---|---|---|
| 883 | 2-(N-methyl-N-methoxysulfamoyl)-methylphenyl | H | C6H5 | OC2H5 | N | N | C—CH3 | 180–187 |
| 884 | 2,6-dichlorophenyl | CH3 | CH3 | OCH3 | N | N | C—CH3 | 174–181 |
| 885 | 2,6-dichlorophenyl | H | C6H5 | OCH3 | N | N | C—CH3 | 171–185 |
| 886 | 2,6-dichlorophenyl | H | 2-(F2HCO)phenyl | OCH3 | N | N | C—CH3 | 190 |
| 887 | 2,6-dichlorophenyl | H | 2-(F3C)phenyl | OCH3 | N | N | C—CH3 | 180 |
| 888 | 2,6-dichlorophenyl | H | 3-(CF3)phenyl | OCH3 | N | N | C—CH3 | 180 |
| 889 | 2,6-dichlorophenyl | H | 2-F-phenyl | OCH3 | N | N | C—CH3 | 224–225 |
| 890 | 2,6-dichlorophenyl | H | 4-F-phenyl | OCH3 | N | N | C—CH3 | 220–221 |
| 891 | 2,6-dichlorophenyl | H | 2-Cl-phenyl | OCH3 | N | N | C—CH3 | 212 |

| | | | | | | | | |
|---|---|---|---|---|---|---|---|---|
| 892 | 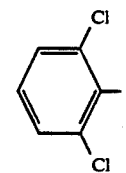 2,6-Cl₂-C₆H₃ | H | 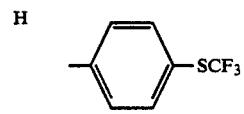 4-SCF₃-C₆H₄ | OCH₃ | N | N | C—CH₃ | 147–149 |
| 893 | 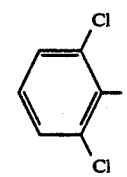 2,6-Cl₂-C₆H₃ | H | 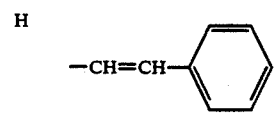 —CH=CH-C₆H₅ | OCH₃ | N | N | C—CH₃ | 211–215 |
| 894 | 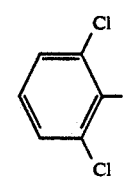 2,6-Cl₂-C₆H₃ | —(CH₂)₅— | | OCH₃ | N | N | C—CH₃ | 208 |
| 895 | 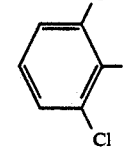 2,6-Cl₂-C₆H₃ | H | CH(CH₃)₂ | OCH₃ | N | N | C—CH₃ | 198–202 |
| 896 | 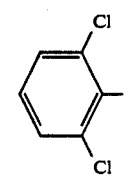 2,6-Cl₂-C₆H₃ | CH₃ | CH₂CH(CH₃)₂ | OCH₃ | N | N | C—CH₃ | 167–169 |
| 897 | 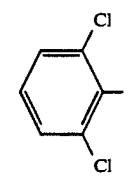 2,6-Cl₂-C₆H₃ | H | C(CH₃)₃ | OCH₃ | N | N | C—CH₃ | 194 |
| 898 | 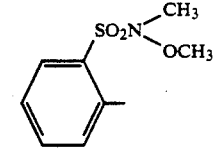 | H | 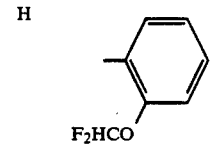 2-F₂HCO-C₆H₄ | OCH₃ | N | N | C—CH₃ | 165–169 |
| 899 | 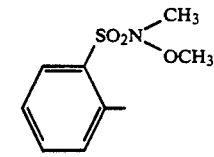 | H | 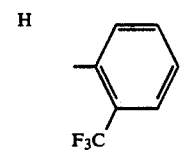 3-CF₃-C₆H₄ | OCH₃ | N | N | C—CH₃ | 163–188 |
| 900 | 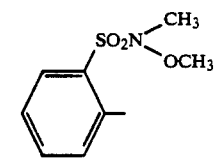 | H | 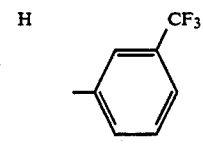 3-CF₃-C₆H₄ | OCH₃ | N | N | C—CH₃ | 204–206 |

-continued
| | 211 | | | 212 | | | | |
|---|---|---|---|---|---|---|---|---|
| 901 | 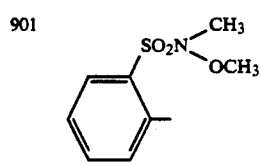 | H | 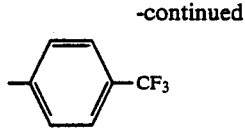 | OCH$_3$ | N | N | C—CH$_3$ | 207–209 |
| 902 | 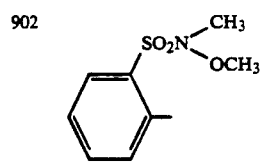 | H | 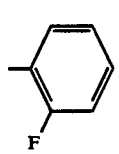 | OCH$_3$ | N | N | C—CH$_3$ | 220–223 |
| 903 | 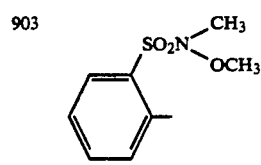 | H | 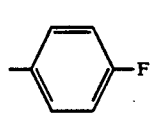 | OCH$_3$ | N | N | C—CH$_3$ | 208–209 |
| 904 | 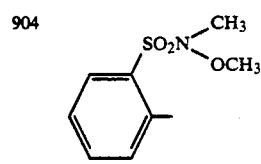 | H | 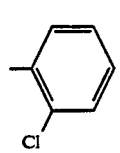 | OCH$_3$ | N | N | C—CH$_3$ | 205–210 |
| 905 | 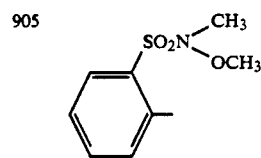 | H | 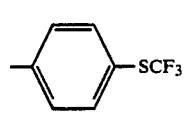 | OCH$_3$ | N | N | C—CH$_3$ | 206 |
| 906 | 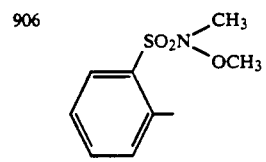 | H | 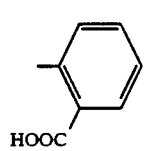 | OCH$_3$ | N | N | C—CH$_3$ | 216 |
| 907 | 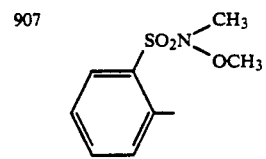 | H | 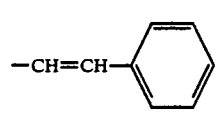 | OCH$_3$ | N | N | C—CH$_3$ | 226–228 |
| 908 | 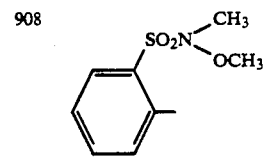 | —(CH$_2$)$_5$— | | OCH$_3$ | N | N | C—CH$_3$ | 190–198 |
| 909 | 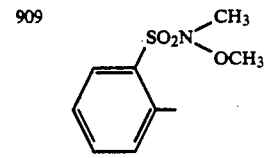 | H | CH(CH$_3$)$_2$ | OCH$_3$ | N | N | C—CH$_3$ | 155–159 |
| 910 | 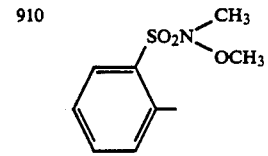 | H | C(CH$_3$)$_3$ | OCH$_3$ | N | N | C—CH$_3$ | $^1$H NMR*)δ= 4,04 ppm (OCH$_3$) |

| No. | (col 213 structure) | R1 | R2 | OCH₃ | N | N | C-R | mp |
|---|---|---|---|---|---|---|---|---|
| 911 | 2-CH₃-C₆H₄-SO₂N(CH₃)(OCH₃) | CH₃ | CH₂CH(CH₃)₂ | OCH₃ | N | N | C—CH₃ | 161–163 |
| 912 | 2-CH₃-C₆H₄-SO₂N(CH₃)(OCH₃) | H | CH₃ | OCH₃ | N | N | C—CH₃ | 149 |
| 913 | 2-CH₃-C₆H₄-SO₂N(CH₃)(OCH₃) | H | 2-methylfuryl | OCH₃ | N | N | C—CH₃ | 208 |
| 914 | 2,6-dichlorophenyl | H | 2-methylfuryl | OCH₃ | N | N | C—CH₃ | 210–215 |
| 915 | 2-CH₃-C₆H₄-SO₂N(CH₃)(OCH₃) | H | 2-pyridyl | OCH₃ | N | N | C—CH₃ | 186 |
| 916 | 2-CH₃-C₆H₄-SO₂N(CH₃)(OCH₃) | H | 3-pyridyl | OCH₃ | N | N | C—CH₃ | 180–185 |
| 917 | 2-CH₃-C₆H₄-SO₂N(CH₃)(OCH₃) | H | 4-pyridyl | OCH₃ | N | N | C—CH₃ | 175–178 |
| 918 | 2-COOC₃H₇-C₆H₄ | CH₃ | CH₃ | OCH₃ | N | N | C—C₂H₅ | 145–148 |
| 919 | 2-OCHF₂-C₆H₄ | H | C(CH₃)₃ | OCH₃ | N | N | C—OCH₃ | 153–156 |
| 920 | 2-OCHF₂-C₆H₄ | CH₃ | CH₂CH(CH₃)₂ | OCH₃ | N | N | C—OCH₃ | 163 |

| | | | | | | | | |
|---|---|---|---|---|---|---|---|---|
| 921 | 2-SO₂N(CH₃)₂, 6-CH₃ phenyl | H | C(CH₃)₃ | OCH₃ | N | N | C—OCH₃ | 136 |
| 922 | 2-Cl, 6-CH₃ phenyl | H | C₆H₅ | OCH₃ | N | N | C—CH₃ | 181 |
| 923 | 2-Cl, 6-CH₃ phenyl | CH₃ | CH₃ | OCH₃ | N | N | C—CH₃ | 175–176 |
| 924 | 2-Cl, 6-CH₃ phenyl | H | 2-(OCHF₂)phenyl | OCH₃ | N | N | C—CH₃ | 167 |
| 925 | 2-Cl, 6-CH₃ phenyl | H | 2-CF₃ phenyl | OCH₃ | N | N | C—CH₃ | 151 |
| 926 | 2-Cl, 6-CH₃ phenyl | H | 3-CF₃ phenyl | OCH₃ | N | N | C—CH₃ | 172 |
| 927 | 2-Cl, 6-CH₃ phenyl | H | 4-CF₃ phenyl | OCH₃ | N | N | C—CH₃ | 129–132 |
| 928 | 2-Cl, 6-CH₃ phenyl | H | 2-F phenyl | OCH₃ | N | N | C—CH₃ | 182 |
| 929 | 2-Cl, 6-CH₃ phenyl | H | 4-F phenyl | OCH₃ | N | N | C—CH₃ | 202 |

-continued
| | | | | | | | | |
|---|---|---|---|---|---|---|---|---|
| 930 | 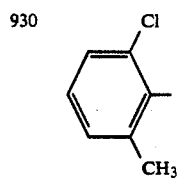 | H | 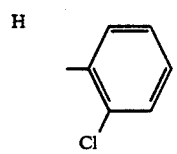 | OCH$_3$ | N | N | C—CH$_3$ | 208 |
| 931 | 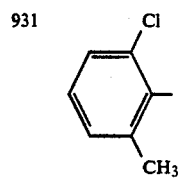 | H | 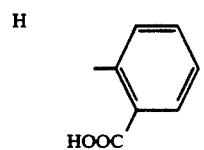 | OCH$_3$ | N | N | C—CH$_3$ | 172–173 |
| 932 | 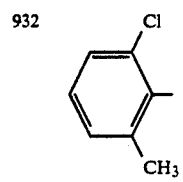 | H | 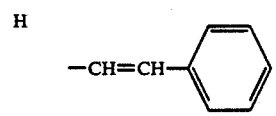 | OCH$_3$ | N | N | C—CH$_3$ | 180–183 |
| 933 | 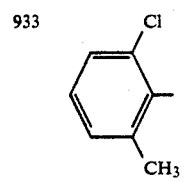 | —(CH$_2$)$_5$— | | OCH$_3$ | N | N | C—CH$_3$ | 195 |
| 934 | 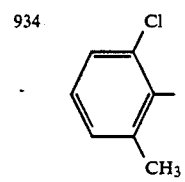 | H | CH(CH$_3$)$_2$ | OCH$_3$ | N | N | C—CH$_3$ | 148 |
| 935 | 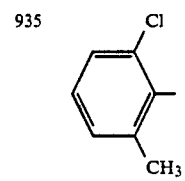 | H | C(CH$_3$)$_3$ | OCH$_3$ | N | N | C—CH$_3$ | 157 |
| 936 | 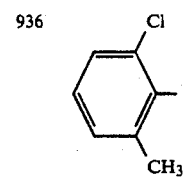 | CH$_3$ | CH$_2$CH(CH$_3$)$_2$ | OCH$_3$ | N | N | C—CH$_3$ | 130 |
| 937 | 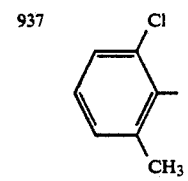 | H | 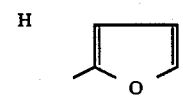 | OCH$_3$ | N | N | C—CH$_3$ | 160 |
| 938 | 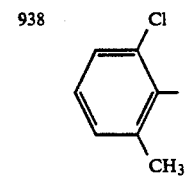 | H | 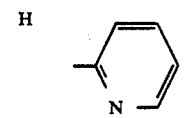 | OCH$_3$ | N | N | C—CH$_3$ | 161 |

-continued
| | | | | | | | |
|---|---|---|---|---|---|---|---|
| 939 | 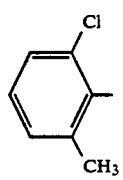 | H | 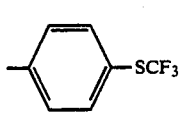 | OCH₃ | N | N | C—CH₃ | 140 |
| 940 | 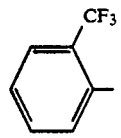 | H | 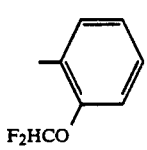 | OCH₃ | N | N | C—CH₃ | 177 |
| 941 | 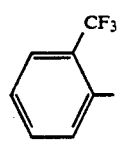 | H | 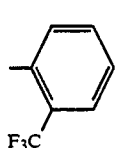 | OCH₃ | N | N | C—CH₃ | 193 |
| 942 | 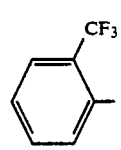 | H | 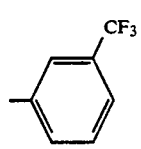 | OCH₃ | N | N | C—CH₃ | 183 |
| 943 | 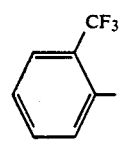 | H | 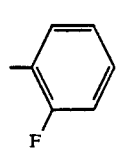 | OCH₃ | N | N | C—CH₃ | 201-203 |
| 944 | 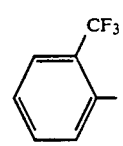 | H | 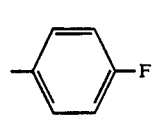 | OCH₃ | N | N | C—CH₃ | 209 |
| 945 | 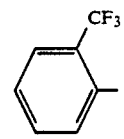 | H | 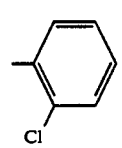 | OCH₃ | N | N | C—CH₃ | 184 |
| 946 | 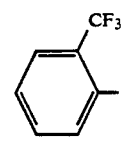 | H | 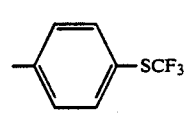 | OCH₃ | N | N | C—CH₃ | 149 |
| 947 | 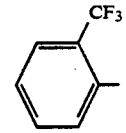 | H | 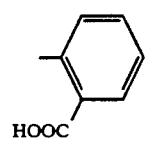 | OCH₃ | N | N | C—CH₃ | 150 |
| 948 | 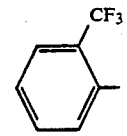 | H | —CH=CH—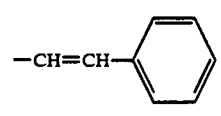 | OCH₃ | N | N | C—CH₃ | 184 |

-continued
| | | | | | | | |
|---|---|---|---|---|---|---|---|
| 949 | 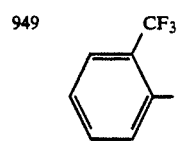 | —(CH$_2$)$_5$— | | OCH$_3$ | N N | C—CH$_3$ | 153 |
| 950 | 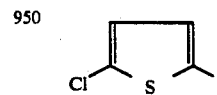 | H | C$_6$H$_5$ | OCH$_3$ | N N | C—OCH$_3$ | 185 |
| 951 | 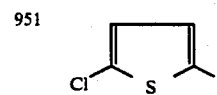 | CH$_3$ | CH$_3$ | OCH$_3$ | N N | C—CH$_3$ | 148 |
| 952 | 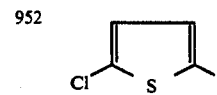 | H | C$_6$H$_5$ | OCH$_3$ | N N | C—CH$_3$ | 206 |
| 953 | 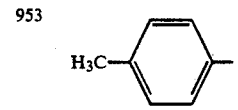 | CH$_3$ | CH$_3$ | OCH$_3$ | N N | C—CH$_3$ | 149 |
| 954 | 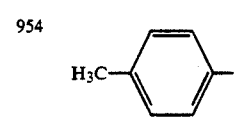 | H | C$_6$H$_5$ | OCH$_3$ | N N | C—CH$_3$ | 153 |
| 955 | 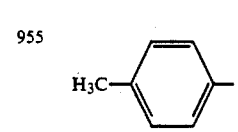 | CH$_3$ | CH$_3$ | OCH$_3$ | N N | C—OCH$_3$ | 185 |
| 956 | 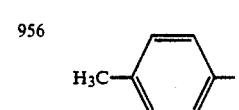 | H | C$_6$H$_5$ | OCH$_3$ | N N | C—OCH$_3$ | 164 |
| 957 | 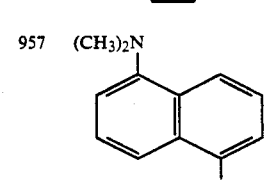 | CH$_3$ | CH$_3$ | OCH$_3$ | N N | C—CH$_3$ | 210 |
| 958 | 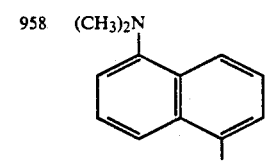 | H | C$_6$H$_5$ | OCH$_3$ | N N | C—CH$_3$ | 241 |
| 959 | 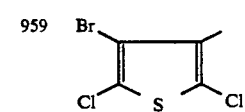 | H | C$_6$H$_5$ | OCH$_3$ | N N | C—OCH$_3$ | 176 |
| 960 | 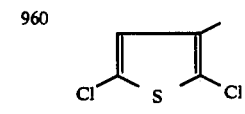 | CH$_3$ | CH$_3$ | OCH$_3$ | N N | C—OCH$_3$ | 136 |
| 961 | 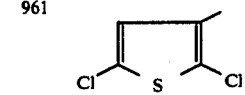 | H | C$_6$H$_5$ | OCH$_3$ | N N | C—OCH$_3$ | 145 |

-continued
| | | | | | | | | |
|---|---|---|---|---|---|---|---|---|
| 962 | 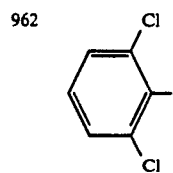 | H | 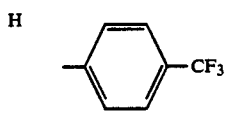 | OCH$_3$ | N | N | C—OCH$_3$ | 183 |
| 963 | 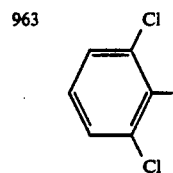 | H | 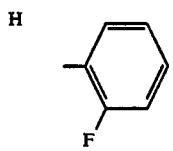 | OCH$_3$ | N | N | C—OCH$_3$ | 180–184 |
| 964 | 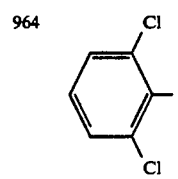 | H | 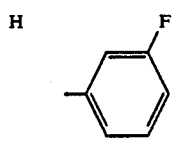 | OCH$_3$ | N | N | C—OCH$_3$ | 174–180 |
| 965 | 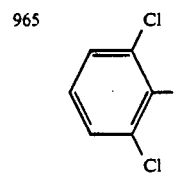 | H | 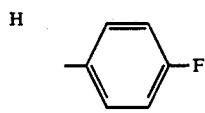 | OCH$_3$ | N | N | C—OCH$_3$ | 186–188 |
| 966 | 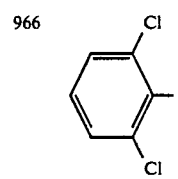 | H | 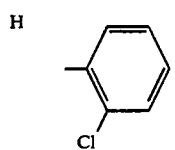 | OCH$_3$ | N | N | C—OCH$_3$ | 221 |
| 967 | 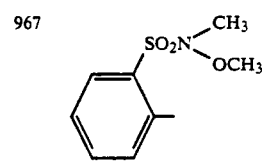 | H | 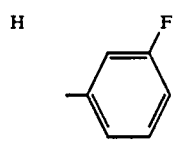 | OCH$_3$ | N | N | C—CH$_3$ | 216 |
| 968 | 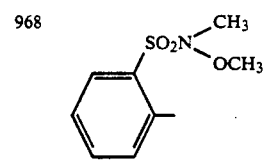 | H | 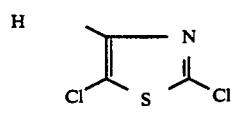 | OCH$_3$ | N | N | C—CH$_3$ | 177 |
| 969 | 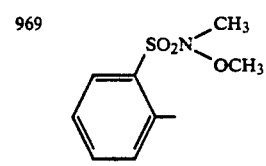 | H | 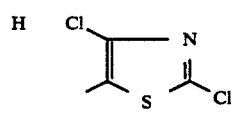 | OCH$_3$ | N | N | C—CH$_3$ | 199–204 |
| 970 | 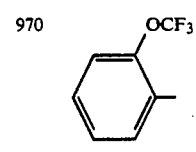 | H | 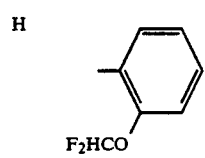 | OCH$_3$ | N | N | C—OCH$_3$ | 188–190 |

5,213,608
-continued
| | | | | | | | | |
|---|---|---|---|---|---|---|---|---|
| 971 | 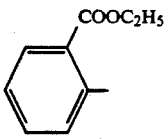 | CH₃ | CH₂CH(CH₃)₂ | OCH₃ | N | N | C—OCH₃ | 150–153 |
| 972 | 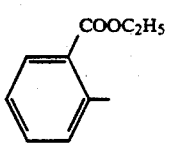 | H | CH₃ | OCH₃ | N | N | C—OCH₃ | 140–145 |
| 973 | 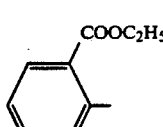 | H | 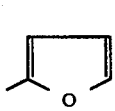 | OCH₃ | N | N | C—OCH₃ | 184 |
| 974 | 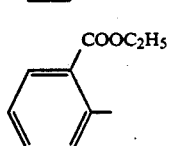 | H | 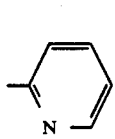 | OCH₃ | N | N | C—OCH₃ | 148 |
| 975 | 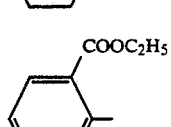 | H | 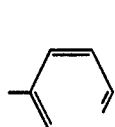 | OCH₃ | N | N | C—OCH₃ | 146 |
| 976 | 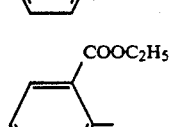 | H | 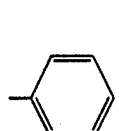 | OCH₃ | N | N | C—CH₃ | 168 |
| 977 | 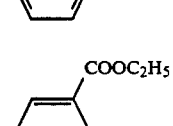 | H | 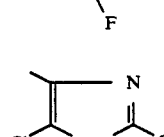 | OCH₃ | N | N | C—CH₃ | 156 |
| 978 | 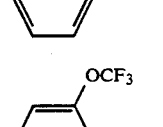 | H |  | OCH₃ | N | N | C—CH₃ | 152 |
| 979 | 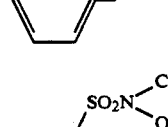 | H | 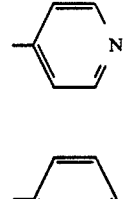 | OCH₃ | N | N | C—CH₃ | 175 |
| 980 | 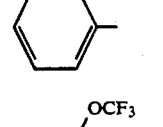 | H | 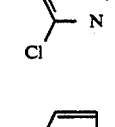 | OCH₃ | N | N | C—CH₃ | 149 |
| 981 | 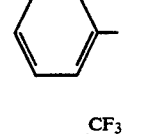 | H | 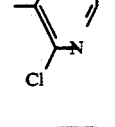 | OCH₃ | N | N | C—CH₃ | 173–175 |

-continued
| | | | | | | | | |
|---|---|---|---|---|---|---|---|---|
| 982 | 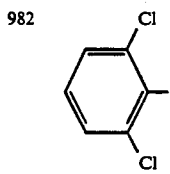 | H | 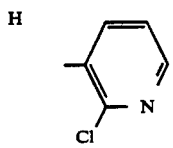 | OCH$_3$ | N | N | C—CH$_3$ | 215 |
| 983 | 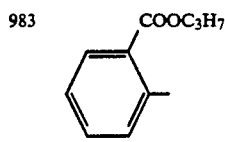 | CH$_3$ | CH$_3$ | OC$_2$H$_5$ | N | N | C—CH$_3$ | 146-148 |
| 984 | 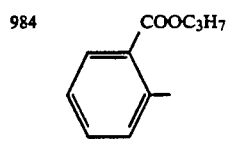 | H | C$_6$H$_5$ | OC$_2$H$_5$ | N | N | C—CH$_3$ | 155-158 |
| 985 | 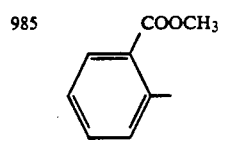 | H | C$_6$H$_5$ | CH$_3$ | N | N | C—CH$_3$ | 212-214 |
| 986 | 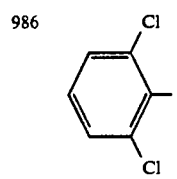 | H | 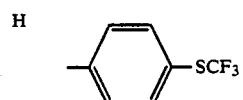 | OCH$_3$ | N | N | C—OCH$_3$ | 173-174 |
| 987 | 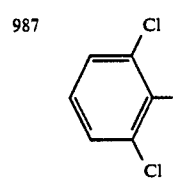 | H | 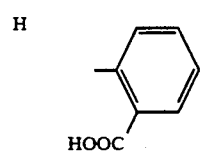 | OCH$_3$ | N | N | C—OCH$_3$ | 190-194 |
| 988 | 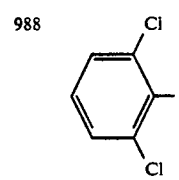 | H | 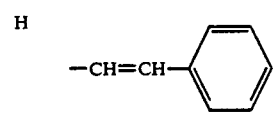 | OCH$_3$ | N | N | C—OCH$_3$ | 190-196 |
| 989 | 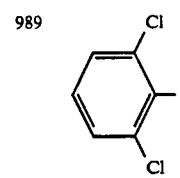 | —(CH$_2$)$_5$— | | OCH$_3$ | N | N | C—OCH$_3$ | 223 |
| 990 | 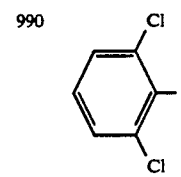 | H | CH(CH$_3$)$_2$ | OCH$_3$ | N | N | C—OCH$_3$ | 175-179 |
| 991 | 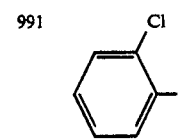 | H | C$_6$H$_5$ | CH$_3$ | N | N | C—CH$_3$ | 190 |

-continued

| # | Ar | R1 | R2 | X | A | B | Y | mp |
|---|---|---|---|---|---|---|---|---|
| 992 | 2-OCHF₂-C₆H₄ | H | C₆H₅ | CH₃ | N | N | C—CH₃ | 175 |
| 993 | 2-OCH₃-C₆H₄ | H | C₆H₅ | OC₂H₅ | N | N | C—CH₃ | 197–199 |
| 994 | 4-NC-C₆H₄ | H | C₆H₅ | OCH₃ | N | N | C—OCH₃ | 226–230 |
| 995 | 4-NC-C₆H₄ | CH₃ | CH₃ | OCH₃ | N | N | C—OCH₃ | 190 |
| 996 | 2-OCH₃-C₆H₄ | H | C₆H₅ | OCH₃ | N | N | C—C₂H₅ | 195–199 |
| 997 | 2-OCH₃-C₆H₄ | H | C₆H₅ | OCH₃ | N | N | C—CH₃ | 166–168 |
| 998 | 2-OCH₃-C₆H₄ | CH₃ | CH₃ | OCH₃ | N | N | C—CH₃ | 167–168 |
| 999 | 2-CF₃-C₆H₄ | H | C₆H₅ | CH₃ | N | N | C—CH₃ | 201–203 |
| 1000 | C₆H₅ | CH₃ | CH₃ | OCH₃ | N | N | C—OCH₃ | 185–187 |
| 1001 | C₆H₅ | H | C₆H₅ | OCH₃ | N | N | C—OCH₃ | 203–205 |
| 1002 | 3-CF₃-C₆H₄ | H | C₆H₅ | OCH₃ | N | N | C—CH₃ | 194–198 |
| 1003 | 2-OCH₃-C₆H₄ | CH₃ | CH₃ | OC₂H₅ | N | N | C—CH₃ | 176–178 |

-continued

| No. | Ar | R1 | R2 | X | A | B | D | mp (°C) |
|---|---|---|---|---|---|---|---|---|
| 1004 | 4-Br-C6H4 | H | C6H5 | OCH3 | N | N | C—CH3 | 224–226 |
| 1005 | 3-Cl-4-F-C6H3 | H | C6H5 | OCH3 | N | N | C—CH3 | 181–183 |
| 1006 | 2,5-dichloro-3-bromo-4-methyl-thien-yl | H | C6H5 | OCH3 | N | N | C—CH3 | 174–175 |
| 1007 | 2-CN-C6H4 | CH3 | CH3 | OCH3 | N | N | C—CH3 | 180–182 |
| 1008 | 2-CN-C6H4 | H | C6H5 | OCH3 | N | N | C—CH3 | 214–216 |
| 1009 | 2,6-Cl2-C6H3 | H | C(CH3)3 | OCH3 | N | N | C—OCH3 | 171–172 |
| 1010 | 2,6-Cl2-C6H3 | CH3 | CH2CH(CH3)2 | OCH3 | N | N | C—OCH3 | 150–156 |
| 1011 | 2,6-Cl2-C6H3 | H | CH3 | OCH3 | N | N | C—OCH3 | 145–150 |
| 1012 | 2,6-Cl2-C6H3 | H | 2-furyl | OCH3 | N | N | C—OCH3 | 140 |
| 1013 | 2,6-Cl2-C6H3 | H | 2-pyridyl | OCH3 | N | N | C—OCH3 | 169–174 |

| # | R1 (aryl) | R2 | R3 | col4 | col5 | col6 | col7 | mp |
|---|---|---|---|---|---|---|---|---|
| 1014 | 2,6-diCl-phenyl | H | 3-pyridyl | OCH₃ | N | N | C—OCH₃ | 177 |
| 1015 | 2,6-diCl-phenyl | H | 4-pyridyl | OCH₃ | N | N | C—OCH₃ | 114–120 |
| 1016 | 2,6-diCl-phenyl | H | 2-Cl-3-pyridyl | OCH₃ | N | N | C—OCH₃ | 196–199 |
| 1017 | phenyl | CH₃ | CH₃ | OCH₃ | N | N | C—CH₃ | 173 |
| 1018 | phenyl | H | C₆H₅ | OCH₃ | N | N | C—CH₃ | 186 |
| 1019 | 2-COOC₂H₅-phenyl | H | 4-pyridyl | OCH₃ | N | N | C—OCH₃ | 193 |
| 1020 | 2-COOC₂H₅-phenyl | H | 2-Cl-3-pyridyl | OCH₃ | N | N | C—OCH₃ | 171 |
| 1021 | 2-COOC₂H₅-phenyl | H | 5-Cl-4-methyl-2-Cl-thiazolyl | OCH₃ | N | N | C—OCH₃ | 153–156 |
| 1022 | 2-COOC₂H₅-phenyl | H | 4-Cl-5-methyl-2-Cl-thiazolyl | OCH₃ | N | N | C—OCH₃ | 205 |
| 1023 | 2-OCF₃-phenyl | H | 3-CF₃-phenyl | OCH₃ | N | N | C—OCH₃ | 162–169 |
| 1024 | 2-OCF₃-phenyl | H | 3-CF₃-phenyl | OCH₃ | N | N | C—OCH₃ | 145 |

| No. | Ar1 | R | Ar2/R' | | | | | mp |
|---|---|---|---|---|---|---|---|---|
| 1025 | 2-OCF₃-phenyl | H | 4-CF₃-phenyl | OCH₃ | N | N | C—OCH₃ | 158 |
| 1026 | 2-OCF₃-phenyl | H | 2-F-phenyl | OCH₃ | N | N | C—OCH₃ | 204 |
| 1027 | 2-OCF₃-phenyl | H | 3-F-phenyl | OCH₃ | N | N | C—OCH₃ | 179 |
| 1028 | 2-OCF₃-phenyl | H | 4-F-phenyl | OCH₃ | N | N | C—OCH₃ | 178–182 |
| 1029 | 2-OCF₃-phenyl | H | 2-Cl-phenyl | OCH₃ | N | N | C—OCH₃ | 190–192 |
| 1030 | 2-OCF₃-phenyl | H | 4-SCF₃-phenyl | OCH₃ | N | N | C—OCH₃ | 142 |
| 1031 | 2-OCF₃-phenyl | H | 2-HOOC-phenyl | OCH₃ | N | N | C—OCH₃ | 223 |
| 1032 | 2-OCF₃-phenyl | H | —CH=CH—phenyl | OCH₃ | N | N | C—OCH₃ | 206 |
| 1033 | 2-OCF₃-phenyl | —(CH₂)₅— | | OCH₃ | N | N | C—OCH₃ | 134 |
| 1034 | 2-OCF₃-phenyl | H | CH(CH₃)₂ | OCH₃ | N | N | C—OCH₃ | 119 |
| 1035 | 2-OCF₃-phenyl | H | C(CH₃)₃ | OCH₃ | N | N | C—OCH₃ | 152–155 |

-continued
| | | | | | | | | |
|---|---|---|---|---|---|---|---|---|
| 1036 | 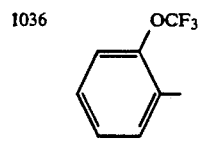 | CH₃ | CH₂CH(CH₃)₂ | | OCH₃ | N | N | C—OCH₃ | 141 |
| 1037 | 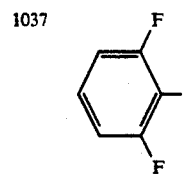 | CH₃ | CH₃ | | OCH₃ | N | N | C—CH₃ | 171 |
| 1038 | 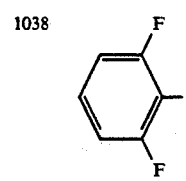 | H | C₆H₅ | | OCH₃ | N | N | C—CH₃ | 236 |
| 1039 | 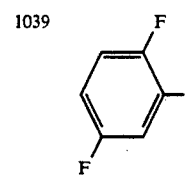 | CH₃ | CH₃ | | OCH₃ | N | N | C—CH₃ | 174–175 |
| 1040 | 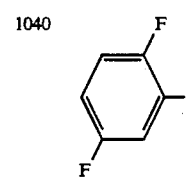 | H | C₆H₅ | | OCH₃ | N | N | C—CH₃ | 193 |
| 1041 | 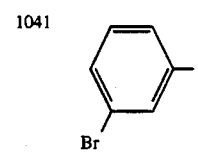 | CH₃ | CH₃ | | OCH₃ | N | N | C—CH₃ | 134 |
| 1042 | 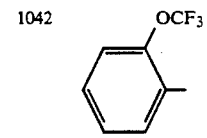 | H | CH₃ | | OCH₃ | N | N | C—OCH₃ | 127–135 |
| 1043 | 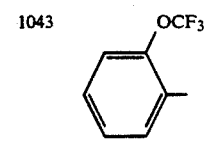 | H | 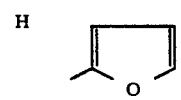 | | OCH₃ | N | N | C—OCH₃ | 176–179 |
| 1044 | 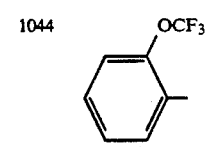 | H | 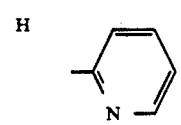 | | OCH₃ | N | N | C—OCH₃ | 151 |
| 1045 | 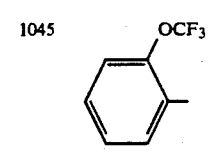 | H | 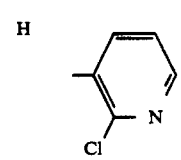 | | OCH₃ | N | N | C—OCH₃ | 186–193 |

-continued

| No. | R1 (aryl) | R2 | R3 | R4 | X | Y | Z | mp (°C) |
|---|---|---|---|---|---|---|---|---|
| 1046 | 2-OCF₃-C₆H₄ | H | C₆H₅ | CH₃ | N | N | C—CH₃ | 193–195 |
| 1047 | 2-COOC₂H₅-C₆H₄ | CH₃ | CH₃ | CH₃ | N | N | C—CH₃ | 103–105 |
| 1048 | 2-COOC₂H₅-C₆H₄ | H | C₆H₅ | CH₃ | N | N | C—CH₃ | 74 |
| 1049 | 2-F-C₆H₄ | H | C₆H₅ | CH₃ | N | N | C—CH₃ | 187 |
| 1050 | 2-SO₂N(C₂H₅)₂-C₆H₄ | H | 4-CF₃-C₆H₄ | OCH₃ | N | N | C—OCH₃ | 205–206 |
| 1051 | 2-SO₂N(C₂H₅)₂-C₆H₄ | H | 3-F-C₆H₄ | OCH₃ | N | N | C—OCH₃ | 180–183 |
| 1052 | 2-SO₂N(C₂H₅)₂-C₆H₄ | H | 2-HOOC-C₆H₄ | OCH₃ | N | N | C—OCH₃ | ¹H NMR*) δ = 3.98 ppm (OCH₃) |
| 1053 | 2-SO₂N(C₂H₅)₂-C₆H₄ | H | 2-Cl-pyridin-3-yl | OCH₃ | N | N | C—OCH₃ | 132–134 |
| 1054 | 2-SO₂N(C₂H₅)₂-C₆H₄ | H | 6-Cl-pyridin-3-yl | OCH₃ | N | N | C—OCH₃ | 222–224 |
| 1055 | 2-COOC₂H₅-C₆H₄ | H | 6-Cl-pyridin-3-yl | OCH₃ | N | N | C—OCH₃ | 204–205 |
| 1056 | 2,6-Cl₂-C₆H₃ | H | 6-Cl-pyridin-3-yl | OCH₃ | N | N | C—OCH₃ | 198–205 |

-continued
| | | | | | | | | |
|---|---|---|---|---|---|---|---|---|
| 1057 | 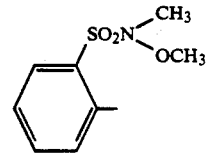 | H | 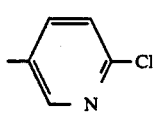 | OCH$_3$ | N | N | C—CH$_3$ | 202-204 |
| 1058 | 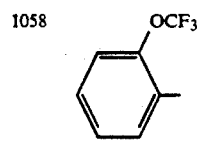 | H | 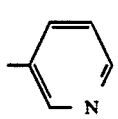 | OCH$_3$ | N | N | C—CH$_3$ | 189 |
| 1059 | 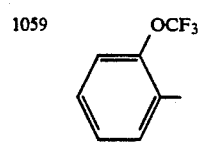 | H | 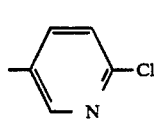 | OCH$_3$ | N | N | C—CH$_3$ | 117-12 |
| 1060 | 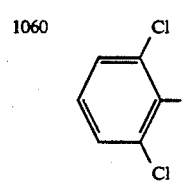 | H | 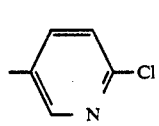 | OCH$_3$ | N | N | C—CH$_3$ | 211-216 |
| 1061 | 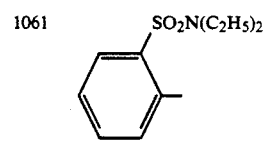 | CH$_3$ | C$_2$H$_5$ | OCH$_3$ | N | N | C—OCH$_3$ | 156-160 |
| 1062 | 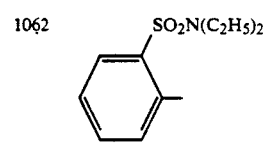 | H | —C=CHC$_2$H$_5$<br>      CH$_3$ | OCH$_3$ | N | N | C—OCH$_3$ | 176 |
| 1063 | 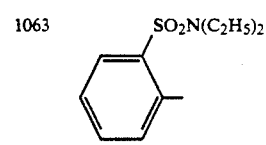 | CH$_3$ | CH$_2$OCH$_3$ | OCH$_3$ | N | N | C—OCH$_3$ | 210 |
| 1064 | 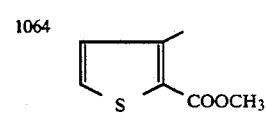 | CH$_3$ | CH$_2$CH(CH$_3$)$_2$ | OCH$_3$ | N | N | C—CH$_3$ | 115 |
| 1065 | 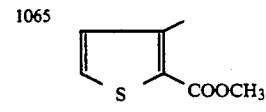 | H | C(CH$_3$)$_3$ | OCH$_3$ | N | N | C—CH$_3$ | 214 |
| 1066 | 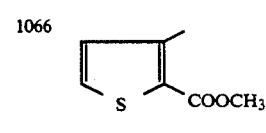 | H | CH(C$_2$H$_5$)$_2$ | OCH$_3$ | N | N | C—CH$_3$ | 159 |
| 1067 | 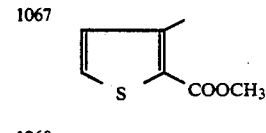 | CH$_3$ | C$_2$H$_5$ | OCH$_3$ | N | N | C—CH$_3$ | 137 |
| 1068 | 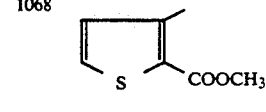 | H | —C=CHC$_2$H$_5$<br>      CH$_3$ | OCH$_3$ | N | N | C—CH$_3$ | 178-185 |

-continued

| # | R1 | R2 | R3 | R4 | X | Y | Z | mp |
|---|---|---|---|---|---|---|---|---|
| 1069 | 3-methyl-thiophene-2-COOCH3 | CH3 | CH2OCH3 | | OCH3 | N | N | C—CH3 | 134–138 |
| 1070 | 2-SO2N(CH3)2-methylphenyl | H | C2H5 | | OCH3 | N | N | C—CH3 | 165–166 |
| 1071 | 2-SO2N(CH3)2-methylphenyl | H | C9H19—n | | OCH3 | N | N | C—CH3 | 111–115 |
| 1072 | 2-SO2N(CH3)2-methylphenyl | H | CH2—C6H5 | | OCH3 | N | N | C—CH3 | 97–104 |
| 1073 | 3-methyl-thiophene-2-COOCH3 | H | C9H19-n | | OCH3 | N | N | C—CH3 | 112–113 |
| 1074 | 2-SO2N(C2H5)2-methylphenyl | H | CH(C2H5)2 | | OCH3 | N | N | C—OCH3 | 120 |
| 1075 | 2-F-methylphenyl | CH3 | CH3 | | SCH3 | N | N | C—CH3 | 166 |
| 1076 | 2-F-methylphenyl | CH3 | CH3 | | OC2H5 | N | N | C—CH3 | 144 |
| 1077 | 2-SO2N(C2H5)2-methylphenyl | H | C2H5 | | OCH3 | N | N | C—OCH3 | 125 |
| 1078 | 2-SO2N(C2H5)2-methylphenyl | H | —(CH2)8—CH3 | | OCH3 | N | N | C—OCH3 | 104 |
| 1079 | 2-SO2N(C2H5)2-methylphenyl | H | —CH2—C6H5 | | OCH3 | N | N | C—OCH3 | 158 |
| 1080 | 2-SO2N(C2H5)2-methylphenyl | CH3 | CH2CH(CH3)2 | | OCH3 | N | N | C—CH3 | 158 |

-continued

| No. | R1 | R2 | R3 | R4 | X | Y | Z | mp |
|---|---|---|---|---|---|---|---|---|
| 1081 | 2-SO₂N(C₂H₅)₂-C₆H₄ | H | CH₃ | | OCH₃ | N | N | C—CH₃ | 158 |
| 1082 | 2-SO₂N(C₂H₅)₂-C₆H₄ | H | 5-methylfuran-2-yl | | OCH₃ | N | N | C—CH₃ | 230 |
| 1083 | 2-SO₂N(C₂H₅)₂-C₆H₄ | H | pyridin-4-yl | | OCH₃ | N | N | C—CH₃ | 196 |
| 1084 | 2-SO₂N(C₂H₅)₂-C₆H₄ | H | 6-chloropyridin-3-yl | | OCH₃ | N | N | C—CH₃ | 240 |
| 1085 | 2-SO₂N(C₂H₅)₂-C₆H₄ | H | 2-chloropyridin-3-yl | | OCH₃ | N | N | C—CH₃ | 195 |
| 1086 | 2-SO₂N(C₂H₅)₂-C₆H₄ | H | 4,5-dichloro-2-methylthiazol | | OCH₃ | N | N | C—CH₃ | 166 |
| 1087 | 2-SO₂N(C₂H₅)₂-C₆H₄ | H | 4,5-dichloro-2-methylthiazol isomer | | OCH₃ | N | N | C—CH₃ | 179 |
| 1088 | 2-SO₂N(C₂H₅)₂-C₆H₄ | H | C₂H₅ | | OCH₃ | N | N | C—CH₃ | 160 |
| 1089 | 2-SO₂N(C₂H₅)₂-C₆H₄ | H | —(CH₂)₈—CH₃ | | OCH₃ | N | N | C—CH₃ | 98 |
| 1090 | 2-SO₂N(C₂H₅)₂-C₆H₄ | H | —CH₂—C₆H₅ | | OCH₃ | N | N | C—CH₃ | 180 |
| 1091 | 2-SO₂N(CH₃)₂-C₆H₄ | H | CH(C₂H₅)₂ | | OCH₃ | N | N | C—CH₃ | 124 |

-continued

| # | Ar | R1 | R2 | X | A | B | E | mp |
|---|---|---|---|---|---|---|---|---|
| 1092 | 2-CH3-C6H4-SO2N(CH3)2 | CH3 | C2H5 | OCH3 | N | N | C—CH3 | 190 |
| 1093 | 2-CH3-C6H4-SO2N(CH3)2 | H | —C(CH3)=CHC2H5 | OCH3 | N | N | C—CH3 | 145 |
| 1094 | 2-CH3-C6H4-SO2N(CH3)2 | CH3 | CH2OCH3 | OCH3 | N | N | C—CH3 | 195 |
| 1095 | 2-CH3-C6H4-SO2N(CH3)(OCH3) | H | 3-F-C6H4 | OCH3 | N | N | C—OCH3 | 164 |
| 1096 | 2-CH3-C6H4-SO2N(CH3)(OCH3) | H | 2-HOOC-C6H4 | OCH3 | N | N | C—OCH3 | 198 |
| 1097 | 2-thienyl | CH3 | CH3 | OCH3 | N | N | C—CH3 | 200 |
| 1098 | 2-thienyl | H | C6H5 | OCH3 | N | N | C—CH3 | 212 |
| 1099 | 2-Cl-3-CH3-C6H3 | H | 3-F-C6H4 | OCH3 | N | N | C—CH3 | 188 |
| 1100 | 2-Cl-3-CH3-C6H3 | H | 3-pyridyl | OCH3 | N | N | C—CH3 | 172 |
| 1101 | 2-Cl-3-CH3-C6H3 | H | 4-pyridyl | OCH3 | N | N | C—CH3 | 196 |

-continued

| # | Ar | R1 | R2 | X | Y | Z | W | mp |
|---|---|---|---|---|---|---|---|---|
| 1102 | 2-Cl, 6-CH₃-phenyl | H | 2-Cl-pyridin-5-yl | OCH₃ | N | N | C—CH₃ | 134 |
| 1103 | 2-Cl, 6-CH₃-phenyl | H | 2-Cl-pyridin-3-yl | OCH₃ | N | N | C—CH₃ | 198 |
| 1104 | 2-SO₂N(CH₃)₂-phenyl | H | C(CH₃)₃ | OCH₃ | N | N | C—CH₃ | 160 |
| 1105 | 2-SO₂N(CH₃)₂-phenyl | H | C₂H₅ | OCH₃ | N | N | C—OCH₃ | 150 |
| 1106 | 2-SO₂N(CH₃)₂-phenyl | H | —(CH₂)₈—CH₃ | OCH₃ | N | N | C—OCH₃ | 99 |
| 1107 | 2-SO₂N(CH₃)₂-phenyl | H | —CH₂—C₆H₅ | OCH₃ | N | N | C—OCH₃ | 124 |
| 1108 | 2-SO₂N(CH₃)₂-phenyl | H | —C(CH₃)=CHC₂H₅ | OCH₃ | N | N | C—OCH₃ | 159 |
| 1109 | 2-SO₂N(CH₃)₂-phenyl | CH₃ | CH₂OCH₃ | OCH₃ | N | N | C—OCH₃ | 166 |
| 1110 | 2-CF₃-phenyl | H | 2-Cl-pyridin-5-yl | OCH₃ | N | N | C—CH₃ | 176 |
| 1111 | 2-CF₃-phenyl | H | pyridin-4-yl | OCH₃ | N | N | C—OCH₃ | 143 |
| 1112 | 2-CF₃-phenyl | H | 2-Cl-pyridin-5-yl | OCH₃ | N | N | C—OCH₃ | 163 |

| | | | | | | | | |
|---|---|---|---|---|---|---|---|---|
| 1113 | 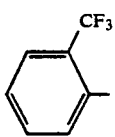 2-CF3-C6H4 | H | 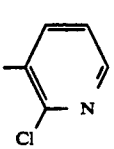 2-Cl-pyridin-3-yl | OCH3 | N | N | C—OCH3 | 149 |
| 1114 | 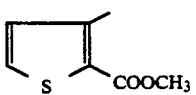 3-methyl-2-(COOCH3)-thiophene | H | —CH2—C6H5 | OCH3 | N | N | C—CH3 | 99 |
| 1115 | 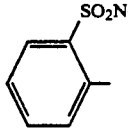 2-SO2N(CH3)2-C6H4 | H | —(CH2)3—CH3 | OCH3 | N | N | C—OCH3 | 164 |
| 1116 | 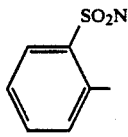 2-SO2N(CH3)2-C6H4 | H | —(CH2)4—CH3 | OCH3 | N | N | C—OCH3 | 133 |
| 1117 | 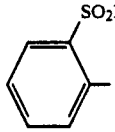 2-SO2N(CH3)2-C6H4 | H | —(CH2)6—CH3 | OCH3 | N | N | C—OCH3 | 135 |
| 1118 | 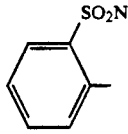 2-SO2N(CH3)2-C6H4 | H | —(CH2)7—CH3 | OCH3 | N | N | C—OCH3 | 110 |
| 1119 | 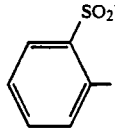 2-SO2N(CH3)2-C6H4 | H | —(CH2)3—CH3 | OCH3 | N | N | C—CH3 | 154 |
| 1120 | 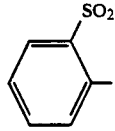 2-SO2N(CH3)2-C6H4 | H | —(CH2)4—CH3 | OCH3 | N | N | C—CH3 | 148 |
| 1121 | 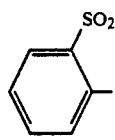 2-SO2N(CH3)2-C6H4 | H | —(CH2)6—CH3 | OCH3 | N | N | C—CH3 | 136 |
| 1122 | 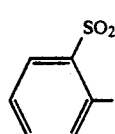 2-SO2N(CH3)2-C6H4 | H | —(CH2)7—CH3 | OCH3 | N | N | C—CH3 | 135 |
| 1123 | 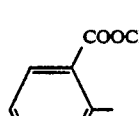 2-COOCH2CH2Cl-C6H4 | H | 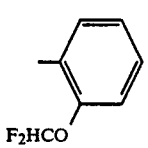 2-OCHF2-C6H4 | OCH3 | N | N | C—CH3 | 160 |

-continued

| | | | | | | | | |
|---|---|---|---|---|---|---|---|---|
| 1124 | COOCH$_2$CH$_2$Cl (phenyl) | H | 2-CF$_3$-phenyl | OCH$_3$ | N | N | C—CH$_3$ | 154 |
| 1125 | COOCH$_2$CH$_2$Cl (phenyl) | H | 3-CF$_3$-phenyl | OCH$_3$ | N | N | C—CH$_3$ | 181 |
| 1126 | COOCH$_2$CH$_2$Cl (phenyl) | H | 4-CF$_3$-phenyl | OCH$_3$ | N | N | C—CH$_3$ | 129 |
| 1127 | COOCH$_2$CH$_2$Cl (phenyl) | H | 2-F-phenyl | OCH$_3$ | N | N | C—CH$_3$ | 165 |
| 1128 | COOCH$_2$CH$_2$Cl (phenyl) | H | 3-F-phenyl | OCH$_3$ | N | N | C—CH$_3$ | 164 |
| 1129 | COOCH$_2$CH$_2$Cl (phenyl) | H | 4-F-phenyl | OCH$_3$ | N | N | C—CH$_3$ | 176 |
| 1130 | COOCH$_2$CH$_2$Cl (phenyl) | H | 2-Cl-phenyl | OCH$_3$ | N | N | C—CH$_3$ | 120 |
| 1131 | COOCH$_2$CH$_2$Cl (phenyl) | H | 4-SCF$_3$-phenyl | OCH$_3$ | N | N | C—CH$_3$ | 145 |
| 1132 | COOCH$_2$CH$_2$Cl (phenyl) | H | 2-HOOC-phenyl | OCH$_3$ | N | N | C—CH$_3$ | 208 |
| 1133 | COOCH$_2$CH$_2$Cl (phenyl) | H | —CH=CH—phenyl | OCH$_3$ | N | N | C—CH$_3$ | 194 |
| 1134 | COOCH$_2$CH$_2$Cl (phenyl) | —(CH$_2$)$_5$— | | OCH$_3$ | N | N | C—CH$_3$ | 154 |

| No. | R1 | R2 | R3 | R4 | X | Y | Z | mp |
|---|---|---|---|---|---|---|---|---|
| 1135 | 2-(COOCH₂CH₂Cl)-C₆H₄ | H | CH(CH₃)₂ | OCH₃ | N | N | C—CH₃ | 141 |
| 1136 | 2-(COOCH₂CH₂Cl)-C₆H₄ | H | C(CH₃)₃ | OCH₃ | N | N | C—CH₃ | 126 |
| 1137 | 2-(COOCH₂CH₂Cl)-C₆H₄ | CH₃ | CH₂CH(CH₃)₂ | OCH₃ | N | N | C—CH₃ | 96 |
| 1138 | 2-(COOCH₂CH₂Cl)-C₆H₄ | H | CH₃ | OCH₃ | N | N | C—CH₃ | 134 |
| 1139 | 2-(COOCH₂CH₂Cl)-C₆H₄ | H | 2-furyl | OCH₃ | N | N | C—CH₃ | 145 |
| 1140 | 2-(COOCH₂CH₂Cl)-C₆H₄ | H | 2-pyridyl | OCH₃ | N | N | C—CH₃ | 169 |
| 1141 | 2-(COOCH₂CH₂Cl)-C₆H₄ | H | 3-pyridyl | OCH₃ | N | N | C—CH₃ | 148 |
| 1142 | 2-(COOCH₂CH₂Cl)-C₆H₄ | H | 4-pyridyl | OCH₃ | N | N | C—CH₃ | 150 |
| 1143 | 2-(COOCH₂CH₂Cl)-C₆H₄ | H | 6-chloro-3-pyridyl | OCH₃ | N | N | C—CH₃ | 188 |
| 1144 | 2-(COOCH₂CH₂Cl)-C₆H₄ | H | 2-chloro-3-pyridyl | OCH₃ | N | N | C—CH₃ | 137 |
| 1145 | 2-(COOCH(CH₃)₂)-C₆H₄ | H | 2-(OCHF₂)-C₆H₄ | OCH₃ | N | N | C—CH₃ | 184 |

-continued
| | | | | | | | | |
|---|---|---|---|---|---|---|---|---|
| 1146 | 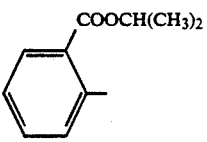 COOCH(CH₃)₂ | H | 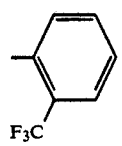 F₃C | OCH₃ | N | N | C—CH₃ | 139 |
| 1147 | 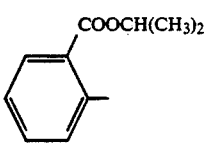 COOCH(CH₃)₂ | H | 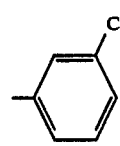 CF₃ | OCH₃ | N | N | C—CH₃ | 170 |
| 1148 | 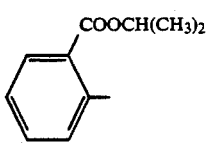 COOCH(CH₃)₂ | H | 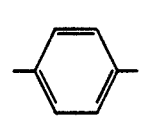 CF₃ | OCH₃ | N | N | C—CH₃ | 215 |
| 1149 | 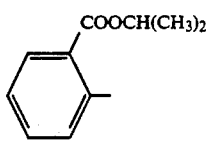 COOCH(CH₃)₂ | H | 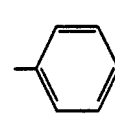 SCF₃ | OCH₃ | N | N | C—CH₃ | 174 |
| 1150 | 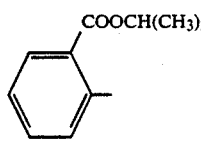 COOCH(CH₃)₂ | H | 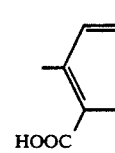 HOOC | OCH₃ | N | N | C—CH₃ | 209 |
| 1151 | 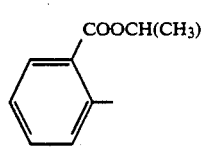 COOCH(CH₃)₂ | —(CH₂)₅— | | OCH₃ | N | N | C—CH₃ | 186 |
| 1152 | 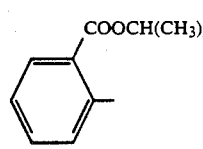 COOCH(CH₃)₂ | H | 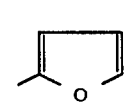 | OCH₃ | N | N | C—CH₃ | 144 |
| 1153 | 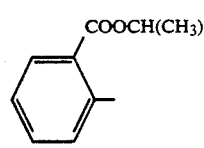 COOCH(CH₃)₂ | H | 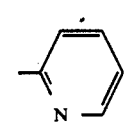 | OCH₃ | N | N | C—CH₃ | 185 |
| 1154 | 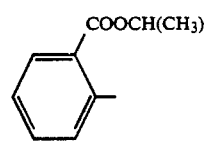 COOCH(CH₃)₂ | H | 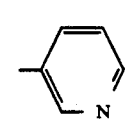 | OCH₃ | N | N | C—CH₃ | 181 |
| 1155 | 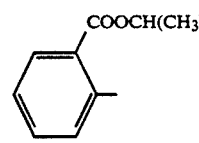 COOCH(CH₃)₂ | H | 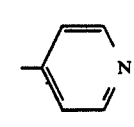 | OCH₃ | N | N | C—CH₃ | 183 |
| 1156 | 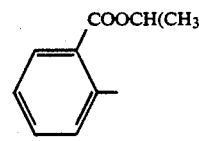 COOCH(CH₃)₂ | H | 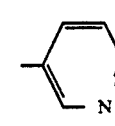 Cl | OCH₃ | N | N | C—CH₃ | 182 |

| # | R1 | R2 | R3 | R4 | R5 | R6 | R7 | # |
|---|---|---|---|---|---|---|---|---|
| 1157 | 2-COOCH(CH3)2-phenyl | H | 3-methyl-2-chloropyridin-yl | | OCH3 | N | N | C—CH3 | 157 |
| 1158 | 2-COOC3H7-phenyl | H | 2-methyl-6-(F2HCO)-phenyl | | OCH3 | N | N | C—CH3 | 143 |
| 1159 | 2-COOC3H7-phenyl | H | 2-methyl-6-(F3C)-phenyl | | OCH3 | N | N | C—CH3 | 150 |
| 1160 | 2-COOC3H7-phenyl | H | 3-CF3-phenyl | | OCH3 | N | N | C—CH3 | 158 |
| 1161 | 2-COOC3H7-phenyl | H | 4-CF3-phenyl | | OCH3 | N | N | C—CH3 | 169 |
| 1162 | 2-COOC3H7-phenyl | H | 2-methyl-6-F-phenyl | | OCH3 | N | N | C—CH3 | 144 |
| 1163 | 2-COOC3H7-phenyl | H | 3-F-phenyl | | OCH3 | N | N | C—CH3 | 156 |
| 1164 | 2-COOC3H7-phenyl | H | 4-SCF3-phenyl | | OCH3 | N | N | C—CH3 | 143 |
| 1165 | 2-COOC3H7-phenyl | —(CH2)5— | | | OCH3 | N | N | C—CH3 | 134 |
| 1166 | 2-COOC3H7-phenyl | H | 2-methylfuran-yl | | OCH3 | N | N | C—CH3 | 141 |
| 1167 | 2-COOC3H7-phenyl | H | 2-methylpyridin-yl | | OCH3 | N | N | C—CH3 | 129 |

-continued
| No. | | | | | | | | |
|---|---|---|---|---|---|---|---|---|
| 1168 | 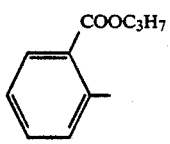 COOC₃H₇ | H | 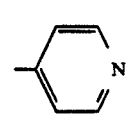 (4-pyridyl) | OCH₃ | N | N | C—CH₃ | 142 |
| 1169 | 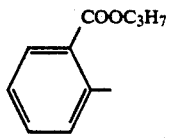 COOC₃H₇ | H | 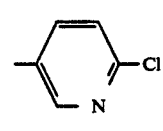 (6-Cl-pyridyl) | OCH₃ | N | N | C—CH₃ | 164 |
| 1170 | 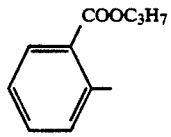 COOC₃H₇ | H | 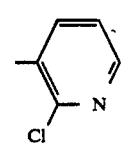 (2-Cl-pyridyl) | OCH₃ | N | N | C—CH₃ | 139 |
| 1171 | 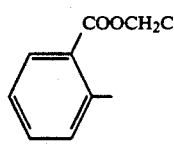 COOCH₂CH₂OCH₃ | H | 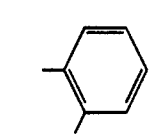 HOOC | OCH₃ | N | N | C—CH₃ | 189 |
| 1172 | 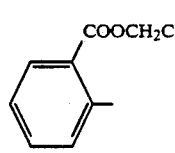 COOCH₂CH₂OCH₃ | H | 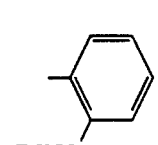 F₂HCO | OCH₃ | N | N | C—CH₃ | 154 |
| 1173 | 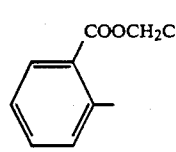 COOCH₂CH₂OCH₃ | H | 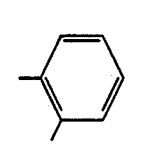 F₃C | OCH₃ | N | N | C—CH₃ | 167 |
| 1174 | 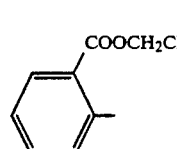 COOCH₂CH₂OCH₃ | H | 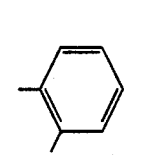 F | OCH₃ | N | N | C—CH₃ | 144 |
| 1175 | 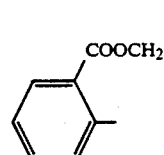 COOCH₂CH₂OCH₃ | H | 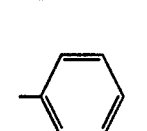 F | OCH₃ | N | N | C—CH₃ | 154 |
| 1176 | 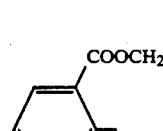 COOCH₂CH₂OCH₃ | H | 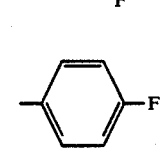 F | OCH₃ | N | N | C—CH₃ | 190 |
| 1177 | 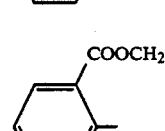 COOCH₂CH₂OCH₃ | H | 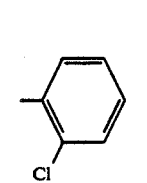 Cl | OCH₃ | N | N | C—CH₃ | 141 |

-continued

| | | | | | | | | |
|---|---|---|---|---|---|---|---|---|
| 1178 | 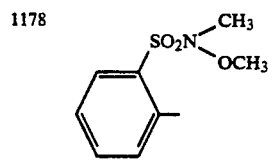 | H | 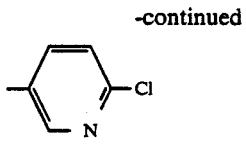 | OCH$_3$ | N | N | C—OCH$_3$ | 211 |
| 1179 | 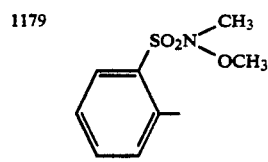 | H | 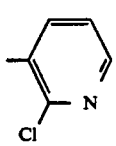 | OCH$_3$ | N | N | C—OCH$_3$ | 199 |
| 1180 | 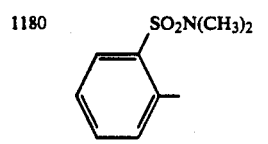 SO$_2$N(CH$_3$)$_2$ | H | CH$_3$ | OCH$_3$ | N | N | C—OCH$_3$ | 167 |
| 1181 | 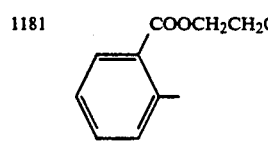 COOCH$_2$CH$_2$OCH$_3$ | H | 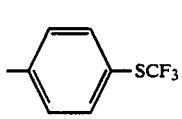 | OCH$_3$ | N | N | C—CH$_3$ | 161 |
| 1182 | 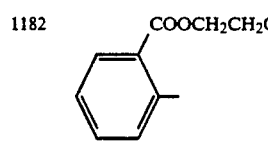 COOCH$_2$CH$_2$OCH$_3$ | H | 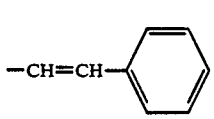 —CH=CH— | OCH$_3$ | N | N | C—CH$_3$ | 189 |
| 1183 | 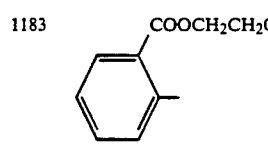 COOCH$_2$CH$_2$OCH$_3$ | —(CH$_2$)$_5$— | | OCH$_3$ | N | N | C—CH$_3$ | 138 |
| 1184 | 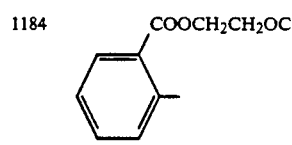 COOCH$_2$CH$_2$OCH$_3$ | H | CH(CH$_3$)$_2$ | OCH$_3$ | N | N | C—CH$_3$ | 127 |
| 1185 | 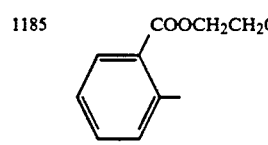 COOCH$_2$CH$_2$OCH$_3$ | H | C(CH$_3$)$_3$ | OCH$_3$ | N | N | C—CH$_3$ | 129 |
| 1186 | 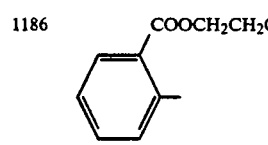 COOCH$_2$CH$_2$OCH$_3$ | CH$_3$ | —CH$_2$CH(CH$_3$)$_2$ | OCH$_3$ | N | N | C—CH$_3$ | 128 |
| 1187 | 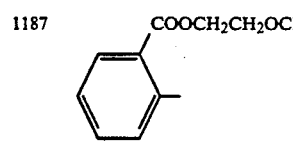 COOCH$_2$CH$_2$OCH$_3$ | H | CH$_3$ | OCH$_3$ | N | N | C—CH$_3$ | 151 |
| 1188 | 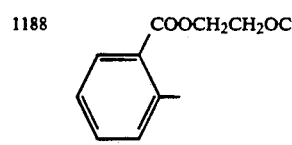 COOCH$_2$CH$_2$OCH$_3$ | H | 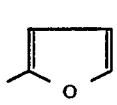 | OCH$_3$ | N | N | C—CH$_3$ | 140 |

| | | | | | | | | |
|---|---|---|---|---|---|---|---|---|
| 1189 | 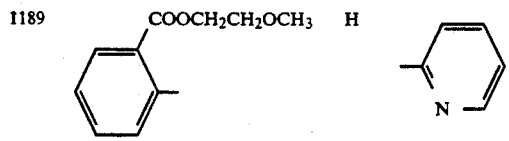 | H | 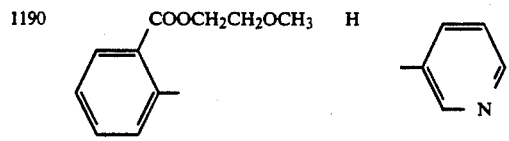 | OCH$_3$ | N | N | C—CH$_3$ | 146 |
| 1190 | 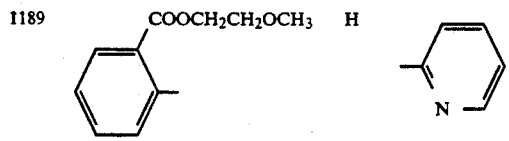 | H | 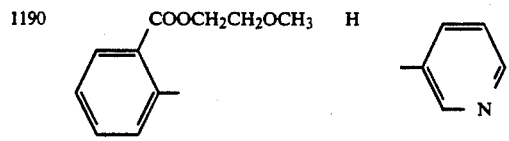 | OCH$_3$ | N | N | C—CH$_3$ | 119 |
| 1191 | 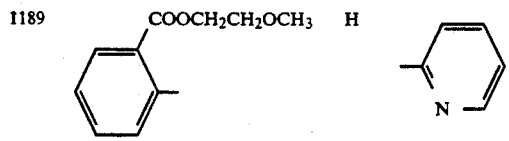 | H | 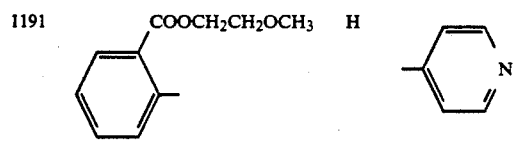 | OCH$_3$ | N | N | C—CH$_3$ | 138 |
| 1192 | 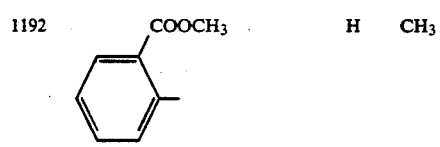 | H | CH$_3$ | OCH$_3$ | N | N | C—CH$_3$ | 153 |
| 1193 | 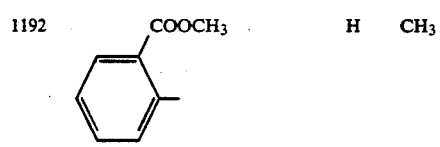 | H | 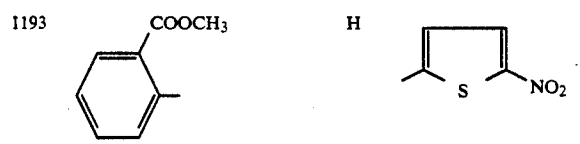 | OCH$_3$ | N | N | C—CH$_3$ | 208 |
| 1194 | 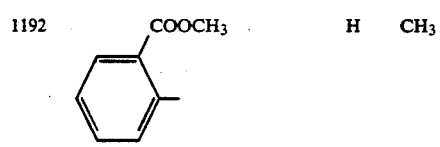 | CH$_3$ | 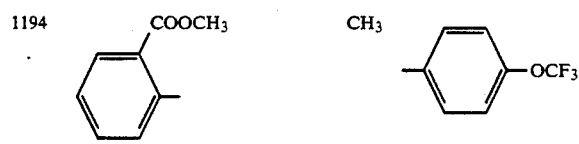 | OCH$_3$ | N | N | C—CH$_3$ | 222 |
| 1195 | 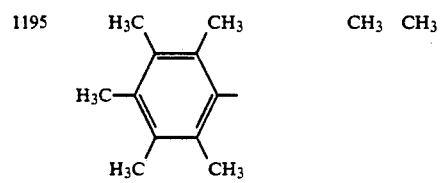 | CH$_3$ | CH$_3$ | OCH$_3$ | N | N | C—CH$_3$ | 224 |
| 1196 | 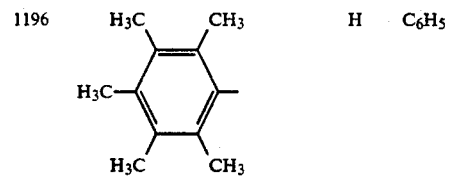 | H | C$_6$H$_5$ | OCH$_3$ | N | N | C—CH$_3$ | 205 |
| 1197 | 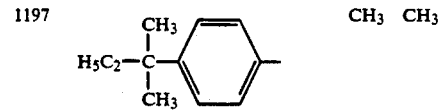 | CH$_3$ | CH$_3$ | OCH$_3$ | N | N | C—CH$_3$ | 136 |
| 1198 | 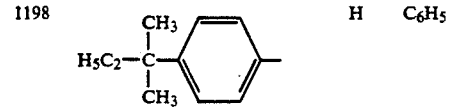 | H | C$_6$H$_5$ | OCH$_3$ | N | N | C—CH$_3$ | 231 |
| 1199 | 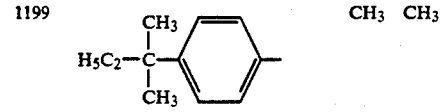 | CH$_3$ | CH$_3$ | OCH$_3$ | N | N | C—OCH$_3$ | 136 |

-continued

| No. | R1 | R2 | R3 | R4 | X | Y | Z | mp |
|---|---|---|---|---|---|---|---|---|
| 1200 | 4-(2-methylbutan-2-yl)phenyl | H | C6H5 | OCH3 | N | N | C—OCH3 | 220 |
| 1201 | 2-(SO2N(CH3)2)phenyl | CH3 | CH3 | CH3 | N | CH | CH | 204 |
| 1202 | 2-(SO2N(CH3)2)phenyl | H | 4-HO-C6H4 | CH3 | N | CH | CH | 143 |
| 1203 | 2-(SO2N(CH3)2)phenyl | H | 3-HO-C6H4 | CH3 | N | CH | CH | 153 |
| 1204 | 2-(SO2N(CH3)2)phenyl | H | 2-HOOC-C6H4 | CH3 | N | CH | CH | 220 |
| 1205 | 2-(SO2N(CH3)2)phenyl | H | 4-CH3-C6H4 | CH3 | N | CH | CH | 234 |
| 1206 | 2-(SO2N(CH3)2)phenyl | H | 3-CH3-C6H4 | CH3 | N | CH | CH | 216 |
| 1207 | 2-(SO2N(CH3)2)phenyl | H | 2-Cl-C6H4 | CH3 | N | CH | CH | 171 |
| 1208 | 2-(SO2N(CH3)2)phenyl | H | 3-Cl-C6H4 | CH3 | N | CH | CH | 218 |
| 1209 | 2-(SO2N(CH3)2)phenyl | H | 4-Cl-C6H4 | CH3 | N | CH | CH | 234 |
| 1210 | 2-(SO2N(CH3)2)phenyl | H | 2,4-Cl2-C6H3 | CH3 | N | CH | CH | 221 |

| | | | | | | | |
|---|---|---|---|---|---|---|---|
| 1211 | 2-SO$_2$N(CH$_3$)$_2$-C$_6$H$_4$ | H | 2-COOCH$_3$-C$_6$H$_4$ | CH$_3$ | N | CH | CH | 238 |
| 1212 | 2-SO$_2$N(CH$_3$)$_2$-C$_6$H$_4$ | C$_6$H$_5$ | C$_6$H$_5$ | CH$_3$ | N | CH | CH | 228 |
| 1213 | 2-SO$_2$N(CH$_3$)$_2$-C$_6$H$_4$ | CH$_3$ | C$_6$H$_5$ | CH$_3$ | N | CH | CH | 243 |
| 1214 | 2-OCF$_3$-C$_6$H$_4$ | H | C$_6$H$_5$ | OCH$_3$ | N | CH | C—CH$_3$ | 213 |
| 1215 | 2-CF$_3$-C$_6$H$_4$ | H | C$_6$H$_5$ | OCH$_3$ | N | CH | C—CH$_3$ | 214 |
| 1216 | 2-COOCH$_2$CH$_2$Cl-C$_6$H$_4$ | H | C$_6$H$_5$ | —CH$_2$OCH$_3$ | N | CH | C—OCH$_3$ | 192 |
| 1217 | 2-COOCH$_3$-C$_6$H$_4$ | —(CH$_2$)$_5$— | | OCH$_3$ | N | CH | —COCH$_3$ | 196 |
| 1218 | 2-COOC$_2$H$_5$-C$_6$H$_4$ | H | C$_6$H$_5$ | —CH$_2$OCH$_3$ | N | CH | C—OCH$_3$ | 177 |
| 1219 | 2-COOC$_2$H$_5$-C$_6$H$_4$ | —(CH$_2$)$_5$— | | —CH$_2$OCH$_3$ | N | CH | C—OCH$_3$ | 75 |
| 1220 | 2-Br-C$_6$H$_4$ | H | C$_6$H$_5$ | —CH$_2$OCH$_3$ | N | CH | C—OCH$_3$ | 215 |
| 1221 | 2-F-C$_6$H$_4$ | H | C$_6$H$_5$ | —CH$_2$OCH$_3$ | N | CH | C—OCH$_3$ | 228 |

-continued

| | | | | | | | | |
|---|---|---|---|---|---|---|---|---|
| 1222 | 2-(COOCH₃)C₆H₄-CH₂- | H | C₆H₅ | OCH₃ | N | CH | C—OCH₃ | 188 |
| 1223 | 2-(COOCH₃)C₆H₄-CH₂- | H | 4-Cl-C₆H₄- | OCH₃ | N | CH | C—OCH₃ | 212 |
| 1224 | 2-(COOCH₃)C₆H₄-CH₂- | H | 4-CH₃-C₆H₄- | OCH₃ | N | CH | C—OCH₃ | 194 |
| 1225 | 2-(COOCH(CH₃)₂)C₆H₄- | CH₃ | CH₃ | OCH₃ | N | CH | C—OCH₃ | 192 |
| 1226 | 2-(COOCH(CH₃)₂)C₆H₄- | CH₃ | CH₃ | OCH₃ | N | N | C—OCH₃ | 187 |
| 1227 | 2-(C₆H₅)C₆H₄- | CH₃ | CH₃ | OCH₃ | N | CH | C—CH₃ | 193 |
| 1228 | 2-(C₆H₅)C₆H₄- | H | C₆H₅ | OCH₃ | N | CH | C—CH₃ | 92 |
| 1229 | 2-(C₆H₅)C₆H₄- | H | N(CH₃)₂ | OCH₃ | N | CH | C—CH₃ | 134 |
| 1230 | 2-(COOCH(CH₃)₂)C₆H₄- | H | C₆H₅ | OCH₃ | N | CH | C—OCH₃ | 197 |
| 1231 | 2-(COOCH(CH₃)₂)C₆H₄- | CH₃ | CH₃ | CH₃ | N | CH | C—CH₃ | 171 |
| 1232 | 4-((CH₃)₂CH)C₆H₄- | H | C₆H₅ | CH₃ | N | CH | C—CH₃ | 201 |

-continued

| # | R1 | R2 | R3 | | | | mp |
|---|---|---|---|---|---|---|---|
| 1233 | 2-COOCH(CH₃)₂-C₆H₄ | H | C₆H₅ | CH₃ | N | CH C—CH₃ | 208 |
| 1234 | 2-COOCH(CH₃)₂-C₆H₄ | H | C₆H₅ | OCH₃ | N | N C—OCH₃ | 182 |
| 1235 | 4-(CH₃)₂CH-C₆H₄ | H | C₆H₅ | OCH₃ | N | CH C—OCH₃ | 182 |
| 1236 | 2-C₆H₅-C₆H₄ | H | 2-Cl-C₆H₄ | OCH₃ | N | CH C—OCH₃ | 205 |
| 1237 | 2-C₆H₅-C₆H₄ | H | 3-Cl-C₆H₄ | OCH₃ | N | CH C—OCH₃ | 178 |
| 1238 | 2-SCH₃-C₆H₄ | CH₃ | CH₃ | OCH₃ | N | CH C—CH₃ | 144 |
| 1239 | 2-SCH₃-C₆H₄ | H | C₆H₅ | OCH₃ | N | CH C—CH₃ | 228 |
| 1240 | 2-SCH₃-C₆H₄ | H | C(CH₃)₃ | OCH₃ | N | N C—OCH₃ | 168 |
| 1241 | 2-SCH₃-C₆H₄ | H | 2-Cl-C₆H₄ | OCH₃ | N | N C—OCH₃ | 214 |
| 1242 | 2-SCH₃-C₆H₄ | H | 3-Cl-C₆H₄ | OCH₃ | N | N C—OCH₃ | 178 |
| 1243 | 2-SCH₃-C₆H₄ | H | 4-Cl-C₆H₄ | OCH₃ | N | N C—OCH₃ | 207 |

-continued
| | | | | | | | | |
|---|---|---|---|---|---|---|---|---|
| 1244 | 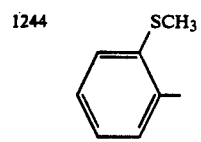 | H | 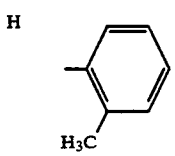 | OCH₃ | N | N | C—OCH₃ | 192 |
| 1245 | 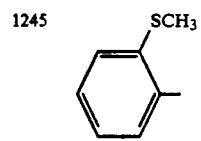 | H | 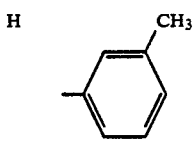 | OCH₃ | N | N | C—OCH₃ | 193 |
| 1246 | 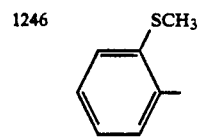 | H | 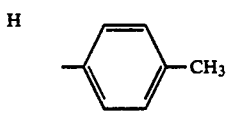 | OCH₃ | N | N | C—OCH₃ | 216 |
| 1247 | 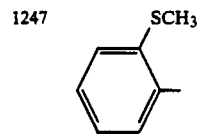 | H | 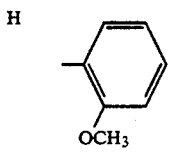 | OCH₃ | N | N | C—OCH₃ | 221 |
| 1248 | 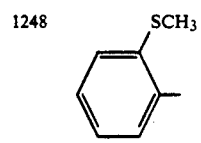 | H | 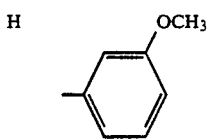 | OCH₃ | N | N | C—OCH₃ | 213 |
| 1249 | 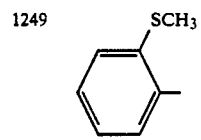 | H | 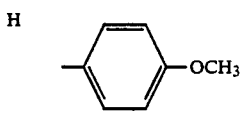 | OCH₃ | N | N | C—OCH₃ | 208 |
| 1250 | 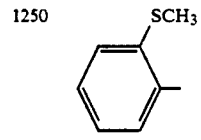 | H | 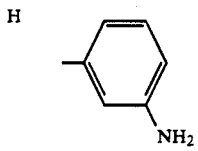 | OCH₃ | N | N | C—OCH₃ | (amorphous) |
| 1251 | 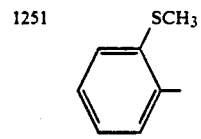 | H | 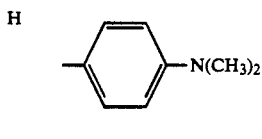 | OCH₃ | N | N | C—OCH₃ | 198 |
| 1252 | 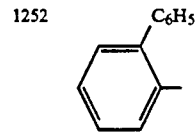 | H | 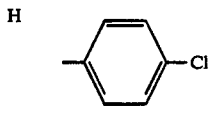 | OCH₃ | N | CH | C—OCH₃ | 228 |
| 1253 | 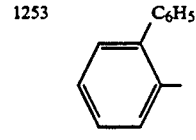 | H | 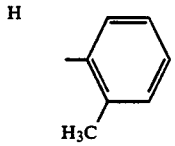 | OCH₃ | N | CH | C—OCH₃ | 192 |
| 1254 | 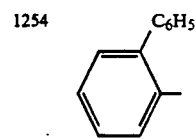 | H | 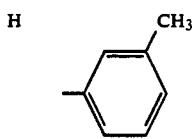 | OCH₃ | N | CH | C—OCH₃ | 189 |

| | | | | | | | | |
|---|---|---|---|---|---|---|---|---|
| 1255 | 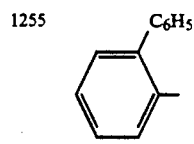 | H | 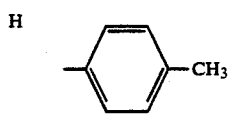 | OCH$_3$ | N | CH | C—OCH$_3$ | 208 |
| 1256 | 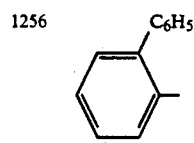 | H | 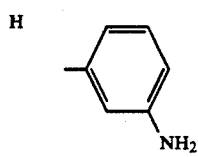 | OCH$_3$ | N | CH | C—OCH$_3$ | 202 |
| 1257 | 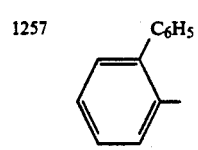 | H | 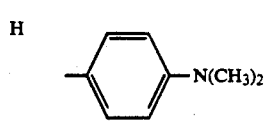 | OCH$_3$ | N | CH | C—OCH$_3$ | 232 |
| 1258 | 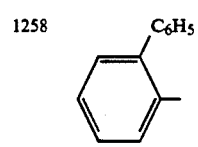 | H | 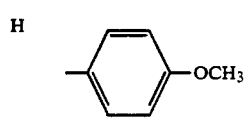 | OCH$_3$ | N | CH | C—OCH$_3$ | 224 |
| 1259 | 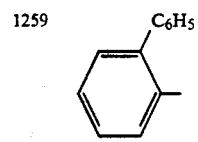 | H | 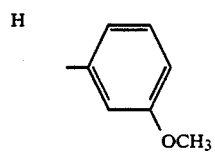 | OCH$_3$ | N | CH | C—OCH$_3$ | 201 |
| 1260 | 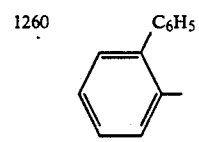 | H | 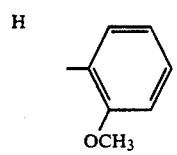 | OCH$_3$ | N | CH | C—OCH$_3$ | 198 |
| 1261 | 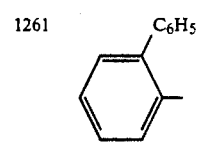 | H | 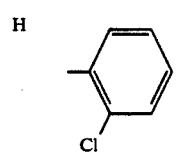 | OCH$_3$ | N | N | C—OCH$_3$ | 206 |
| 1262 | 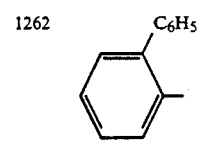 | H | 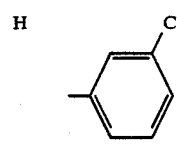 | OCH$_3$ | N | N | C—OCH$_3$ | 112 |
| 1263 | 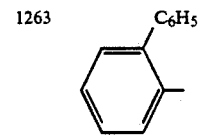 | H | 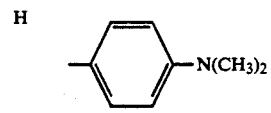 | OCH$_3$ | N | N | C—OCH$_3$ | 211 |
| 1264 | 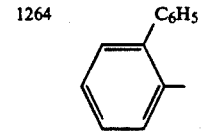 | H | 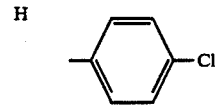 | OCH$_3$ | N | N | C—OCH$_3$ | 204 |
| 1265 | 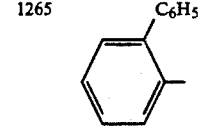 | H | 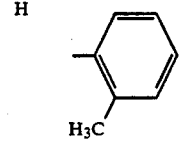 | OCH$_3$ | N | N | C—OCH$_3$ | 201 |

-continued
| | | | | | | | | |
|---|---|---|---|---|---|---|---|---|
| 1266 | 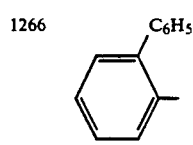 | H | 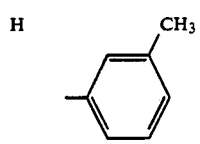 | OCH₃ | N | N | C—OCH₃ | 176 |
| 1267 | 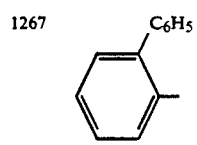 | H | 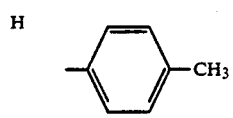 | OCH₃ | N | N | C—OCH₃ | 187 |
| 1268 | 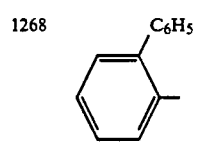 | H | 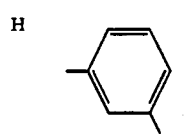 | OCH₃ | N | N | C—OCH₃ | 169 |
| 1269 | 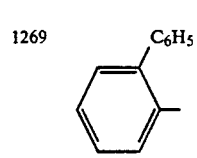 | H | 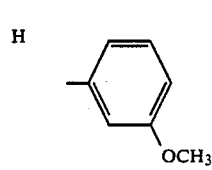 | OCH₃ | N | N | C—OCH₃ | 176 |
| 1270 | 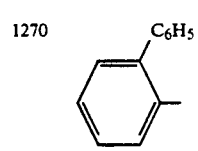 | H | 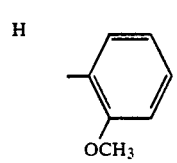 | OCH₃ | N | N | C—OCH₃ | 214 |
| 1271 | 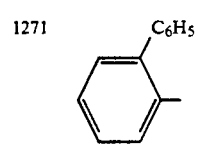 | H | 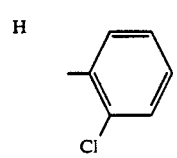 | OCH₃ | N | N | C—CH₃ | 199 |
| 1272 | 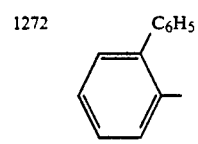 | H | 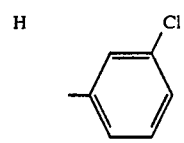 | OCH₃ | N | N | C—CH₃ | 124 |
| 1273 | 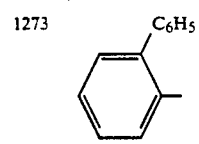 | H | 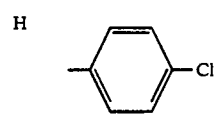 | OCH₃ | N | N | C—CH₃ | 198 |
| 1274 | 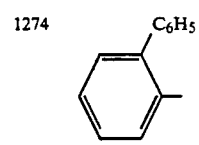 | H | 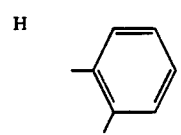 | OCH₃ | N | N | C—CH₃ | 204 |
| 1275 | 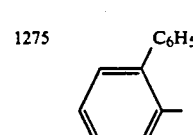 | H | 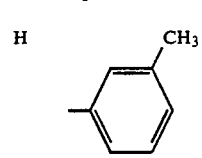 | OCH₃ | N | N | C—CH₃ | 198 |
| 1276 | 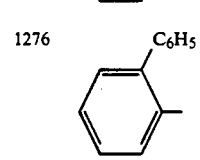 | H | 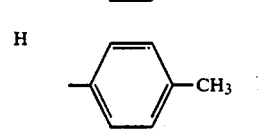 | OCH₃ | N | N | C—CH₃ | 203 |

-continued
| | | | | | | | | |
|---|---|---|---|---|---|---|---|---|
| 1277 | 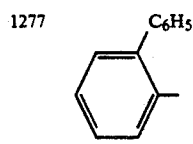 | H | 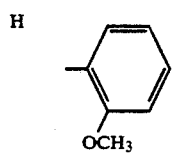 | OCH$_3$ | N | N | C—CH$_3$ | 216 |
| 1278 | 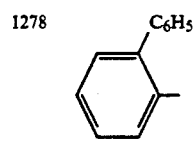 | H | 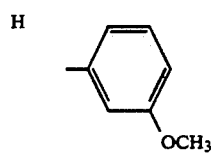 | OCH$_3$ | N | N | C—CH$_3$ | 193 |
| 1279 | 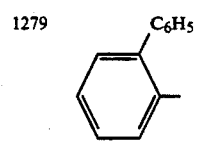 | H | 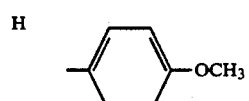 | OCH$_3$ | N | N | C—CH$_3$ | 207 |
| 1280 | 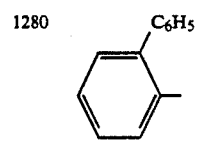 | H | 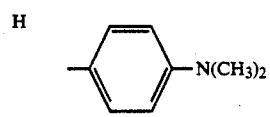 | OCH$_3$ | N | N | C—CH$_3$ | 219 |
| 1281 | 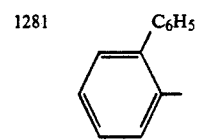 | H | C$_6$H$_5$ | CH$_3$ | N | N | C—CH$_3$ | 208 |
| 1282 | 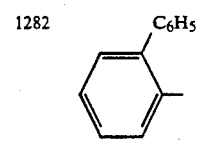 | H | 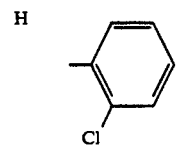 | CH$_3$ | N | N | C—CH$_3$ | 204 |
| 1283 | 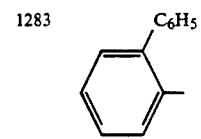 | H | 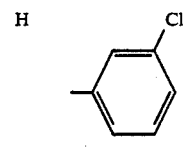 | CH$_3$ | N | N | C—CH$_3$ | 189 |
| 1284 | 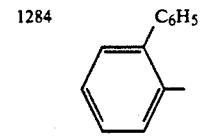 | H | 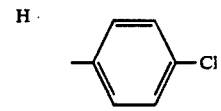 | CH$_3$ | N | N | C—CH$_3$ | 232 |
| 1285 | 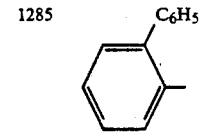 | H | 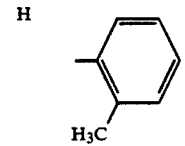 | CH$_3$ | N | N | C—CH$_3$ | 209 |
| 1286 | 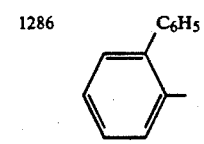 | H | 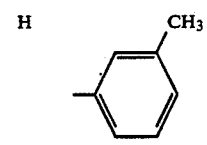 | CH$_3$ | N | N | C—CH$_3$ | 212 |
| 1287 | 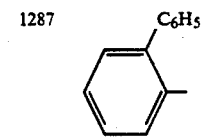 | H | 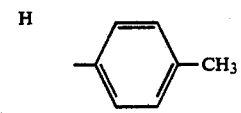 | CH$_3$ | N | N | C—CH$_3$ | 217 |

-continued
| | | | | | | | | |
|---|---|---|---|---|---|---|---|---|
| 1288 | 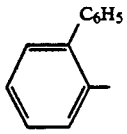 | H | 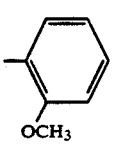 | CH$_3$ | N | N | C—CH$_3$ | 205 |
| 1289 | 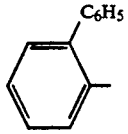 | CH$_3$ | CH$_3$ | CH$_3$ | N | N | C—CH$_3$ | 206 |
| 1290 | 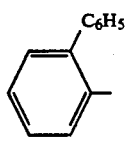 | H | 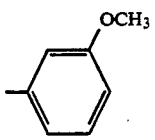 | CH$_3$ | N | N | C—CH$_3$ | 204 |
| 1291 | 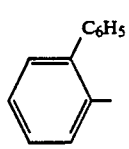 | H | 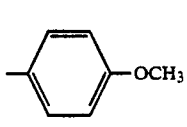 | CH$_3$ | N | N | C—CH$_3$ | 208 |
| 1292 | 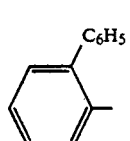 | H | 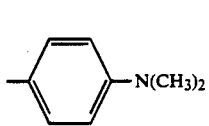 | CH$_3$ | N | N | C—CH$_3$ | 206 |
| 1293 | 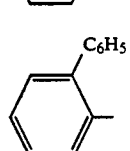 | CH$_3$ | CH$_3$ | OC$_2$H$_5$ | N | N | C—CH$_3$ | 185 |
| 1294 | 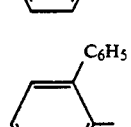 | H | C$_6$H$_5$ | OC$_2$H$_5$ | N | N | C—CH$_3$ | 158 |
| 1295 | 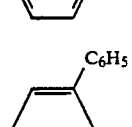 | H | 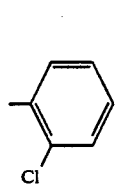 | OC$_2$H$_5$ | N | N | C—CH$_3$ | 182 |
| 1296 | 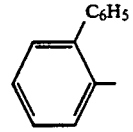 | H | 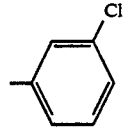 | OC$_2$H$_5$ | N | N | C—CH$_3$ | 108 |
| 1297 | 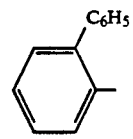 | H | 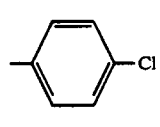 | OC$_2$H$_5$ | N | N | C—CH$_3$ | 165 |
| 1298 | 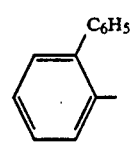 | H | 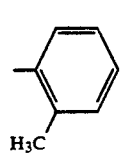 | OC$_2$H$_5$ | N | N | C—CH$_3$ | 182 |

-continued

| No. | R1 | R2 | R3 | R4 | | | mp |
|---|---|---|---|---|---|---|---|
| 1299 | o-C6H5-phenyl | H | 3-CH3-phenyl | OC2H5 | N | N C—CH3 | 164 |
| 1300 | o-C6H5-phenyl | H | 4-CH3-phenyl | OC2H5 | N | N C—CH3 | 174 |
| 1301 | o-C6H5-phenyl | H | 2-OCH3-phenyl | OC2H5 | N | N C—CH3 | 211 |
| 1302 | o-C6H5-phenyl | H | 3-OCH3-phenyl | OC2H5 | N | N C—CH3 | 162 |
| 1303 | o-C6H5-phenyl | H | 4-OCH3-phenyl | OC2H5 | N | N C—CH3 | 176 |
| 1304 | o-C6H5-phenyl | H | 3-NH2-phenyl | CH3 | N | N C—CH3 | 131 |
| 1305 | o-C6H5-phenyl | CH3 | CH3 | OC2H5 | N | CH C—OC2H5 | 194 |
| 1306 | o-C6H5-phenyl | H | C6H5 | OC2H5 | N | CH C—OC2H5 | 201 |
| 1307 | o-C6H5-phenyl | H | 2-Cl-phenyl | OC2H5 | N | CH C—OC2H5 | 204 |
| 1308 | o-C6H5-phenyl | H | 3-Cl-phenyl | OC2H5 | N | CH C—OC2H5 | 182 |
| 1309 | o-C6H5-phenyl | H | 4-Cl-phenyl | OC2H5 | N | CH C—OC2H5 | 224 |

| | | | | | | | | |
|---|---|---|---|---|---|---|---|---|
| 1310 | 2-C₆H₅-C₆H₄ | H | 2-CH₃-C₆H₄ | OC₂H₅ | N | CH | C—OC₂H₅ | 197 |
| 1311 | 2-C₆H₅-C₆H₄ | H | 3-CH₃-C₆H₄ | OC₂H₅ | N | CH | C—OC₂H₅ | 177 |
| 1312 | 2-C₆H₅-C₆H₄ | H | 4-CH₃-C₆H₄ | OC₂H₅ | N | CH | C—OC₂H₅ | 218 |
| 1313 | 2-C₆H₅-C₆H₄ | H | 2-OCH₃-C₆H₄ | OC₂H₅ | N | CH | C—OC₂H₅ | 202 |
| 1314 | 2-C₆H₅-C₆H₄ | H | 3-OCH₃-C₆H₄ | OC₂H₅ | N | CH | C—OC₂H₅ | 175 |
| 1315 | 2-C₆H₅-C₆H₄ | H | 4-OCH₃-C₆H₄ | OC₂H₅ | N | CH | C—OC₂H₅ | 165 |
| 1316 | 2-C₆H₅-C₆H₄ | H | 4-N(CH₃)₂-C₆H₄ | OC₂H₅ | N | CH | C—OC₂H₅ | 232 |
| 1317 | 2-C₆H₅-C₆H₄ | H | 3-NH₂-C₆H₄ | OC₂H₅ | N | CH | C—OC₂H₅ | 175 |
| 1318 | 4-Cl-2-CH₃-C₆H₃ | CH₃ | CH₃ | OCH₃ | N | CH | C—OCH₃ | 182 |
| 1319 | 4-Cl-2-CH₃-C₆H₃ | H | C₆H₅ | OCH₃ | N | CH | C—OCH₃ | 192 |

-continued
| | | | | | | | |
|---|---|---|---|---|---|---|---|
| 1320 | 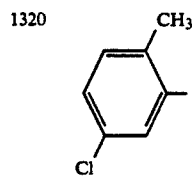 | H | 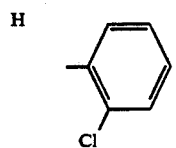 | OCH₃ | N | CH C—OCH₃ | 208 |
| 1321 | 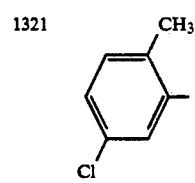 | H | 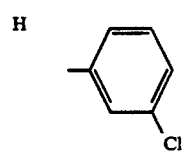 | OCH₃ | N | CH C—OCH₃ | 215 |
| 1322 | 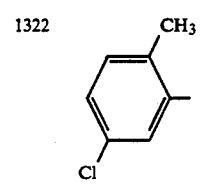 | H | 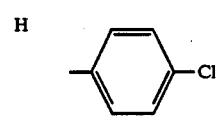 | OCH₃ | N | CH C—OCH₃ | 207 |
| 1323 | 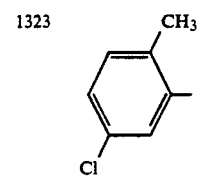 | H | 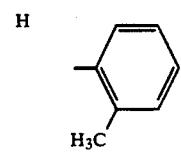 | OCH₃ | N | CH C—OCH₃ | 206 |
| 1324 | 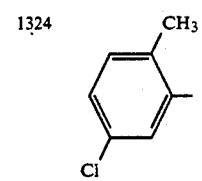 | H | 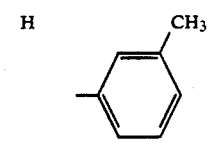 | OCH₃ | N | CH C—OCH₃ | 217 |
| 1325 | 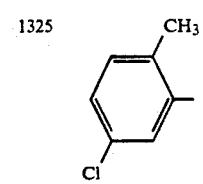 | H | 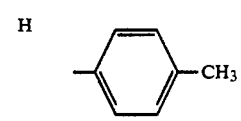 | OCH₃ | N | CH C—OCH₃ | 219 |
| 1326 | 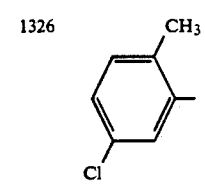 | H | 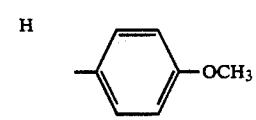 | OCH₃ | N | CH C—OCH₃ | 238 |
| 1327 | 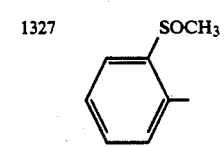 | H | 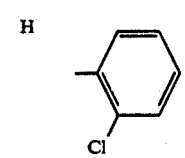 | OCH₃ | N | CH C—OCH₃ | 215 |
| 1328 | 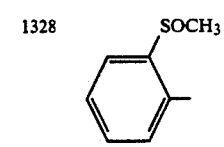 | H | 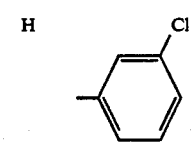 | OCH₃ | N | CH C—OCH₃ | 222 |

-continued
| | | | | | | | |
|---|---|---|---|---|---|---|---|
| 1329 | 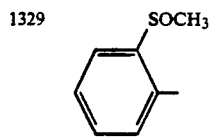 | H | 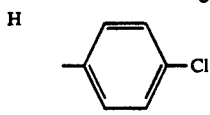 | OCH₃ | N | CH C—OCH₃ | 233 |
| 1330 | 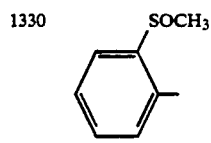 | H | 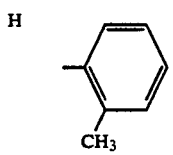 | OCH₃ | N | CH C—OCH₃ | 224 |
| 1331 | 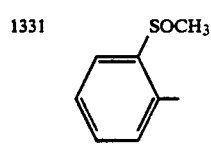 | H | 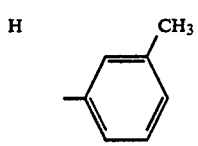 | OCH₃ | N | CH C—OCH₃ | 202 |
| 1332 | 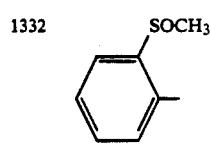 | H | 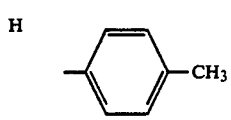 | OCH₃ | N | CH C—OCH₃ | 230 |
| 1333 | 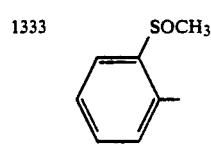 | H | 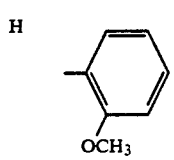 | OCH₃ | N | CH C—OCH₃ | 210 |
| 1334 | 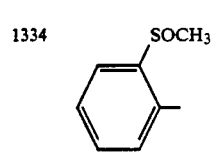 | H | 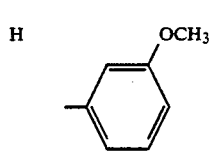 | OCH₃ | N | CH C—OCH₃ | 213 |
| 1335 | 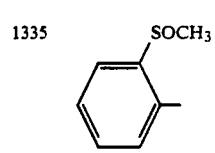 | H | 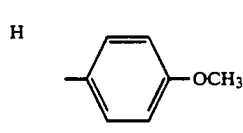 | OCH₃ | N | CH C—OCH₃ | 246 |
| 1336 | 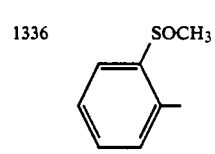 | H | 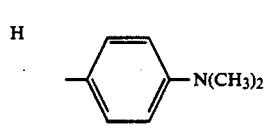 | OCH₃ | N | CH C—OCH₃ | 226 |
| 1337 | 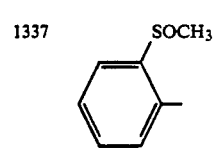 | H | 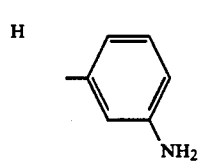 | OCH₃ | N | CH C—OCH₃ | 205 |
| 1338 | 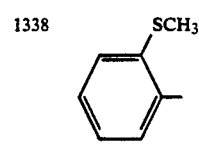 | CH₃ | CH₃ | OC₂H₅ | N | CH C—OC₂H₅ | 175 |
| 1339 | 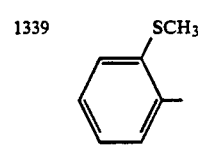 | H | C₆H₅ | OC₂H₅ | N | CH C—OC₂H₅ | 183 |

| | | | | | | | | |
|---|---|---|---|---|---|---|---|---|
| 1340 | 2-(SO₂CH₃)-C₆H₄ | CH₃ | CH₃ | | OCH₃ | N | CH | C—OCH₃ | 222 |
| 1341 | 2-(SO₂CH₃)-C₆H₄ | H | C₆H₅ | | OCH₃ | N | CH | C—OCH₃ | 211 |
| 1342 | 2-(C₆H₅)-C₆H₄ | CH₃ | CH₃ | | OC₂H₅ | N | N | C—OCH₃ | 160 |
| 1343 | 2-(C₆H₅)-C₆H₄ | H | C₆H₅ | | OC₂H₅ | N | N | C—OCH₃ | 112 |
| 1344 | 2-(C₆H₅)-C₆H₄ | H | 2-Cl-C₆H₄ | | OC₂H₅ | N | N | C—OCH₃ | 181 |
| 1345 | 2-(C₆H₅)-C₆H₄ | H | 3-Cl-C₆H₄ | | OC₂H₅ | N | N | C—OCH₃ | 151 |
| 1346 | 2-(C₆H₅)-C₆H₄ | H | 4-Cl-C₆H₄ | | OC₂H₅ | N | N | C—OCH₃ | 177 |
| 1347 | 2-(C₆H₅)-C₆H₄ | H | 3-CH₃-C₆H₄ | | OC₂H₅ | N | N | C—OCH₃ | 177 |
| 1348 | 2-(C₆H₅)-C₆H₄ | H | 3-NH₂-C₆H₄ | | OC₂H₅ | N | N | C—CH₃ | 149 |
| 1349 | 2-(CO₂CH₃)-C₆H₄ | CH₃ | CH₃ | | CH₃ | N | N | C—CH₃ | |
| 1350 | 2-F-C₆H₄ | CH₃ | CH₃ | | CH₃ | N | N | C—CH₃ | |

| # | Ar | R1 | R2 | R3 | X | Y | Z | |
|---|---|---|---|---|---|---|---|---|
| 1351 | 2-CF3-C6H4 | CH3 | CH3 | CH3 | N | N | C—CH3 | |
| 1352 | 2-F-C6H4 | H | C6H5 | OCH3 | N | N | C—OCH3 | 208 |
| 1353 | 2-SO2N(CH3)2-C6H4 | H | C6H5 | CH3 | N | N | C—CH3 | |
| 1354 | 2-OCHF2-C6H4 | H | C6H5 | OCH3 | N | N | C—C2H5 | |
| 1355 | 2,6-Cl2-C6H3-CH2— | CH3 | CH3 | CH3 | N | N | C—CH3 | |
| 1356 | 2-Cl-C6H4-CH2— | H | C6H5 | OCH3 | N | N | C—CH3 | |
| 1357 | 2,6-Cl2-C6H3-CH2— | H | C6H5 | CH3 | N | N | C—CH3 | |
| 1358 | 3-methyl-2-CO2CH3-thienyl | CH3 | CH3 | CH3 | N | N | C—CH3 | |
| 1359 | 3-methyl-2-CO2CH3-thienyl | H | C6H5 | CH3 | N | N | C—CH3 | |
| 1360 | 3-methyl-2-CO2CH3-thienyl | CH3 | CH3 | OCH3 | N | N | C—C2H5 | |
| 1361 | 3-methyl-2-CO2CH3-thienyl | H | C6H5 | OCH3 | N | N | C—C2H5 | |

| No. | Aryl | R1 | R2 | X | A | B | Y | mp |
|---|---|---|---|---|---|---|---|---|
| 1362 | 2-CN-C6H4-CH2- | CH3 | CH3 | OCH3 | N | N | C—CH3 | |
| 1363 | 2-CN-C6H4-CH2- | H | C6H5 | OCH3 | N | N | C—CH3 | |
| 1364 | 2,3,5,6-tetramethylphenyl | CH3 | CH3 | OCH3 | N | N | C—OCH3 | 211 |
| 1365 | 5-N(CH3)2-naphth-1-yl | CH3 | CH3 | OCH3 | N | N | C—OCH3 | 154 |
| 1366 | 2-Cl-6-CH3-phenyl | CH3 | CH3 | OCH3 | N | N | C—OCH3 | 200 |
| 1367 | 2,4-Cl2-phenyl | CH3 | CH3 | OCH3 | N | N | C—CH3 | 100 |
| 1368 | 2,5-F2-phenyl | CH3 | CH3 | OCH3 | N | N | C—CH3 | 165 |
| 1369 | 4-Cl-phenyl | CH3 | CH3 | OCH3 | N | N | C—CH3 | 152 |
| 1370 | 3-Cl-phenyl | CH3 | CH3 | OCH3 | N | N | C—CH3 | 142 |
| 1371 | 2,4-Br2-phenyl | CH3 | CH3 | OCH3 | N | N | C—CH3 | 194 |

-continued

| # | Ar | R1 | R2 | X1 | X2 | X3 | X4 | mp |
|---|---|---|---|---|---|---|---|---|
| 1372 | 3,5-(F₃C)₂-C₆H₃- | CH₃ | CH₃ | OCH₃ | N | N | C—OCH₃ | |
| 1373 | 2-CN-C₆H₄- | CH₃ | CH₃ | OCH₃ | N | N | C—OCH₃ | |
| 1374 | 3,5-(F₃C)₂-C₆H₃- | CH₃ | CH₃ | OCH₃ | N | N | C—CH₃ | 172 |
| 1375 | 3-Cl-4-F-C₆H₃- | CH₃ | CH₃ | OCH₃ | N | N | C—CH₃ | |
| 1376 | 2-SO₂CH₃-C₆H₄- | CH₃ | CH₃ | OCH₃ | N | N | C—CH₃ | 224 |
| 1377 | 4-NC-C₆H₄- | CH₃ | CH₃ | OCH₃ | N | N | C—CH₃ | 165 |
| 1378 | 2-CH₃-4-F-C₆H₃- | CH₃ | CH₃ | OCH₃ | N | N | C—OCH₃ | |
| 1379 | 2-CH₃-4-F-C₆H₃- | CH₃ | CH₃ | OCH₃ | N | N | C—CH₃ | |
| 1380 | 2-Br-C₆H₄- | CH₃ | CH₃ | OCH₃ | N | N | C—CH₃ | |
| 1381 | 2-OCH₃-4-OCH₃-C₆H₃- | CH₃ | CH₃ | OCH₃ | N | N | C—OCH₃ | 184 |

| | | | | | | | | |
|---|---|---|---|---|---|---|---|---|
| 1382 | 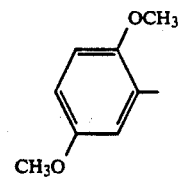 | CH₃ | CH₃ | | OCH₃ | N | N | C—CH₃ | 164 |
| 1383 | 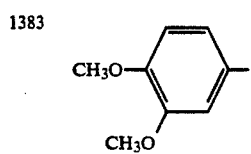 | CH₃ | CH₃ | | OCH₃ | N | N | C—OCH₃ | 116 |
| 1384 | 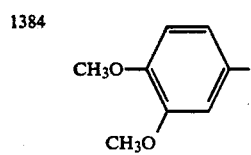 | CH₃ | CH₃ | | OCH₃ | N | N | C—CH₃ | 216 |
| 1385 | 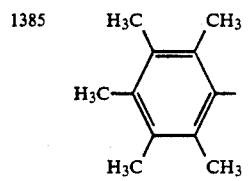 | H | C₆H₅ | | OCH₃ | N | N | C—OCH₃ | 208 |
| 1386 | 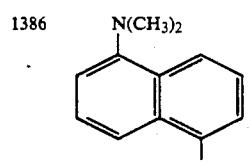 | H | C₆H₅ | | OCH₃ | N | N | C—OCH₃ | 197 |
| 1387 | 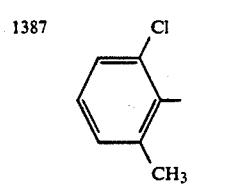 | H | C₆H₅ | | OCH₃ | N | N | C—OCH₃ | 198 |
| 1388 | 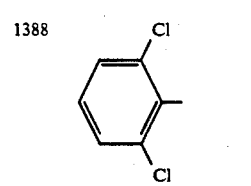 | H | C₆H₅ | | OCH₃ | N | N | C—OCH₃ | 206 |
| 1389 | 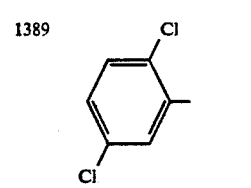 | H | C₆H₅ | | OCH₃ | N | N | C—OCH₃ | 131 |
| 1390 | 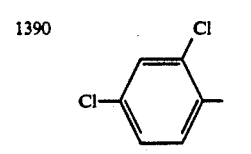 | H | C₆H₅ | | OCH₃ | N | N | C—OCH₃ | 157 |

-continued

| No. | Ar | R | R' | X | A | B | Y | mp |
|---|---|---|---|---|---|---|---|---|
| 1391 | 2,5-diCl-C6H3 | H | C6H5 | OCH3 | N | N | C—CH3 | |
| 1392 | 2,4-diCl-C6H3 | H | C6H5 | OCH3 | N | N | C—CH3 | 163 |
| 1393 | 2,4-diF-C6H3 | H | C6H5 | OCH3 | N | N | C—OCH3 | |
| 1394 | 3-Cl-C6H4 | H | C6H5 | OCH3 | N | N | C—OCH3 | 142 |
| 1395 | 4-Cl-C6H4 | H | C6H5 | OCH3 | N | N | C—OCH3 | 163 |
| 1396 | 3-Br-C6H4 | H | C6H5 | OCH3 | N | N | C—OCH3 | |
| 1397 | 2,6-diF-C6H3 | H | C6H5 | OCH3 | N | N | C—OCH3 | 196 |
| 1398 | 2,4-diF-C6H3 | H | C6H5 | OCH3 | N | N | C—CH3 | 216 |
| 1399 | 3-Cl-C6H4 | H | C6H5 | OCH3 | N | N | C—CH3 | 162 |
| 1400 | 4-Cl-C6H4 | H | C6H5 | OCH3 | N | N | C—CH3 | 204 |
| 1401 | 4-F-C6H4 | H | C6H5 | OCH3 | N | N | C—CH3 | 200 |

| | | | | | | | | |
|---|---|---|---|---|---|---|---|---|
| 1402 | 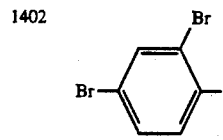 | H | C$_6$H$_5$ | | OCH$_3$ | N | N | C—CH$_3$ | 182 |
| 1403 | 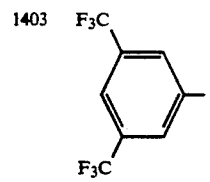 | H | C$_6$H$_5$ | | OCH$_3$ | N | N | C—OCH$_3$ | |
| 1404 | 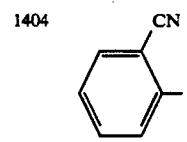 | H | C$_6$H$_5$ | | OCH$_3$ | N | N | C—OCH$_3$ | |
| 1405 | 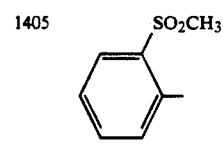 | H | C$_6$H$_5$ | | OCH$_3$ | N | N | C—OCH$_3$ | |
| 1406 | 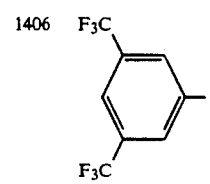 | H | C$_6$H$_5$ | | OCH$_3$ | N | N | C—CH$_3$ | 187 |
| 1407 | 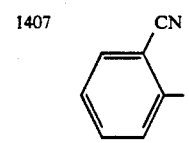 | H | C$_6$H$_5$ | | OCH$_3$ | N | N | C—CH$_3$ | |
| 1408 | 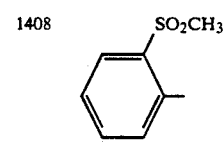 | H | C$_6$H$_5$ | | OCH$_3$ | N | N | C—CH$_3$ | 205 |
| 1409 | 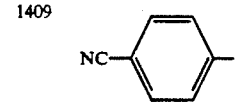 | H | C$_6$H$_5$ | | OCH$_3$ | N | N | C—CH$_3$ | 243 |
| 1410 | 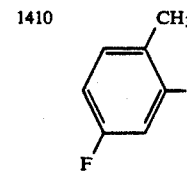 | H | C$_6$H$_5$ | | OCH$_3$ | N | N | C—OCH$_3$ | |
| 1411 | 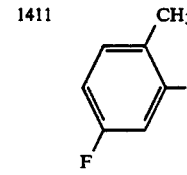 | H | C$_6$H$_5$ | | OCH$_3$ | N | N | C—CH$_3$ | |

-continued

| | | | | | | | | |
|---|---|---|---|---|---|---|---|---|
| 1412 | 2-Br-C6H4 | H | C6H5 | OCH3 | N | N | C—OCH3 | 192 |
| 1413 | 2-Br-C6H4 | H | C6H5 | OCH3 | N | N | C—CH3 | |
| 1414 | 2,4-(CH3O)2-C6H3 | H | C6H5 | OCH3 | N | N | C—OCH3 | 215 |
| 1415 | 2,4-(CH3O)2-C6H3 | H | C6H5 | OCH3 | N | N | C—CH3 | 193 |
| 1416 | 3,4-(CH3O)2-C6H3 | H | C6H5 | OCH3 | N | N | C—OCH3 | 159 |
| 1417 | 3,4-(CH3O)2-C6H3 | H | C6H5 | OCH3 | N | N | C—CH3 | 174 |
| 1418 | 2-OCH3-C6H4 | H | C6H5 | OCH3 | N | N | C—OCH3 | |
| 1419 | 2-Cl-6-CH3-C6H3 | CH3 | CH2CH(CH3)2 | OCH3 | N | N | C—OCH3 | |
| 1420 | 2-Cl-6-CH3-C6H3 | H | CH3 | OCH3 | N | N | C—OCH3 | |
| 1421 | 2-Cl-6-CH3-C6H3 | H | pyridyl | OCH3 | N | N | C—OCH3 | 185 |

-continued
| | | | | | | | | |
|---|---|---|---|---|---|---|---|---|
| 1422 | 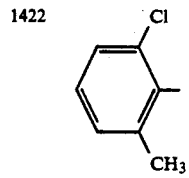 | H | 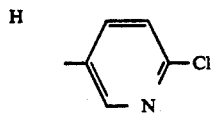 | OCH₃ | N | N | C—OCH₃ | 191 |
| 1423 | 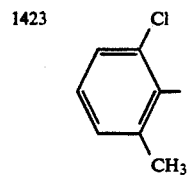 | H | 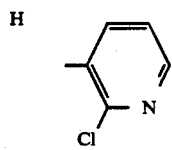 | OCH₃ | N | N | C—OCH₃ | 189 |
| 1424 | 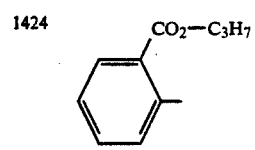 | H | 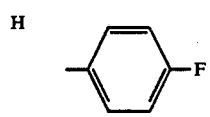 | OCH₃ | N | N | C—CH₃ | 167 |
| 1425 | 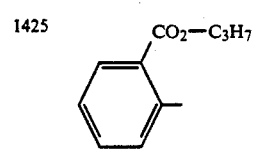 | H | 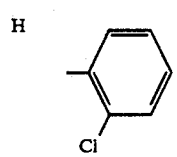 | OCH₃ | N | N | C—CH₃ | 143 |
| 1426 | 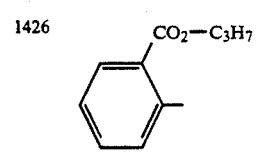 | H | 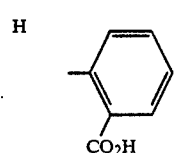 | OCH₃ | N | N | C—CH₃ | |
| 1427 | 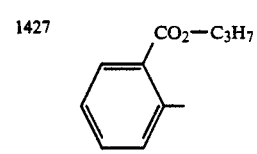 | H | 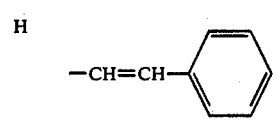 | OCH₃ | N | N | C—CH₃ | 182 |
| 1428 | 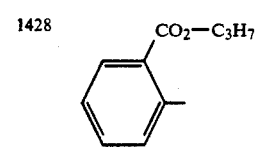 | H | CH(CH₃)₂ | OCH₃ | N | N | C—CH₃ | 145 |
| 1429 | 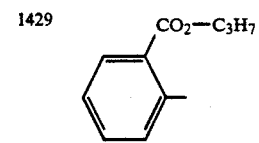 | H | —C(CH₃)₃ | OCH₃ | N | N | C—CH₃ | 149 |
| 1430 | 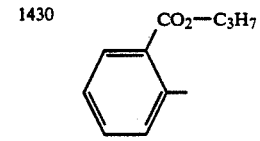 | CH₃ | CH₂CH(CH₃)₂ | OCH₃ | N | N | C—CH₃ | |
| 1431 | 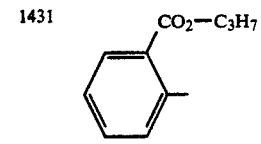 | H | CH₃ | OCH₃ | N | N | C—CH₃ | 134 |

-continued

| | | | | | | | | |
|---|---|---|---|---|---|---|---|---|
| 1432 | 2-(CO₂—C₃H₇)-phenyl | H | pyridin-3-yl | OCH₃ | N | N | C—CH₃ | 150 |
| 1433 | 2-(COOCH(CH₃)₂)-phenyl | H | 3-(CF₃)-phenyl | OCH₃ | N | N | C—CH₃ | |
| 1434 | 2-(COOCH(CH₃)₂)-phenyl | H | 4-(CF₃)-phenyl | OCH₃ | N | N | C—CH₃ | 168 |
| 1435 | 2-(COOCH(CH₃)₂)-phenyl | H | 6-chloropyridin-3-yl | OCH₃ | N | N | C—CH₃ | |
| 1436 | 2-(COOCH(CH₃)₂)-phenyl | H | 2-chloropyridin-3-yl | OCH₃ | N | N | C—CH₃ | |
| 1437 | 2-(CO₂CH₂CH₂OCH₃)-phenyl | H | 6-chloropyridin-3-yl | OCH₃ | N | N | C—CH₃ | 134 |
| 1438 | 2-(CO₂CH₂CH₂OCH₃)-phenyl | H | 2-chloropyridin-3-yl | OCH₃ | N | N | C—CH₃ | 131 |
| 1439 | 2-(SO₂N(CH₃)₂)-phenyl | H | CH₃CH₂CH₂ | OCH₃ | N | N | C—OCH₃ | |
| 1440 | 2-(SO₂N(CH₃)₂)-phenyl | H | CH₃SCH₂CH₂ | OCH₃ | N | N | C—OCH₃ | 172 |
| 1441 | 2-(SO₂N(CH₃)₂)-phenyl | H | CH₃CH₂CH₂ | OCH₃ | N | N | C—CH₃ | 167 |
| 1442 | 2-(SO₂N(CH₃)₂)-phenyl | H | CH₃SCH₂CH₂ | OCH₃ | N | N | C—CH₃ | 161 |

| | | | | | | | | |
|---|---|---|---|---|---|---|---|---|
| 1443 | 2-SO₂N(C₂H₅)₂-phenyl | H | CH₃ | | OCH₃ | N | N | C—OCH₃ |
| 1444 | 2-SO₂N(C₂H₅)₂-phenyl | CH₃ | CH₂CH(CH₃)₂ | | OCH₃ | N | N | C—OCH₃ |
| 1445 | 2-SO₂N(C₂H₅)₂-phenyl | H | —C(CH₃)₃ | | OCH₃ | N | N | C—OCH₃ |
| 1446 | 2-SO₂N(C₂H₅)₂-phenyl | —(CH₂)₅— | | | OCH₃ | N | N | C—OCH₃ |
| 1447 | 2-SO₂N(C₂H₅)₂-phenyl | H | —CH(CH₃)₂ | | OCH₃ | N | N | C—OCH₃ |
| 1448 | 2-SO₂N(C₂H₅)₂-phenyl | H | CH₃CH₂CH₂— | | OCH₃ | N | N | C—OCH₃ | 154 |
| 1449 | 2-SO₂N(C₂H₅)₂-phenyl | H | CH₃SCH₂CH₂— | | OCH₃ | N | N | C—OCH₃ | 141 |
| 1450 | 2-SO₂N(C₂H₅)₂-phenyl | CH₃ | —CH₂CH(CH₃)₂ | | OCH₃ | N | N | C—CH₃ |
| 1451 | 2-SO₂N(C₂H₅)₂-phenyl | H | C(CH₃)₃ | | OCH₃ | N | N | C—CH₃ |
| 1452 | 2-SO₂N(C₂H₅)₂-phenyl | —(CH₂)₅— | | | OCH₃ | N | N | C—CH₃ |
| 1453 | 2-SO₂N(CH₃)₂-phenyl | H | —CH(CH₃)₂ | | OCH₃ | N | N | C—CH₃ |

-continued

| | | | | | | | | |
|---|---|---|---|---|---|---|---|---|
| 1454 | 2-SO$_2$N(C$_2$H$_5$)$_2$-phenyl | H | CH$_3$CH$_2$CH$_2$— | OCH$_3$ | N | N | C—CH$_3$ | 163 |
| 1455 | 2-SO$_2$N(C$_2$H$_5$)$_2$-phenyl | H | CH$_3$SCH$_2$CH$_2$— | OCH$_3$ | N | N | C—CH$_3$ | 153 |
| 1456 | 2-SO$_2$N(CH$_3$)$_2$-phenyl | H | CH$_3$(CH$_2$)$_5$— | OCH$_3$ | N | N | C—OCH$_3$ | 102 |
| 1457 | 2-SO$_2$N(CH$_3$)$_2$-phenyl | H | CH$_3$(CH$_2$)$_9$— | OCH$_3$ | N | N | C—OCH$_3$ | 108 |
| 1458 | 2-SO$_2$N(CH$_3$)$_2$-phenyl | H | CH$_3$(CH$_2$)$_{10}$— | OCH$_3$ | N | N | C—OCH$_3$ | 112 |
| 1459 | 2-SO$_2$N(CH$_3$)$_2$-phenyl | H | CH$_3$(CH$_2$)$_{11}$— | OCH$_3$ | N | N | C—OCH$_3$ | 105 |
| 1460 | 2-SO$_2$N(CH$_3$)$_2$-phenyl | H | CH$_3$(CH$_2$)$_{12}$— | OCH$_3$ | N | N | C—OCH$_3$ | |
| 1461 | 2-SO$_2$N(CH$_3$)$_2$-phenyl | H | CH$_3$(CH$_2$)$_5$— | OCH$_3$ | N | N | C—CH$_3$ | 108 |
| 1462 | 2-SO$_2$N(CH$_3$)$_2$-phenyl | H | CH$_3$(CH$_2$)$_9$— | OCH$_3$ | N | N | C—CH$_3$ | 105 |
| 1463 | 2-SO$_2$N(CH$_3$)$_2$-phenyl | H | CH$_3$(CH$_2$)$_{10}$— | OCH$_3$ | N | N | C—CH$_3$ | 113 |
| 1464 | 2-SO$_2$N(CH$_3$)$_2$-phenyl | H | CH$_3$(CH$_2$)$_{11}$— | OCH$_3$ | N | N | C—CH$_3$ | |

-continued

| No. | Ar | R1 | R2 | X | A | B | E | mp |
|---|---|---|---|---|---|---|---|---|
| 1465 | 2-(SO$_2$N(CH$_3$)$_2$)C$_6$H$_4$ | H | CH$_3$(CH$_2$)$_{12}$— | OCH$_3$ | N | N | C—CH$_3$ | 105 |
| 1466 | 3-methyl-2-(CO$_2$CH$_3$)thiophene | H | CH$_3$CH$_2$— | OCH$_3$ | N | N | C—CH$_3$ | |
| 1467 | 3-methyl-2-(CO$_2$CH$_3$)thiophene | H | CH$_3$CH$_2$CH$_2$— | OCH$_3$ | N | N | C—CH$_3$ | 149 |
| 1468 | 3-methyl-2-(CO$_2$CH$_3$)thiophene | H | CH$_3$SCH$_2$CH$_2$— | OCH$_3$ | N | N | C—CH$_3$ | 150 |
| 1469 | 2-methylthiophene | CH$_3$ | CH$_3$ | OCH$_3$ | N | N | C—OCH$_3$ | |
| 1470 | 2-methylthiophene | H | C$_6$H$_5$ | OCH$_3$ | N | N | C—OCH$_3$ | |
| 1471 | 5-chloro-2-methylthiophene | CH$_3$ | CH$_3$ | OCH$_3$ | N | N | C—OCH$_3$ | |
| 1472 | 3,5-dichloro-2-methylthiophene | H | C$_6$H$_5$ | OCH$_3$ | N | N | C—CH$_3$ | |
| 1473 | 4-bromo-3,5-dichloro-2-methylthiophene | CH$_3$ | CH$_3$ | OCH$_3$ | N | N | C—OCH$_3$ | |
| 1474 | 4-bromo-3,5-dichloro-2-methylthiophene | CH$_3$ | CH$_3$ | OCH$_3$ | N | N | C—CH$_3$ | |
| 1475 | 4,5-dibromo-2-methylthiophene | CH$_3$ | CH$_3$ | OCH$_3$ | N | N | C—OCH$_3$ | |
| 1476 | 4,5-dibromo-2-methylthiophene | CH$_3$ | CH$_3$ | OCH$_3$ | N | N | C—CH$_3$ | |
| 1477 | 4,5-dibromo-2-methylthiophene | H | C$_6$H$_5$ | OCH$_3$ | N | N | C—OCH$_3$ | |
| 1478 | 4,5-dibromo-2-methylthiophene | H | C$_6$H$_5$ | OCH$_3$ | N | N | C—CH$_3$ | |

-continued

| # | R1 | R2 | R3 | R4 | | | | |
|---|---|---|---|---|---|---|---|---|
| 1479 | 3,5-dimethylisoxazol-4-yl (H3C, CH3 on isoxazole) | CH3 | CH3 | | OCH3 | N | N | C—OCH3 |
| 1480 | 3,5-dimethylisoxazol-4-yl | CH3 | CH3 | | OCH3 | N | N | C—CH3 |
| 1481 | 3,5-dimethylisoxazol-4-yl | H | C6H5 | | OCH3 | N | N | C—OCH3 |
| 1482 | 3,5-dimethylisoxazol-4-yl | H | C6H5 | | OCH3 | N | N | C—CH3 |
| 1483 | 5-chloro-1,3,4-trimethylpyrazol-... | CH3 | CH3 | | OCH3 | N | N | C—OCH3 |
| 1484 | 5-chloro-1,3,4-trimethylpyrazol | CH3 | CH3 | | OCH3 | N | N | C—CH3 |
| 1485 | 5-chloro-1,3,4-trimethylpyrazol | H | C6H5 | | OCH3 | N | N | C—OCH3 |
| 1486 | 5-chloro-1,3,4-trimethylpyrazol | H | C6H5 | | OCH3 | N | N | C—CH3 |
| 1487 | 2-SO2N(C2H5)2-phenyl | H | 2-HO2C-phenyl | | OCH3 | N | N | C—CH3 | 212 |
| 1488 | 2-CO2CH2CH2OCH3-phenyl | H | 3-CF3-phenyl | | OCH3 | N | N | C—CH3 | 144 |
| 1489 | 3-CF3-phenyl | CH3 | CH3 | | OCH3 | N | N | C—CH3 | 109 |
| 1490 | 4-Br-phenyl | CH3 | CH3 | | OCH3 | N | N | C—CH3 | 134 |

-continued

| | | | | | | | | |
|---|---|---|---|---|---|---|---|---|
| 1491 | [2-methyl-thiophene-3-carboxylate, CO₂CH₃] | H | CH₃(CH₂)₃— | OCH₃ | N | N | C—CH₃ | 134 |
| 1492 | [2-methyl-thiophene-3-carboxylate, CO₂CH₃] | H | CH₃(CH₂)₄— | OCH₃ | N | N | C—CH₃ | 120 |
| 1493 | [2-methyl-thiophene-3-carboxylate, CO₂CH₃] | H | CH₃(CH₂)₁₂— | OCH₃ | N | N | C—CH₃ | 189 |
| 1494 | [2-methyl-thiophene-3-carboxylate, CO₂CH₃] | H | CH₃(CH₂)₁₀— | OCH₃ | N | N | C—CH₃ | 110 |
| 1495 | [2-methyl-thiophene-3-carboxylate, CO₂CH₃] | H | CH₃(CH₂)₁₁— | OCH₃ | N | N | C—CH₃ | 103 |
| 1496 | [2-methyl-thiophene-3-carboxylate, CO₂CH₃] | H | CH₃(CH₂)₉— | OCH₃ | N | N | C—CH₃ | 120 |
| 1497 | [2-COOCH(CH₃)₂-phenyl] | H | —CH=CH—phenyl | OCH₃ | N | N | C—CH₃ | 173 |
| 1498 | [2-COOCH(CH₃)₂-phenyl] | H | —CH(CH₃)₂ | OCH₃ | N | N | C—CH₃ | 178 |
| 1499 | [2-COOCH(CH₃)₂-phenyl] | H | —C(CH₃)₃ | OCH₃ | N | N | C—CH₃ | 166 |
| 1500 | [2-COOCH(CH₃)₂-phenyl] | CH₃ | —CH₂CH(CH₃)₂ | OCH₃ | N | N | C—CH₃ | 154 |
| 1501 | [2-COOCH(CH₃)₂-phenyl] | H | [2-F-phenyl] | OCH₃ | N | N | C—CH₃ | 188 |
| 1502 | [2-COOCH(CH₃)₂-phenyl] | H | [3-F-phenyl] | OCH₃ | N | N | C—CH₃ | 184 |

-continued

| | 323 | | | | 324 | | | | |
|---|---|---|---|---|---|---|---|---|---|
| 1503 | 2-(COOCH(CH$_3$)$_2$)-phenyl | H | 4-F-phenyl | OCH$_3$ | N | N | C—CH$_3$ | 206 |
| 1504 | 2-(COOCH(CH$_3$)$_2$)-phenyl | H | 2-Cl-phenyl | OCH$_3$ | N | N | C—CH$_3$ | 168 |
| 1505 | 3-methyl-2-(CO$_2$CH$_3$)-thienyl | H | —(CH$_2$)$_5$CH$_3$ | OCH$_3$ | N | N | C—CH$_3$ | 117 |
| 1506 | 3-methyl-2-(CO$_2$CH$_3$)-thienyl | H | —(CH$_2$)$_7$CH$_3$ | OCH$_3$ | N | N | C—CH$_3$ | 111 |
| 1507 | 2-(CO$_2$—C$_3$H$_7$)-phenyl | H | 2-Cl-phenyl | OCH$_3$ | N | N | C—CH$_3$ | 143 |
| 1508 | 2-(CO$_2$—C$_3$H$_7$)-phenyl | H | 2-CO$_2$H-phenyl | OCH$_3$ | N | N | C—CH$_3$ | |
| 1509 | 2-(CO$_2$—C$_3$H$_7$)-phenyl | H | —CH=CH—phenyl | OCH$_3$ | N | N | C—CH$_3$ | 182 |
| 1510 | 2-(CO$_2$—C$_3$H$_7$)-phenyl | H | CH(CH$_3$)$_2$ | OCH$_3$ | N | N | C—CH$_3$ | 145 |
| 1511 | 2-(CO$_2$—C$_3$H$_7$)-phenyl | H | —C(CH$_3$)$_3$ | OCH$_3$ | N | N | C—CH$_3$ | 149 |
| 1512 | 2-(CO$_2$—C$_3$H$_7$)-phenyl | CH$_3$ | CH$_2$CH(CH$_3$)$_2$ | OCH$_3$ | N | N | C—CH$_3$ | 136 |
| 1513 | 2-(CO$_2$—C$_3$H$_7$)-phenyl | H | CH$_3$ | OCH$_3$ | N | N | C—CH$_3$ | 134 |

-continued

| # | R1 | R2 | R3 | R4 | R5 | R6 | R7 | mp |
|---|---|---|---|---|---|---|---|---|
| 1514 | 2-(CO₂-C₃H₇)-phenyl | H | 3-pyridyl | | OCH₃ | N | N | C—CH₃ | 150 |
| 1515 | 2-(COOCH(CH₃)₂)-phenyl | H | 3-(CF₃)-phenyl | | OCH₃ | N | N | C—CH₃ | 170 |
| 1516 | 2-(CO₂CH₂CH₂OCH₃)-phenyl | H | 4-(CF₃)-phenyl | | OCH₃ | N | N | C—CH₃ | 168 |
| 1517 | 2-(COOCH(CH₃)₂)-phenyl | H | 6-chloro-3-pyridyl | | OCH₃ | N | N | C—CH₃ | 182 |
| 1518 | 2-(COOCH(CH₃)₂)-phenyl | H | 2-chloro-3-pyridyl | | OCH₃ | N | N | C—CH₃ | 157 |
| 1519 | 2-(CO₂CH₂CH₂OCH₃)-phenyl | H | 6-chloro-3-pyridyl | | OCH₃ | N | N | C—CH₃ | 134 |
| 1520 | 2-(CO₂CH₂CH₂OCH₃)-phenyl | H | 2-chloro-3-pyridyl | | OCH₃ | N | N | C—CH₃ | 131 |
| 1521 | 2-(SO₂N(CH₃)₂)-phenyl | H | CH₃CH₂CH₂ | | OCH₃ | N | N | C—OCH₃ | |
| 1522 | 2-(SO₂N(CH₃)₂)-phenyl | H | CH₃SCH₂CH₂ | | OCH₃ | N | N | C—OCH₃ | 172 |
| 1523 | 2-(SO₂N(CH₃)₂)-phenyl | H | CH₃CH₂CH₂ | | OCH₃ | N | N | C—CH₃ | 167 |
| 1524 | 2-(SO₂N(CH₃)₂)-phenyl | H | CH₃SCH₂CH₂ | | OCH₃ | N | N | C—CH₃ | 161 |

-continued

| No. | Ar | R1 | R2 | X | A | B | Y | mp |
|---|---|---|---|---|---|---|---|---|
| 1525 | 2-SO₂N(C₂H₅)₂-phenyl | H | CH₃ | OCH₃ | N | N | C—OCH₃ | |
| 1526 | 2-SO₂N(C₂H₅)₂-phenyl | CH₃ | CH₂CH(CH₃)₂ | OCH₃ | N | N | C—OCH₃ | |
| 1527 | 2-SO₂CH₃-phenyl | CH₃ | CH₃ | CH₃ | N | CH | C—CH₃ | 287 |
| 1528 | 2-SO₂CH₃-phenyl | H | C₆H₅ | CH₃ | N | CH | C—CH₃ | 273 |
| 1529 | 2-SO₂CH₃-phenyl | H | 4-CH₃-phenyl | CH₃ | N | CH | C—CH₃ | 248 |
| 1530 | 2-SO₂CH₃-phenyl | H | 2-Cl-phenyl | CH₃ | N | CH | C—CH₃ | 248 |
| 1531 | 2-SO₂CH₃-phenyl | H | 3-Cl-phenyl | CH₃ | N | CH | C—CH₃ | 265 |
| 1532 | 2-COOCH(CH₃)₂-phenyl | H | CH₃ | OCH₃ | N | N | C—CH₃ | |
| 1533 | 2-SO₂N(C₂H₅)₂-phenyl | H | 4-CH₃-phenyl | OCH₃ | N | N | C—CH₃ | |
| 1534 | 2-COOCH(CH₃)₂-phenyl | H | 4-CH₃-phenyl | OCH₃ | N | N | C—CH₃ | |
| 1535 | 2-SO₂N(CH₃)(OCH₃)-phenyl | H | 4-CH₃-phenyl | OCH₃ | N | N | C—CH₃ | |

-continued
| | | | | | | | | |
|---|---|---|---|---|---|---|---|---|
| 1536 | 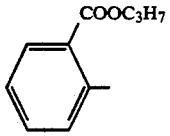 (COOC₃H₇) | H | 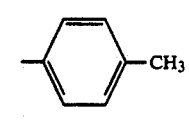 (CH₃) | OCH₃ | N | N | C—CH₃ | |
| 1537 | 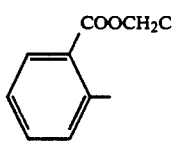 (COOCH₂CH₂Cl) | H | 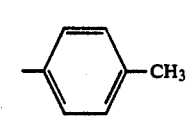 (CH₃) | OCH₃ | N | N | C—CH₃ | |
| 1538 | 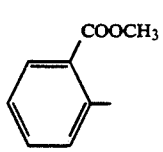 (COOCH₃) | H | 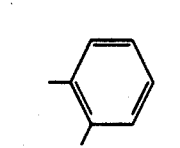 (HOOC) | OCH₃ | N | N | C—OCH₃ | |
| 1539 | 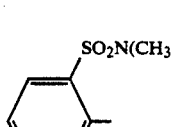 (SO₂N(CH₃)₂) | C₂H₅ | C₂H₅ | | CH₃ | N | CH CH | 167 |
| 1540 | 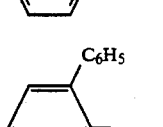 (C₆H₅) | H | 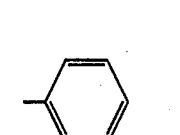 (CH₃) | OC₂H₅ | N | N | C—OCH₃ | 150 |
| 1541 | 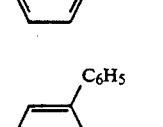 (C₆H₅) | H | 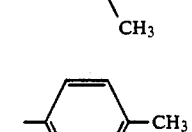 (CH₃) | OC₂H₅ | N | N | C—OCH₃ | 151 |
| 1542 | 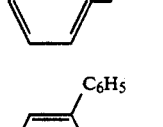 (C₆H₅) | H | 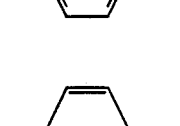 (OCH₃) | OC₂H₅ | N | N | C—OCH₃ | 189 |
| 1543 | 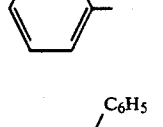 (C₆H₅) | H | 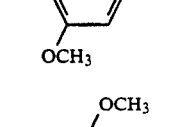 (OCH₃) | OC₂H₅ | N | N | C—OCH₃ | 170 |
| 1544 | 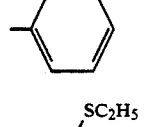 (SC₂H₅) | H | C₆H₅ | OCH₃ | N | CH | C—OCH₃ | 231 |
| 1545 | 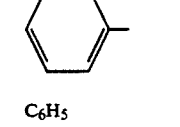 (SC₂H₅) | H | 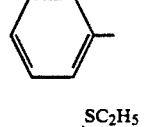 (Cl) | OCH₃ | N | CH | C—OCH₃ | 200 |
| 1546 |  (SC₂H₅) | H | 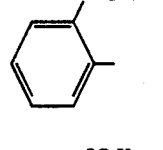 (Cl) | OCH₃ | N | CH | C—OCH₃ | 210 |

-continued

| | | | | | | | | |
|---|---|---|---|---|---|---|---|---|
| 1547 | 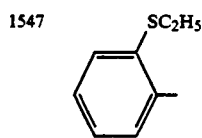 | H | 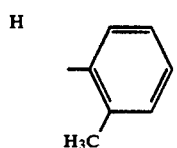 | OCH₃ | N | CH | C—OCH₃ | 210 |
| 1548 | 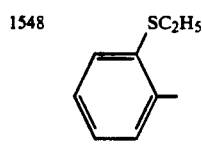 | H | 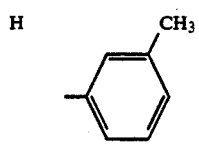 | OCH₃ | N | CH | C—OCH₃ | 212 |

*)The ¹H-NMR spectra were taken up in deuterochloroform (CDCl₃) with tetramethylsilane (TMS) as the internal standard. The chemical shift is indicated as a d value in ppm.

Starting Substances of the Formula (II):

EXAMPLE (II-1)

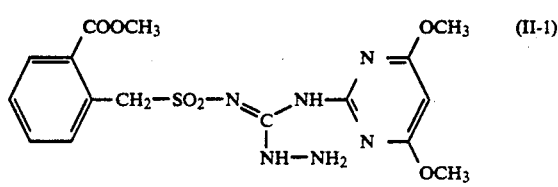 (II-1)

1.3 g (0.025 mole of hydrazine hydrate are added at an initial temperature of 20° C. to a suspension of 15.9 g (0.025 mol) of N'-(4,6-dimethoxy-pyrimidin-2-yl)N''-methoxy-N''-(2-methoxycarbonyl-phenylsulphonyl)-N'''(2-methoxycarbonyl-benzulsulphonyl)-guanidine in 100 ml of methanol, with stirring, during which process the reaction mixture reaches a temperature of 30° C. and a clear solution is formed. The product which precipitates in crystalline form after four hours, stirring at 20° C. to 30° C. is isolated by filtration with suction.

9.5 g (89% of theory) of N'-(4,6-dimethoxypyrimidin-2-yl)-N''-amino-N'''-(2-methoxycarbonyl-benzylsulphonyl)-guanidine of melting point 166° C. are obtained.

EXAMPLE (II-2)

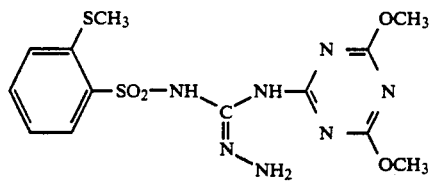

1.0 g (0.02 mol) of hydrazine hydrate is added with stirring at 20° C. to a mixture of 8.3 g (0.02 mol) of N'-(4,6-dimethoxy-s-triazin-2-yl)-N''-(2-methylthphenylsulphonyl)-S-methyl-isothiourea and 80 ml of methylene chloride, and this mixture is stirred for 30 minutes at 20° C. It is then concentrated, the residue is triturated with ethanol, and the product which is obtained in crystalline form is isolated by filtration with suction.

5.5 g (69% of theory) of N'-(4,6-dimethoxy-s-triazin-2-yl)-N''-amino-N'''-(2-methylthio-phenylsulphonyl)-guanidine of melting point 147° C. are obtained.

Examples of compounds of the foumula (II) which can be also prepared analogously to Examples (II-1) and (II-2) are listed in Table 4 below ("decomp. denotes "decomposition").

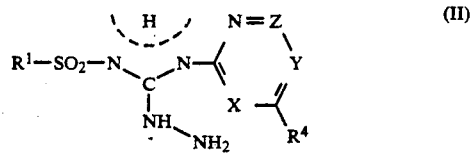 (II)

The abovementioned compounds (II-1) and (II-2) as well as the individual compounds (II-3) to (II-94) which are mentioned in Table 4 are new as such and also have herbicidal properties themselves; these compounds are likewise the subject of the invention.

TABLE 4

| | Examples of the starting substances of the formula (II) | | | | | |
|---|---|---|---|---|---|---|
| Ex. No. | R¹ | R⁴ | X | Y | Z | Melting point (°C.) |
| II-3 | 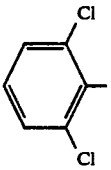 | OCH₃ | N | N | C—OCH₃ | 132 (decomp.) |

TABLE 4-continued

| Examples of the starting substances of the formula (II) | | | | | | |
|---|---|---|---|---|---|---|
| Ex. No. | R¹ | R⁴ | X | Y | Z | Melting point (°C.) |
| II-4 | 2-SO₂N(CH₃)₂-phenyl | OCH₃ | N | N | C—OCH₃ | 143 (decomp.) |
| II-5 | 2-OCF₃-phenyl | CH₃ | N | N | C—OC₂H₅ | 224 |
| II-6 | 2-COOCH₃-phenyl | CH₃ | N | N | C—OC₂H₅ | 121 (decomp.) |
| II-7 | 2-SO₂CH₃-phenyl | OCH₃ | N | N | C—OCH₃ | 153 (decomp.) |
| II-8 | 2-COOCH₃-phenyl | OCH₃ | N | N | C—OCH₃ | 170 (decomp.) |
| II-9 | 2-CF₃-phenyl | OCH₃ | N | N | C—OCH₃ | 155 (decomp.) |
| II-10 | 2,6-di-F-phenyl | OCH₃ | N | N | C—OCH₃ | 124 (decomp.) |
| II-11 | 2-Cl-benzyl | OCH₃ | N | N | C—OCH₃ | 170 (decomp.) |
| II-12 | 2-COOCH₃-benzyl | CH₃ | N | N | C—OCH₃ | 150 (decomp.) |
| II-13 | 2-COOCH₃-benzyl | OCH₃ | N | N | C—OCH₃ | 178 (decomp.) |

TABLE 4-continued

Examples of the starting substances of the formula (II)

| Ex. No. | R¹ | R⁴ | X | Y | Z | Melting point (°C.) |
|---|---|---|---|---|---|---|
| II-14 | 2-(COOCH₃)-C₆H₄-CH₂- | CH₃ | N | N | C—CH₃ | 138 (decomp.) |
| II-15 | 2-(COOCH₃)-C₆H₄-CH₂- | C₂H₅ | N | N | C—OCH₃ | 150 (decomp.) |
| II-16 | 2-(COOCH₃)-C₆H₄-CH₂- | CH₃ | N | N | C—OC₂H₅ | 141 (decomp.) |
| II-17 | 2-(COOCH₃)-C₆H₄-CH₂- | CH₃ | N | N | C—N(CH₃)₂ | 193 (decomp.) |
| II-18 | 2-(OCHF₂)-C₆H₄- | C₂H₅ | N | N | C—OCH₃ | 212 (decomp.) |
| II-19 | 2-(OCHF₂)-C₆H₄- | CH₃ | N | N | C—OCH₃ | 225 |
| II-20 | 2-Cl-C₆H₄- | C₂H₅ | N | N | C—OCH₃ | 133 (decomp.) |
| II-21 | 2,6-Cl₂-C₆H₃- | C₂H₅ | N | N | C—OCH₃ | 105 (decomp.) |
| II-22 | 2-(OCF₃)-C₆H₄-CH₂- | CH₃ | N | N | C—SCH₃ | 217 |
| II-23 | 2-(OCHF₂)-C₆H₄-CH₂- | C₂H₅ | N | N | C—OCH₃ | 190 |

TABLE 4-continued

| Ex. No. | R¹ | R⁴ | X | Y | Z | Melting point (°C.) |
|---|---|---|---|---|---|---|
| II-24 | 2-(OCHF$_2$)-benzyl | CH$_3$ | N | N | C—OC$_2$H$_5$ | 188 |
| II-25 | 2-(OCHF$_2$)-benzyl | CH$_3$ | N | N | C—SCH$_3$ | 148 (decomp.) |
| II-26 | 2-(OCHF$_2$)-benzyl | CH$_3$ | N | N | C—CH$_3$ | 133 (decomp.) |
| II-27 | 2-(SO$_2$N(CH$_3$)$_2$)-phenyl | CH$_3$ | N | N | C—CH$_3$ | 145 (decomp.) |
| II-28 | 2-Cl-benzyl | CH$_3$ | N | N | C—OC$_2$H$_5$ | 136 (decomp.) |
| II-29 | 2-Cl-benzyl | CH$_3$ | N | N | C—SCH$_3$ | 169 (decomp.) |
| II-30 | 2,6-diCl-benzyl | CH$_3$ | N | N | C—OC$_2$H$_5$ | 177 |
| II-31 | 3-methyl-2-(COOCH$_3$)-thienyl | CH$_3$ | N | N | C—SCH$_3$ | 137 |
| II-32 | 3-methyl-2-(COOCH$_3$)-thienyl | CH$_3$ | N | N | C—OC$_2$H$_5$ | 65 |
| II-33 | 2-Cl-benzyl | CH$_3$ | N | N | C—OCH$_3$ | 163 (decomp.) |
| II-34 | 2,6-diCl-benzyl | CH$_3$ | N | N | C—OCH$_3$ | 166 (decomp.) |

TABLE 4-continued

Examples of the starting substances of the formula (II)

| Ex. No. | R¹ | R⁴ | X | Y | Z | Melting point (°C.) |
|---|---|---|---|---|---|---|
| II-35 | 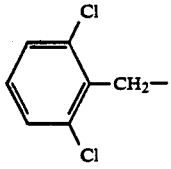 2,6-dichlorobenzyl | OCH₃ | N | N | C—OCH₃ | 164 (decomp.) |
| II-36 | 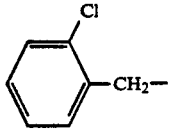 2-chlorobenzyl | CH₃ | N | N | C—CH₃ | 167 (decomp.) |
| II-37 | 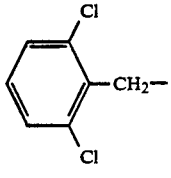 2,6-dichlorobenzyl | CH₃ | N | N | C—SCH₃ | 238 (decomp.) |
| II-38 | 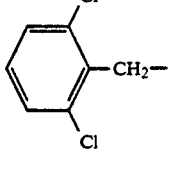 2,6-dichlorobenzyl | C₂H₅ | N | N | C—OCH₃ | 218 |
| II-39 | 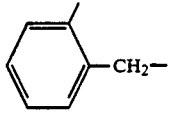 2-chlorobenzyl | C₂H₅ | N | N | C—OCH₃ | 203 |
| II-40 | 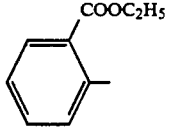 2-(ethoxycarbonyl)benzyl | CH₃ | N | N | C—SCH₃ | 125 (decomp.) |
| II-41 | 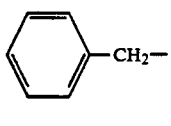 benzyl | CH₃ | N | N | C—OCH₃ | 217 (decomp.) |
| II-42 | 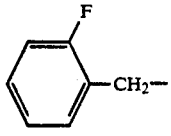 2-fluorobenzyl | CH₃ | N | N | C—OCH₃ | 204 |
| II-43 | 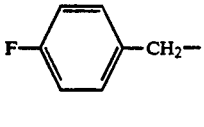 4-fluorobenzyl | CH₃ | N | N | C—OCH₃ | 218 (decomp.) |
| II-44 | 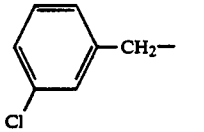 3-chlorobenzyl | CH₃ | N | N | C—OCH₃ | 195 (decomp.) |

TABLE 4-continued

Examples of the starting substances of the formula (II)

| Ex. No. | R¹ | R⁴ | X | Y | Z | Melting point (°C.) |
|---|---|---|---|---|---|---|
| II-45 | 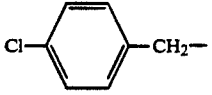 4-Cl-C₆H₄-CH₂- | CH₃ | N | N | C—OCH₃ | 232 (decomp.) |
| II-46 | 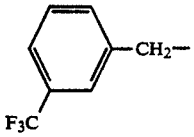 3-F₃C-C₆H₄-CH₂- | CH₃ | N | N | C—OCH₃ | 211 (decomp.) |
| II-47 | 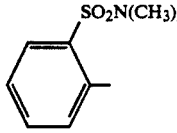 2-SO₂N(CH₃)₂-C₆H₄- | CH₃ | N | N | C—OCH₃ | 136 (decomp.) |
| II-48 | 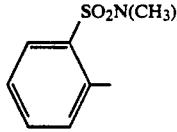 2-SO₂N(CH₃)₂-C₆H₄- | OCH₃ | N | CH | C—OCH₃ | 142 |
| II-49 | 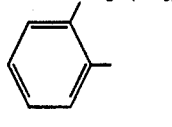 2-SO₂N(CH₃)₂-C₆H₄- | CH₃ | N | CH | CH | 172 |
| II-50 | 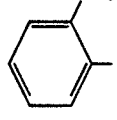 2-CF₃-C₆H₄- | CH₃ | N | CH | CH | 148 |
| II-51 | 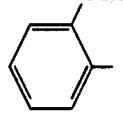 2-OCH₃-C₆H₄- | CH₃ | N | CH | C—CH₃ | 141 |
| II-52 | 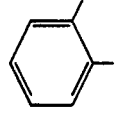 2-OC₂H₅-C₆H₄- | CH₃ | N | CH | C—CH₃ | 171 |
| II-53 | 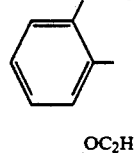 2-OCH₃-C₆H₄- | OCH₃ | N | CH | C—OCH₃ | 194 |
| II-54 | 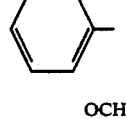 2-OC₂H₅-C₆H₄- | OCH₃ | N | CH | C—OCH₃ | 186 |
| II-55 | 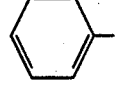 2-OCH₃-C₆H₄- | CH₃ | N | CH | CH | 124 |

TABLE 4-continued

Examples of the starting substances of the formula (II)

| Ex. No. | R¹ | R⁴ | X | Y | Z | Melting point (°C.) |
|---|---|---|---|---|---|---|
| II-56 | 2-OC₂H₅-C₆H₄- | CH₃ | N | CH | CH | 178 |
| II-57 | 2-OCF₃-C₆H₄-CH₂- | CH₃ | N | CH | C—CH₃ | 151 |
| II-58 | 2-CN-C₆H₄-CH₂- | CH₃ | N | CH | C—CH₃ | 162 |
| II-59 | 2,6-Cl₂-C₆H₃-CH₂- | CH₃ | N | CH | C—CH₃ | 205 |
| II-60 | 2-F-6-Cl-C₆H₃-CH₂- | CH₃ | N | CH | C—CH₃ | 197 |
| II-61 | 2-CN-C₆H₄-CH₂- | CH₃ | N | CH | C—OCH₃ | 192 |
| II-62 | 2,5-Cl₂-C₆H₃-CH₂- | CH₃ | N | CH | C—OCH₃ | 204 |
| II-63 | 2-COOCH₃-C₆H₄-CH₂- | CH₃ | N | CH | C—OCH₃ | 166 |
| II-64 | 2-[SO₂—N(CH₃)(OCH₃)]-C₆H₄- | CH₃ | N | CH | C—OCH₃ | 176 |
| II-65 | 2-OCF₃-C₆H₄- | OCH₃ | N | CH | C—CH₂OCH₃ | 225 |

TABLE 4-continued

Examples of the starting substances of the formula (II)

| Ex. No. | R¹ | R⁴ | X | Y | Z | Melting point (°C.) |
|---|---|---|---|---|---|---|
| II-66 | 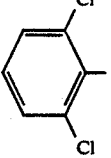 2,6-dichlorophenyl | CH₃ | N | CH | CH | 162 |
| II-67 | 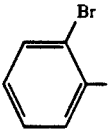 2-bromophenyl | CH₃ | N | CH | CH | 131 |
| II-68 | 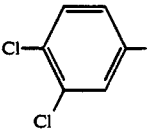 3,4-dichlorophenyl | CH₃ | N | CH | CH | 132 |
| II-69 | 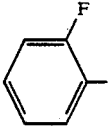 2-fluorophenyl | CH₃ | N | CH | CH | 108 |
| II-70 | 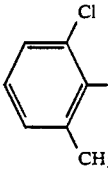 2-chloro-3-methylphenyl | CH₃ | N | CH | CH | 102 |
| II-71 | 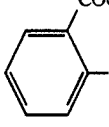 2-methoxycarbonylphenyl | OCH₃ | N | C—CH₃ | CH | 153 |
| II-72 | 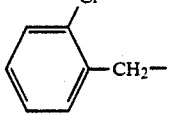 2-chlorobenzyl | CH₃ | N | CH | CH | 154 |
| II-73 | 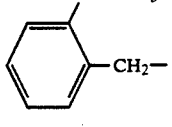 2-methoxycarbonylbenzyl | OCH₃ | N | CH | C—Cl | 145 |
| II-74 | 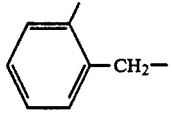 2-chlorobenzyl | OCH₃ | N | CH | C—OCH₃ | 150 |
| II-75 | 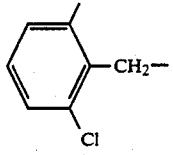 2,6-dichlorobenzyl | OCH₃ | N | CH | C—OCH₃ | 188 |

TABLE 4-continued

Examples of the starting substances of the formula (II)

| Ex. No. | R¹ | R⁴ | X | Y | Z | Melting point (°C.) |
|---|---|---|---|---|---|---|
| II-76 | 2-Cl-phenyl | OCH₃ | N | CH | C—OCH₃ | 153 |
| II-77 | naphthyl | OCH₃ | N | N | C—OCH₃ | 89 |
| II-78 | 2-C₆H₅-phenyl | CH₃ | N | CH | C—CH₃ | 164 |
| II-79 | 2-SCH₃-phenyl | OCH₃ | N | CH | C—OCH₃ | 198 |
| II-80 | 2-SCH₃-phenyl | CH₃ | N | CH | C—CH₃ | 146 |
| II-81 | 2-SOCH₃-phenyl | CH₃ | N | CH | C—CH₃ | 192 |
| II-82 | 2-SCH(CH₃)₂-phenyl | OCH₃ | N | CH | C—OCH₃ | 194 |
| II-83 | 2-SOCH₃-phenyl | OCH₃ | N | CH | C—OCH₃ | 149 |
| II-84 | 2-F,6-Cl-benzyl | CH₃ | N | N | C—OCH₃ | 231 (decomp.) |
| II-85 | 2,4-Cl₂-benzyl | CH₃ | N | N | C—OCH₃ | 233 (decomp.) |
| II-86 | benzyl | OCH₃ | N | N | C—OCH₃ | 156 (decomp.) |

TABLE 4-continued

Examples of the starting substances of the formula (II)

| Ex. No. | $R^1$ | $R^4$ | X | Y | Z | Melting point (°C.) |
|---|---|---|---|---|---|---|
| II-87 | 2-F-C$_6$H$_4$-CH$_2$- | OCH$_3$ | N | N | C—OCH$_3$ | 218 |
| II-88 | 4-F-C$_6$H$_4$-CH$_2$- | OCH$_3$ | N | N | C—OCH$_3$ | 225 |
| II-89 | 3-Cl-C$_6$H$_4$-CH$_2$- | OCH$_3$ | N | N | C—OCH$_3$ | 220 |
| II-90 | 3-CF$_3$-C$_6$H$_4$-CH$_2$- | OCH$_3$ | N | N | C—OCH$_3$ | 189 |
| II-91 | 2-F-6-Cl-C$_6$H$_3$-CH$_2$- | OCH$_3$ | N | N | C—OCH$_3$ | 214 |
| II-92 | 2-CF$_3$-C$_6$H$_4$-CH$_2$- | CH$_3$ | N | CH | C—OCH$_3$ | 187 |
| II-93 | 2-OCF$_3$-C$_6$H$_4$- | CH$_3$ | N | CH | C—OCH$_3$ | 135 |
| II-94 | 2-CF$_3$-C$_6$H$_4$- | CH$_3$ | N | CH | C—OCH$_3$ | 140 |

Use Examples

In the following Use Examples, the compound listed below is used as comparison substance:

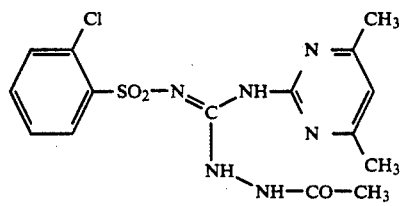

(A)

N'-4,6-dimethyl-pyrimidin-2-yl)-N'''-acetylamino-N'''-(2-chloro-phenylsulphonyl)-guanidine (disclosed in EP-A 121,082).

The formulae of the compounds according to the invention which are used for the Use Examples are listed individually below, using the numbering for the Preparation Examples ("Example No.").

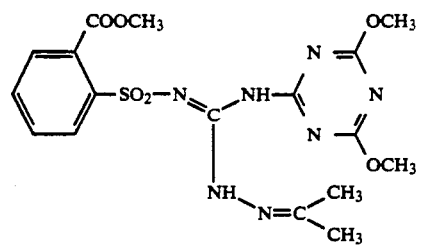
(3)
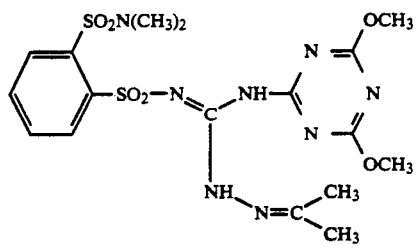
(68)
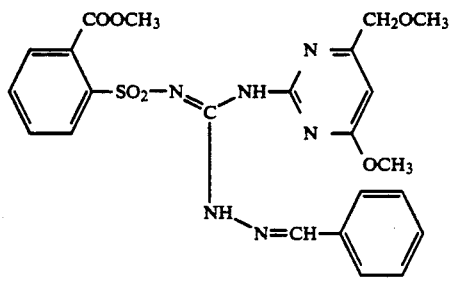
(5)
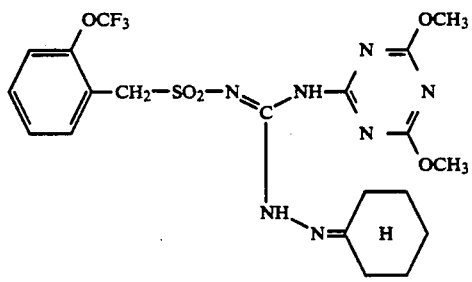
(72)
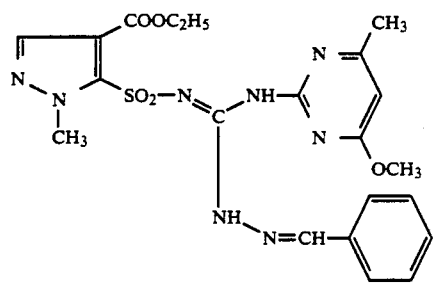
(9)
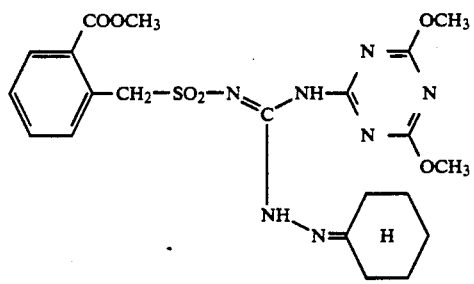
(71)
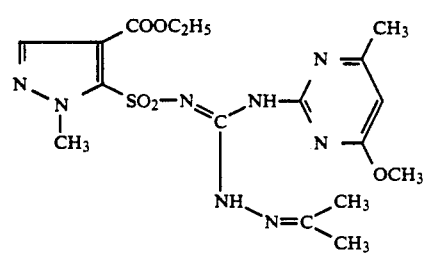
(10)
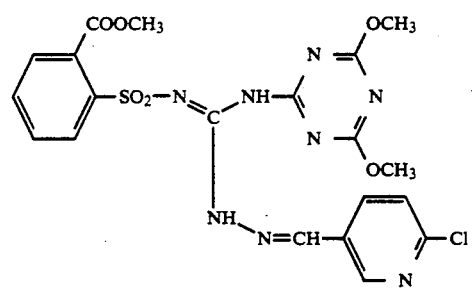
(73)
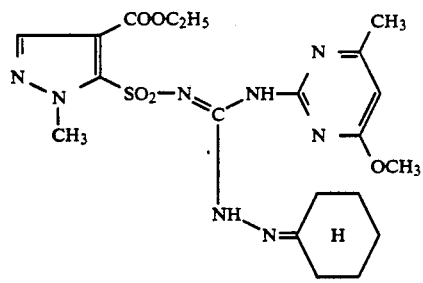
(11)
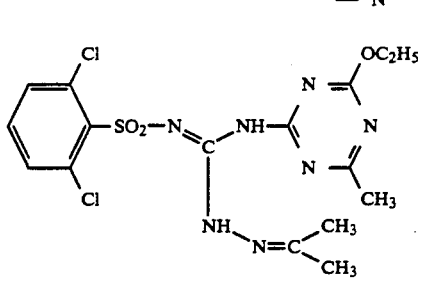
(80)
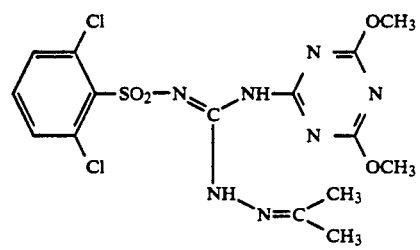
(67)
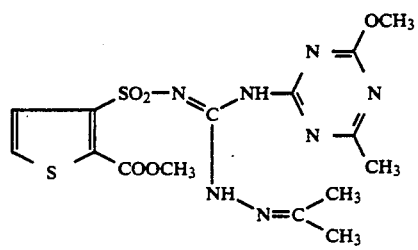
(83)

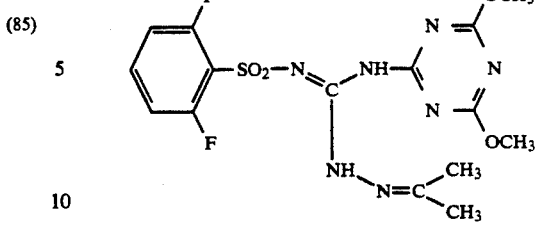
(85)
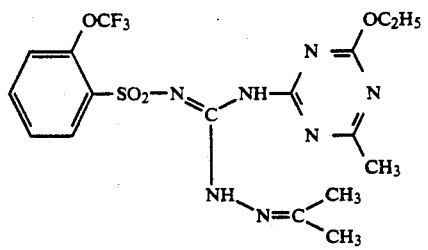
(86)
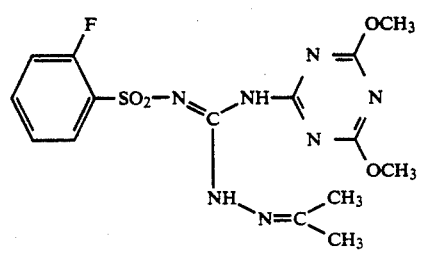
(87)
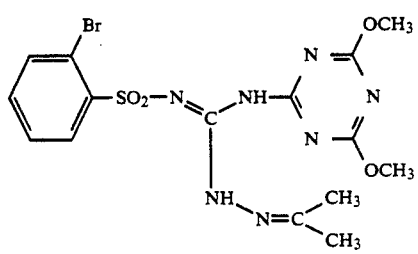
(88)
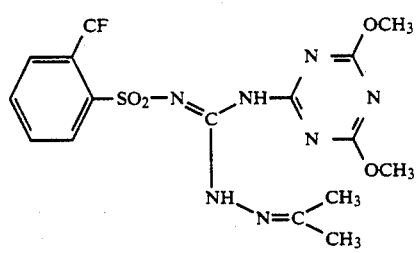
(92)
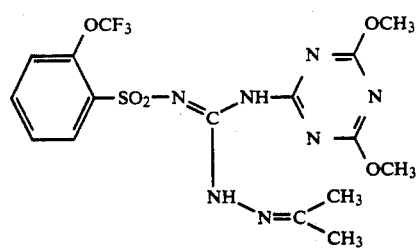
(93)
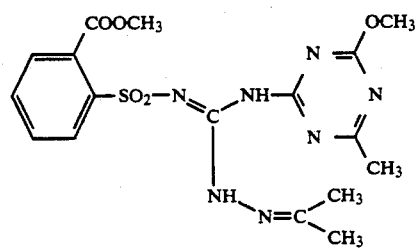
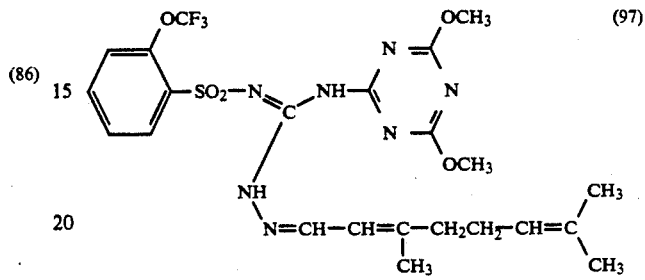
(95)
(97)
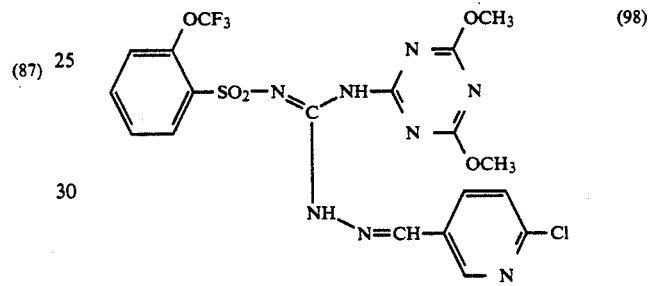
(98)
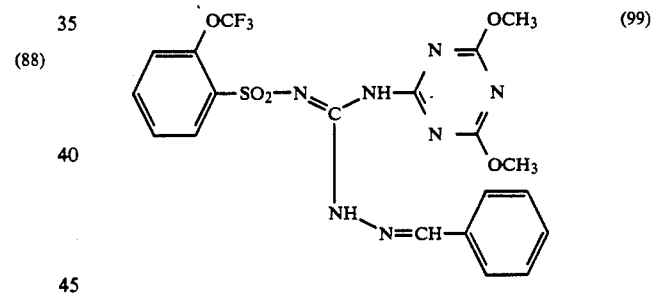
(99)
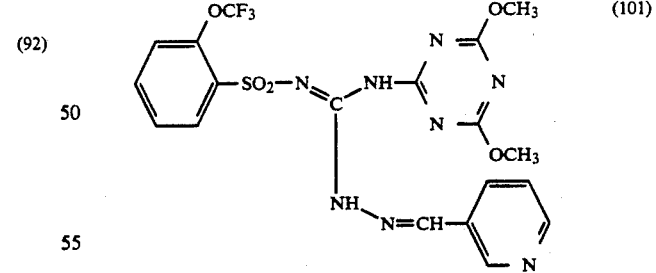
(101)
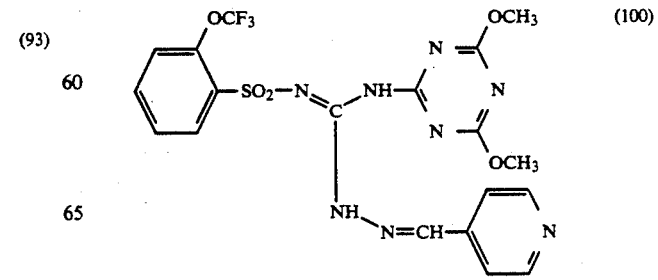
(100)

355
-continued
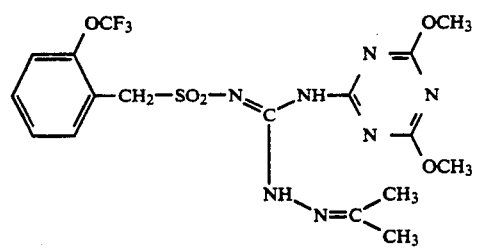 (102)
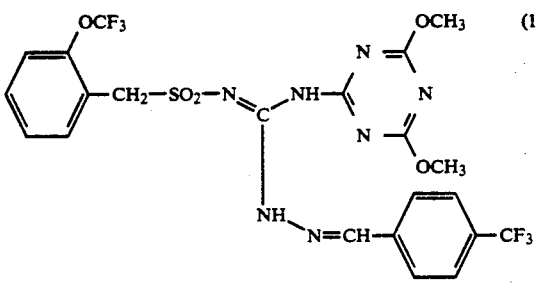 (106)
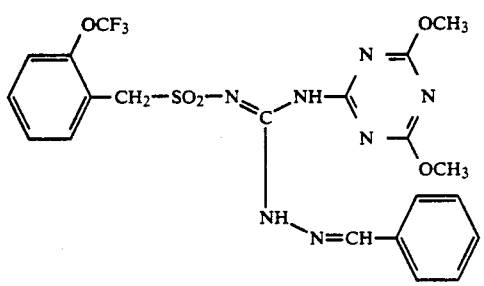 (107)
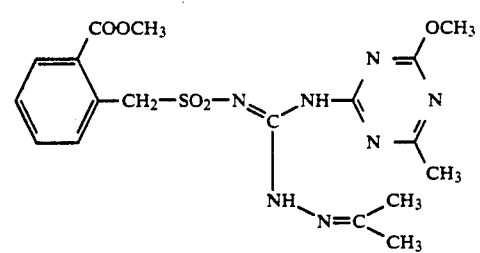 (108)
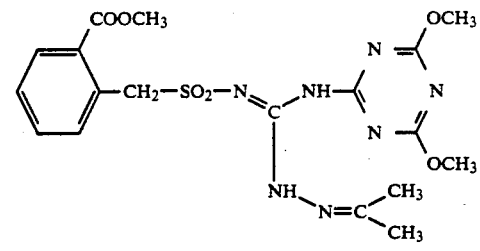 (109)
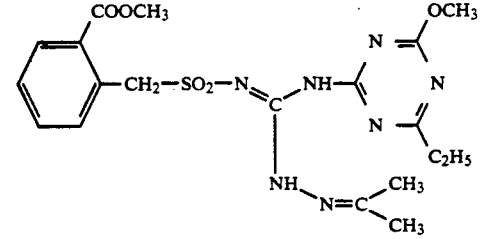 (111)
356
-continued
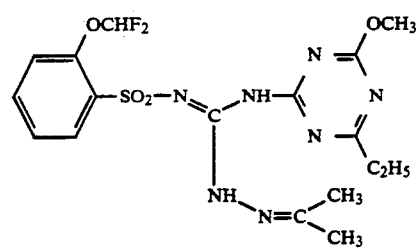 (115)
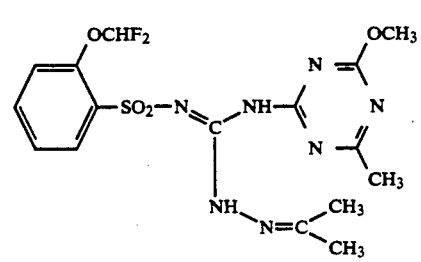 (116)
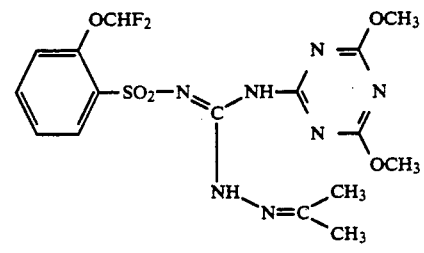 (117)
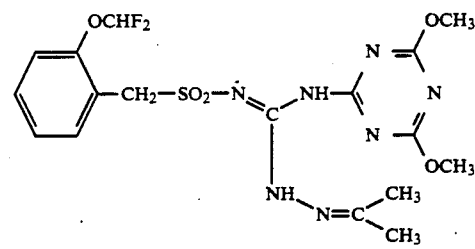 (123)
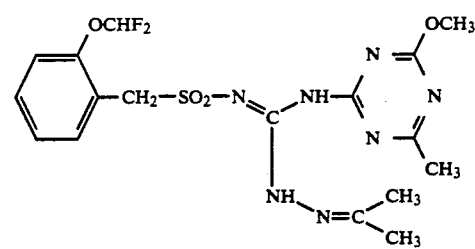 (125)
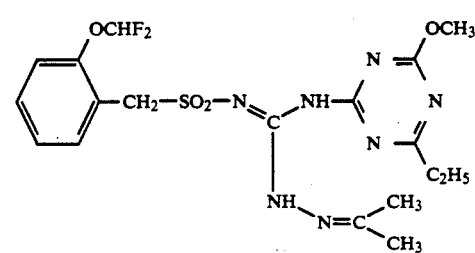 (126)

-continued

-continued (283) 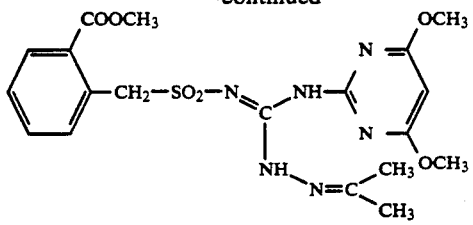

(284) 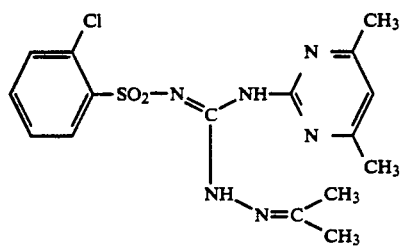

(285) 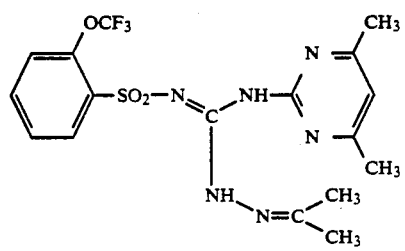

(286) 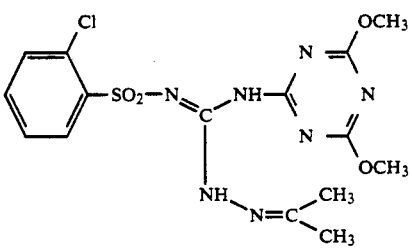

(287) 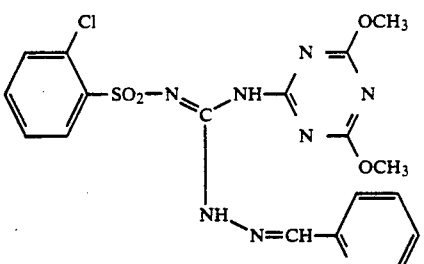

(291) 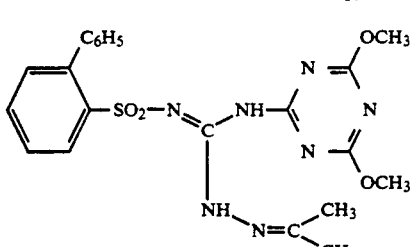

EXAMPLE A

Pre-Emergence Test

Solvent: 5 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of the active compound. It is expedient to keep constant the amount of water per unit area. The concentration of the active compound in the preparation is of no importance, only the amount of active compound applied per unit area being decisive. After three weeks, the degree of damage to the plants is rated in % damage in comparison to the development of the untreated control. The figures denote:

0% = no action (like untreated control)

100% = total destruction

A clearly superior activity compared with the prior art is shown in this test, for example, by the compounds of the following Preparation Examples: 3, 67, 68, 80, 83, 85, 87, 88, 92, 93, 95, 99, 101, 108, 116, 117, 258, 269, 270, 271, 272, 273, 275, 276, 278, 284, 285 and 286.

EXAMPLE B

Post-Emergence Test

Solvent: 5 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

Test plants which have a height of 5–15 cm are sprayed with the preparation of the active compound in such a way as to apply the particular amounts of active compound desired per unit area. The concentration of the spray liquor is so chosen that the particular amounts of active compound desired are applied in 1,000 l of water/ha. After three weeks, the degree of damage to the plants is rated in % damage in comparison to the development of the untreated control. The figures denote:

0% = no action (like untreated control)

100% = total destruction

A clearly superior activity compared with the prior art is shown in this test, for example, by the compounds of the following Preparation Examples: 5, 9, 10, 11, 67, 68, 71, 72, 73, 80, 83, 86, 87, 88, 93, 95, 97, 98, 99, 100, 101, 102, 106, 107, 108, 109, 111, 115, 116, 117, 123, 125, 126, 127, 128, 257, 269, 270, 276, 278, 283, 286, 287 and 291.

We claim:

1. A substituted sulphonylamidinohydrazone of the formula

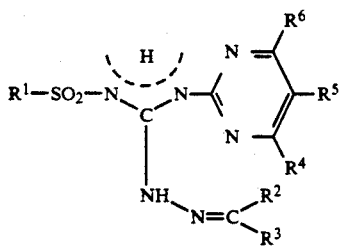

in which $R^1$ represents the radical

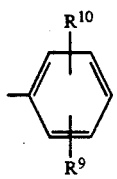

where $R^9$ and $R^{10}$ are identical or different and represent hydrogen, fluorine, chlorine, bromine, iodine, cyano, nitro, $C_1-C_6$-alkyl (which is optionally substituted by fluorine, chlorine, bromine, cyano, carboxyl, $C_1-C_4$-alkoxycarbonyl, $C_1-C_4$-alkylaminocarbonyl, di-($C_1-C_4$-alkyl)-amino-carbonyl, hydroxyl, $C_1-C_4$-alkoxy, formyloxy, $C_1-C_4$-alkyl-carbonyloxy, $C_1-C_4$-alkoxy-carbonyloxy, $C_1-C_4$-alkylaminocarbonyloxy, $C_1-C_4$-alkylthio, $C_1-C_4$-alkylsulphinyl, $C_1-C_4$-alkylsulphonyl, di-($C_1-C_4$-alkyl)-aminosulphonyl, $C_3-C_6$-cycloalkyl or phenyl), or represent $C_2-C_6$-alkenyl (which is optionally substituted by fluorine, chlorine, bromine, cyano, $C_1-C_4$-alkoxy-carbonyl, carboxyl or phenyl), or represent $C_2-C_6$-alkinyl (which is optionally substituted by fluorine, chlorine, bromine, cyano, $C_1-C_4$-alkoxy-carbonyl, carboxyl or phenyl), or represent $C_1-C_4$-alkoxy (which is optionally substituted by fluorine, chlorine, bromine, cyano, carboxyl, $C_1-C_4$-alkoxy-carbonyl, $C_1-C_4$-alkoxy, $C_1-C_4$-alkylthio, $C_1-C_4$-alkylsulphinyl or $C_1-C_4$-alkylsulphonyl), or represent $C_1-C_4$-alkylthio (which is optionally substituted by fluorine, chlorine, bromine, cyano, carboxyl, $C_1-C_4$-alkoxy-carbonyl, $C_1-C_4$-alkylthio, $C_1-C_4$-alkylsulphinyl or $C_1-C_4$-alkylsulphonyl), or represent $C_3-C_6$-alkenyloxy (which is optionally substituted by fluorine, chlorine, bromine, cyano or $C_1-C_4$-alkoxy-carbonyl), or represent $C_2-C_6$-alkenylthio (which is optionally substituted by fluorine, chlorine, bromine, cyano, nitro, $C_1-C_3$-alkylthio or $C_1-C_4$-alkoxycarbonyl), $C_3-C_6$-alkinyloxy or $C_3-C_6$-alkinylthio, or represent the radical —$S(O)_p$—$R^{11}$ where p represents the numbers 1 or 2 and $R^{11}$ represents $C_1-C_4$-alkyl (which is optionally substituted by fluorine, chlorine, bromine, cyano or $C_1-C_4$-alkoxy-carbonyl), $C_3-C_6$-alkenyl, $C_3-C_6$-alkinyl, phenyl, $C_1-C_4$-alkoxy, $C_1-C_4$-alkoxy-$C_1-C_4$-alkylamino, $C_1-C_4$-alkylamino or di-($C_1-C_4$-alkyl)-amino, or represents the radical —$NHOR^{12}$ where $R^{12}$ represents $C_1-C_{12}$-alkyl (which is optionally substituted by fluorine, chlorine, cyano, $C_1-C_4$-alkoxy, $C_1-C_4$-alkylthio, $C_1-C_4$-alkylsulphinyl, $C_1-C_4$-alkylsulphonyl, $C_1-C_4$-alkyl-carbonyl, $C_1-C_4$-alkoxycarbonyl, $C_1-C_4$-alkylamino-carbonyl or di-($C_1-C_4$-alkyl)amino-carbonyl, or represents $C_3-C_6$-alkenyl (which is optionally substituted by fluorine, chlorine or bromine), $C_3-C_6$-alkinyl, $C_3-C_6$-cycloalkyl, $C_3-C_6$-cycloalkyl-$C_1-C_2$-alkyl, phenyl-$C_1-C_2$-alkyl (which is optionally substituted by fluorine, chlorine, nitro, cyano, $C_1-C_4$-alkyl, $C_1-C_4$-alkoxy or $C_1-C_4$-alkoxy-carbonyl), or represents benzyhydryl, or represents phenyl (which is optionally substituted by fluorine, chlorine, nitro, cyano, $C_1-C_4$-alkyl, trifluoromethyl, $C_1-C_4$-alkoxy, $C_1-C_2$-fluoroalkoxy, $C_1-C_4$-alkylthio, trifluoromethylthio or $C_1-C_4$-alkoxycarbonyl), or $R^9$ and $R^{10}$ furthermore represent phenyl or phenoxy, or represent amino, $C_1-C_4$-alkylcarbonylamino, $C_1-C_4$-alkoxy-carbonylamino, $C_1-C_4$-alkylaminocarbonyl-amino or di-($C_1-C_4$-alkyl)amino-carbonylamino, or represent the radical —SO—$R^{13}$ where $R^{13}$ represents $C_1-C_6$-alkyl, $C_1-C_6$-alkoxy (which is optionally substituted by fluorine, chlorine, methoxy or ethoxy), or represents $C_3-C_6$-cycloalkoxy, $C_3-C_6$-alkenyloxy, $C_1-C_4$-alkylthio, $C_1-C_4$-alkylamino, $C_1-C_4$-alkoxyamino, $C_1-C_4$-alkoxy-$C_1-C_4$-alkyl-amino or di-($C_1-C_4$-alkyl)-amino (each of which is optionally substituted by fluorine and/or chlorine), or $R^9$ and $R^{10}$ furthermore represent $C_1-C_4$-alkylsulphonyloxy, di-($C_1-C_4$-alkyl)-aminosulphonylamino or thiazolyloxy, or represent the radical —CH=N—$R^{14}$ where $R^{14}$ represents $C_1-C_6$-alkyl which is optionally substituted by fluorine, chlorine, cyano, carboxyl, $C_1-C_4$-alkoxy, $C_1-C_4$-alkylthio, $C_1-C_4$-alkylsulphinyl or $C_1-C_4$-alkylsulphonyl, or represents benzyl which is optionally substituted by fluorine or chlorine, or represents $C_3-C_6$-alkenyl or $C_3-C_6$-alkinyl, each of which is optionally substituted by fluorine or chlorine, or represents phenyl which is optionally substituted by fluorine, chlorine, bromine, $C_1-C_4$-alkyl, $C_1-C_4$-alkoxy, trifluoromethyl, trifluoromethoxy or trifluoromethylthio, or represents $C_1-C_6$-alkoxy, $C_3-C_6$-alkenoxy, $C_3-C_6$-alkinoxy or benzyloxy, each of which is optionally substituted by fluorine and/or chlorine, or represents amino, $C_1-C_4$-alkylamino, di-($C_1-C_4$-alkyl)-amino, phenylamino, $C_1-C_4$-alkyl-carbonylamino, $C_1-C_4$-alkoxy-carbonylamino or $C_1-C_4$-alkylsulphonylamino, or represents phenylsulphonylamino which is optionally substituted by fluorine, chlorine, bromine or methyl; or $R^1$ represents the radical

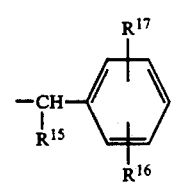

where $R^{15}$ represent hydrogen or $C_1-C_4$-alkyl, $R^{16}$ and $R^{17}$ are identical or different and represent hydrogen, fluorine, chlorine, bromine, nitro, cyano, $C_1$–$C_4$-alkyl (which is optionally substituted by fluorine and/or chlorine), $C_1$–$C_4$-alkoxy (which is optionally substituted by fluorine and/or chlorine), carboxyl, $C_1$–$C_4$-alkoxycarbonyl, $C_1$–$C_4$-alkylsulphonyl or di-($C_1$–$C_4$-alkyl)-aminosulphonyl; or $R^1$ represents the radical

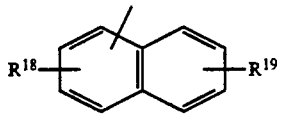

where $R^{18}$ and $R^{19}$ are identical or different and represent hydrogen, fluorine, chlorine, bromine, nitro, cyano, dimethylamino, $C_1$–$C_4$-alkyl (which is optionally substituted by fluorine and/or chlorine) or $C_1$–$C_4$-alkoxy (which is optionally substituted by fluorine and/or chlorine); or $R^1$ represents the radical

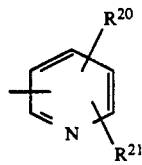

where $R^{20}$ and $R^{21}$ are identical or different and represent hydrogen, fluorine, chlorine, bromine, nitro, cyano, $C_1$–$C_4$-alkyl (which is optionally substituted by fluorine and/or chlorine), $C_2$–$C_4$-alkenyl (which is optionally substituted by fluorine and/or chlorine), $C_1$–$C_4$-alkoxy (which is optionally substituted by fluorine and/or chlorine), or represent $C_1$–$C_4$-alkylthio, $C_1$–$C_4$-alkylsulphinyl or $C_1$–$C_4$-alkylsulphonyl (each of which is optionally substituted by fluorine and/or chlorine), and also represent di-($C_1$–$C_4$-alkyl)-aminosulphonyl, $C_1$–$C_4$-alkoxy-carbonyl, dimethylaminocarbonyl or dioxolanyl; or $R^1$ represents the radical

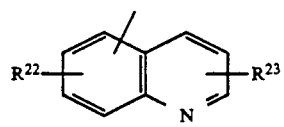

where $R^{22}$ and $R^{23}$ are identical or different and represent hydrogen, fluorine, chlorine, bromine, $C_1$–$C_4$-alkyl (which is optionally substituted fluorine and/or bromine), $C_1$–$C_4$-alkoxy (which is optionally substituted by fluorine and/chlorine), or represent $C_1$–$C_4$-alkylthio, $C_1$–$C_4$-alkylsulphinyl or $C_1$–$C_4$-alkylsulphonyl (each of which is optionally substituted by fluorine and/or chlorine), or represent di-($C_1$–$C_4$-alkyl)-aminosulphonyl; or $R^1$ represents the radical

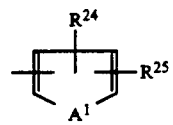

where $R^{24}$ and $R^{25}$ are identical or different and represent hydrogen, fluorine, chlorine, bromine, cyano, nitro, $C_1$–$C_4$-alkyl (which is optionally substituted by fluorine, chlorine, $C_1$–$C_4$-alkoxy and/or $C_1$–$C_4$-halogenoalkoxy), $C_1$–$C_4$-alkoxy (which is optionally substituted by fluorine and/or chlorine), or $C_1$–$C_4$-alkylthio, $C_1$–$C_4$-alkylsulphinyl or $C_1$–$C_4$-alkylsulphonyl (each of which is optionally substituted by fluoride and/or chlorine), di-($C_1$–$C_4$-alkyl)aminosulphonyl, $C_1$–$C_4$-alkoxy-carbonyl, dioxolanyl or 2-thiazolyl, and $A^1$ represents oxygen, sulphur or the N—$Z^1$ group where
$Z^1$ represents hydrogen, $C_1$–$C_4$-alkyl (which is optionally substituted by fluorine, chlorine, bromine or cyano), $C_3$–$C_6$-cycloalkyl, benzyl, phenyl (which is optionally substituted by fluorine, chlorine, bromine or nitro), $C_1$–$C_4$-alkylcarbonyl, $C_1$–$C_4$-alkoxy-carbonyl or di-($C_1$–$C_4$-alkyl)-aminocarbonyl; or $R^1$ represents the radical

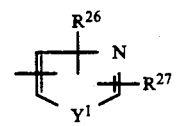

where $R^{26}$ represents hydrogen, $C_1$–$C_5$-alkyl or halogen,
$R^{27}$ represents hydrogen or $C_1$–$C_5$-alkyl and
$Y^1$ represents oxygen, sulphur or the N—$R^{28}$ group where
$R^{28}$ represents hydrogen or $C_1$–$C_5$-alkyl; or $R^1$ represents the radical

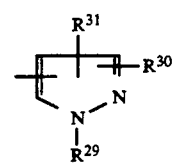

where $R^{23}$ represents hydrogen, $C_1$–$C_4$-alkyl, phenyl or (iso)quinolinyl,
$R^{30}$ represents hydrogen, halogen, cyano, nitro, $C_1$–$C_4$-alkyl (which is optionally substituted by fluorine and/or chlorine), $C_1$–$C_4$-alkoxy (which is optionally substituted by fluorine and/or chlorine), dioxolanyl or $C_1$–$C_4$-alkoxy-carbonyl, and
$R^{31}$ represents hydrogen, halogen or $C_1$–$C_4$-alkyl; or $R^1$ represents the radical

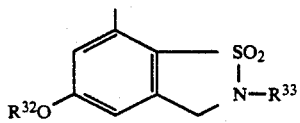

where
R$^{32}$ represents C$_1$-C$_3$-alkyl and
R$^{33}$ represents C$_1$-C$_4$-alkyl; or
R$^1$ represents the radical

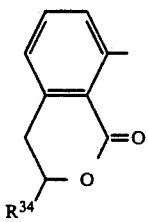

where
R$^{34}$ represents hydrogen or methyl; or
R$^1$ represents the radical

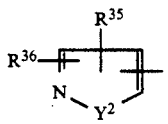

where
R$^{35}$, represents hydrogen, halogen or C$_1$-C$_4$-alkyl,
R$^{36}$ represents hydrogen, halogen, C$_1$-C$_4$-alkyl, C$_1$-C$_4$-halogenoalkyl, C$_1$-C$_4$-alkoxy or C$_1$-C$_4$-halogenoalkoxy, Y$^2$ represents oxygen or sulphur; or
R$^1$ represents pentamethylphenyl,
R$^2$ represent hydrogen, or represents C$_1$-C$_6$-alkyl which is optionally substituted by fluorine, chlorine and/or bromine, or represents phenyl or benzyl, each of which is optionally substituted by fluorine, chlorine, bromine, C$_1$-C$_4$-alkyl and/or C$_1$-C$_4$-alkoxy,
R$^3$ represents hydrogen, or represents C$_1$-C$_{20}$-alkyl, C$_2$-C$_{10}$-alkenyl, C$_2$-C$_{10}$-alkinyl or C$_4$-C$_{10}$-alkadienyl, each of which is optionally substituted by fluorine, chlorine and/or bromine, or represents C$_1$-C$_4$-alkoxy-C$_1$-C$_4$-alkyl, or represents C$_1$-C$_4$-alkyl-thio-C$_1$-C$_4$-alkyl, or represents phenyl which is optionally substituted by fluorine, chlorine, bromine, carboxyl, cyano, nitro, amino, C$_1$-C$_4$-alkyl (which is optionally substituted by fluorine and/or chlorine), C$_1$-C$_4$-alkoxy (which is optionally substituted by fluorine and/or chlorine), C$_1$-C$_4$-alkylthio (which is optionally substituted by fluorine and/or chlorine), di-(C$_1$-C$_4$-alkyl)-amino, C$_1$-C$_4$-alkoxy-carbonyl and/or phenoxy (which is optionally substituted by fluorine, chlorine and/or trifluoromethyl), or represents naphthyl, or represents pyridyl, pyrrolyl, furyl, thiazolyl or thienyl, each of which is optionally substituted by cyano, nitro, fluorine, chlorine, bromine, C$_1$-C$_4$-alkyl and/or C$_1$-C$_4$-alkoxy, or represents dithienyl, or represents phenyl-C$_1$-C$_2$-alkyl or phenylethenyl, each of which is optionally substituted by fluorine, chlorine, bromine, C$_1$-C$_4$-alkyl and/or C$_1$-C$_4$-alkoxy, or represents C$_1$-C$_6$-alkoxy, C$_1$-C$_6$-alkoxy-carbonyl or di-(alkyl)-amino, or together with R$^2$ represents C$_2$-C$_6$-alkanediyl which is optionally substituted by fluorine, chlorine, bromine, C$_1$-C$_4$-alkyl and/or C$_1$-C$_4$-alkoxy-carbonyl, R$^4$ represents hydrogen, fluorine, chlorine, bromine, C$_1$-C$_4$-alkyl, C$_1$-C$_4$-halogenoalkyl, C$_1$-C$_2$-alkoxy-C$_1$-C$_2$-alkyl, bis-(C$_1$-C$_2$-alkoxy)-C$_1$-C$_2$-alkyl, C$_1$-C$_4$-alkoxy, C$_1$-C$_4$-halogenoalkoxy, C$_1$-C$_4$-alkylthio, C$_1$-C$_4$-halogenoalkylthio, amino, C$_1$-C$_4$-alkylamino, dimethylamino or diethylamino, and R$^5$ represents hydrogen, halogen, cyano, C$_1$-C$_4$-alkyl, formyl, C$_1$-C$_4$-alkyl-carbonyl or C$_1$-C$_4$-alkoxy-carbonyl, and R$^6$ represents hydrogen, fluorine, chlorine, bromine, C$_1$-C$_4$-alkyl, trifluoromethyl, C$_1$-C$_4$-alkoxy, difluoromethoxy, C$_1$-C$_4$-alkylthio, C$_1$-C$_4$-alkylamino, dimethylamino or diethylamino.

2. A compound according to claim 1, in which
R$^1$ represents the radical

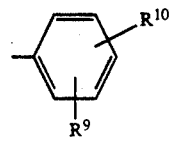

where
R$^9$ represents fluorine, chlorine, bromine, cyano, methyl, trifluoromethyl, methoxy, ethoxy, difluoromethoxy, trifluoromethoxy, C$_1$-C$_3$-alkylthio, C$_1$-C$_3$-alkylsulphinyl, C$_1$-C$_3$-alkylsulphonyl, phenylsulphonyl, dimethylaminosulphonyl, diethylaminosulphonyl, N-methoxy-N-methylaminosulphonyl, phenyl, phenoxy or C$_1$-C$_3$-alkoxycarbonyl, and R$^{10}$ represents hydrogen, fluorine, chlorine, bromine, methyl or methoxy; or
R$^1$ represents the radical

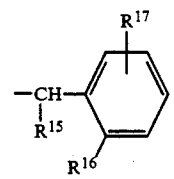

where
R$^{15}$ represents hydrogen,
R$^{16}$ represents fluorine, chlorine, bromine, cyano, methyl, methoxy, ethoxy, difluoromethoxy, trifluoromethoxy, methoxycarbonyl, ethoxycarbonyl, methylsulphonyl or dimethylaminosulphonyl, and
R$^{17}$ represents hydrogen or chlorine; or
R$^1$ represents the radical

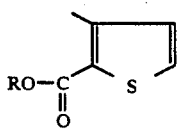

where
R represents C$_1$-C$_2$-alkyl; or
R$^1$ represents the radical

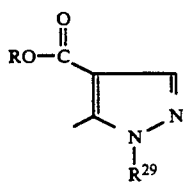

where
R$^{29}$ represents methyl or phenyl and
R represents C$_1$–C$_2$-alkyl, or
R$^1$ represents naphthyl;
R$^2$ represents hydrogen, C$_1$–C$_4$-alkyl or phenyl,
R$^3$ represents C$_1$–C$_{10}$-alkyl, C$_2$–C$_{10}$-alkenyl or C$_4$–C$_{10}$-alkadienyl, or represents phenyl which is optionally substituted by fluorine, chlorine, bromine, carboxyl, cyano, nitro, methyl, ethyl, trifluoromethyl, methoxy, ethoxy, difluoromethoxy, trifluoromethoxy, methylthio, ethylthio, difluoromethylthio, trifluoromethylthio, dimethylamino and/or phenoxy (which is optionally substituted by fluorine, chlorine and/or trifluoromethyl), or represents pyridyl, furyl, thiazolyl or thienyl, each of which is optionally substituted by cyano, nitro, fluorine, chlorine, bromine, methyl, ethyl, methoxy or ethoxy, or represents dithienyl, or represents benzyl or phenylethenyl, or represents C$_1$–C$_4$-alkoxy, C$_1$–C$_4$-alkoxy-carbonyl or dimethylamino, or together with R$^2$ represents butane-1,4-diyl (tetramethylene) or pentane-1,5-diyl (pentamethylene),
R$^4$ represents hydrogen, fluorine, chlorine, bromine, methyl, methoxymethyl, trifluoromethyl, methoxy, ethoxy, difluoromethoxy, methylthio, ethylthio, amino, methylamino, ethylamino, dimethylamino or diethylamino,
R$^5$ represents hydrogen, fluorine, chlorine or methyl, and
R$^6$ represents hydrogen, fluorine, chlorine, bromine, methyl, ethyl, trifluoromethyl, methoxy, ethoxy, propoxy, isopropoxy, difluoromethoxy, methylthio, ethylthio, methylamino, ethylamino, dimethylamino or diethylamino.

3. A compound according to claim 1, wherein such compound is N'-(4,6-dimethoxy-pyrimidin-2-yl)-N''-(1-methylethylideneamino)-N'''-(2-methylthio-phenysulphonyl)-guanidine of the formula

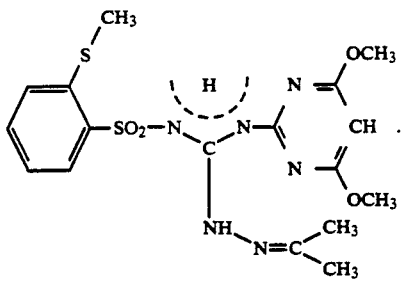

4. A compound according to claim 1, wherein such compound is N'-(4,6-dimethoxy-pyrimidin-2-yl)-N''-(benzylideneamino)-N'''-(2-methylsulphinyl-phenylsulphonyl)-guanidine of the formula

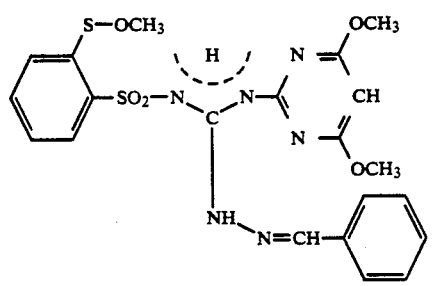

5. A herbicidal composition comprising a herbicidally effective amount of a compound according to claim 1 and a diluent.

6. A method of combating unwanted vegetation which comprises applying to such vegetation or to a locus from which it is desired to exclude such vegetation a herbicidal composition comprising a herbicidally effective amount of a compound according to claim 1.

7. The method according to claim 6, wherein such compound is
N'-(4,6-dimethoxy-pyrimidin-2-yl)-N'''-(1-methylethylideneamino)-N''''-(2-methylthio-phenylsulphonyl)-guanidine and
N'(4,6-dimethoxy-pyrimidin-2-yl)-N''-(benzylideneamino)-N'''-(2-methylsulphinyl-phenylsulphonyl)-guanidine.

* * * * *